(12) United States Patent
Edwards et al.

(10) Patent No.: US 12,398,426 B2
(45) Date of Patent: Aug. 26, 2025

(54) METHODS OF DETECTING INHERITED MYOPATHIES IN HORSES

(71) Applicant: UNM RAINFOREST INNOVATIONS, Albuquerque, NM (US)

(72) Inventors: Jeremy Scott Edwards, Albuquerque, NM (US); Paul Szauter, Albuquerque, NM (US); Robert B. Sinclair, Columbus, NC (US); Kirsten Dimmler, St. Paul, MN (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 1118 days.

(21) Appl. No.: 17/263,757

(22) PCT Filed: May 23, 2019

(86) PCT No.: PCT/US2019/033717
§ 371 (c)(1),
(2) Date: Jan. 27, 2021

(87) PCT Pub. No.: WO2020/033026
PCT Pub. Date: Feb. 13, 2020

(65) Prior Publication Data
US 2021/0180137 A1 Jun. 17, 2021

Related U.S. Application Data

(60) Provisional application No. 62/737,295, filed on Sep. 27, 2018, provisional application No. 62/717,072, filed on Aug. 10, 2018.

(51) Int. Cl.
*C12Q 1/68* (2018.01)
*C12P 19/34* (2006.01)
*C12Q 1/6883* (2018.01)

(52) U.S. Cl.
CPC ..... *C12Q 1/6883* (2013.01); *C12Q 2600/156* (2013.01)

(58) Field of Classification Search
CPC .................................................. C12Q 1/6883
See application file for complete search history.

(56) References Cited

PUBLICATIONS

Submitted SNP (ss) ss3044218992 from "European Variation Archive", Aug. 30, 2017, obtained online and printed from https://www.ebi.ac.uk/eva/?variant&accessionID=ss3044218992 (Year: 2017).*
Lobo, I. (2008) Genetics and Statistical Analysis. Nature Education 1(1):109 (Year: 2008).*
Ronald A. Thisted, "What is a P-value?" Departments of Statistics and Health Studies, The University of Chicago. Jun. 8, 1998, pp. 1-6. (Year: 1998).*
Durward-Akhurst SA, et al. "Predicted genetic burden and frequency of phenotype-associated variants in the horse". Sci Rep. Apr. 10, 2024;14(1):8396 (Year: 2024).*
GenBank Locus:CM000382, "Equus caballus chromosome 6, whole genome shotgun sequence". REGION: 23480600 . . . 23480640 Apr. 25, 2014. From https://www.ncbi.nlm.nih.gov/nuccore/CM000382.2. (Year: 2014).*
GenBank XM_023642648 "PREDICTED: Equus caballus collagen type VI alpha 3 chain (COL6A3), transcript variant X5, mRNA" Jan. 23, 2018, from https://www.ncbi.nlm.nih.gov/nucleotide/XM_023642648.1. (Year: 2018).*
Schaefer et al. "Developing a 670k genotyping array to tag ~2M SNPs across 24 horse breeds" BMC Genomics (2017) 18:565 (Year: 2017).*
Affymetrix Technical Note "Linking Whole-genome Amplification to SNP Genotyping" 2008, from https://assets.thermofisher.com/TFS-Assets/LSG/brochures/wga_snp_technote.pdf (Year: 2008).*
Broad Institute Horse Genome Project (https://www.broadinstitute.org/horse/horse-genome-project) . (Year: 2007).*
Thunes C. Feeding Horses with Neuromuscular Disorders. May 2015 (online) https://thehorse.com/112050/feeding-horses-with-neuromuscular-disorders/.
Wackermann K. PSSM2 beim Pferd—die Trainings-Intoleranz. Mar. 2022 (online) https://www.st-georg.de/wissen/pssm2-beim-pferd-die-trainings-intoleranz/.
Wackermann K. PSSM2 in horses (english translation). Mar. 2022 (online) https://www.st-georg.de/wissen/pssm2-beim-pferd-die-trainings-intoleranz/.
Moro LN, et al. Generation of myostatin edited horse embryos using CRISPR/Cas9 technology and somatic cell nuclear transfer. Scientific Reports, 2020;10:15587 https://doi.org/10.1038/s41598-020-72040-4.
Ablondi M, et al. Performance of Swedish Warmblood fragile foal syndrome carriers and breeding prospects. Genetics Selection Evolution, 2022;54:4.
Hames M. EquiSeq Review. EquiSeq Facebook Page, May 1, 2022. https://www.facebook.com/EquiSeq1/posts/2697622740380203.
Szauter P. Genetic Basis of Exercise Intolerance in Arabian. Al Khamsa Annual Meeting and Convention, Oct. 13, 2019.
Equiseq. Warmblood Fragile Foal Syndrome (WFFS). Aug. 2, 2016 (online) http://equiseq.com/learning_center/health/warmblood-fragile-foal-syndrome-wffs.
Aurino S, et al. Candidate-gene testing for orphan limb-girdle muscular dystrophies. Acta Myologica, 2008;27:90-97.
Ferlini A, et al. The medical genetics of dystrophinopathies: Molecular genetic diagnosis and its impact on clinical practice. Neuromuscular Disorders, 2013;23:4-14.
Foroud T, et al. A mutation in myotilin causes spheroid bosy myopathy. Neurology, 2005;65(12):abstract.
Kley RA, et al. Impairment of protein degradation in myofibrillar myopathy caused by FLNC/filamin C mutations. Autophagy, 2013;9:422-423.

(Continued)

*Primary Examiner* — Stephen T Kapushoc
(74) *Attorney, Agent, or Firm* — Henry D. Coleman; R. Neil Sudol

(57) ABSTRACT

This disclosure describes detecting four genetically distinct kinds of inherited myopathy in horses, referred to as Polysaccharide Storage Myopathy type 2 (PSSM2), or in some cases as Myofibrillar Myopathy (MFM).

28 Claims, 36 Drawing Sheets
Specification includes a Sequence Listing.

(56) References Cited

PUBLICATIONS

Mykkanen AK, et al. MCT1, MCT3 and CD147 gene polymorphisms in healthy horses and horses with myopathy. Veterinary Science, 2011;91:473-477.

Nandelstadh, P; et al. A Class III PDZ Binding Motif in the Myotilin and FATZ Families Binds Enigma Family Proteins: a Common Link for Z-Disc Myopathies. Molecular and Cellular Biology, 2009;822-834.

Selcen D, Engel AG. Mutations in myotilin cause myofibrillar myopathy. Neurology, 2004;62(8):abstract.

Herrick K., et al. 144 Lack of Correspondence Between Commercial Genetic Test Variants . . . . Journal of Equine Veterinary Science 100 (2021) 103607.

Horse Genome Project. Broad Institute Dec. 11, 2023.

GenBank NCBI Reference Sequence XM_014739030.1 Equus caballus filamin C, gamma (FLNC) mRNA.

Valberg, et al. Commercial Genetic Testing for Type 2 Polysaccharide Storage Myopathy . . . . Equine Vet. Jour. 2021, 53:690-700.

Valberg, et al., Absence of myofibrillar myopathy in Quarter Horses . . . . Equine Vet. Jour. 2023; 55:230-238.

Van Nandelstadh, et al., A Class III PDZ Binding Motif . . . . Molecular and Cellular Biology, Feb. 2009, pp. 822-834.

Williams, et al., Integrated proteomic and pranscriptomic profiling identifies . . . . BMC Genomics (2021) 22:438.

Williams, et al., Candidate gene expression and coding sequence variants . . . . Equine Vet. Jour. 2020; May 26.

* cited by examiner

FIG. 1

```
31,307,949    TTCAGTTCTA AATCATGATA ATTTAAGGAA AAGTGCCAGC TATAACCACT
              ATGTTTACCC GAAAGACAAA ATTCTAATTT ATTGTTATTA TTATTATTCC
              CAAGGCATGT TTTTATTGTC TTTTTCCTCC TTAGAAAATT AATATATATT
              TATTGTAGAA AACTTGGAAA ATACAGCACA ATGAAGAGAA TAAAAATCAC
              TCACCCACCT TCCGATTGTT ATTAACAAAA TAACATTCTT CTATTTTAGT
              ATGCTGTTTT TTTTAAAAAG AGTTAATCCA TAAAGAAATA ACTGTTGATT
              AGAAATTAGA ACCAGTAAAT ATCTTTTTTC CATGAAACTT GTTTTAATAT
              TTTTAAATTT CATCTTTTTA AAAATATTTT GCCTACATTT AAGAAGCACA
              GATATTTACG AAACTTCATT TACTAAAAGT TCAATGGAGA AAAGTCTTAA
              TTTATTTCTC AGAATGTGAG AAATCCTTAC ATCTTATAAA GAATAAAGTG
              GGGTCATGTC GCCACGTAAG TTTGACCTCT GAGGGAATTG TTAGTAAAGA
              ATGTTCGAGC CACTTCAAAA CGTCAGCCTC CAGGGTCCGA GGTGGGGATT
              GTGCCAACGG CTGCATGAAG TGAACCGGGC TGCATCCTTG GCCCAGCTCT
              GGGATCTAAC ACTGGTGGCT TATTTGGGGC AGCCTGGCAG CTCTTTTGCA
              GAACTGTGGG ATTTTACAGC TGCAAGGTAC CTTGATGGGA AAATATGACT
              GTTCTTACAA TGCTCCTCCT AATCTTTTTT TAATTTCCTT CCCAAGAAGC
              CAGCAGGGAG GGTGGTCCCC GAGATTTCTG GCTTTCTTTG TGGCGAGGTC
              GGGGGAGGTG GGTGCCTGAC TGTTTTCCCC TTCCTCCTGC TCATGCCCCT
              TCCTGGCTTT CAGATCAGGG TCCAGGTGAT CGAGGGGCGC CAGCTGCCAG
              GGGTGAACAT CAAGCCTGTG GTCAAGGTCA CCGCGGCCAG GCAGACCAAG
31,306,949    (C/T)
              GGACTCGGAT TCACAGGGGA AACAGCCCGC TCTTCAACGA GGTGGGAGAC
              ATGGCGTTTT AGGGCTGGTA GCTTGGTGGG CCTTCCAGAT TGGGAGCACC
              CGGCAGATAC CTGGCAATTC TTTCAGTTTT TGTTCATGGC GCTAACTTTG
              GTTTGAGAGG TGTGCCAGGT CCTGAGTACG TTATCTGAGG AACTGGAGAG
              AGCGTTCTAG TTCTTATTCC TCTCCCGGC TCCTCGTGCT CCACATCCCT
              GTCTTCCTGT GGGGCCAGCC ACCCATGCTG TCCTGGAGAT GACAACCTCT
              GAGAGGTCAG GGGTGGAACA CCCCAGAACT TGTCGAGTCC TCAGAGCTCA
              GGGCCGGGCA GAGCTCACTC TGTGCTTTCC GTGTGGACCA GACCTGAAGG
              CTGTGGGTGT GGCCGACCCT CTTCCCAGCC TGGGGGTCAA CAGGCTCTCG
              TTTATCTTCT TTTCGCCCTG AACCAACAGA CTCTCTTCTT CAACGTGTTT
              GACTCTCCCT CGGAGCTGTT TGACGAGGCC GTCTTTATCA CGGTACGTCT
              CAGGGATCAA GGCGTGCTCT GTGGGCCGTG TGTACACACA TGCATTCAGT
              GTGCATGTGT GTGTATGCAC GTAGGGGTGT GAGTGTGAGA GTGTGTAGGA
              GAAGCCTTAG GGCCCGGGGC CTGGGTGATG TGGGGAGCTC GCTGCTAAGC
              TCTGCTGGTC ACAAAAGTGC CTTCAGCAGC TCAGATGAGG CAGCAGCCCA
              GTGGGGAGAC CCCCCGCTGC TCAGCACCCC CAGGTGCCTC AGGCCAGGTC
              CTGATATCAT TCCTGCAGGG GATACTTTGA TTTTCCTCTT TTTTTCTTTG
              TCCACTTGCC TGCTTCTGGC CAAGATTGCC TCTCTCTGAG CCTCAGCTCT
              TTGTTTTTCT TCCCTCTGAA AGGCAGTATA GTTTGGTGAA AAGCGTGGGC
              TTTGGAGCCA AACTGTCTGG ATTCTAGTCC TGCCTGTGCC ATGTAGGGGC    31,305,949

(SEQ ID NO:1)
```

FIG. 2

```
764   ATACAGGAGG AGAGGAGGAC ACCGAGGACC AGGGGCTCAC GGGAGATGAG
      GCAGAGCCAT TCTTGGATCA GAACGGAGCC CCAGGCCCCG GGGCTCCCAC
      CACCCTGAAG AAGCCACCTT CCCATCCTCC CCCCTACCAT CCTGGGGGGA
      AAAGGAAGAG AAGCACGCCT GCGCCCAGAA AGCTGCTTTC GGATAAACCA
      CAGGACTTCC AGATCAGGGT CCAGGTGATC GAGGGGCGCC AGCTGCCAGG
      GGTGAACATC AAGCCTGTGG TCAAGGTCAC CGCGGCCAGG CAGACCAAGC
      GGACTCGGAT TCACAGGGGA AACAGCCCGC TCTTCAACGA GACTCTCTTC
      TTCAACGTGT TTGACTCTCC CTCGGAGCTG TTTGACGAGG CCGTCTTTAT
      CACGGTGGTA GACTCCTGTT CGCTCCGGAC AGATGCCCTC ATCGGGGAGT
      TCCGGATGGA TGTGGGTACC ATCTACAGAG AGCCCCGACA CGCCTATCTC
      AGGAAGTGGC TGCTGCTCTC GGACCCTGAC GATTTCTCTG CTGGGCCCAA
      AGGCTACCTG AAAGCAAGCC TTTGTGTGCT GGGGCCTGGA GACGAAGCTC
      CGCTGGAGAG AAAGGACCCC TCTGAAGACA AGGAGGACAT TGAAAGCAAT
      CTGCTCAGGC CAACTGGCAT GGCCCTTCGA GGAGCGCACT TCTGTCTGAA
      GGTCTTCAGG GCTGAGGACT TACCACAGAT GGACGATGCC GTGGTGGACA
      GCGTGAAGCA GATCTTCGGC TTTGACAGTA ACAAGAAGAA CCTGGTGGAT
      CCCTTCGTCG AGGTCAGCTT TGCGGGGAAA ATGCTCTGCA GCAAGATCCT
      GGAGAAGATG GCCAACCCTC AGTGGAACCA GAGCATCACG CTGCCTGTCA
      TGTTTCCCTC CATGTCTGAA AAAATGAGGA TTCGTGTCAT AGACTGGGAC
      CGCCTCACCC ACAATGACAT CGTGGCCACC ACCTACCTGA ATATGTCGAA
      AATCTCTGCC CCTGGAGGAG AAATAGCAG                        1792

(SEQ ID NO:2)

764   ATACAGGAGG AGAGGAGGAC ACCGAGGACC AGGGGCTCAC GGGAGATGAG
      GCAGAGCCAT TCTTGGATCA GAACGGAGCC CCAGGCCCCG GGGCTCCCAC
      CACCCTGAAG AAGCCACCTT CCCATCCTCC CCCCTACCAT CCTGGGGGGA
      AAAGGAAGAG AAGCACGCCT GCGCCCAGAA AGCTGCTTTC GGATAAACCA
      CAGGACTTCC AGATCAGGGT CCAGGTGATC GAGGGGCGCC AGCTGCCAGG
      GGTGAACATC AAGTCTGTGG TCAAGGTCAC CGCGGCCAGG CAGACCAAGC
      GGACTCGGAT TCACAGGGGA AACAGCCCGC TCTTCAACGA GACTCTCTTC
      TTCAACGTGT TTGACTCTCC CTCGGAGCTG TTTGACGAGG CCGTCTTTAT
      CACGGTGGTA GACTCCTGTT CGCTCCGGAC AGATGCCCTC ATCGGGGAGT
      TCCGGATGGA TGTGGGTACC ATCTACAGAG AGCCCCGACA CGCCTATCTC
      AGGAAGTGGC TGCTGCTCTC GGACCCTGAC GATTTCTCTG CTGGGCCCAA
      AGGCTACCTG AAAGCAAGCC TTTGTGTGCT GGGGCCTGGA GACGAAGCTC
      CGCTGGAGAG AAAGGACCCC TCTGAAGACA AGGAGGACAT TGAAAGCAAT
      CTGCTCAGGC CAACTGGCAT GGCCCTTCGA GGAGCGCACT TCTGTCTGAA
      GGTCTTCAGG GCTGAGGACT TACCACAGAT GGACGATGCC GTGGTGGACA
      GCGTGAAGCA GATCTTCGGC TTTGACAGTA ACAAGAAGAA CCTGGTGGAT
      CCCTTCGTCG AGGTCAGCTT TGCGGGGAAA ATGCTCTGCA GCAAGATCCT
      GGAGAAGATG GCCAACCCTC AGTGGAACCA GAGCATCACG CTGCCTGTCA
      TGTTTCCCTC CATGTCTGAA AAAATGAGGA TTCGTGTCAT AGACTGGGAC
      CGCCTCACCC ACAATGACAT CGTGGCCACC ACCTACCTGA ATATGTCGAA
      AATCTCTGCC CCTGGAGGAG AAATAGCAG                        1792

(SEQ ID NO:3)
```

FIG. 3

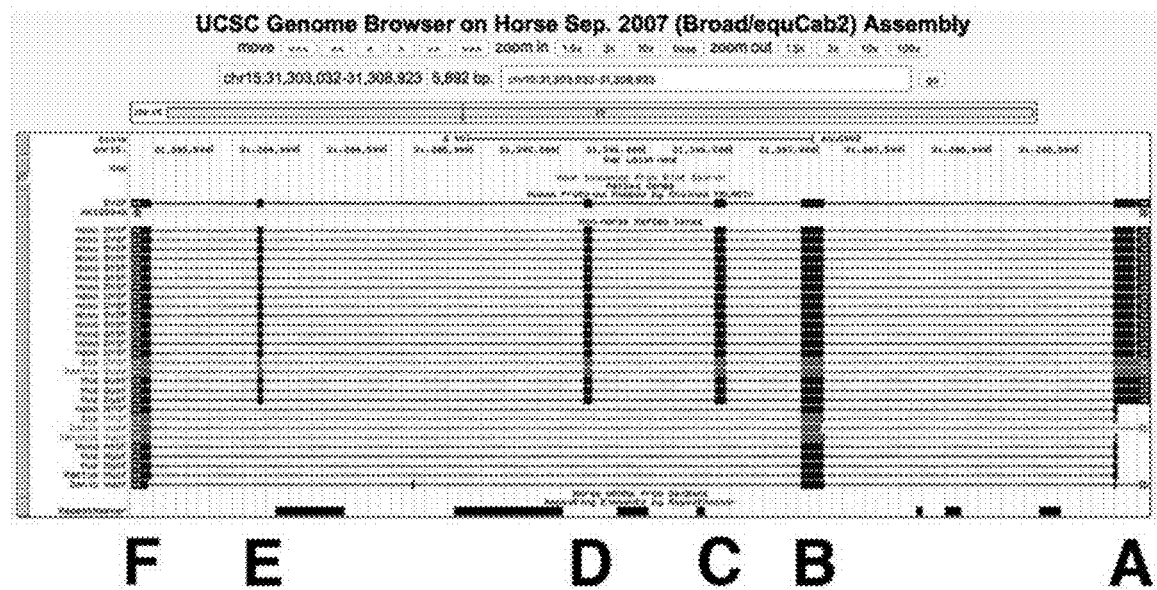

Exon Sequences

A
    31,308,932    ctcctcccag ATACAGGAGG AGAGGAGGAC ACCGAGGACC AGGGGCTCAC
                       GGGAGATGAG GCAGAGCCAT TCTTGGATCA GAACGGAGCC CCAGGCCCCG
                       GGGCTCCCAC CACCCTGAAG AAGCCACCTT CCCATCCTCC CCCCTACCAT
                       CCTGGGGGGA AAAGGAAGAG AAGCACGCCT GCGCCCAGAA AGCTGCTTTC
                       GGATAAACCA CAGGACTTCC AGgtgatgca cc              31,308,701
                       (SEQ ID NO:4)

B
    31,307,046    tggctttcag ATCAGGGTCC AGGTGATCGA GGGGCGCCAG CTGCCAGGGG
                       TGAACATCAA GCCTGTGGTC AAGGTCACCG CGGCCAGGCA GACCAAGCGG
                       ACTCGGATTC ACAGGGGAAA CAGCCCGCTC TTCAACGAGg tgggagaca   31,306,989
                       (SEQ ID NO:5)

C
    31,306,479    gaaccaacag ACTCTCTTCT TCAACGTGTT TGACTCTCCC TCGGAGCTGT
                       TTGACGAGGC CGTCTTTATC ACGgtacgtc tca             31,306,397
                       (SEQ ID NO:6)

D
    31,305,709    ttcoctccag GTGGTAGACT CCTGTTCGCT CCGGACAGAT GCCCTCATCG
                       GGGAGTTCCG Ggtaattagt t                       31,305,639
                       (SEQ ID NO:7)

E
    31,303,803    ctgattgcag ATGGATGTGG GTACCATCTA CAGAGAGCCC Cgtgagtcat
                       att                                                                  31,303,753
                       (SEQ ID NO:8)

F
    31,303,157    tctctcttag GACACGCCTA TCTCAGGAAG TGGCTGCTGC TCTCGGACCC
                       TGACGATTTC TCTGCTGGGC CCAAAGGCTA CCTGAAAGCA AGCCTTTGTG
                       TGCTGGGGCC TGAGACGAA GCTCCGgtga gtcatt         31,303,022
                       (SEQ ID NO:9)

FIG. 4

```
154    TGGEEDTEDQ GLTGDEAEPF LDQNGAPGPG APTTLKKPPS HPPPYHPGGK
       RKRSTPAPRK LLSDKPQDFQ IRVQVIEGRQ LPGVNIKPVV KVTAARQTKR
       TRIHRGNSPL FNETLFFNVF DSPSELFDEA VFITVVDSCS LRTDALIGEF
       RMDVGTIYRE PRHAYLRKWL LLSDPDDFSA GPKGYLKASL CVLGPGDEAP
       LERKDPSEDK EDIESNLLRP TGMALRGAHF CLKVFRAEDL PQMDDAVVDS
       VKQIFGPDSN KKNLVDPFVE VSFAGKMLCS KILEKMANPQ WNQSITLPVM
       FPSMSEKMRI RVIDWDRLTH NDIVATTYLN MSKISAPGGE IA              495

(SEQ ID NO:10)

154    TGGEEDTEDQ GLTGDEAEPF LDQNGAPGPG APTTLKKPPS HPPPYHPGGK
       RKRSTPAPRK LLSDKPQDFQ IRVQVIEGRQ LPGVNIKPVV KVTAARQTKW
       TRIHRGNSPL FNETLFFNVF DSPSELFDEA VFITVVDSCS LRTDALIGEF
       RMDVGTIYRE PRHAYLRKWL LLSDPDDFSA GPKGYLKASL CVLGPGDEAP
       LERKDPSEDK EDIESNLLRP TGMALRGAHF CLKVFRAEDL PQMDDAVVDS
       VKQIFGPDSN KKNLVDPFVE VSFAGKMLCS KILEKMANPQ WNQSITLPVM
       FPSMSEKMRI RVIDWDRLTH NDIVATTYLN MSKISAPGGE IA              495

(SEQ ID NO:11)
```

FIG. 5

```
                 5'-ccgag atttctggct ttct-3' (SEQ ID NO:14)
31,307,136   GGTCCCGAG ATTTCTGGCT TTCTTTGTGG CGAGGTCGGG GGAGGTGGGT

GCCTGACTGT TTTCCCCTTC CTCCTGCTCA TGCCCCTTCC TGGCTTTCAG 31,307,036   ATC AGG GTC CAG GTG ATC GAG GGG CGC CAG CTG CCA GGG
31,307,036   ATC AGG GTC CAG GTG ATC GAG GGG CGC CAG CTG CCA GGG

GTG AAC ATC AAG CCT GTG GTC AAG GTC ACC GCG GCC AGG
             GTG AAC ATC AAG CCT GTG GTC AAG GTC ACC GCG GCC AGG

CAG ACC AAG CGG ACT CGG ATT CAC AGG GGA AAC AGC CCG
             CAG ACC AAG TGG ACT CGG ATT CAC AGG GGA AAC AGC CCG

CTC TTC AAC GAG (SEQ ID NO:12)    31,306,906
             CTC TTC AAC GAG (SEQ ID NO:13)    31,306,906

GTGGGAGACA TGGCGTTTTA GGGCTGGTAG CTTGGTGGGC CTTCCAGATT

GGGAGCACCC GGCAGATACC TGGCAATTCT TTCAGTTTTT GTTCATGGCG

CTAACTTTGG TTTGAGAGGT GTGCCAGGTC CTGAGTACGT TATCTGAGGA

ACTGGAGAGA GGGTTCTAGT TCTTATTCCT GTCCCGGGCT CCTGGTGCTC

CACATCCCTG TCTTCCTGTG GGGCCAGCCA CCCATGCTGT CCTGGAGATG

ACAACCTCTG AGAGGTCAGG GGTGGAACAC CCCAGAACTT GTCGAGTCCT    31,306,608
                        (SEQ ID NO:15) 3'-tgtg gggtcttgaa cagctc-5'
```

FIG 6

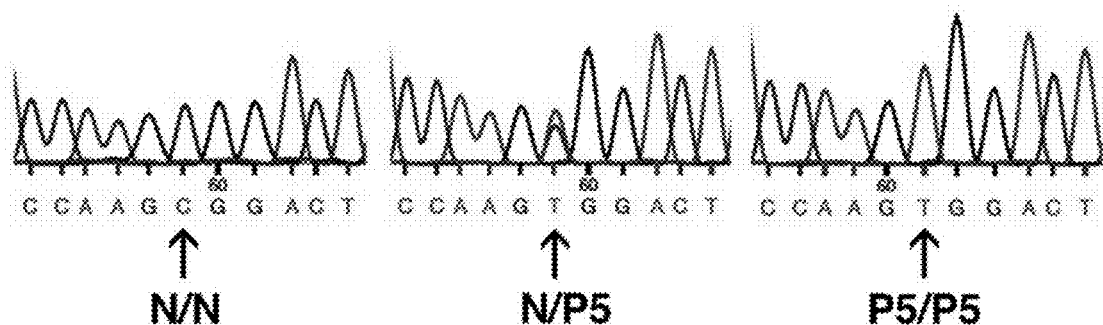

FIG. 7

```
377  ATGCTGAGGG TCTTCATCCT CTATGCCGAG AACGTCCACA CACCCGACAC
     CGACATCAGC GATGCCTACT GCTCCGCGGT GTTTGCAGGG GTGAAGAAGA
     GAACCAAAGT CATCAAGAAC AGCGTGAACC CTGTATGGAA TGAGGGATTT
     GAATGGGACC TCAAGGGCAT CCCCCTGGAC CAGGGCTCTG AGCTTCATGT
     GGTGGTCAAA GACCATGAGA CGATGGGGAG GAACAGGTTC CTGGGGGAAG
     CCAAGGTCCC ACTCCGAGAG GTCCTCGCCA CCCCTAGTCT GTCCGCCAGC
     TTCAATGCCC CCCTGCTGGA CACCAAGAAG CAGCCCACAG GGCCTCGCT
     GGTCCTGCAG GTGTCCTACA CACCGCTGCC TGGAGCTGTG CCCCTGTTCC
     CGCCCCCTAC TCCTCTGGAG CCCTCCCCGA CTCTGCCTGA CCTGGATGTA
     GTGGCAGACA CAGGAGGAGA GGAAGACACA GAGGACCAGG GACTCACTGG
     AGATGAGGCG GAGCCATTCC TGGATCAAAG CGGAGGCCCG GGGCTCCCA
     CCACCCCAAG GAAACTACCT TCACGTCCTC CGCCCCACTA CCCCGGGATC
     AAAAGAAAGC GAAGTGCGCC TACATCTAGA AAGCTGCTGT CAGACAAACC
     GCAGGATTTC CAG**ATCAGGG TCCAGGTGAT CGAGGGGCGC CAGCTGCCGG
     GGGTGAACAT CAAGCCTGTG GTCAAGGTTA CCGCTGCAGG GCAGACCAAG
     CGGACGCGGA TCCACAAGGG AAACAGCCCA CTCTTCAATG AG**ACTCTTTT
     CTTCAACTTG TTTGACTCTC CTGGGGAGCT GTTTGATGAG CCCATCTTTA
     TCACGGTGGT AGACTCTCGT TCTCTCAGGA CAGATGCTCT CCTCGGGGAG
     TTCCGGATGG ACGTGGGCAC CATTTACAGA GAGCCCCGGC ACGCCTATCT
     CAGGAAGTGG CTGCTGCTCT CAGACCCTGA TGACTTCTCT GCTGGGGCCA
     GAGGCTACCT GAAAACAAGC TTTGTGTGC TGGGCCTGG GGACGAAGCG
     CCTCTGGAGA GAAAAGACCC CTCTGAAGAC AAGGAGGACA TTGAAAGCAA
     CCTGCTCCGG CCCACAGGCG TAGCCCTGCG AGGAGCCCAC TTCTGCCTGA
     AGGTCTTCCG GGCCGAGGAC TTGCCGCAGA TGGACGATGC CGTGATGGAC
     AACGTGAAAC AGATCTTTGG CTTCGAGAGT AACAAGAAGA ACTTGGTGGA
     CCCCTTTGTG GAGGTCAGCT TTGCGGGGAA AATGCTGTGC AGCAAGATCT
     TGGAGAACAC GGCCAACCCT CAGTGGAACC AGAACATCAC ACTGCCTGCC
     ATGTTTCCCT CCATGTGCGA AAAAATGAGG ATTCGTATCA TAGACTGGGA
     CCGCCTGACT CACAATGACA TCGTGGCTAC CACCTACCTG AGTATGTCGA
     AAATCTCTGC CCCTGGAGGA GAAATAGAAG AGGAGCCTGC AGGTGCTGTC
     AAGCCTTCGA AAGCCTCAGA CTTGGATGAC TACCTGGGCT TCCTCCCCAC
     TTTTGGGCCC TGCTACATCA ACCTCTATGG CAGTCCCAGA GAGTTCACAG
     GCTTCCCAGA CCCCTACACA GAGCTCAACA CAGGCAAGGG GGAAGGTGTG
     GCTTATCGTG GCCGGCTTCT GCTCTCCCTG GAGACCAAGC TGGTGGAGCA
     CAGTGAACAG AAGGTGGAGG ACCTTCCTGC GGATGACATC CTCCCGGGTGG
     AGAAGTACCT TAGGAGGCGC AAGTACTCCC TGTTTGCGGC CTTCTACTCA
     GCCACCATGC TGCAGGATGT GGATGATGCC ATCCAGTTTG AGGTCAGCAT
     CGGAACTAC GGGAACAAGT TCGACATGAC CTGCCTGCCG CTGGCCTCCA
     CCACTCAGTA CAGCCGTGCA GTCTTTGACG GGTGCCACTA CTACTACCTA
     CCCTGGGGTA ACGTGAAACC TGTGGTGGTG CTGTCATCCT ACTGGGAGGA
     CATCAGCCAT AGAATCGAGA CTCAGAACCA GCTGCTTGGG ATTGCTGACC
     GGCTGGAAGC TGGCCTGGAG CAGGTCCACC TGGCCCTGAA GGCGCAGTGC
     TCCACGGAGG ACGTGGACTC GCTGGTGGCT CAGCTGACGG ATGAGCTCAT
     CGCAGGCTGC AGCCAGCCTC TGGGTGACAT CCATGAGACA CCCTCTGCCA
     CCCACCTGGA CCAGTACCTG TACCAGCTGC GCACCCATCA CCTGAGCCAA
     ATCACTGAGG CTGCCCTGGC CCTGAAGCTC GGCCACAGTG AGCTCCCTGC
     AGCTCTGGAG CAGGCGGAGG ACTGGCTCCT GCGTCTGCGT GCCCTGGCAG
     AGGAGCCCCA GAACAGCCTG CCGGACATCG TCATCTGGAT GCTGCAGGGA
     GACAAGCGTG TGGCATACCA GCGGGTGCCC GCCCACCAAG TCCTCTTCTC
     CCGGCGGGT GCCAACTACT GTGGCAAGAA TTGTGGGAAG CTACAGACAA
     TCTTTCTGAA ATATCCGATG GAGAAGGTGC CTGGCGCCCG GATGCCAGTG
     CAGATACGGG TCAAGCTGTG GTTTGGGCTC TCAGTGGATG AGAAGGAGTT
     CAACCAGTTT GCTGAGGGGA AGCTGTCTGT CTTTGCTGAA ACCTATGAGA
     ACGAGACTAA GTTGGCCCTT GTTGGGAACT GGGCACAAC GGGCCTCACC
     TACCCCAAGT TTCTGACGT CACGGGCAAG ATCAAGCTAC CCAAGGACAG
     CTTCCGCCCC TCGGCCGGCT GGACCTGGGC TGGAGATTGG TTCGTGTGTC
     CGGAGAAGAC TCTGCTCCAT GACATGGACG CCGGTCACCT GAGCTTCGTG
     GAAGAGGTGT TTGAGAACCA GACCCGGCTT CCCGGAGGCC AGTGGATCTA
     CATGAGTGAC AACTACACCG ATGTGAACGG GGAGAAGGTG CTTCCCAAGG
     ATGACATTGA GTGCCACTGG GGCTGGAAGT GGGAAGATGA GGAATGGTCC
     ACAGACCTCA ACCGGCTGTT CGATGAGCAA GGCTGGGAGT ATAGCATCAC
```

Fig. 7 (continued)

```
CATCCCCCCG GAGCGGAAGC CGAAGCACTG GGTCCCTGCT GAGAAGATGT
ACTACACACA CCGACGGCGG CGCTGGGTGC GCCTGCGCAG GAGGGATCTC
AGCCAAATGG AAGCACTGAA AAGGCACAGG CAGGCGGAGG CGGAGGGCGA
GGGCTGGGAG TACGCCTCTC TTTTTGGCTG GAAGTTCCAC CTCGAGTACC
GCAAGACAGA TGCCTTCCGC CGCCGCCGCT GGCGCCGTCG CATGGAGCCA
CTGGAGAAGA CGGGGCCTGC AGCTGTGTTT GCCCTTGAGG GGGCCCTGGG
CGGCGTGATG GATGACAAGA GTGAAGATTC CATGTCCGTC TCCACCTTGA
GCTTCGGTGT GAACAGACCC ACGATTTCCT GCATATTCGA CTATGGGAAC
CGCTACCATC TACGCTGCTA CATGTACCAG GCCCGGGACC TGGCTGCGAT
GGACAAGGAC TCTTTTTCTG ATCCCTATGC CATCGTCTCC TTCCTGCACC
AGAGCCAGAA GACGGTGGTG GTGAAGAACA CCCTTAACCC CACCTGGGAC
CAGACGCTCA TCTTCTACGA GATCGAGATC TTTGGCGAGC CGGCCACAGT
TGCTGAGCAA CCGCCCAGCA TTGTGGTGGA GCTGTACGAC CATGACACTT
ATGGTGCAGA CGAGTTTATG GGTCGCTGCA TCTGTCAACC GAGTCTGGAA
CGGATGCCAC GGCTGGCCTG GTCCCACTG ACGAGGGGCA GCCAGCCGTC
GGGGGAGCTG CTGGCCTCTT TTGAGCTCAT CCAGAGAGAG AAGCCGGCCA
TCCACCATAT TCCTGGTTTT GAGGTGCAGG AGACATCAAG GATCCTGGAT
GAGTCTGAGG ACACAGACCT GCCCTACCCA CCACCCCAGA GGGAGGCCAA
CATCTACATG GTTCCTCAGA ACATCAAGCC AGCGCTCCAG CGTACCGCCA
TCGAGATCCT GGCATGGGGC CTGCGGAACA TGAAGAGTTA CCAGCTGGCC
AACATCTCCT CCCCCAGCCT CGTGGTAGAG TGTGGGGGCC AGACGGTGCA
GTCCTGTGTC ATCAGGAACC TCCGGAAGAA CCCCAACTTT GACATCTGCA
CCCTCTTCAT GGAAGTGATG CTGCCCAGGG AGGAGCTCTA CTGCCCCCCC
ATCACCGTCA AGGTCATCGA TAACCGCCAG TTTGGCCGCC GGCCTGTGGT
GGGCCAGTGT ACCATCCGCT CCCTGGAGAG CTTCCTGTGT GACCCCTACT
CGGCGGAGAG TCCATCCCCA CAGGGTGGCC CAGACGATGT GAGCCTACTC
AGTCCTGGGG AAGACGTGCT CATCGACATT GATGACAAGG AGCCCCTCAT
CCCCATCCAG GAGGAAGAGT TCATCGATTG GTGGAGCAAA TTCTTTGCCT
CCATAGGGGA GAGGGAAAAG TGCGGCTCCT ACCTGGAGAA GGATTTTGAC
ACCCTGAAGG TCTATGACAC ACAGCTGGAG AATGTGGAGG CCTTTGAGGG
CCTGTCTGAC TTTTGTAACA CCTTCAAGCT GTACCGGGGC AAGACGCAGG
AGGAGACAGA AGATCCATCT GTGATTGGTG AATTTAAGGG CCTCTTCAAA
ATTTATCCCC TCCCAGAAGA CCCAGCCATC CCCATGCCCC CAAGACAGTT
CCACCAGCTG GCCGCCCAGG GACCCCAGGA GTGCTTGGTC CGTATCTACA
TTGTCCGAGC ATTTGGCCTG CAGCCCAAGG ACCCCAATGG AAAGTGTGAT
CCTTACATCA AGATCTCCAT AGGGAAGAAA TCAGTGAGTG ACCAGGATAA
CTACATCCCC TGCACGCTGG AGCCCGTATT TGGAAAGATG TTCGAGCTGA
CCTGCACTCT GCCTCTGGAG AAGGACCTAA AGATACACTCT CTATGACTAT
GACCTCCTCT CCAAGGACGA AAAGATCGGT GAGACGGTCG TCGACCTGGA
GAACAGGCTG CTGTCCAAGT TTGGGCTCG CTGTGGACTC CCACAGACCT
ACTGTGTCTC TGGACCGAAC CAGTGGCGGG ACCAGCTCCG CCCCTCCCAG
CTCCTCCACC TCTTCTGCCA GCAGCATAGA GTCAAGGCAC CTGTGTACCG
GACAGACCGT GTAATGTTTC AGGATAAAGA ATATTCCATT GAAGAGATAG
AGGCTGGCAG GATCCCAAAC CCACACCTGG GCCCAGTGGA GGAGCGTCTG
GCTCCGCATG TGCTTCAGCA GCAGGGCCTG GTCCCGGAGC ACGTGGAGTC
ACGGCCCCTC TACAGCCCCC TGCAGCCAGA CATCGAGCAG GGGAAGCTGC
AGATGTGGGT CGACCTATTT CCGAAGGCCC TGGGGCGGCC TGGACCTCCC
TTCAACATCA CCCCACGGAG AGCCAGAAGG TTTTTCCTGC GTTGTATTAT
CTGGAATACC AGAGATGTGA TCCTGGATGA CCTGAGCCTC ACGGGGGAGA
AGATGAGCGA CATTTATGTG AAAGGTTGGA TGATTGGCTT TGAAGAACAC
AAGCAAAAGA CAGACGTGCA TTATCGTTCC CTGGGAGGTG AAGGCAACTT
CAACTGGAGG TTCATTTTCC CCTTCGACTA CCTGCCAGCT GAGCAAGTCT
GTACCATTGC CAAGAAGGAT GCCTTCTGGA GGCTGGACAA GACTGAGAGC
AAAATCCCAG CACGAGTGGT GTTCCAGATC TGGGACAATG ACAAGTTCTC
CTTTGATGAT TTTCTGGGCT CCCTGCAGCT CGATCTCAAC CGCATGCCCA
AGCCAGCCAA GACAGCCAAG AAGTGCTCCT TGGACCAGCT GGATGATGCT
TTCCACCCAG AATGGTTTGT GTCCCTTTTT GAGCAGAAAA CAGTGAAGGG
CTGGTGGCCC TGTGTAGCAG AAGAGGGTGA GAAGAAAATA CTGGCGGGCA
AGCTGGAAAT GACCTTGGAG ATTGTAGCAG AGAGTGAGCA TGAGGAGCGG
CCTGCTGGCC AGGGCCGGGA TGAGCCCAAC ATGAACCCTA AGCTTGAGGA
CCCAAGGCGC CCCGACACCT CCTTCCTGTG GTTTACCTCC CCATACAAGA
CCATGAAGTT CATCCTGTGG CGGCGTTTCC GGTGGGCCAT CATCCTCTTC
ATCATCCTCT TCATCCTGCT GCTGTTCCTG GCCATCTTCA TCTACGCCTT
```

Fig. 7 (continued)

```
CCCGAACTAT GCTGCCATGA AGCTGGTGAA GCCCTTCAGC TGA            6619
(SEQ ID NO:16)
```

FIG. 8

```
1    MLRVFILYAE NVHTFDTDIS DAYCSAVFAG VKKRTKVIKN SVNFVWNEGF
     EWDLKGIFLD QGSELHVVVK DHETMGRNRF LGEAKVFLRE VLATFSLSAS
     FNAPLLDTKK QPTGASLVLQ VSYTPLPGAV PLFPPFTFLE PSPTLPDLDV
     VADTGGEEDT EDQGLTGDEA EPFLDQSGGP GAPTTPRKLP SRPPPHYPGI
     KRKRSAPTSR KLLSDKPQDF QIRVQVIEGR QLPGVNIKPV VKVTAAGQTK
     RTRIHKGNSP LFNETLFFNL FDSPGELFDE PIFITVVDSR SLRTDALLGE
     FRMDVGTIYR EPRHAYLRKW LLLSDPDDFS AGARSYLKTS LCVLGPGDEA
     PLERKDPSED KEDIESNLLR PTGVALRGAH FCLKVFRAED LPQMDDAVMD
     NVKQIFGFES NKKNLVDPFV EVSFAGKMLC SKILEKTANP QWNQNITLPA
     MFPSMCEKMR IRIIDWDRLT HNDIVATTYL SMSKISAPGG EIEEEPAGAV
     KPSKASDLDD YLGFLPTFGP CYINLYGSPR EFTGFPDPYT ELNTGKGEGV
     AYRGRLLLSL ETKLVEHSEQ KVEDLPADDI LRVEKYLRRR KYSLFAAFYS
     ATMLQDVDDA IQFEVSIGNY GNKFDMTCLF LASTTQYSRA VFDGCHYYYL
     PWGNVKPVVV LSSYWEDISH RIETQNQLLG IADRLEAGLE QVHLALKAQC
     STEDVDSLVA QLTDELIAGC SQPLGDIHET PSATHLDQYL YQLRTHHLSQ
     ITEAALALKL GHSELPAALE QAEDWLLRLR ALAEEPQNSL PDIVIWMLQG
     DKRVAYQRVP AHQVLFSRRG ANYCGKNCGK LQTIFLKYPM EKVPGARMFV
     QIRVKLWFGL SVDEKEFNQF AEGKLSVFAE TYENETKLAL VGNWGTTGLT
     YPKFSDVTGK IKLPKDSFRP SAGWTWAGDW FVCPEKTLLH DMDAGHLSFV
     EEVFENQTRL PGGQWIYMSD NYTDVNGEKV LPKDDIECPL GWKWEDEEWS
     TDLNRAVDEQ GWEYSITIPP ERKPKHWVPA EKMYYTHRRR RWVRLRRRDL
     SQMEALKRHR QAEAEGEGWE YASLFGWKFH LEYRKTDAFR RRRWRRRMEP
     LEKTGPAAVF ALEGALGGVM DDKSEDSMSV STLSFGVNRP TISCIFDYGN
     RYHLRCYMYQ ARDLAAMDKD SFSDPYAIVS FLHQSQKTVV VKNTLNPTWD
     QTLIFYEIEI FGEPATVAEQ PPSIVVELYD HDTYGADEFM GRCICQPSLE
     RMPRLAWFPL TRGSQPSGEL LASFELIQRE KPAIHHIPGF EVQETSRILD
     ESEDTDLPYP PPQREANIYM VPQNIKPALQ RTAIEILAWG LRNMKSYQLA
     NISSFSLVVE CGGQTVQSCV IRNLRKNPNF DICTLFMEVM LPREELYCFP
     ITVKVIDNRQ FGRRPVVGQC TIRSLESFLC DPYSAESPSP QGGPDDVSLL
     SPGEDVLIDI DDKEPLIPIQ EEEFIDWWSK FFASIGEREK CGSYLEKDFD
     TLKVYDTQLE NVEAFEGLSD FCNTFKLYPG KTQEETEDPS VIGEFKGLFK
     IYPLPEDPAI PMPPRQFHQL AAQGPQECLV RIYIVRAFSL QPKDFNGKCD
     FYIKISIGKK SVSDQDNYIP CTLEPVFGKM FELTCTLPLE KDLKITLYDY
     DLLSKDEKIG ETVVDLENRL LSKFGARCGL PQTYCVSGPN QWRDQLRPSQ
     LLHLFCQQHR VKAPVYRTDR VMFQDKEYSI EEIEAGRIFN PHLGPVEERL
     ALHVLQQQGL VPEHVESRFL YSPLQFDIEQ GKLQMWVDLF PKALGRPGFP
     FNITFRPARR FFLRCIIWNT RDVILDDLSL TGERMSDIYV KGWMIGFEEH
     KQKTDVHYRS LGGEGNFNWR FIFPFDYLPA EQVCTIAKKD AFWRLDKTES
     KIPARVVFQI WDNDKFSFDD FLGSLQLDLN RMPKPAKTAK KCSLDQLDDA
     FHPEWFVSLF EQKTVKGWWP CVAEEGEKKI LAGKLEMTLE IVAESEHEER
     PAGQGRDEPN MNPKLEDPRR PDTSFLWFTS PYKTMKFILW RRFRWAIILF
     IILFILLLFL AIFIYAFPNY AAMKLVKPFS                   2080

(SEQ ID NO:17)
```

FIG. 9
```
NP_003485.1     220  FQIRVQVIEGRQLPGVNIKPVVKVTAAGQTKRTRIHRGNSPLFNE  264  (SEQ ID NO:18)
                     ********************************* ****+*******
XP_023474694.1  222  FQIRVQVIEGRQLPGVNIKPVVKVTAARQTKRTRIHRGNSPLFNE  266  (SEQ ID NO:19)
R253W           222  FQIRVQVIEGRQLPGVNIKPVVKVTAARQTKWTRIHRGNSPLFNE  266  (SEQ ID NO:20)
```
FIG. 10
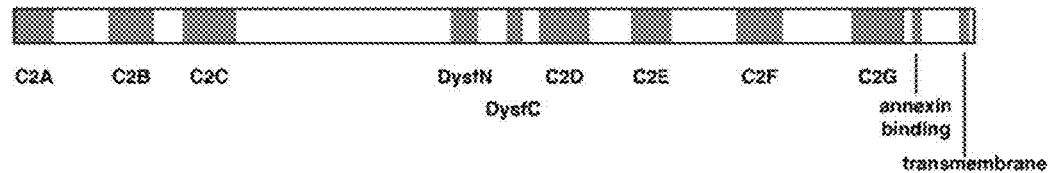
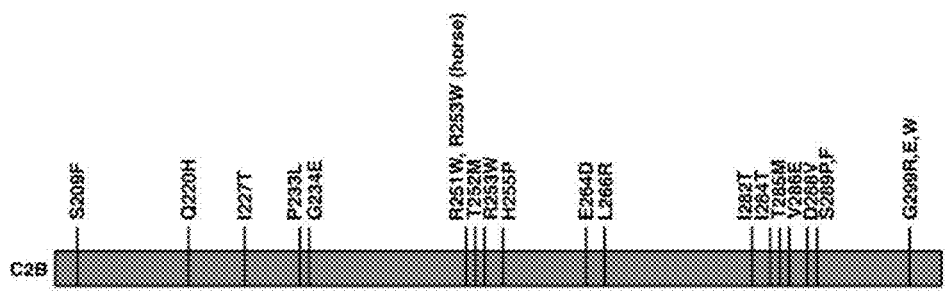

```
31,226,630   GACTCTTTTT TCTCCACGTC GGGTCTAGGG TGCAGATGAG TTTATGGGAC
             GCTGCATCTG TCAGCCGACT CTGGAACGGA TGCCCCGGCT GACCTGGTTC
             CCACTGACTA GGGGCAGCCA GCCGGCGGGC GAGCTGCTGG CCTCTTTTGA
             GCTCATCCAG AGAGAGAAGG TGAGGCTGGT CCCCATCCTG ATCCAGGAAG
             CCCAGACAGG GAGTACATGG TAGGAGAGGG TAGGGGGCAC AGGCAGGGAT
             GCCCCGAAGG AGGGGAGGGG CTGCCGATAC ATCCTTCTCC CCCCACCAGG
             CCTGCTCAGT GGGGAGCACT GAACCGCCAC CTCTGGAATT CAGGCTTCCT
             GCTGAGACTG GTTTTGCCCC TCTTTTCTGA CCCCAAGTT AGGCTACTGT
             CTAAACATTG GGGTAGAATG TTGGAATCTG GGCTGTGCTG GAATGTCTGA
             GTCCTCTGGC CATTGGATGT ATTTTTCCCT GGGTCATATC CTGACGTGGT
             TTCTGAGAGG AGGACCTCCG TGATCTGGTC GGGGAGACTT AATTGTGATG
             GTGGCACCCA GGGACAGGTA AGGTCAGGAC CTCCGGTGTA GTGTTGGCTC
             TGCCATGGCC TGGCTGTGCG ACCCTGGGCC AGGCACTTCC CTGCTGTGAA
             ATAGGGGGTT TGGGTTAGAA CCATATCTTC AGCTTTGCTC TTAGAGTGAT
             GTGAACCCCA GGTGTAAGCT GGATGGAAGT CAGGCTACTC TGGGTCAAGT
             GTCTGGAGGG GGCACACAGT ATGCTGCAAC CTGGCTTCCC CTGGCACCTG
             GCTGCCAACT CCCGGGCACC TCCAAGGAGT CCCTAGGTTG CAAACTCCCA
             ACTGTGATCA CTGACATATT CCATGAGTGT CATTTTGTGG CTGAAGGTGT
             GTTTGCCTGG CCCGGACAGA AAGGAGGGTG ATGGGGCCTT GGGTGACAGG
             CACTGACCAA AGCTCTTTTT TCTACCCCGC AGCCGGCCAT CTACCACATT
31,225,630   (C/A)
             CTGGTTTTGA GGTAAGTCTT GCTCTTCCCT CTTCTTCTTC AAACTCATGG
             CCCGCCTCTG TGTGTTTGCA GCCCCCTATG AGCTAGGAAG GGCAGTCAGG
             TGTATACCAC CACTGGCCCG CCTTCAGGGA TGGGGTGGGT GAGGGCCGGG
             GTCCCTGGCC AGCTCAGGCC TTTCCCGCCC TTCTTCCCTG AGACTCAGAC
             TGTACGACC TCATGGTCAT CCAGCCCACG GGCTCTCAGC TGGGCTGCAT
             GTTAGAATCC CTTCGGCAGC TTGAAAAATC ACCAGTGCTC AGGCCCCACC
             CCAGACCAGA TGGAACACAG TCTCTGGGCA TGTGGCCCAG GCATTGGTAT
             CTTTCAGAGC TTCCCAGGGG ATTTTAATGT GCTGCTAGGG CTGAGCACCA
             TCGACTTAGC CCAGTGGTTC TCAGTGTGAT ATCACCTGGG ATGTTGTTAG
             AAATGCCGAT TCTTGGCTCC TGCTTCACAC CTACTGAAGC AAACTCTGAG
             GGGCAGTGCA GCAACCTGCA AATTAACAAG CCTCCAGGGG ATTCTGATGC
             CCACTCGAGT TTCAGAAGCT CTGGCTTAGA CCATCTTCCC CAACTCATTG
             TTCCCCCCAT GACCGGTTTT CCTCCTCTA CTAGTGATGG GGGCTCTGTT
             CCCTTCTCCC TGCTCTCCTT CCTTCTCCTG GGGCATGGT AGAAAATGCA
             GACCCTTTCC TGGTACCCAG GCTAATTTGA TTCAGGAGAT ACTGTTCTCA
             GTCAGGTCA GCTGCATCTT GGAGGAGCGG TCATCCGGTC TGTCGTTGGA
             TGCCTTCCCC CTTACAAGGC AGTCCACGCA ATCTGCAGAC AGTTTTTACC
             ATGCAGGCCT TCCTTCACCC CTGTCTCTGC TCCACCCCCG GCATCCCTCA
             GCCCCCTCTC TCTCCTGCTC CCTCTCCTGT CCAGCCCAAG CTCCCGCTCT
             CAGGTCTGCC AGCCCCTGGG GATCCAGATT CTTTCTCCCT GGCTCTCCAA   31,224,630
```

(SEQ ID NO:56)

FIG. 14

```
3,727    AGACCCACGA TTTCCTGCAT CTTCGACTAC GGGAACCGCT ACCATCTACG
         CTGCTACATG TACCAGGCCC GGGACCTGCC CGCCATGGAC AAGGACTCTT
         TTTCTGATCC CTACGCAATC GTCTCCTTCC TGCACCAGAG CCAGAAGACA
         GTGGTGGTGA AGAACACCCT GAACCCCACC TGGGACCAGA CACTCATCTT
         CTATGAGATC GAGATCTTTG GTGAGCCGCC CAGCATCGCC GAGCAGCCGC
         CCAGCATCGT GGTGGAGCTA TACGACCATG ACACCTACGG TGCAGATGAG
         TTTATGGGAC GCTGCATCTG TCAGCCGACT CTGGAACGGA TGCCCCGGCT
         GACCTGGTTC CCACTGACTA GGGGCAGCCA GCCGGCGGGC GAGCTGCTGG
         CCTCTTTTGA GCTCATCCAG AGAGAGAAGC CGGCCATCTA CCACATTCCT
         GGTTTTGAG                                                    4,185

(SEQ ID NO:57)

3,727    AGACCCACGA TTTCCTGCAT CTTCGACTAC GGGAACCGCT ACCATCTACG
         CTGCTACATG TACCAGGCCC GGGACCTGCC CGCCATGGAC AAGGACTCTT
         TTTCTGATCC CTACGCAATC GTCTCCTTCC TGCACCAGAG CCAGAAGACA
         GTGGTGGTGA AGAACACCCT GAACCCCACC TGGGACCAGA CACTCATCTT
         CTATGAGATC GAGATCTTTG GTGAGCCGCC CAGCATCGCC GAGCAGCCGC
         CCAGCATCGT GGTGGAGCTA TACGACCATG ACACCTACGG TGCAGATGAG
         TTTATGGGAC GCTGCATCTG TCAGCCGACT CTGGAACGGA TGCCCCGGCT
         GACCTGGTTC CCACTGACTA GGGGCAGCCA GCCGGCGGGC GAGCTGCTGG
         CCTCTTTTGA GCTCATCCAG AGAGAGAAGC CGGCCATCTA CCACATTACT
         GGTTTTGAG                                                    4,185

(SEQ ID NO:58)
```

FIG. 15

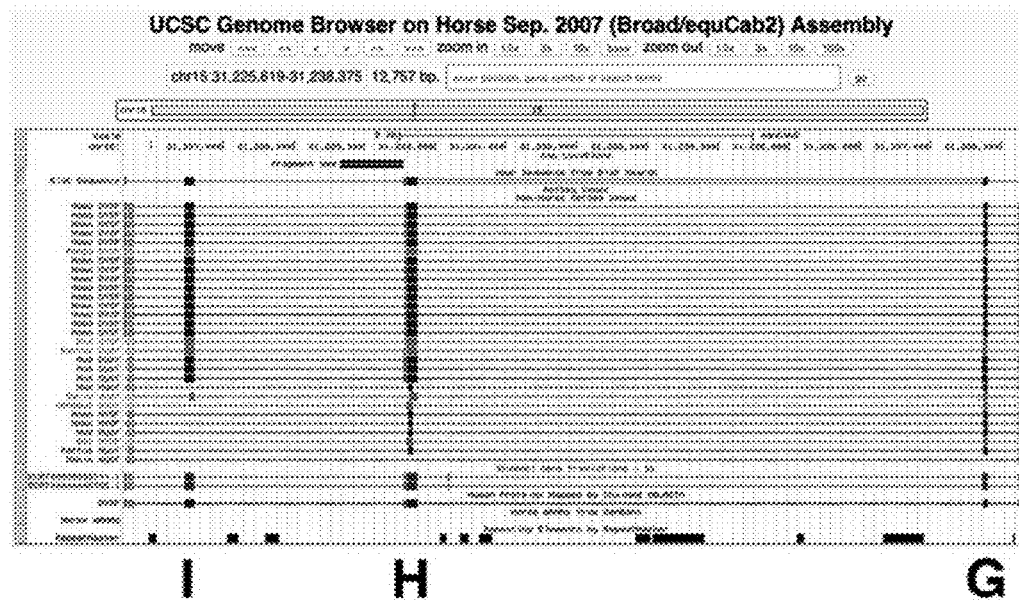

I   31,225,558   tacccccgcag CCGGCCATCT ACCACATTCC TGGTTTTGAG gtaagtcttg 31,225,609
(SEQ ID NO:59)

FIG. 16

1,141   RPTISCIFDY GNRYHLRCYM YQARDLPAMD KDSFSDPYAI VSFLHQSQKT
VVVKNTLNPT WDQTLIFYEI EIFGEPPSIA EQPPSIVVEL YDHDTYGADE
FMGRCICQPT LERMPRLTWF PLTRGSQPAG ELLASFELIQ REKPAIYHIP
GFE   1,293

(SEQ ID NO:60)

1,141   RPTISCIFDY GNRYHLRCYM YQARDLPAMD KDSFSDPYAI VSFLHQSQKT
VVVKNTLNPT WDQTLIFYEI EIFGEPPSIA EQPPSIVVEL YDHDTYGADE
FMGRCICQPT LERMPRLTWF PLTRGSQPAG ELLASFELIQ REKPAIYHIT
GFE   1,293

(SEQ ID NO:61)

FIG. 17

```
               5'-ggttgca aactcccaac tgt-3' (SEQ ID NO:64)
               ACTGGTTGCA AACTCCCAAC TGTGATCACT GACATATTCC ATGAGTGTCA

TTTTGTGGCT GAAGGTGTGT TTGCCTGGCC CGGACAGAAA GGAGGGTGAT

GGGGCCTTGG GTGACAGGCA CTGACCAAAG CTCTTTTTTC TACCCCGCAG 31,225,648     CCG GCC ATC TAC CAC ATT CCT GGT TTT GAG (SEQ ID NO:62)     31,225,619
31,225,648     CCG GCC ATC TAC CAC ATT ACT GGT TTT GAG (SEQ ID NO:63)     31,225,619

GTAAGTCTTG CTCTTCCCTC TTCTTCTTCA AACTCATGGC CCGCCTCTGT

GTGTTTGCAG CCCCCTATGA GCTAGGAAGG GCAGTCAGGT GTATACCACC

ACCGGCCCGC CTTCAGGGAT GGGGTGGGTG AGGGCCGGGG TCCCTGGCCA

GCTCAGGCT TTCCCGCCCT TCTTCCCTGA GACTCAGACT GTAGGGACCT

CATGGTCATC CAGCCCACGG GCTCTCAGCT GGGCTGCATG TTAGAATCCC
                                                                  3'-g
               TTGGCAGCT TGAAAAATCA
               aagccgtcga acttttag-5' (SEQ ID NO:65)
```

FIG. 18
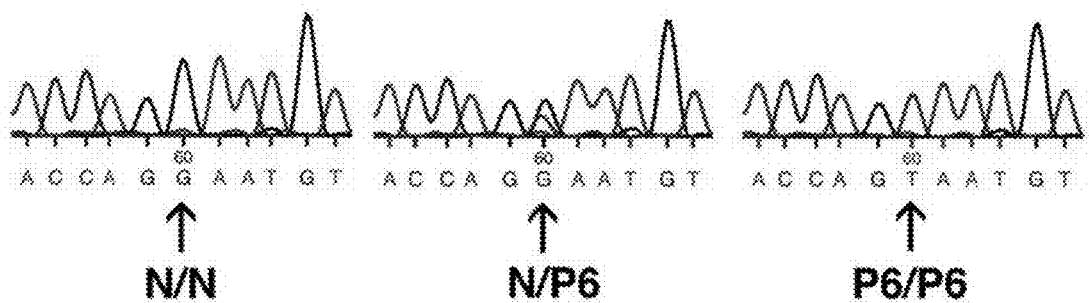
FIG. 19
```
human       1261  TRGSQPSGELLASFELIQREKPAIHHIPGFEVQETSRILDESEDTDLPYPPPQREANIYM  1320
(SEQ ID NO:66)
                  ******+*********************+********+** **+***************
horse       1263  TRGSQPAGELLASFELIQREKPAIYHIPGFEVQDTSGILEESEDTDLPYPPPQREANIYM  1322
(SEQ ID NO:67)
P1290T      1263  TRGSQPAGELLASFELIQREKPAIYHITGFEVQDTSGILEESEDTDLPYPPPQREANIYM  1322
(SEQ ID NO:68)
```
FIG. 20
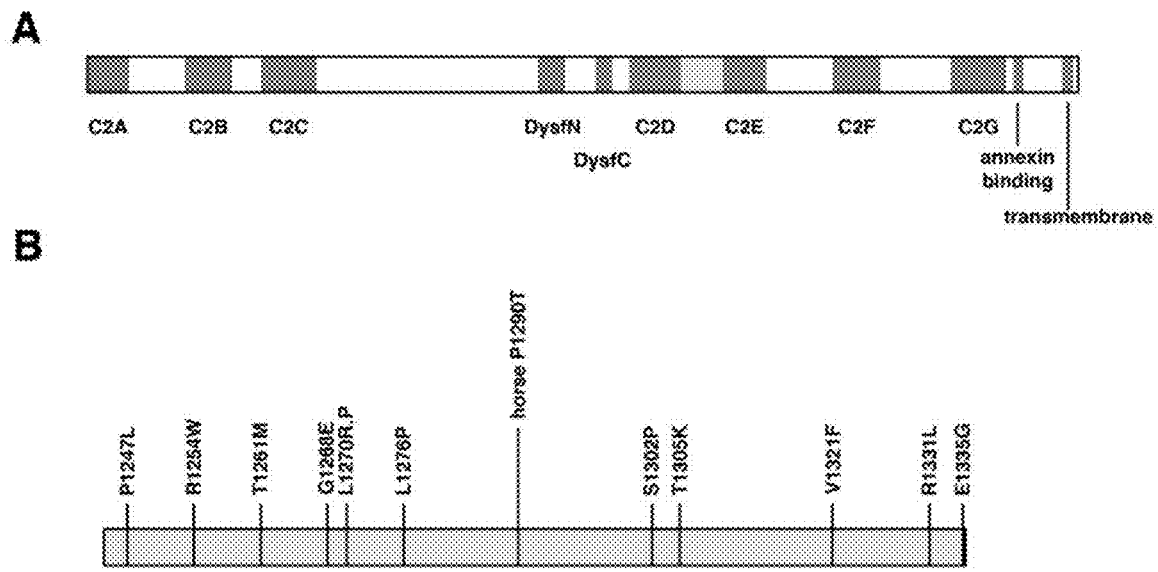

FIG. 21

```
SEQ ID NO:69    TRGSQPSGELLASFELIQREKPAIHHI-PGFEVQ-ETSRILDESEDTDLFYPPPQREANIYM
SEQ ID NO:70    -RGSQPSGELLASFELIQREKPAIHHI-PGFEVQ-ETSRILDESEDTDLPYPPPQREANIYM
SEQ ID NO:71    TRGSQPAGELLAAFELIQREKPAIHHI-PGFEMR-ETSRILDETEDTDLPYPPPQREANIYM
SEQ ID NO:72    TRGSQPAGELLASFELIQREKPAIHHI-PGFEVQ-DTSRILEESEDTDLPYPPPQREANIYM
SEQ ID NO:73    TRGNQPAGELLASFELIQREKPAIHHI-PGFEVQ-DTAGILEESEDTDLFYPPPQREANIYM
SEQ ID NO:74    -RGSQPAGELLASFELIQREKPAIHHI-PGFEVQ-DTSGILEESEDTDLPYPPPQREANIYM
SEQ ID NO:75    TRGSQPAGELLASFELIQREKPAIHHI-PGFEVQ-DTTGILEESEDTDLFYPPPQREANIYM
SEQ ID NO:76    TRGSQPAGELLASFELIQREKPAIHHI-PGFEVQ-DTSGILEESEDTDLPYPPPQREANIYM
SEQ ID NO:77    TKGSQPTGELLASFELIQREKPAIHHI-PGFEVQ-ETSRILDESEDTDLFYPPPQREANIYM
SEQ ID NO:78    TRGSQPTGELLASFELIQREKPAIHRI-PGFEVQ-ETSRILDESEDTDLFYPPPQREANIYM
SEQ ID NO:79    TRGSQPMGELLASFELIQREKPAIHHI-PGFEVQ-ETSRILDESEDTDLFYPPPQREANIYM
SEQ ID NO:80    -RGSQPSGELLASFELIQREKPAIYRI-PGFEVQ-DTSRILDESEDTDLPYPPPQREANVYM
SEQ ID NO:81    -RGGQPSGELLAAFELIQREKPAIHHI-PGFEVQ-DASRILDEAEDTDLPYPPPQREANVHM
SEQ ID NO:82    -RGSQPSGELLASFELIQREKPAIHRI-PGFEVQ-DTARILDESEDTDLPYPPPQREANIYV
SEQ ID NO:83    -RGSQASGELLASFELIQREKPAIYHI-PGFEVQ-DTSRILDESEDTDLPYPPPQREANVYM
SEQ ID NO:84    TRGGQPAGELLAAFELIQREKPAIHHI-PGFEMR-ETSRILDETEDTDLPYPPPQREANIYM
SEQ ID NO:85    TRGSQPAGELLAAFELIQREKPAIHHI-PGFEMH-ETSSILEETEDTDLPYPPPQREANIYM
SEQ ID NO:86    TRGSQPAGELLAAFELIQREKPAIHHI-PGFEMH-ETSKTLDETEDTDLFYPPPQREANIYM
SEQ ID NO:87    -RGSQPAGELLASFELIQREKPAIYHI-PGFEVQ-DTSRILDESEDTDLPYPPPQREANIYV
SEQ ID NO:88    TRGNQPAGELLASFELIQREKPAIHHI-PGFEVQ-DTSRILDESEDTDLPYPPPQREANIYM
SEQ ID NO:89    -RGSQPAGELLASFELIQREKPAIYHI-PGFEVQ-DTSRILDESEDTDLPYPPPQREANVYV
SEQ ID NO:90    -RSSQPAGELLASFELIQREKPAIHHI-PGFEVQ-DTSRILDESEDADLFYPPPQREVNIYM
SEQ ID NO:91    -RGSQPAGELLASFELIQREKPAIHHI-PGFEVH-DTSGILDESEDTDLPYPPPQREANIYM
SEQ ID NO:92    TRGSQPAGELLASFELIQREKPAIHHI-PGFEVQ-DTSRILDESEDTDLPYPPPQREANIYM
SEQ ID NO:93    TRGSQPAGELLASFELIQREKPAIHHI-PGFEVQ-DASRILEESEDTDLPYPPPQREANIYM
SEQ ID NO:94    TRGSQPAGELLASFELIQREKPAIYHI-PGFEVQ-DTSRILEESEDTDLFYPPPQREANIYI
SEQ ID NO:95    TRGSQPAGELLASFELIQREKPAIYHI-PGFEVQ-DTSGILEESEDTDLPYPPPQREANIYM
SEQ ID NO:96    TRGSQLAGELLASFELIQREKPAIYHL-PGFEVQ-DTSGILEESEDTDLFYPPPQREANIYM
SEQ ID NO:97    TRGSQAAGELLASFELIQREKPAIHHI-PGFEVQ-DTSRILEESEDTDLPYPPPQREANIYM
SEQ ID NO:98    TRGNQPAGELLASFELIQREKPAIHHI-PGFEVQ-DTSGILEESEDTDLFYPPPQREANIYM
SEQ ID NO:99    VPGSQPAGELLASFELIQREKPAIHHI-PGFEVQ-DTSGILDESEDTDLPYPPPQREANIYM
SEQ ID NO:100   TRGNQPAGELLASFELIQREKPAIYHI-PGFEVQ-DTSGILEESEDTDLPYPPPQREANIYM
SEQ ID NO:101   VRGSRPAGELLAAFELIMREKPATHRI-PGFEPE-EISGVADEIGDTDLFYPPPQREANIYV
SEQ ID NO:102   TKKNKPAGDLLAAFELIQREKPSTHHSDPGFDPAVRTSRPLGKAGDSDLFYPPPQREPNV--
CLUSTAL          : .:  *;***;****  ****;  :*   ***;       :     :  *;********** *;
P1290T                                     T
```

FIG. 22

```
47,660,977   CTTCCAGATT TGCTCCCTGT TACTGCATTT CTAAATTTTA CTTGAGATTC
             ATTCTTTCCT TGTGAGGGCA ACTATCAGCT ATCATACTCA AGAATGAAGC
             AAGTGCTTTC CCACATGTAT TATCTTAATC CTCTACTTTG AGGCAAGTAT
             TTTCTCCCTT ATTTACTGAT AAGTAGAAAC ACACACATAC AAACACGTGC
             ACAAGGTTCA AGGAGAGTAA ATAATTTGCC CATGAAAGAT CTAACTCAGT
             TCCTTATTAA ATCTTTAAAT CATGACTCCA GGCTAATGTA GTCTACATCC
             TACATCTACA TATTTGTATA TGCCTATAT TTTTTTTTTT TTTTGAGGA
             AGATTGTGAG CTGACGTCTA TTGCCAATCT TCCTCTTTTT GCTTAAGGAA
             GACCTGAGCT AACATCTGTG CCATCTTCCT GTATTTGTA TGTGGGCCAC
             TGCCACAGCA TTACTTGATG ACCGGTGTGT AGGTCTGTGC CTGGGATCCG
             AACCCCAGGC CACCAAAGCG GAGCGTGTGA ACTTAACCAC TACGCCACCA
             GGCCGGCCCC TCCTTAGATA TTTTTAATGT TCATATAGAT TATGTGGTAT
             TATCATCTGT AGGATAAATG TATGCCATTC AAATGTTTTC TTTGGAACTC
             TCTCCAGTGA CACTTTTAGC TGTAAAATTT TGTGAACAGA TTTTCTGCTG
             GCCATTCTAA ATAACACAAA ATAACTATAT ATTGTGTTTC CTTTTATAC
             TCACTAGAAT AACTTCTTTA TCGCCTTTA TATATAGGTT GTATTGCTGG
             GAAAATACAA TGCACAGGGC TTAGGTTCAG ATCATGAATT AATGCTGAGA
             TGTACCAAAG GACAAGAATA CGTCAAAGTC GTCATGCAAA ATGGGCGAAT
             GATGGGAGCT GTCTTAATTG GTGAAACCGA TTTAGAAGAA ACATTTGAAA
             ACTTGATTTT AAACCAGATG AATCTTTCAG CATACGGAGA AGATCTGCTG
47,661,977   (G/C)
             ATCCAGATAT TGACATAGAA GATTATTTTG ACTAAAAAGG TCATTCCAAG
             AACCACATAA AGTTCCAAAT AAGACAAAAA AGTCACACAT CAATAAAGTA
             AATGATTGCA CTGATTTAAT GATGACCACA TTGAAGTTAA AAGTACAGAA
             GTGATAATGA TTTCAGTGGA AAAATATTAA AAAATAAATT CTAAAGATAA
             AATCAATTCA AGTAACTTAT TTACAGATTT TTTTCCTAAC ACAAAATTGA
             CCAATTATGT AAGAATTCTC AAGTTATTCA TTTCTGTGTT TTAAACGTAC
             ACACATTCAT TTGTGATTTT AGCTTTGGAG CACATTTAGC TAGGCTGTTA
             TCTGCTCAGC CCACAACTTG GTCTTGGTTA GTAGACCAGA GCCATTCTTT
             GATTGGAAAA CGTCAAGAAG CTTGTAATTT TATTTTACTT AGAGATGCCG
             CAATATCTTC TTGCTAATAT TATTTGTATT GATACCTTAT TCCTTTTTTG
             TTTGAATTCT ACAGCTATTA TTTTAACCTG AAATCATTCA CTTTCTGTCA
             TGAGCCTGTG ACTTTTCAGT ACAATAACAC TACCATCAAA AGAGAGTTAT
             GTGAAAAGAA AAAATATAGC TAGGTATATC ACGGCATAAA GAGCTTAAGA
             CAGTTATGTG AACTTACTCT TTTAAGGAGT TTACATAAAA AAAGATTTAT
             TTTCCCTTGT TTCATACTGT AAATTTATAC AATTCATGCT CTCAAATTTT
             CAAAAGATCT CAAATTCTCA AGTCCTCAAT TCTTTAGAGA TAAGTTCTTA
             AAATATAGCT CCATTGTAT AAAACATTAA TGAAATTGTC TTAAAAATTA
             AACTTTGATT AACTACAAAA ATAATGGTGT AAACATGCAT AAACTGTTCT
             GTTCTTGGAA AATTTAGATA CACTCATGCA TCATCAATTT TTCTTTTCTT
             AGCCCCTGTG TTCTTAGCCT CAGATTGCTG AAGCATGTTT GCAGACTTCT   47,662,977

(SEQ ID NO:103)
```

FIG. 23

```
238  AGGTTTCCAG AGTATTGGAA GAATTTGATG TTGAAGAACA GCCAAATACC
     ATGTTAGAAA ATCGCTTTCC CAACATTAAG GTTATAGAAT CTGGAGTAAA
     GCAACTGAAG AGTGAAGAAC ACTGCATTTT AACAGAAGAT GGCAATCAGC
     ATGTATATAA GAAACTCTGT CTGTGTGCTG GAGCTAAACC AAAGTTGATA
     TGTGAAGGAA ATCCTTATGT ATTAGGAATC CGTGACACAG ACAGTGCTCA
     GGAATTTCAG AAACAGCTTA CTAAGGCTAA AAGAATAATG ATCATAGGCA
     ATGGTGGGAT CGCACTTGAA TTAGTGTATG AAATTGAAGG CTGTGAAGTC
     ATTTGGGTCA TTAAAGACAA AGCTATTGGG AATACGTTCT TCGATGCAGG
     AGCAGCTGAA TTCTTGACTT CAAAGCTCAT CGCTGAAAAA CCAGAGGGTA
     AAATTGCACA TAGAAGAACC AGATATACAA CTGAAGGAAG GAAAAAGGAA
     GCACGAACCA AAGGTGATGC TGCTAATGTA GGCAGTGCCC TGGGACCTGA
     CTGGCATGAA GGCTTGAATC TTAAAGGAAC AAAAGAGTTT TCTCATAAGA
     TTCACATTGA AACTATGTGT GAAGTAAAGA AAATCTACCT TCAGGAAGAA
     TTTAGAATTT CCAAGAAAAA GTCCTTGACT TTTCCAAGAG ACCATAATAA
     TCAGTCAGTT TCAACTGATA AAGAGATATG GCCTGTATAT GTGGAATTGA
     CCAATGAAAA GATATATGGC TGCGATTTCA TTGTCAGTGC TACAGGAGTT
     ACACCAAATA TAGAACCTTT CCTCTGTGGC AACAATTTTG ATCTAGGAGA
     AGATGGTGGC CTGAAAGTGA ATAATCATAT GCACACGTCC CTTCCTGACA
     TCTATGCTGC AGGTGACATC TGCACTGCCT CCTGGGAACC CAGCCCAGTG
     TGGCAGCAGA TGAGGCTGTG GACGCAGGCT AGACAGATGG GATGGTATGC
     AGCCAAGTGC ATGGCTGCAG CTACTTTAGG AGACTCCATT GACATGGATT
     TCAGCTTCGA ACTGTTTGCT CATGTAACAA AATTTTTTAA CTATAAGGTT
     GTATTGCTGG GAAAATACAA TGCACAGGGC TTAGGTTCAG ATCATGAATT
     AATGCTGAGA TGTACCAAAG GACAAGAATA CGTCAAAGTC GTCATGCAAA
     ATGGGCGAAT GATGGGAGCT GTCTTAATTG GTGAAACCGA TTTAGAAGAA
     ACATTTGAAA ACTTGATTTT AAACCAGATG AATCTTTCAG CATATGGAGA
     AGATCTGCTG GATCCAGATA TTGACATAGA AGATTATTTT GACTAA        1583

(SEQ ID NO:104)

238  AGGTTTCCAG AGTATTGGAA GAATTTGATG TTGAAGAACA GCCAAATACC
     ATGTTAGAAA ATCGCTTTCC CAACATTAAG GTTATAGAAT CTGGAGTAAA
     GCAACTGAAG AGTGAAGAAC ACTGCATTTT AACAGAAGAT GGCAATCAGC
     ATGTATATAA GAAACTCTGT CTGTGTGCTG GAGCTAAACC AAAGTTGATA
     TGTGAAGGAA ATCCTTATGT ATTAGGAATC CGTGACACAG ACAGTGCTCA
     GGAATTTCAG AAACAGCTTA CTAAGGCTAA AAGAATAATG ATCATAGGCA
     ATGGTGGGAT CGCACTTGAA TTAGTGTATG AAATTGAAGG CTGTGAAGTC
     ATTTGGGTCA TTAAAGACAA AGCTATTGGG AATACGTTCT TCGATGCAGG
     AGCAGCTGAA TTCTTGACTT CAAAGCTCAT CGCTGAAAAA CCAGAGGGTA
     AAATTGCACA TAGAAGAACC AGATATACAA CTGAAGGAAG GAAAAAGGAA
     GCACGAACCA AAGGTGATGC TGCTAATGTA GGCAGTGCCC TGGGACCTGA
     CTGGCATGAA GGCTTGAATC TTAAAGGAAC AAAAGAGTTT TCTCATAAGA
     TTCACATTGA AACTATGTGT GAAGTAAAGA AAATCTACCT TCAGGAAGAA
     TTTAGAATTT CCAAGAAAAA GTCCTTGACT TTTCCAAGAG ACCATAATAA
     TCAGTCAGTT TCAACTGATA AAGAGATATG GCCTGTATAT GTGGAATTGA
     CCAATGAAAA GATATATGGC TGCGATTTCA TTGTCAGTGC TACAGGAGTT
     ACACCAAATA TAGAACCTTT CCTCTGTGGC AACAATTTTG ATCTAGGAGA
     AGATGGTGGC CTGAAAGTGA ATAATCATAT GCACACGTCC CTTCCTGACA
     TCTATGCTGC AGGTGACATC TGCACTGCCT CCTGGGAACC CAGCCCAGTG
     TGGCAGCAGA TGAGGCTGTG GACGCAGGCT AGACAGATGG GATGGTATGC
     AGCCAAGTGC ATGGCTGCAG CTACTTTAGG AGACTCCATT GACATGGATT
     TCAGCTTCGA ACTGTTTGCT CATGTAACAA AATTTTTTAA CTATAAGGTT
     GTATTGCTGG GAAAATACAA TGCACAGGGC TTAGGTTCAG ATCATGAATT
     AATGCTGAGA TGTACCAAAG GACAAGAATA CGTCAAAGTC GTCATGCAAA
     ATGGGCGAAT GATGGGAGCT GTCTTAATTG GTGAAACCGA TTTAGAAGAA
     ACATTTGAAA ACTTGATTTT AAACCAGATG AATCTTTCAG CATATGGAGA
     AGATCTGCTG CATCCAGATA TTGACATAGA AGATTATTTT GACTAA        1583

(SEQ ID NO:105)
```

Exon 12

47,661,754   ttatatatag GTTGTATTGC TGGGAAAATA CAATGCACAG GGCTTAGGTT
             CAGATCATGA ATTAATGCTG AGATGTACCA AAGGACAAGA ATACGTCAAA
             GTCGTCATGC AAAATGGGCG AATGATGGGA GCTGTCTTAA TTGGTGAAAC
             CGATTTAGAA GAAACATTTG AAAACTTGAT TTTAAACCAG ATGAATCTTT
             CAGCATACGG AGAAGATCTG CTGGATCCAG ATATTGACAT AGAAGATTAT
             TTTGACTAAa aaggtcatt                                    47,662,022

(SEQ ID NO:106)

FIG. 25

```
 56   VSRVLEEFDV EEQPNTMLEN RFPNIKVIES GVKQLKSEEH CILTEDGNQH
      VYKKLCLCAG AKPKLICEGN PYVLGIRDTD SAQEFQKQLT KAKRIMIIGN
      GGIALELVYE IEGCEVIWVI KDKAIGNTFF DAGAAEFLTS KLIAEKPEGK
      IAHRRTRYTT EGRKKEARTK GDAANVGSAL GPDWHEGLNL KGTKEFSHKI
      HIETMCEVKK IYLQEEFRIS KKKSLTFPRD HNNQSVSTDK EIWPVYVELT
      NEKIYGCDFI VSATGVTPNI EPFLCGNNFD LGEDGGLKVN NHMHTSLPDI
      YAAGDICTAS WEPSPVWQQM RLWTQARQMG WYAAKCMAAA TLGDSIDMDF
      SFELFARVTK FFNYKVVLLG KYNAQGLGSD HELMLRCTKG QEYVKVVMQN
      GRMMGAVLIG ETDLEETFEN LILNQMNLSA YGEDLLDPDI DIEDYFD      502

(SEQ ID NO:107)

56   VSRVLEEFDV EEQPNTMLEN RFPNIKVIES GVKQLKSEEH CILTEDGNQH
      VYKKLCLCAG AKPKLICEGN PYVLGIRDTD SAQEFQKQLT KAKRIMIIGN
      GGIALELVYE IEGCEVIWVI KDKAIGNTFF DAGAAEFLTS KLIAEKPEGK
      IAHRRTRYTT EGRKKEARTK GDAANVGSAL GPDWHEGLNL KGTKEFSHKI
      HIETMCEVKK IYLQEEFRIS KKKSLTFPRD HNNQSVSTDK EIWPVYVELT
      NEKIYGCDFI VSATGVTPNI EPFLCGNNFD LGEDGGLKVN NHMHTSLPDI
      YAAGDICTAS WEPSPVWQQM RLWTQARQMG WYAAKCMAAA TLGDSIDMDF
      SFELFARVTK FFNYKVVLLG KYNAQGLGSD HELMLRCTKG QEYVKVVMQN
      GRMMGAVLIG ETDLEETFEN LILNQMNLSA YGEDLLHPDI DIEDYFD      502

(SEQ ID NO:108)
```

FIG. 26

```
                                                                  5'-c
47,661,614  TTCTTTGGAA CTCTCTCCAG TGACACTTTT AGCTGTAAAA TTTTGTGAAC agattttctg ctggccatt-3' (SEQ ID NO:111)
            AGATTTTCTG CTGGCCATTC TAAATAACAC AAAATAACTA TATATTGTGT

TTCCTTTTTA TACTCACTAG AATAACTTCT TTATCGCCTT TTATATATAG 47,661,764  GTT GTA TTG CTG GGA AAA TAC AAT GCA CAG GGC TTA GGT
47,661,764  GTT GTA TTG CTG GGA AAA TAC AAT GCA CAG GGC TTA GGT

TCA GAT CAT GAA TTA ATG CTG AGA TGT ACC AAA GGA CAA
            TCA GAT CAT GAA TTA ATG CTG AGA TGT ACC AAA GGA CAA

GAA TAC GTC AAA GTC GTC ATG CAA AAT GGG CGA ATG ATG
            GAA TAC GTC AAA GTC GTC ATG CAA AAT GGG CGA ATG ATG

GGA GCT GTC TTA ATT GGT GAA ACC GAT TTA GAA GAA ACA
            GGA GCT GTC TTA ATT GGT GAA ACC GAT TTA GAA GAA ACA

TTT GAA AAC TTG ATT TTA AAC CAG ATG AAT CTT TCA GCA
            TTT GAA AAC TTG ATT TTA AAC CAG ATG AAT CTT TCA GCA

TAT GGA GAA GAT CTG CTG GAT CCA GAT ATT GAC ATA GAA
            TAT GGA GAA GAT CTG CTG CAT CCA GAT ATT GAC ATA GAA

GAT TAT TTT GAC TAA (SEQ ID NO:109) 47,662,012
            GAT TAT TTT GAC TAA (SEQ ID NO:110) 47,662,012

AAAGGTCATT CCAAGAACCA CATAAAGTTC CAAATAAGAC AAAAAAGTCA

CACATCAATA AAGTAAATGA TTGCACTGAT TTAATGATGA CCACATTGAA    47,662,112
            (SEQ ID NO:112) 3'-aacgtgacta aattactact ggt-5'
```

FIG. 27

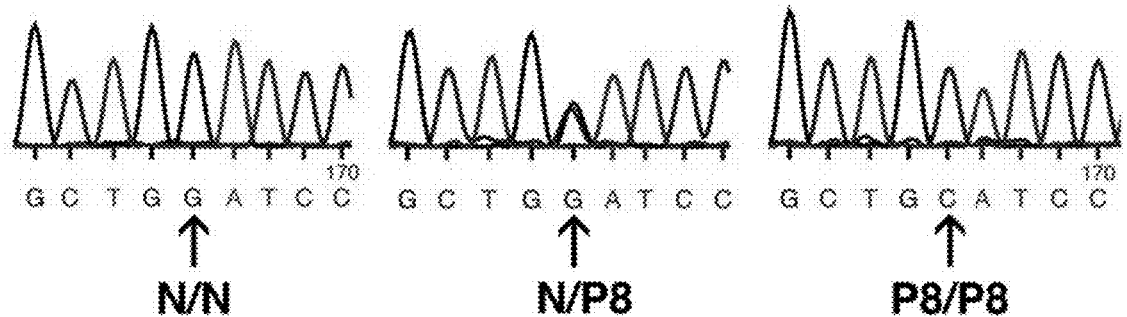

FIG. 28

```
619  TGAAATTGAA GGCTGTGAAG TGATTTGGGC CATTAAAGAT AAAGCTATAG
     GGAATACTTT CTTCGATGCA GGAGCAGCTG AATTCTTGAC TTCAAAGCTC
     ATTGCTGAAA AATCAGAGGC TAAAATTGCA CATAAAAGAA CCAGATATAC
     AACTGAAGGA AGGAAAAAGG AAGCTAGAAG CAAATCTAAA GCAGATAATG
     TAGGAAGTGC ATTGGGACCA GATTGGCATG AAGGCTTGAA TCTTAAAGGA
     ACAAAAGAGT TTTCTCATAA GATTCACCTT GAAACTATGT GTGAAGTAAA
     GAAAATCTAC CTTCAGGATG AGTTTAGAAT TTTGAAGAAA AAGTCCTTCA
     CTTTTCCAAG AGACCATAAG TCAGTTACAG CTGATACAGA GATGTGGCCT
     GTCTATGTGG AATTGACCAA TGAAAAGATA TATGGCTGCG ATTTCATTGT
     CAGTGCTACA GGAGTTACAC CAAATGTAGA ACCTTTTCTC CATGGTAACA
     GTTTTGATCT AGGAGAAGAT GGTGGCCTGA AAGTGGATGA TCATATGCAC
     ACATCCCTTC CTGATATCTA TGCTGCCGGT GACATCTGTA CTACATCCTG
     GCAGCTGAGC CCAGTCTGGC AGCAGATGAG GCTGTGGACC CAGGCTAGAC
     AGATGGGATG GTATGCAGCA AAGTGCATGG CTGCAGCGAG TTCAGGAGAC
     TCTATTGACA TGGATTTCAG CTTTGAACTG TTTGCTCATG TGACAAAATT
     TTTTAACTAT AAGGTTGTAC TGCTGGGAAA ATACAATGCA CAGGGCTTAG
     GTTCAGATCA TGAATTAATG CTGAGATGTA CCAAAGGACG AGAATACATC
     AAAGTCGTCA TGCAAAATGG ACGAATGATG GGAGCTGTCT TAATTGGTGA
     AACCGATTTA GAAGAAACAT TTGAAAACCT AATCTTAAAC CAAATGAATC
     TTTCATCATA TGGAGAAGAT CTGCTAGATC CAAATATTGA TATAGAAGAT
     TATTTTGACT AA                                        1630
```

(SEQ ID NO:113)

FIG. 29

```
56   ISKILEEFDV EEQSSTMLGK RFPNIKVIES GVKQLKSEEH CIVTEDGNQH
     VYKKLCLCAG AKPKLICEGN PYVLGIRDTD SAQEFQKQLT KAKRIMIIGN
     GGIALELVYE IEGCEVIWAI KDKAIGNTFF DAGAAEFLTS KLIAEKSEAK
     IAHKRTRYTT EGRKKEARSK SKADNVGSAL GPDWHEGLNL KGTKEFSHKI
     HLETMCEVKK IYLQDEFRIL KKKSFTFPRD HKSVTADTEM WPVYVELTNE
     KIYGCDFIVS ATGVTPNVEP FLHGNSFDLG EDGGLKVDDH MHTSLPDIYA
     AGDICTTSWQ LSPVWQQMRL WTQARQMGWY AAKCMAAASS GDSIDMDFSF
     ELFAHVTKFF NYKVVLLGKY NAQGLGSDHE LMLRCTKGRE YIKVVMQNGR
     MMGAVLIGET DLEETFENLI LNQMNLSSYG EDLLDPNIDI EDYFD   500
```

(SEQ ID NO:114)

FIG. 30

Human
VVLLGKYNAQGLGSDHELMLRCTKGREYIKVVMQNGRMMGAVLIGETDLEETFENLILNQMNLSSYGEDLLDPNIDIEDYFD
(SEQ ID NO:115)

Horse
VVLLGKYNAQGLGSDHELMLRCTKGQEYVKVVMQNGRMMGAVLIGETDLEETFENLILNQMNLSAYGEDLLDPDIDIEDYFD
(SEQ ID NO:116)

Horse D492H
VVLLGKYNAQGLGSDHELMLRCTKGQEYVKVVMQNGRMMGAVLIGETDLEETFENLILNQMNLSAYGEDLLHPDIDIEDYFD
(SEQ ID NO:117)

```
Human       419  VVLLGKYNAQGLGSDHELMLRCTKGREYIKVVMQNGRMMGAVLIGETDLE  468
                 *************************  *** ******************
Horse       421  VVLLGKYNAQGLGSDHELMLRCTKGQEYVKVVMQNGRMMGAVLIGETDLE  470
Horse D492H 421  VVLLGKYNAQGLGSDHELMLRCTKGQEYVKVVMQNGRMMGAVLIGETDLE  470

Human       469  ETFENLILNQMNLSSYGEDLLDPNIDIEDYFD  500
                 ************** ****** * ********
Horse       471  ETFENLILNQMNLSAYGEDLLDPDIDIEDYFD  502
Horse D492H 471  ETFENLILNQMNLSAYGEDLLHPDIDIEDYFD  502
```

FIG. 31

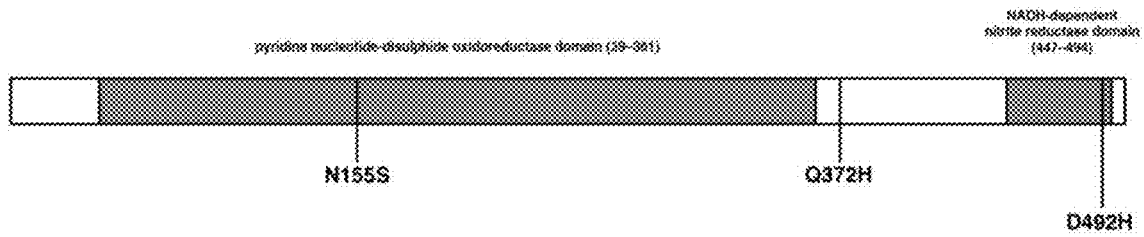

FIG. 32

```
(SEQ ID NO:118)  TKGQEYIKVVMQNGRMMGAVLIGETDLEETFENLILNQMNLSSYGEDLLDPNIDIEDYFD
(SEQ ID NO:119)  TKGQEYVKVVMQNGRMMGAVLIGETDLEETFENLILNQMNLSSYGEDLLDPNIDIEDYFD
(SEQ ID NO:120)  TRGQEYVKVVMQNGRMMGAVLIGETDLEETFENLILNQMDLSSYGEDLLDPNIDIEDYFD
(SEQ ID NO:121)  TKGQEYVKVVMQNGRMMGAVLIGETDLEETFENLILNQMDLSSYGEDLLDPNIDIEDYFD
(SEQ ID NO:122)  TKGQEYVKVVMQNGRMMGAVLIGETNLEETFENLILNQMNLSSYGEDLLDPNIDIEDYFD
(SEQ ID NO:123)  TKGQEYVKVVMQNGRMMGAVLIGETDLEETFENLILNQMNLSAYGEDLLDPDIDIEDYFD
(SEQ ID NO:124)  TKGQEYIKAVLQNGRMMGAVLIGETDLEETFENLILNQMNLSAYGEDLLDPNIDIEDYFD
(SEQ ID NO:125)  TKGQEYVKVVMQNGRMMGAVLIGETDLEETFENLILNQMDLSSYGEDLLDPNIDLEDYFD
(SEQ ID NO:126)  TKGREYIKVVMQNGRMMGAVLIGETDLEETFENLILNQMNLSSYGEDLLDPNIDIEDYFD
(SEQ ID NO:127)  TKGQEYIKVVMQNGRMMGAVLIGETDLEETFENLILNQMNLSQYGEDLLDPNIDIEDYFD
(SEQ ID NO:128)  TRGQEYIKVVMHNGRMMGAVLIGETDLEETFENLILNQMDLSSYGEDLLNPDIDIEDYFD
(SEQ ID NO:129)  TRGQEYVKVVMQNGRMMGAVLIGETDLEETFENLILNQMDLSSYGEDLLDPDIDIEDYFD
(SEQ ID NO:130)  TRGQEYVKVVMQNGRMMGAVLIGETDLEETFENLILNQMDLSSYGEDLLDPDIDIEDYFD
(SEQ ID NO:131)  TKGQEYVKVVMQNGRMMGAVLIGETDLEETFENLILNQMDLSPYGEDLLDPNIDIEDYFD
(SEQ ID NO:132)  TKGQEYIKVIMQNGRMMGAVLIGETDLEETFENLILNQMDLSSYGEDLLDPNIDIEDYFD
(SEQ ID NO:133)  TKGQEYVKVVMQHGRMMGAVLIGETDLEETFENLILNQTDLSSYGEDLLDPNIDLEDYFD
(SEQ ID NO:134)  TKGQEYIKVVMQNGIRMGAVLIGETDLEETFENLILNQMDLSPYGEDLLDPNIDIEDYFD
(SEQ ID NO:135)  TKGQEYVKAVLQNGRMMGAVLIGETDLEETFENLILNQMNLSAYGEDLLDPNIDIEDYFD
(SEQ ID NO:136)  TKGQEYVKVVMQNGRMMGAVLIGETDLEETFENLILNQTDLSSYGEDLLDPNIDLEDYFD
(SEQ ID NO:137)  TKGQEYVKVVMQNGRMMGAILIGETDLEETFENLILNQMNLSAYGEDLLDPDIDIEDYFD
(SEQ ID NO:138)  TKGQEYVKVVMQNGRMMGAILIGETDLEETFENLILNQMNLSAYGEDLLDPNIDIEDYFD
(SEQ ID NO:139)  TKGQEYVKVVMQNGRMMGAILIGETNLEETFENLILNQMNLSAYGEDLLDPSIDIEDYFD
(SEQ ID NO:140)  TKGQEYVKVVMQNGRMMGAVLIGETDLEETFENLILNQMDLSAYGEDLLNPDIDIEDYFD
(SEQ ID NO:141)  TKGHEYVKVVMQNGRMMGAVLIGETDLEETFENLILNQMDLSAYGEDLLNPDIDIEDYFD
(SEQ ID NO:142)  TKGQEYVKVVMQNGRMVGAVLIGETDLEETFENLILNQMDLSAYGEDLLNPDIDIEDYFD
(SEQ ID NO:143)  TKGQEYVKVVMQNGRMMGAVLIGETDLEETFENLILNQMDLSAYGEDLLNPNIDIEDYFD
(SEQ ID NO:144)  TKGHEYVKVVMQNGRMMGAVLIGETDLEETFENLILNPMDLSAYGEDLLNPDIDIEDYFD
(SEQ ID NO:145)  TKGHEYVKVVMQNGRMMGAVLIGETDLEETFENLILNPMDLSAYGEDLLNPDIDIEDYFD
(SEQ ID NO:146)  TKGHEYIKVVMQNGRMMGAVLIGETDLEETFENLILNQMDLSAYGEDLLNPDIDIEDYFD
(SEQ ID NO:147)  TKGHEYVKVVMQNGRMMGAVLIGETDLEETFENLILNQIDLSAYGEDLLNPDIDLEDYFD
(SEQ ID NO:148)  TKGQEYVKAVMQNGRMVGAVLIGETDLEETFENLILNQMDLSAYGEDLLNPDIDIEDYFD
(SEQ ID NO:149)  TKGQEYVKVVMQSGPMVGAVLIGDTDLEETFENLILNQMDLSAYGEDLLNPDVDIEDYFD
(SEQ ID NO:150)  TKGQEYVKVVMQNGRMMGAVLIGETDLEETFENLILNQMDLSRYGEDLLDPNIDIEDYFD
(SEQ ID NO:151)  TKGLEYVKVVMQNGRMLGAVLIGETDLEETFENLILNQMDLSRYGEDLLDPNIDIEDYFD
(SEQ ID NO:152)  TKGQEYVKVVMQNGRMLGAVLIGETDLEETFENLILNQMDLSRYGEDLLDPNIDIEDYFD
(SEQ ID NO:153)  TKGQEYIKVVMQNGRMLGAVLIGETDLEETFENLILNQMDLSRYGENLLDPNIDIEDYFD
(SEQ ID NO:154)  TKGQEYIKVVMQNGRMLGAVLIGETDLEETFENLILNQMDLSPYGEDLLDPNIDIEDYFD
(SEQ ID NO:155)  TKGQEYIKVVMQHGRMLGAVLIGETDLEETFENLILNQMDLSPYGEDLLDPNIDIEDYFD
(SEQ ID NO:156)  TKGEYIKVVMQHGRMLGAVLIGETDLEETFENLILNQMDLSRYGKDLLDPNIDIEDYFD
(SEQ ID NO:157)  TKGQEYVKVVLQNGRMMGAILIGETDLEETFENLMLNQMDLSAYGEELLNPDIDIEDYFD
(SEQ ID NO:158)  TTGQEYVKTVMQNGRMKGAVLIGETDLEETFENLILNQMDLSAYGEDLLNPNIDIEDYFD
(SEQ ID NO:159)  TKGHEYVKAVMQNGRMMGAVLIGETNLEETFENLILNQMDLSSYGEELLNPNIDIEDYFD
(SEQ ID NO:160)  TKGHEYVKVVLSGGRMLGAVLIGETDLEETFENLILNQMDLTPYGEELLNPNIDIEDYFD
(SEQ ID NO:161)  TRGHEYVKLVMQGGRMVGALLIGDTDLEETFENLILNQTDLSSYGERLLDPNIDIEDYFD
(SEQ ID NO:162)  TKGQEYVKVVLTGGRMVGAVLIGETDLEETFENLILNQMDLSRYGEELLNPNIDIEDYFD
         CLUSTAL * * **:* ::  *:* **:***:*:********:**: :*: **: **:*.:*:*****
           D492H                                                       H
```

FIG. 33

```
23,481,621    TTAGAATTCT GGGGTGGCTG GAGGTGTGTT TGCTCTCTAG CTGCAAAGAT
              AAACGTTTGC AAGACCTGTC ATACGAAGAC CTGAGAAGTT TCCCTAAAAT
              GTGGTCTCAG GGTACTTAA GTTTGTTTA AGAAAAGAGA AGAGTTCGTA
              GCTTTTCTTG TTTCAGGCTC TATAAAACCT GTAAGTTTTT GTAGGTGACC
              ATTGCGGGA CCGGCCTCTT CTTGTCCATG AGGCCAGAGT AGCCTGGGC
              ATCGTGCTTC CTGGGGAGGA AGAAGCATTG CCCCCCTGTT GGGGCAGAGA
              GTGGGTGCTG ACCGCATGGT CAGGGTCTGT CAGAGGCAGG TGGACGTTCT
              GTGGATGGGA TGTGACTGAA GGGACCCGTC TCTTGAGCCT CACATTCATA
              TCATCACGAA TATTTTCTG AGCACCTGAT CCTGCGGCG TGGCTTTCCT
              CGCACATGTG GCTCATTCC CTGACTTGTG TTGTTTTCAG GGTGACTCAG
              GGCGGACAG CCAGCAGAGA GGACCCAAAG GAGAAACCGG AGACCTCGGG
              CCCATGGTAC GATGTCCTT GTTCCCAGAC TCTCCTGTGC TGGAGGCCAG
              AGAAACAAAG CTCACACTGG CTCGCCAGGG GCGAAGGAC CATGGAAGTG
              GTCTTTGAGG CTGGGGAGCA TATGCGGTCA GGAACAGAGG GCCCCGTGAA
              GCCCACCCTG TGTGCCCATG AAGGACGTTT CCATTGTGGA ACAGAAGCAA
              GCCCTACCGA GAGGAGCTTC TTCTGGGCAG AAGTTGTGCT CTTTAGATAT
              TTACGAAAGC GCTTGTCAAG CCAAAGGCTG TGGGGGCGGG CACGTACCTA
              AGTCTAGCGC ACCTCACGAC AGAGTACCGA CCTTCCTCTG CCTATCCATC
              CCTTTTCCTG TAGTGTCTCG TGCAATATTC CAGAGTTCCT GCTCTTCTTT
              GCAGATGAAA ATCTTACACC AATTTTCTTC CCCACGCCAG GGTCTGCCTG
23,480,621    (G/C)
              GAGTGATGGT GTCTCGGGAA GTCCTGGAGA ACCAGGGAGG GACGTGAGTG
              TCTCTTACAG CTTTGGAGGG AGGTGGCGGG GCCTCTGTGC TGGTATTTAG
              CAGGTGCCCT CCAGATCTTC CAGACACTGC CTGGGGCGTT GTTACCCAGC
              AACTCTTTGT TTAAAGAATT TAAAGAGATT TCTGAAACCT TTGTCACCCA
              AATCTTGATG CTTATGGAAA ACATTCGTCC TTATTGTTTG AGCTGTGCCC
              CATCTGTGCC CGTCTCTTCT CCCACCTCA GTCCCGCTTA CTCCCCTCCC
              CAAAACTCAC CGAACAGACA CTTTTTAAAG TATTGTCTTC CCAGCTTTCA
              AGTATCTGGC CAGGTTTTAT CCCACTAAAT GTTAAAAAA ATCCAACAG
              AAACACGAAA ACGGGGCGG GGGGGGGGA TGAGGGAATA TGGGCAGGG
              AGGCTGCTGG GGTTGTATAT TTGTGGTTGC TTTAGAATT GTTTTTCGTG
              TGCTGCTGTA GCTCAAGCAA GGAAACGAGA CTCAGTTTTC TAGTGAATCG
              CTTTTTGAAA TCGCTTTCCC AAGGCATTTC AGAAATGCCC TTTGTAGATT
              AGCTGATTGC ATGCCTAGTC TTTGAGTCTT TCTGGAAGAG CTGCTAAAGC
              CAAAGGGATA AAGATCGTCT TTAGGAAGCC AGTGGAATGC TTCCAGGGCC
              CAGGGGCAAG ATGGTCTGGA AGCTCATACA TCCTCTGGGG TGCGTCAGGA
              TGCTGGGGC GGGTGCCCAG GCAGGTCTC TGCTCAGAAG CTGCCTGGGA
              CTATGCAGCC TTGAACGGGG CCCCCTCAGC TGTCTCCCA GTGGCAGCGA
              CACATTTAGG GATCAGCAGC TGGACAATCG GGGGGTGTA TGCTGAGGTG
              AGCGCTCTGA AAAGAAGTAA CTCTCACCTG TAATCAGATG ATATATCATG
              GGCCAAAGTT TGCTTTTAAA ATTCAGAAGA AGACTTAAAA TTTGAAAATG    23,479,621
(SEQ ID NO:163)
```

FIG. 34

```
6,356      GGACAAAGGG GAGACCGAGG GCCCATCGGC AGCATCGGGC CAAAGGGTGT
           TCCCGGAGAA GACGGCTACC GAGGGTACCC CGGTGATGAG GGTGGGCCCG
           GTGATCGGGG TCCACCGGGT GTGAACGGCA CTCAAGGTTT CCAGGGCTGC
           CCCGGGCAGA GAGGAATAAA GGGCTCTCGT GGATTCCCAG GAGAGAAGGG
           TGAATTAGGA GAAATCGGAC TTGATGGTCT TGACGGTGAA GATGGAGACA
           AAGGATTGCC TGGGTCTTCT GGAGAGAAAG GGAATCCTGG AAGGAGGGGT
           GACAAAGGAC CTAAAGGAGA CCAAGGGGAA AGAGGAGATG TTGGAATTAG
           GGGCGACCCG GGTGACTCAG GGCGGGACAG CCAGCAGAGA GGACCCAAAG
           GAGAAACCGG AGACCTCGGG CCCATGGGTC TGCCTGGGAG TGATGGTGTC
           TCGGGAAGTC CTGGAGAACC AGGGAGGGAC GGTGGCTTTG GCCGAAGGGG
           ACCACCAGGA GCTAAGGGCA ACAAGGGCGG TCCTGGCCAG CAGGGCACCG
           TGGGAGAGCA GGGGACCAGA GGTGCACAGG GTCCACCTGG TTCCACCGGT
           CCTCCAGGGC TGATCGGCGA ACAAGGCATT CCTGGACCTC GGGGAAGCGG
           AGGTGCTGTG GGCGTCCCTG GAGAACGCGG CCGAACCGGT CCCTTGGGAA
           GAAAGGGCGA GCCTGGAGAG CCGGGAGCGA AGGGAGGACT CGGGCCCCGG
           GGCCCCCGTG GGGAAACGGG AGATGACGGG CGAGACGGAG TTGGCAGTGA
           AGGACAAAAA GGCAAAAAAG GAGAAAGAGG ATTCCCTGGA TACCCAGGTC
           CAAAGGGTAC CCGTGGTGAG CCAGGGACAG ACGGAACACT AGGACCCAAA
           GGCGTCAGAG GCCGAAGGGG AGACTCAGGA CCTCCAGGGG CAGCTGGACA
           GAAGGGAGAC CCTGGTTACC CGGGACCATC TGGTCTCAAA GGCAACAGAG
           GCGACTCG                                              7,363
```

(SEQ ID NO:164)

```
6,356      GGACAAAGGG GAGACCGAGG GCCCATCGGC AGCATCGGGC CAAAGGGTGT
           TCCCGGAGAA GACGGCTACC GAGGGTACCC CGGTGATGAG GGTGGGCCCG
           GTGATCGGGG TCCACCGGGT GTGAACGGCA CTCAAGGTTT CCAGGGCTGC
           CCCGGGCAGA GAGGAATAAA GGGCTCTCGT GGATTCCCAG GAGAGAAGGG
           TGAATTAGGA GAAATCGGAC TTGATGGTCT TGACGGTGAA GATGGAGACA
           AAGGATTGCC TGGGTCTTCT GGAGAGAAAG GGAATCCTGG AAGGAGGGGT
           GACAAAGGAC CTAAAGGAGA CCAAGGGGAA AGAGGAGATG TTGGAATTAG
           GGGCGACCCG GGTGACTCAG GGCGGGACAG CCAGCAGAGA GGACCCAAAG
           GAGAAACCGG AGACCTCGGG CCCATGGGTC TGCCTGCGAG TGATGGTGTC
           TCGGGAAGTC CTGGAGAACC AGGGAGGGAC GGTGGCTTTG GCCGAAGGGG
           ACCACCAGGA GCTAAGGGCA ACAAGGGCGG TCCTGGCCAG CAGGGCACCG
           TGGGAGAGCA GGGGACCAGA GGTGCACAGG GTCCACCTGG TTCCACCGGT
           CCTCCAGGGC TGATCGGCGA ACAAGGCATT CCTGGACCTC GGGGAAGCGG
           AGGTGCTGTG GGCGTCCCTG GAGAACGCGG CCGAACCGGT CCCTTGGGAA
           GAAAGGGCGA GCCTGGAGAG CCGGGAGCGA AGGGAGGACT CGGGCCCCGG
           GGCCCCCGTG GGGAAACGGG AGATGACGGG CGAGACGGAG TTGGCAGTGA
           AGGACAAAAA GGCAAAAAAG GAGAAAGAGG ATTCCCTGGA TACCCAGGTC
           CAAAGGGTAC CCGTGGTGAG CCAGGGACAG ACGGAACACT AGGACCCAAA
           GGCGTCAGAG GCCGAAGGGG AGACTCAGGA CCTCCAGGGG CAGCTGGACA
           GAAGGGAGAC CCTGGTTACC CGGGACCATC TGGTCTCAAA GGCAACAGAG
           GCGACTCG                                              7,363
```

(SEQ ID NO:165)

Exon 26

23,480,641  cccacgccagGGTCTGCCGGTCTGCCTGGGAGTGATGGTGTCTCGGGAAGTCCTGGAGAACCAGGGAGGGAC
            gtgagtgtct  23,480,568

(SEQ ID NO:156)

FIG. 36

```
2,037      GQRGDRGPIG SIGPKGVPGE DGYRGYPGDE GGPGDRGPPG VNGTQGFQGC
           PGQRGIKGSR GFPGEKGELG EIGLDGLDGE DGDKGLPGSS GEKGNPGRRG
           DKGPKGDQGE RGDVGIRGDP GDSGRDSQQR GPKGETGDLG PMGLPGSDGV
           SGSPGEPGRD GGFGRRGPPG AKGNKGGPGQ QGTVGEQGTR GAQGPPGSTG
           PPGLIGEQGI PGPRGSGGAV GVPGERGRTG PLGRKGEPGE PGAKGGLGPR
           GPRGETGDDG RDGVGSEGQK GKKGERGFPG YPGPKGTRGE PGTDGTLGPK
           GVRGRRGDSG PPGAAGQKGD PGYPGPSGLK GNRGDS                    2,372
(SEQ ID NO:167)

2,037      GQRGDRGPIG SIGPKGVPGE DGYRGYPGDE GGPGDRGPPG VNGTQGFQGC
           PGQRGIKGSR GFPGEKGELG EIGLDGLDGE DGDKGLPGSS GEKGNPGRRG
           DKGPKGDQGE RGDVGIRGDP GDSGRDSQQR GPKGETGDLG PMGLPASDGV
           SGSPGEPGRD GGFGRRGPPG AKGNKGGPGQ QGTVGEQGTR GAQGPPGSTG
           PPGLIGEQGI PGPRGSGGAV GVPGERGRTG PLGRKGEPGE PGAKGGLGPR
           GPRGETGDDG RDGVGSEGQK GKKGERGFPG YPGPKGTRGE PGTDGTLGPK
           GVRGRRGDSG PPGAAGQKGD PGYPGPSGLK GNRGDS                    2,372
(SEQ ID NO:168)
```

FIG. 37

```
                                                            5'-ttcccagac tctcctgtgc
23,481,081   AGACCTCGGG CCCATGGTAC GATGCTCCTT GTTCCCAGAC TCTCCTGTGC t 3' (SEQ ID NO:171)
             TGGAGGCCAG AGAAACAAAG CTCACACTGG CTCGCCAGGG GCCGAAGGAC

CATGGAAGTG GTCTTTGAGG CTGGGGAGCA TATGCGGTCA GGAACAGAGG

GCCCCGTGAA GCCCACCCTG TGTGCCCATG AAGGACGTTT CCATTGTGGA

ACAGAAGCAA GCCCTACCGA GAGGAGCTTC TTCTGGGCAG AAGTTGTGCT

CTTTAGATAT TTACGAAAGC GCTTGTCAAG CCAAAGGCTG TGGGGGCGGG

CACGTACCTA AGTCTAGCGC ACCTCACGAC AGAGTACCGA CCTTCCTCTG

CCTATCCATC CCTTTTCCTG TAGTGTCTCG TGCAATATTC CAGAGTTCCT

GCTCTTCTTT GCAGATGAAA ATCTTACACC AATTTCTTC CCCACGCCAG 23,480,631   GGT CTG CCT GGG AGT GAT GGT GTC TCG GGA AGT CCT GGA
23,480,631   GGT CTG CCT GCG AGT GAT GGT GTC TCG GGA AGT CCT GGA

GAA CCA GGG AGG GAC (SEQ ID NO:169)                    23,480,578
             GAA CCA GGG AGG GAC (SEQ ID NO:170)                    23,480,578

GTGAGTGTCT CTTACAGCTT TGGAGGGAGG TGGCGGGGCC TCTGTGCTGG

TATTTAGCAG GTGCCCTCCA GATCTTCCAG ACACTGCCTG GGCGTTGTT

ACCCAGCAAC TCTTTGTTTA AGAATTTAA AGAGATTTCT GAAACCTTTG

TCACCCAAAT CTTGATGCTT ATGGAAAACA TTCGTCCTTA TTGTTTGATC
                                  (SEQ ID NO:172)        3'-caaactag TGTGCCCCAT CTGTGCCCGT CTCTTCTCCC ACCCCCAGTC CCGCTTACTC    23,480,328
             acacgggta ga-5'
```

FIG. 38

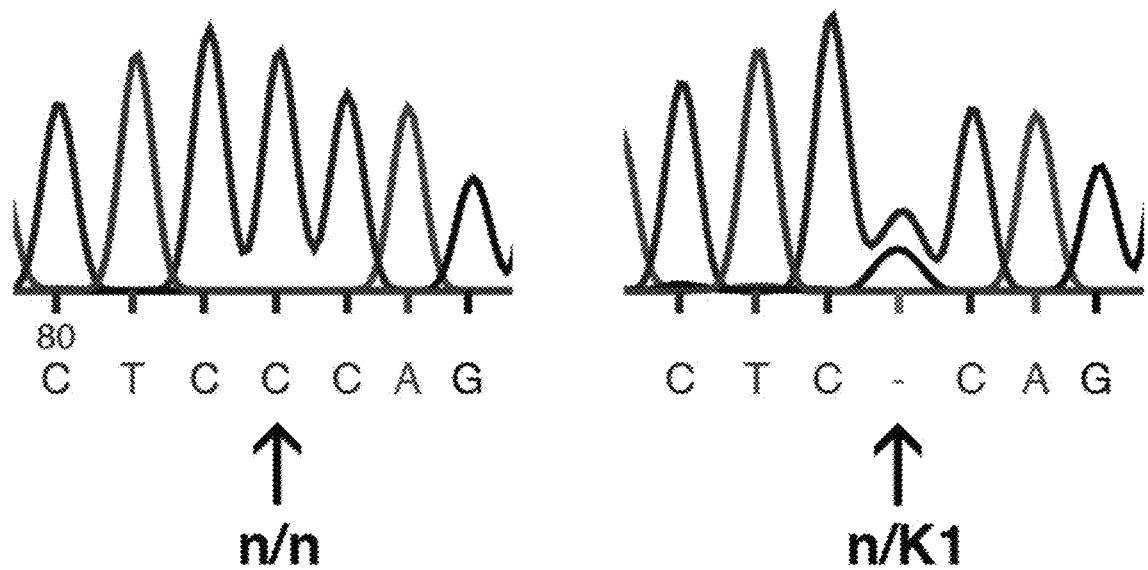

FIG. 39

```
6,397    GGGCAGAGGG GAGACCGCGG GCCCATCGGC AGCATCGGGC CAAAGGGTAT
         TCCTGGAGAA GACGGCTACC GAGGCTATCC TGGTGATGAG GGTGGACCCG
         GTGAGCGTGG TCCGCCTGGT GTGAACGGCA CTCAAGGTTT CCAGGGCTGC
         CCCGGCCAGA GAGGAGTAAA GGGCTCTCGG GGATTCCCAG GAGAGAAGGG
         CGAAGTAGGA GAAATTGGAC TGGATGGTCT GGATGGTGAA GATGGAGACA
         AAGGATTGCC TGGTTCTTCT GGAGAGAAAG GGAATGCTGG AAGAAGGGGT
         GATAAAGGAC CTCGAGGAGA GAAAGGAGAA AGAGGAGATG TTGGGATTCG
         AGGGGACCCG GGTAACCCAG GACAAGACAG CCAGGACAGA GGACCCAAAG
         GAGAAACCGG TGACCTCGGC CCCATGGGTG TCCCAGGGAG AGATGGAGTA
         CCTGGAGGAC CTGGAGAAAC TGGGAAGAAT GGTGGCTTTG GCCGAAGGGG
         ACCCCCCGGA GCTAAGGGCA ACAAGGGCGG TCCTGGCCAG CCGGGCTTTG
         AGGGAGAGCA GGGGACCAGA GGTGCACAGG GCCCAGCTGG TCCTGCTGGT
         CCTCCAGGGC TGATAGGAGA ACAAGGCATT TCTGGACCTC GGGGAAGCGG
         AGGTGCCGCT GGTGCTCCTG GAGAACGAGG CAGAACCGGT CCACTGGGAA
         GAAAGGGTCA GCCCGGAGAG CCAGGACCAA AAGGAGGAAT CGGGAACCGG
         GGCCCTCGTG GGGAGACGGG AGATGACGGG AGAGACGGAG TTGGCAGTGA
         AGGACGCAGA GGCAAAAAAG GAGAAAGAGG ATTCCCTGGA TACCCAGGAC
         CAAAGGGTAA CCCAGGTGAA CCTGGGCTAA ATGGAACAAC AGGACCCAAA
         GGCATCAGAG GCCGAAGGGG AAATTCGGGA CCTCCAGGGA TAGTTGGACA
         GAAGGGAGAC CCTGGCTACC CAGGACCAGC TGGTCCCAAG GCCAACAGCG
         GCGACTCC                                                     7,404

(SEQ ID NO:179)
```

FIG. 40

```
2,038      GQRGDRGPIG SIGPKGIPGE DGYRGYPGDE GGPGERGPPG VNGTQGFQGC
           PGQPGVKGSR GFPGEKGEVG EIGLDGLDGE DGDKGLPGSS GEKGNPGRRG
           DKGPRGEKGE RGDVGIRGDP GNPGQDSQER GPKGETGDLG PMGVPGRDGV
           PGGPGETGKN GGFGRRGPPG AKGNKGGPGQ PGFEGEQGTR GAQGPAGPAG
           PPGLIGEQGI SGFRGSGGAA GAPGERGRTG PLGRKGEPGE PGPKGGIGNR
           GPRGETGDDG RDGVGSEGRR GKKGERGFPG YPGPKGNPGE PGLNGTTGPK
           GIRGRRGNSG PPGIVGQKGD PGYPGPAGPK GNRGDS                    2,373
(SEQ ID NO:174)
```

FIG. 41

```
human  2038 GQRGDRGPIGSIGPKGIPGEDGYRGYPGDEGGPGERGPPGVNGTQGFQGCPGQRGVKGSR 2097
horse  2037 GQRGDRGPIGSIGPKGVPGEDGYRGYPGDEGGPGDRGPPGVNGTQSFQGCPGQRGIKGSR 2096 human  2098 GFPGEKGEVGEIGLDGLDGEDGDKGLPGSSGEKGNPGRRGDKGPRGEKGERGDVGIRGDP 2157
horse  2097 GFPGEKGELGEIGLDGLDGEDGDKGLPGSSGEKGNPGRRGDKGPKGDQGERGDVGIRGDP 2156 human  2158 GNPGQDSQERGPKGETGDLGPMGVPGRDGVPGGPGETGKNGGFGRRGPPGAKGNKGGPGQ 2217
horse  2157 GDSGRDSQQRGPKGETGDLGPMGLPGSDGVSGSPGEPGRDGGFGRRGPPGARGNKGGPGQ 2216
G2182A                            A human  2218 PGFEGEQGTRGAQGPAGPAGPPGLIGEQGISGPRGSGGAAGAPGERGRTGPLGRKGEPGE 2277
horse  2217 QGTVGEQGTRGAQGPPGSTGPPGLIGEQGIPGPRGSGGAVGVPGERGRTGPLGRKGEPGE 2276 human  2278 PGPKGGIGNRGPRGETGDDGRDGVGSEGRRGKKGERGFPGYPGPKGNPGEPGLNGTTGPK 2337
horse  2277 PGAKGGLGPRGPRGETGDDGRDGVGSEQKGKKGERGFPGYPGPKGTRGEPGTDGTLGPK 2336 human  2338 GIRGRRGNSGPPGIVGQKGDPGYPGPAGPKGNRGDS 2373 (SEQ ID NO:175)
horse  2337 GVRGRRGDSGPPGAAGQKGDPGYPGPSGLKGNRGDS 2372 (SEQ ID NO:176)
```

METHODS OF DETECTING INHERITED MYOPATHIES IN HORSES

CROSS-REFERENCE TO RELATED APPLICATION

This application is a United States national phase patent application based upon international patent application number PCT/US19/33717 of international filing date May 23, 2019, which claims the benefit U.S. Provisional Patent Application No. 62/717,072 filed Aug. 10, 2018 and U.S. Provisional Patent Application No. 62/737,295, filed Sep. 27, 2018, all three of which applications are incorporated herein by reference in its entirety.

SEQUENCE LISTING

This application contains a Sequence Listing electronically submitted via EFS-Web to the United States Patent and Trademark Office as an ASCII text file entitled "0310_000142WO01_SL" having a size of 223 kilobytes and created on Apr. 30, 2019. The information contained in the Sequence Listing is incorporated by reference herein.

SUMMARY

This disclosure describes, in one aspect, methods for detecting the presence or absence of a set of biomarkers in a horse. Generally, the method includes obtaining a biological sample from a horse that includes a nucleic acid that includes the coding region for three genes: dysferlin (DYSF), pyridine nucleotide-disulfide oxidoreductase domain-containing protein 1 (PYROXD1), and collagen type VI alpha 3 chain (COL6A3). There are two important biomarkers in DYSF, one important biomarker in PYROXD1, and one important biomarker in COL6A3, to be assayed as follows: (1) Dysferlin (DYSF), determining whether the nucleic acid has the specific substitution of an adenine (A) for a guanine (G) on the forward strand at chr15:31,306,949 of the current horse genome assembly (EquCab2, GCA_000002305.1) as displayed in the UCSC Genome Browser and as shown in FIG. 1, or the equivalent substitution in the complement thereof. This base substitution, known as rs1145077095 in dbSNP, corresponding to position 31,306,949 in SEQ ID NO:1, results in a nonconservative amino acid substitution in the dysferlin (DYSF) protein. The amino acid substitution caused by this base substitution is shown in FIG. 4. FIG. 4 shows the partial sequence of an altered dysferlin with tryptophan (W) substituted for arginine (R) at position 253, with SEQ ID NO:10 showing the partial protein sequence encoded by the wild-type or common allele and SEQ ID NO:11 showing the partial protein sequence encoded by the variant. (2) Dysferlin (DYSF), determining whether the nucleic acid has the specific substitution of a thymine (T) for a guanine (G) on the forward strand at chr15:31,225,630 of the current horse genome assembly (EquCab2, GCA_000002305.1) as displayed in the UCSC Genome Browser and as shown in FIG. 13, or the equivalent substitution in the complement thereof. This base substitution, known as rs1136366555 in dbSNP, corresponding to position 31,225,630 in SEQ ID NO:56, results in a nonconservative amino acid substitution in the dysferlin (DYSF) protein. The amino acid substitution caused by this base substitution is shown in FIG. 16. FIG. 16 shows the partial sequence of an altered dysferlin with threonine (T) substituted for proline (P) at position 1290, with SEQ ID NO:60 showing the partial protein sequence encoded by the wild-type or common allele and SEQ ID NO:61 showing the partial protein sequence encoded by the variant. (3) Pyridine nucleotide-disulfide oxidoreductase domain-containing protein 1 (PYROXD1), determining whether the nucleic acid has the specific substitution of a cytosine (C) for a guanine (G) on the forward strand at chr6:47,661,977 of the current horse genome assembly (EquCab2, GCA_000002305.1) as displayed in the UCSC Genome Browser and as shown in FIG. 22, or the equivalent substitution in the complement thereof. This base substitution, known as rs1136260157 in dbSNP, corresponding to position 47,661,977 in SEQ ID NO:103, results in a nonconservative amino acid substitution in the pyridine nucleotide-disulfide oxidoreductase domain-containing protein 1 (PYROXD1) protein. The amino acid substitution caused by this base substitution is shown in FIG. 25. FIG. 25 shows an altered pyridine nucleotide-disulfide oxidoreductase domain-containing protein 1 (PYROXD1), with histidine (H) substituted for aspartate (D) at position 492, with SEQ ID NO:107 showing the protein sequence encoded by the wild-type or common allele and SEQ ID NO:108 showing the protein sequence encoded by the variant. (4) Collagen type VI alpha 3 chain (COL6A3), determining whether the nucleic acid has the specific substitution of a guanine (G) for a cytosine (C) on the forward strand at chr6:23,480,621 of the current horse genome assembly (EquCab2, GCA_000002305.1) as displayed in the UCSC Genome Browser and as shown in FIG. 33, or the equivalent substitution in the complement thereof. This base substitution, known as rs1139437410 in dbSNP, corresponding to position 23,480,621 in SEQ ID NO:163, results in a nonconservative amino acid substitution in the collagen type VI alpha 3 chain (COL6A3) protein. The amino acid substitution caused by this base substitution is shown in FIG. 36. FIG. 36 shows an altered collagen type VI alpha 3 chain (COL6A3), with alanine (A) substituted for glycine (G) at position 2182, with SEQ ID NO:167 showing the protein sequence encoded by the wild-type or common allele and SEQ ID NO:168 showing the protein sequence encoded by the variant.

In some embodiments, the method further includes amplifying at least a portion of the DYSF, PYROXD1, or COL6A3 coding regions. In some of these embodiments, all or part of (1) Exon B of the DYSF coding region as identified in FIG. 3 (SEQ ID NO:5) is amplified. This specified exon corresponds to the gene models presented in FIG. 2 in this disclosure; the specific base substitutions detected are presented in FIG. 1, even if alternative gene models or different isoforms result in this exon being named or numbered differently. In another aspect, this disclosure describes a method for detecting the presence or absence of a biomarker in a physiological sample. Generally, the method includes obtaining a physiological sample from a horse that includes a nucleic acid that includes at least a portion of SEQ ID NO:1 that includes nucleotide 31,306,949 of SEQ ID NO:1, determining whether the nucleic acid has an adenine (A) substituted for a guanine (G) at nucleotide 31,306,949 on the forward strand of SEQ ID NO:1; this single-nucleotide polymorphism (SNP) is also known as rs1145077095 in dbSNP. (2) Exon I of the DYSF coding region as identified in FIG. 15 (SEQ ID NO:59) is amplified. This specified exon corresponds to the gene models presented in FIG. 14 in this disclosure; the specific base substitutions detected are presented in FIG. 13, even if alternative gene models or different isoforms result in this exon being named or numbered differently. In another aspect, this disclosure describes a method for detecting the presence or absence of a biomarker in a physiological sample. Generally, the method includes obtaining a physiological sample from a horse that includes a nucleic acid that includes at least a portion of SEQ ID NO:56 that includes nucleotide 31,225,630 of SEQ ID NO:56, determining whether the nucleic acid has an thymine (T) substituted for a guanine (G) at nucleotide 31,225,630 of the forward strand of SEQ ID NO:56; this single-nucleotide polymorphism (SNP) is also known as rs1136366555 in dbSNP. (3) Exon 12 of the PYROXD1 coding region, as identified in FIG. 24 (SEQ ID NO:106) is amplified. This specified exon corresponds to the gene models presented in FIG. 23 in this disclosure; the specific base substitutions detected are presented in FIG. 22, even if alternative gene models or different isoforms result in this exon being named or numbered differently. In another aspect, this disclosure describes a method for detecting the presence or absence of a biomarker in a physiological sample. Generally, the method includes obtaining a physiological sample from a horse that includes a nucleic acid that includes at least a portion of SEQ ID NO:103 that includes nucleotide 47,661,977 of SEQ ID NO:103, determining whether the nucleic acid has a cytosine (C) substituted for a guanine (G) at nucleotide 47,661,977 of the forward strand of SEQ ID NO:103; this single nucleotide polymorphism (SNP) is also known as rs1136260157 in dbSNP. (4) Exon 26 of the COL6A3 coding region, as identified in FIG. 35 (SEQ ID NO:166) is amplified. This specified exon corresponds to the gene models presented in FIG. 34 in this disclosure; the specific base substitutions detected are presented in FIG. 33, even if alternative gene models or different isoforms result in this exon being named or numbered differently. In another aspect, this disclosure describes a method for detecting the presence or absence of a biomarker in a physiological sample. Generally, the method includes obtaining a physiological sample from a horse that includes a nucleic acid that includes at least a portion of SEQ ID NO:163 that includes nucleotide 23,480,621 of SEQ ID NO:163, determining whether the nucleic acid has a guanine (G) substituted for a cytosine (C) at nucleotide 23,480,621 of the forward strand of SEQ ID NO:163; this single nucleotide polymorphism (SNP) is also known as rs1139437410 in dbSNP.

In all cases, the nucleotide at the specified position of the forward strand may be inferred by the determination of the nucleotide at the specified position on the reverse (complementary) strand. In some embodiments, the method further includes amplifying at least a portion of the nucleic acid.

In another aspect, this disclosure describes a method for detecting the presence or absence of a biomarker in a physiological sample. Generally, the method includes obtaining a physiological sample from a horse that includes a nucleic acid encoding (1) Dysferlin polypeptide, then determining whether the nucleic acid encodes a dysferlin polypeptide altered as described as follows: a dysferlin polypeptide having, in part, the amino acid sequence of SEQ ID NO:10 (FIG. 4) or a dysferlin polypeptide having a tryptophan (W) substituted for arginine (R) at position 253 as shown in SEQ ID NO:11 (FIG. 4). (2) Dysferlin polypeptide, then determining whether the nucleic acid encodes a dysferlin polypeptide altered as described as follows: a dysferlin polypeptide having, in part, the amino acid sequence of SEQ ID NO:60 (FIG. 16) or a dysferlin polypeptide having a threonine (T) substituted for proline (P) at position 1290 as shown in SEQ ID NO:61 (FIG. 16). (3) Pyridine nucleotide-disulfide oxidoreductase domain-containing protein 1 (PYROXD1) polypeptide, then determining whether the nucleic acid encodes a pyridine nucleotide-disulfide oxidoreductase domain-containing protein 1 polypeptide altered as described as follows: a pyridine nucleotide-disulfide oxidoreductase domain-containing protein 1 polypeptide having, in part, the amino acid sequence of SEQ ID NO:107 (FIG. 25) or a pyridine nucleotide-disulfide oxidoreductase domain-containing protein 1 polypeptide having a histidine (H) for an aspartate (D) at position 492 as shown in SEQ ID NO:108 (FIG. 25). (4) Collagen type VI alpha 3 chain (COL6A3) polypeptide, then determining whether the nucleic acid encodes a collagen type VI alpha 3 chain polypeptide altered as described as follows: a collagen type VI alpha 3 chain polypeptide having, in part, the amino acid sequence of SEQ ID NO:167 (FIG. 36) or a collagen type VI alpha 3 chain polypeptide having an alanine (A) for a glycine (G) at position 2182 as shown in SEQ ID NO:168 (FIG. 36).

The above summary is not intended to describe each disclosed embodiment or every implementation. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1. A portion of the current horse genome assembly (EquCab2, GCA_000002305.1) with coordinates as displayed in the UCSC Genome Browser centered on the chr15:31,306,949 position, the site of a substitution of an adenine (A) for a guanine (G) on the forward strand that results in the substitution of a tryptophan (W) for arginine (R) at amino acid position 253 in dysferlin as shown in FIG. 4 (SEQ ID NO:11). The reverse complement sequence is shown, with the site of a substitution of a thymine (T) for a cytosine (C) as indicated (SEQ ID NO:1). The single nucleotide polymorphism (SNP) defined by this base substitution is identified as rs1145077095 in dbSNP.

FIG. 2. A portion of the normal equine DYSF Coding DNA Sequence (SEQ ID NO:2) and a portion of the mutant DYSF Coding DNA Sequence (SEQ ID NO:3) bearing the C to T mutation at nucleotide position at position 1027 in this figure, corresponding to chr15:31,306,949 as shown in SEQ ID NO:1 (FIG. 1). This sequence is a region of perfect consensus among 21 different experimentally predicted mRNA isoforms. The numbering in FIG. 2 is that of isoform X1 (XM_023618907.1), which for this segment perfectly matches the numbering of isoforms X2 (XM_023618908.1), X3 (XM_023618909.1), X4 (XM_023618910.1), X5 (XM_023618911.1), and X6 (XM_023618912.1). The numbering of the start and end positions for other isoforms is described in detail in the text. In both sequences, the sequence of Exon B as shown in FIG. 3 is indicated in bold. The site of a C to T mutation at nucleotide position 1027, corresponding to 31,306,949 in SEQ ID NO:1 (FIG. 1), and to rs1145077095 in dbSNP, is underlined. The region of sequence comprising Exon B as shown in FIG. 3 is displayed as codons in the correct reading frame for both SEQ ID NO:2 and SEQ ID NO: 3 in FIG. 5.

FIG. 3. A view of the current horse genome assembly (EquCab2, GCA_000002305.1) in the UCSC Genome Browser with exon sequences that match the partial DYSF Coding DNA Sequence (SEQ ID NO:2) and the mutant partial DYSF Coding DNA Sequence (SEQ ID NO:3). The DYSF Coding DNA Sequences correspond to Exons A, B, C, D, E, and F as indicated by the regions of sequence similarity of the translated genomic DNA to DYSF protein sequences from human (Homo), cattle (Bos), rat (Rattus), mouse (Mus), and DYSF protein sequences from the more distantly-related zebrafish (Danio) and African claw-toed frog (Xenopus). Partial matches to the paralogous protein myoferlin (MYOF) from human (Homo), cattle (Bos), mouse (Mus), rat (Rattus), and zebrafish (Danio) are also seen. The sequences of Exons A-F with 10 bp of flanking intron sequence and their coordinates in the current horse assembly are displayed below the image from the UCSC Genome Browser. Sequence IDs are Exon A (SEQ ID NO:4), Exon B (SEQ ID NO:5), Exon C (SEQ ID NO:6.), Exon D (SEQ ID NO:7), Exon E (SEQ ID NO:8), and Exon F (SEQ ID NO:9).

FIG. 4. Models of part of the normal protein sequence encoded by horse DYSF (XP_023474694.1, presented here as SEQ ID NO:10) corresponding to a translation of SEQ ID NO:2 shown in FIG. 2 and part of the altered protein sequence encoded by horse DYSF with the base substitution at chr15:31,306,949 (based on XP_023474694.1, presented here as SEQ ID NO:11) corresponding to a translation of SEQ ID NO:3 shown in FIG. 2. The portion of the protein encoded by Exon B as shown in FIG. 3 is indicated in bold, while amino acid position 253 affected by the base substitution of an adenine (A) for a guanine (G) on the forward strand at the chr15:31,306,949 position, corresponding to rs1145077095 in dbSNP as shown in FIG. 1, is underlined. The amino acid positions in XP_023474694.1 are indicated at the beginning and end of the sequence.

FIG. 5. Horse DYSF Exon B and flanking genomic DNA sequence from which PCR primers to amplify genomic DNA containing the site of the DYSF-R253W mutation would be most appropriately derived. Genomic coordinates are as in FIG. 1. Exon B from chr15:31,307,036 to chr15: 31,306,908 is shown broken into codons in the correct reading frame for the wild-type allele (SEQ ID NO:12) and the DYSF-R253W allele (SEQ ID NO:13). Only the reference sequence from the assembly is shown for the flanking sequences. The codon affected by the G to A mutation site at nucleotide position chr15:31,306,949 on the forward strand, corresponding to rs1145077095 in dbSNP as shown in FIG. 1 (C to T in the reverse complement as shown), is shown in bold, with the position of the base substitution indicated by underlining. The base substitution changes the bold three base codon from one coding for an arginine (CGG) to one coding for a tryptophan (TGG). Example primers used experimentally to amplify genomic DNA containing the mutation site are shown in lower case [5'-CCCGAGATTTCTGGCTTTCT-3' (SEQ ID NO:14) and 5'-CTCGACAAGTTCTGGGGTGT-3'(SEQ ID NO:15)].

FIG. 6. Traces from Sanger DNA sequencing of amplified DYSF genomic DNA using primers shown in FIG. 5 (SEQ ID NO:14 and SEQ ID NO:15). The sequence of the reverse strand is shown. The arrows in the figure indicate nucleotide position chr15:31,306,949, the site of a substitution of a thymine (T) for a cytosine (C) in this position, corresponding to rs1145077095 in dbSNP, that creates the DYSF-R253W variant. The traces show, from left to right, results for a horse homozygous for the wild-type or common allele (N/N), results for a horse heterozygous for the substitution (N/P5), and results for a horse homozygous for the substitution (P5/P5).

FIG. 7. Sequence of the human DYSF coding sequence derived from NM_003494.3 (SEQ ID NO:16). The 5' UTR and 3 UTR have been removed; the sequence begins with the ATG start codon and ends with the TGA stop codon. The numbering of the first and last nucleotides corresponds to that of NM_003494.3. The sequence of the human exon corresponding to Exon B in horse as shown in FIG. 3 is indicated in bold.

FIG. 8. Sequence of the human DYSF protein sequence, equivalent to NP_003485.1 (SEQ ID NO:17). The numbering of the first and last amino acids corresponds to that of NP_003485.1. The sequence encoded by the human exon corresponding to Exon B in horse as shown in FIG. 3 is indicated in bold.

FIG. 9. Comparison of that portion of the protein sequence of DYSF encoded by horse Exon B from wild type (XP_023474694.1, shown here as SEQ ID NO:19) and DYSF-R253W (R253W, shown here as SEQ ID NO:20) to the protein sequence of DYSF encoded by human Exon 7 (NP_003485.1, shown here as SEQ ID NO:18). Between the sequences of the horse and human proteins in the alignment, an asterisk (*) indicates an identical amino acid in that position, while a space ( ) indicates the nonconservative substitution of an arginine (R) in horse for a glycine (G) in human at human position 247, and a plus sign (+) indicates the conservative substitution of an arginine (R) in horse for a lysine (K) in human at human position 256. No other amino acid substitutions are seen in comparison of the human sequence (SEQ ID NO:18) and the wild-type horse sequence (SEQ ID NO:19). The sequence from horse bearing the DYSF-R253W mutation (SEQ ID NO:20) has a nonconservative substitution of a tryptophan (W) for an arginine (R) that is found in human (SEQ ID NO:18) and the wild-type horse sequence (SEQ ID NO:19). This position, corresponding to position 253 in horse (SEQ ID NO:19, SEQ ID NO:20) and position 251 in human (SEQ ID NO:18) is indicated by bold and underlining.

FIG. 10. Features of the dysferlin protein encoded by the human DYSF gene. (A) The canonical human isoform has 2080 amino acids. The protein contains seven C2 calcium-binding domains designated C2A through C2G, shaded in gray. The secondary structure of the protein sequence encoded by each of the C2 domains consists of eight segments assembling into beta sheet, with two different topologies described. Domains C2C, C2D, C2F, and C2G are designated as topology type I, while domains C2A, C2B, and C2E are designated as topology type II (C.Therrien et al. 2006 J. Neurological Sciences 250: 71-78). The positions of four additional conserved domains (DysfN, DysfC, annexin binding, and transmembrane) are also indicated (C.Therrien et al. 2006 J. Neurological Sciences 250: 71-78), also shaded in gray. (B) topology type II C2 calcium-binding domains C2B, C2A, and C2E are shown expanded, with positions of pathogenic missense alleles listed in TABLE 1 (C2B) and TABLE 2 (C2A and C2E) shown. The DYSF-R253W substitution in the horse C2B domain precisely corresponds to the DYSF-R251W substitution in human.

FIG. 11. Amino acid sequences of proteins encoded by the C2B domain of DYSF, including the position of the equine DYSF-R253W substitution. Species included in the analysis are described in the text. The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the position of the DYSF-R253W substitution in horse in bold. The position of the DYSF-R253W substitution is indicated in bold in all of the aligned sequences.

FIG. 12. Sequence comparison of the C2A, C2B, and C2E domains of dysferlin encoded by human DYSF to the C2B domain of dysferlin encoded by horse DYSF. (A) The amino acid sequences of two isoforms of the C2A domain of human dysferlin (SEQ ID NO:51 and SEQ ID NO:52), the C2B domain of human dysferlin (SEQ ID NO:53), the C2E domain of human dysferlin (SEQ ID NO:54), and the C2B domain of horse dysferlin (SEQ ID NO:55), are shown. (B) Clustal Omega was used to align these four sequences. The fifth line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The remaining lines show the position of the horse DYSF-R253W substitution and various pathogenic human substitutions (presented in TABLE 1 and TABLE 2) aligned to the consensus.

FIG. 13. A portion of the current horse genome assembly (EquCab2, GCA_000002305.1) with coordinates as displayed in the UCSC Genome Browser centered on the chr15:31,225,630 position, the site of a substitution of a thymine (T) for a guanine (G) on the forward strand that results in the substitution of a threonine (T) for proline (P) at amino acid position 1290 in dysferlin as shown in FIG. 16 (SEQ ID NO:61). The reverse complement sequence is shown, with the site of a substitution of an adenine (A) for a cytosine (C) as indicated (SEQ ID NO:56). The single nucleotide polymorphism (SNP) defined by this base substitution is identified as rs1136366555 in dbSNP.

FIG. 14. A portion of the normal equine DYSF Coding DNA Sequence (SEQ ID NO:57) and a portion of the mutant DYSF Coding DNA Sequence (SEQ ID NO:58) bearing the C to A mutation at nucleotide position at position 4174 in this figure, corresponding to chr15:31,225,630 as shown in SEQ ID NO:56 (FIG. 13). [This sequence is a region of perfect consensus among 21 different experimentally predicted mRNA isoforms. The numbering in FIG. 2 is that of isoform X1 (XM_023618907.1), which for this segment perfectly matches the numbering of isoforms X2 (XM_023618908.1), X3 (XM_023618909.1), X4 (XM_023618910.1), X5 (XM_023618911.1), and X6 (XM_023618912.1). The numbering of the start and end positions for other isoforms is described in detail in the text.] In both sequences, the sequence of Exon I as shown in FIG. 15 is indicated in bold. The site of a C to A mutation at nucleotide position 4174, corresponding to 31,225,630 in SEQ ID NO:56 (FIG. 13), and to rs1136366555 in dbSNP, is underlined. The region of sequence comprising Exon I as shown in FIG. 15 is displayed as codons in the correct reading frame for both SEQ ID NO:57 and SEQ ID NO: 58 in FIG. 17.

FIG. 15. A view of the current horse genome assembly (EquCab2, GCA_000002305.1) in the UCSC Genome Browser with exon sequences that match the partial DYSF Coding DNA Sequence (SEQ ID NO:57) and the mutant partial DYSF Coding DNA Sequence (SEQ ID NO:58). The DYSF Coding DNA Sequences correspond to Exons G, H, and I as indicated by the regions of sequence similarity of the translated genomic DNA to DYSF protein sequences from human (Homo), orangutan (Pongo), cattle (Bos), mouse (Mus), rat (Rattus) and DYSF protein sequences from the more distantly-related zebrafish (Danio). The sequence of Exon I with 10 bp of flanking intron sequence and its coordinates in the current horse assembly is displayed below the image from the UCSC Genome Browser (SEQ ID NO: 59).

FIG. 16. Models of part of the normal protein sequence encoded by horse DYSF (XP_023474694.1, presented here as SEQ ID NO:60) corresponding to a translation of SEQ ID NO:57 shown in FIG. 14 and part of the altered protein sequence encoded by horse DYSF with the base substitution at chr15:31,225,630 (based on XP_023474694.1, presented here as SEQ ID NO:61) corresponding to a translation of SEQ ID NO:58 shown in FIG. 14. The portion of the protein encoded by Exon I as shown in FIG. 15 is indicated in bold, while amino acid position 1290 affected by the base substitution of a thymine (T) for a guanine (G) at the chr15:31,225,630 position on the forward strand, corresponding to rs1136366555 in dbSNP as shown in FIG. 13 (C to A in the reverse complement as shown), is underlined. The amino acid positions in) XP_023474694.1 are indicated at the beginning and end of the sequence.

FIG. 17. Horse DYSF Exon I and flanking genomic DNA sequence from which PCR primers to amplify genomic DNA containing the site of the DYSF-P1290T mutation would be most appropriately derived. Genomic coordinates are as in FIG. 13. Exon I from chr15:31,225,648 to chr15:31,225,619 is shown broken into codons in the correct reading frame for the wild-type allele (SEQ ID NO:62) and the DYSF-P1290T allele (SEQ ID NO:63). Only the reference sequence from the assembly is shown for the flanking sequences. The codon affected by the G to T mutation site at nucleotide position chr15:31,225,630 on the forward strand, corresponding to rs1136366555 in dbSNP as shown in FIG. 13 (C to A in the reverse complement as shown), is shown in bold, with the position of the base substitution indicated by underlining. The base substitution changes the bold three base codon from one coding for a proline (CCT) to one coding for a threonine (ACT). Example primers used experimentally to amplify genomic DNA containing the mutation site are shown in lower case [5'-GGTTGCAAACTCCCAACTGT-3' (SEQ ID NO:64) and 5 GATTTTTCAAGCTGCCGAAG-3' (SEQ ID NO:65)].

FIG. 18. Traces from Sanger DNA sequencing of amplified DYSF genomic DNA using primers shown in FIG. 17 (SEQ ID NO:64 and SEQ ID NO:65). The sequence of the forward strand is shown. The arrows in the figure indicate nucleotide position chr15:31,225,630, the site of a substitution of an thymine (T) for a guanine (G) in this position, corresponding to rs1136366555 in dbSNP, that creates the DYSF-P1290T variant. The traces show, from left to right, results for a horse homozygous for the wild-type or common allele (N/N), results for a horse heterozygous for the substitution (N/P6), and results for a horse homozygous for the substitution (P6/P6).

FIG. 19. Comparison of that portion of the protein sequence of DYSF encoded by horse Exon I from wild type (XP_023474694.1, shown here as SEQ ID NO:67) and DYSF-P1290T (P1290T, shown here as SEQ ID NO:68) to the protein sequence of DYSF encoded by human (NP_003485.1, shown here as SEQ ID NO:66). Between the sequences of the horse and human proteins in the alignment, an asterisk (*) indicates an identical amino acid in that position, while a space ( ) indicates the nonconservative substitution of a glycine (G) in horse for an arginine (R) in human at human position 1297, and a plus sign (+) indicates the conservative substitution of an alanine (A) in horse for a serine (S) in human at human position 1267, a tyrosine (Y) in horse for a histidine (H) in human position 1285, an aspartic acid (D) in horse for a glutamic acid (E) in human position 1294, and a glutamic acid (E) in horse for an aspartic acid (D) in human position 1300. No other amino acid substitutions are seen in comparison of the human sequence (SEQ ID NO:66) and the wild-type horse sequence (SEQ ID NO:67). The sequence from horse bearing the DYSF-P1290T mutation (SEQ ID NO:68) has a nonconservative substitution of a threonine (T) for a proline (P) that is found in human (SEQ ID NO:66) and the wild-type horse sequence (SEQ ID NO:67). This position, corresponding to position 1290 in horse (SEQ ID NO:67, SEQ ID NO:68) and position 1288 in human (SEQ ID NO:66) is indicated by bold and underlining.

FIG. 20. Features of the dysferlin protein encoded by the human DYSF gene. (A) The canonical human isoform has 2080 amino acids. The protein contains seven C2 calcium-binding domains designated C2A through C2G, shaded in gray. The positions of four additional conserved domains (DysfN, DysfC, annexin binding, and transmembrane) are also indicated (C.Therrien et al. 2006 J. Neurological Sciences 250: 71-78), also shaded in gray. The interdomain region between the C2D and C2E domains, affected by the horse DYSF-P1290T mutation, is indicated in light gray. (B) The interdomain region between the C2D and C2E domains is shown expanded, with positions of pathogenic and potentially pathogenic missense alleles listed in TABLE 3 shown. The horse DYSF-P1290T substitution corresponds to a proline at position 1288 in human, with no pathogenic or potentially pathogenic allele identified at that position in human.

FIG. 21. Amino acid sequences of proteins encoded by the C2D-C2E interdomain region of DYSF, including the position of the equine DYSF-P1290T substitution. Species included in the analysis are described in the text. The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the position of the DYSF-P1290T substitution in horse in bold. The position of the DYSF-P1290T substitution is indicated in bold in all of the aligned sequences.

FIG. 22. A portion of the current horse genome assembly (EquCab2, GCA_000002305.1) with coordinates as displayed in the UCSC Genome Browser centered on the chr6:47,661,977 position, the site of a substitution of a cytosine (C) for a guanine (G) on the forward strand that results in the substitution of a histidine (H) for an aspartate (D) at amino acid position 492 in pyridine nucleotide-disulfide oxidoreductase domain-containing protein 1 (PYROXD1) as shown in FIG. 25 (SEQ ID NO:108). The single nucleotide polymorphism (SNP) defined by this base substitution is identified as rs1136260157 in dbSNP.

FIG. 23. A portion of the normal equine PYROXD1 Coding DNA Sequence (SEQ ID NO:104) and a portion of the mutant PYROXD1 Coding DNA Sequence (SEQ ID NO:105) bearing the G to C mutation at nucleotide position 1548 in this figure, corresponding to chr6:47,661,977 as shown in SEQ ID NO:103 (FIG. 22). This sequence is a region of perfect consensus among five different experimentally predicted mRNA isoforms. The numbering in FIG. 23 is that of isoform X1 (XM_001502130.5). The numbering of the start and end positions for other isoforms is described in detail in the text. In both sequences the sequence of Exon 12 as shown in FIG. 24 is indicated in bold. The site of a G to C mutation at nucleotide position 1548, corresponding to 47,661,977 in SEQ ID NO:103 (FIG. 22), and to rs1136260157 in dbSNP, is underlined. The region of sequence comprising Exon 12 as shown in FIG. 24 is displayed as codons in the correct reading frame for both SEQ ID NO:109 and SEQ ID NO:110 in FIG. 26.

FIG. 25. Models of part of the normal protein sequence encoded by horse PYROXD1 (XP_001502180.3, presented here as SEQ ID NO:107) corresponding to a translation of SEQ ID NO:104 shown in FIG. 23 and part of the altered protein sequence encoded by horse PYROXD1 (adapted from XP_001502180.3, presented here as SEQ ID NO:108) with the base substitution at chr6:47,661,977 corresponding to a translation of SEQ ID NO:105 shown in FIG. 23. The portion of the protein encoded by Exon 12 is indicated in bold, while amino acid position 492 affected by the base substitution of a cytosine (C) for a guanine (G) at the chr6:47,661,977 position on the forward strand as shown in FIG. 22, is underlined. The amino acid positions in XP_001502180.3 are indicated at the beginning and end of the sequence.

FIG. 26. Horse PYROXD1 Exon 12 and flanking genomic DNA sequence from which PCR primers to amplify genomic DNA containing the site of the PYROXD1-D492H mutation would be most appropriately derived. Genomic coordinates are as in FIG. 22. Exon 12 from chr6:47,661,764 to chr6:47,662,012 is shown broken into codons in the correct reading frame for the wild-type allele (SEQ ID NO:109) and the PYROXD1-D492H allele (SEQ ID NO:110). Only the reference sequence from the assembly is shown for the flanking sequences. The codon affected by the G to C mutation site at nucleotide position chr6:47,661,977, as shown in FIG. 22 is shown in bold, with the position of the base substitution indicated by underlining. The base substitution changes the bold three base codon from one coding for an aspartate (GAT) to one coding for a histidine (CAT). Example primers used experimentally to amplify genomic DNA containing the mutation site [5'-CAGAT-TTTCTGCTGGCCATT-3' (SEQ ID NO:111) and 5'-TGGT-CATCATTAAATCAGTGCAA-3' (SEQ ID NO:112)] are shown in lower case in the figure.

FIG. 27. Traces from Sanger DNA sequencing of amplified PYROXD1 genomic DNA using primers shown in FIG. 26 (SEQ ID NO:111 and SEQ ID NO:112). The sequence of the forward strand is shown. The arrows in the figure indicate nucleotide position chr6:47,661,977, the site of a substitution of a cytosine (C) for a guanine (G) in this position that creates the PYROXD1-D492H variant. The traces show, from left to right, results for a horse homozygous for the wild-type or common allele (n/n), results for a horse heterozygous for the substitution (n/P8), and results for a horse homozygous for the substitution (P8/P8).

FIG. 28. Partial sequence of the human PYROXD1 coding sequence derived from NM_024854.4 (SEQ ID NO:113). This sequence is a region of perfect consensus among three different experimentally predicted mRNA isoforms. The numbering of the first and last nucleotides corresponds to that of NM_024854.4. The numbering of the start and end positions for other isoforms is described in the text. The sequence of Exon 12 is indicated in bold. The sequence begins with beginning of the consensus among the three isoforms and ends with the TAA stop codon.

FIG. 29. Partial sequence of the human PYROXD1 protein sequence, showing a translation of SEQ ID NO:113, equivalent to NP_079130.2 (SEQ ID NO:66). The numbering of the first and last amino acids corresponds to that of NP_079130.2.

FIG. 30. Comparison of that portion of the protein sequence of PYROXD1 encoded by horse Exon 12 from wild type (XP_001502180.3, shown here as SEQ ID NO:116) and PYROXD1-D492H (D492H, derived from XP_001502180.3 and shown here as SEQ ID NO:117) to the protein sequence of PYROXD1 encoded by human Exon 12 (NP_079130.2, shown here as SEQ ID NO:115). Between the sequences of the horse and human proteins in the alignment, an asterisk (*) indicates an identical amino acid in that position, while a plus sign (+) indicates the following conservative substitutions: a glutamine (Q) for an arginine (R) at human position 444, a valine (V) for an isoleucine (I) at human position 447, an alanine (A) for a serine (S) at human position 483, and an aspartate (D) for an asparagine (N) at human position 492. The sequence from horse bearing the PYROXD1-D492H mutation (SEQ ID NO:117) has a nonconservative substitution of a histidine (H) for an aspartate (D) at horse position 492, corresponding to human position 490. This position is indicated in bold for all three sequences. The wild-type horse sequence (SEQ ID NO:116) matches the human sequence (SEQ ID NO:115) at this position.

FIG. 31. Features of the pyridine nucleotide-disulfide oxidoreductase domain-containing protein 1 protein encoded by the human PYROXD1 gene. The human protein has 500 amino acids and two domains: the pyridine nucleotide-disulfide oxidoreductase domain (amino acids 39-361) and the NADH-dependent nitrite reductase domain (447-494) as described in O'Grady et al. 2016 Am J Hum Genet. 99:1086-1105. Positions of two human pathogenic missense alleles (N155I and Q372H, O'Grady et al. 2016 Am J Hum Genet. 99:1086-1105 DOI: 10.1016/j.ajhg.2016.09.005) are shown, as is the position of the horse D492H mutation described herein.

FIG. 32. Partial amino acid sequences of proteins encoded by PYROXD1, including the position of the equine PYROXD1-D492H substitution. Species included in the analysis are described in the text. The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the position of the PYROXD1-D492H substitution in horse in bold. The position of the PYROXD1-D492H substitution is indicated in bold in all of the aligned sequences.

FIG. 33. A portion of the current horse genome assembly (EquCab2, GCA_000002305.1) with coordinates as displayed in the UCSC Genome Browser centered on the chr6:23,480,621 position, the site of a substitution of a guanine (G) for a cytosine (C) on the forward strand that results in the substitution of an alanine (A) for a glycine (G) at amino acid position 2182 in collagen type VI alpha 3 chain (COL6A3) as shown in FIG. 36 (SEQ ID NO:168). The reverse complement sequence is shown, with the site of a substitution of a cytosine (C) for a guanine (G) on the reverse strand as indicated (SEQ ID NO:163). The single nucleotide polymorphism (SNP) defined by this base substitution is identified as rs1139437410 in dbSNP.

FIG. 34. A portion of the normal equine COL6A3 Coding DNA Sequence (SEQ ID NO:164) and a portion of the mutant COL6A3 Coding DNA Sequence (SEQ ID NO:165) bearing the G to C mutation at nucleotide position 6792 in this figure, corresponding to chr6:23,480,621 as shown in SEQ ID NO:163 (FIG. 33). The numbering in FIG. 34 is that of the COL6A3 coding sequence (CDS) model XM_023642645.1; the sequence presented comprises the coding sequence for the five collagen-like domains in the middle of the protein. See the text for a discussion of the CDS model in NCBI. In both sequences the sequence of the third collagen-like domain, partially encoded by Exon 26, as shown in FIG. 35 is indicated in bold. The site of a G to C mutation at nucleotide position 6792, corresponding to 23,480,621 in SEQ ID NO:163 (FIG. 33), and to rs1139437410 in dbSNP, is underlined. The region of sequence comprising Exon 26 is displayed as codons in the correct reading frame for both SEQ ID NO:164 and SEQ ID NO:165 in FIG. 37.

FIG. 36. Models of part of the normal protein sequence encoded by horse COL6A3 (XP_023498413.1, presented here as SEQ ID NO:167) corresponding to a translation of SEQ ID NO:164 shown in FIG. 34 and part of the altered protein sequence encoded by horse COL6A3 (adapted from XP_023498413.1, presented here as SEQ ID NO:168) with the base substitution at chr6:23,480,621 corresponding to a translation of SEQ ID NO:165 shown in FIG. 34. The portion of the protein corresponding to all five collagen-like domains is shown; the portion corresponding to the third collagen-like domain, partially encoded by Exon 26, is indicated in bold, while the amino acid at position 2182 affected by the base substitution of a cytosine (C) for a guanine (G) at the chr6:23,480,621 position as shown in FIG. 33, is underlined. The amino acid positions in XP_023498413.1 are indicated at the beginning and end of the sequence.

FIG. 37. Horse COL6A3 Exon 26 and flanking genomic DNA sequence from which PCR primers to amplify genomic DNA containing the site of the COL6A3-G2182A mutation would be most appropriately derived. Genomic coordinates are as in FIG. 33. Exon 26 from chr6:23,480,631 to chr6:23,480,578 is shown broken into codons in the correct reading frame for the wild-type allele (SEQ ID NO:169) and the COL6A3-G2182A allele (SEQ ID NO:170). Only the reference sequence from the assembly is shown for the flanking sequences. The codon affected by the C to G mutation site at nucleotide position chr6:23,480,621 on the forward strand, corresponding to rs1139437410 in dbSNP as shown in FIG. 33 (G to C in the reverse complement as shown), is shown in bold, with the position of the base substitution indicated by underlining. The base substitution changes the bold three base codon from one coding for a glycine (GGG) to one coding for an alanine (GCG). Example primers used experimentally to amplify genomic DNA containing the mutation site [5'-AGATGGGGCACA-GATCAAAC-3' (SEQ ID NO:172) and 5'-TTCCCA-GACTCTCCTGTGCT-3' (SEQ ID NO:171)] are shown in lower case in the figure.

FIG. 38. Traces from Sanger DNA sequencing of amplified COL6A3 genomic DNA using primers shown in FIG. 37 (SEQ ID NO:171 and SEQ ID NO:172). The sequence of the forward strand is shown. The arrows in the figure indicate nucleotide position chr6:23,480,621, the site of a substitution of a cytosine (C) for a guanine (G) in this position on the reverse strand that creates the COL6A3-G2182A variant. The traces show, from left to right, the sequence of the forward strand for a horse homozygous for the wild-type or common allele (n/n), and results for a horse heterozygous for the substitution (n/K1).

FIG. 39. Partial sequence of the human COL6A3 coding sequence derived from NM_004369.3 (SEQ ID NO:173). This sequence is a region of perfect consensus among multiple different experimentally predicted mRNA isoforms. The numbering of the first and last nucleotides corresponds to that of NM_004369.3. The sequence encoding the third collagen-like domain is indicated in bold.

FIG. 40. Partial sequence of the human COL6A3 protein sequence, showing a translation of SEQ ID NO:173, equivalent to NP_004360.2 (SEQ ID NO:174). The numbering of the first and last amino acids corresponds to that of NP_004360.2. The sequence of the third collagen-like domain is indicated in bold.

FIG. 41. Comparison of the portion of the protein sequence of COL6A3 comprising the five collagen-like repeats from human (NP_004360.2, shown here as SEQ ID NO:175) and horse (XP_023498413.1, shown here as SEQ ID NO:176). The position of the COL6A3-G2182A substitution is shown below the horse sequence. Between the sequences of the horse and human proteins in the alignment, an asterisk (*) indicates an identical amino acid in that position, while a plus sign (+) indicates a conservative substitution, and a space ( ) indicates a nonconservative substitution. The positions of glycine residues that are part of the Gly-X-Y structure of the collagen triple helix are indicated by an asterisk (*) in reverse text (white text on a black background) between the horse and human sequences. All of these glycine residues are conserved between human and horse. The horse G2182A sequence has a nonconservative substitution of an alanine (A) for a glycine (G) at position 2182; the wild-type horse sequence matches the human sequence at this position.

FIG. 43. Partial amino acid sequences of proteins encoded by COL6A3, including the position of the equine COL6A3-G2182A substitution. Species included in the analysis are described in the text. The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the position of the COL6A3-G2182A substitution in horse in bold. The position of the COL6A3-G2182A substitution is indicated in bold in all of the aligned sequences.

DETAILED DESCRIPTION OF ILLUSTRATIVE EMBODIMENTS

Figure 24:
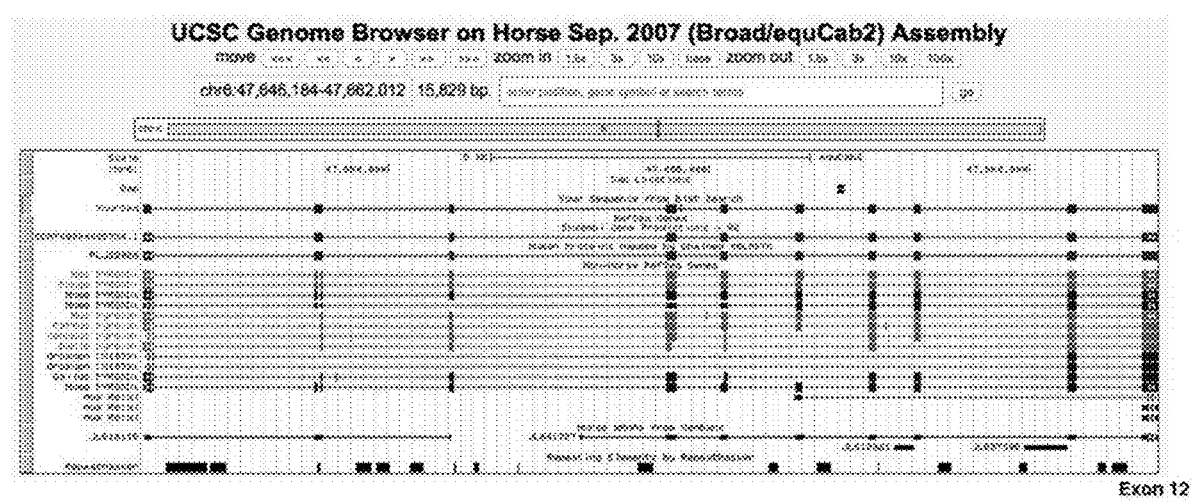
FIG. 24. A view of the current horse genome assembly (EquCab2, GCA_000002305.1) in the UCSC Genome Browser with exon sequences that match the PYROXD1 Coding DNA Sequence (SEQ ID NO:104) and the mutant PYROXD1 Coding DNA Sequence (SEQ ID NO:105) in a BLAT search. The PYROXD1 Coding DNA Sequences in horse correspond to PYROXD1 coding sequences in other species as indicated by the regions of sequence similarity of the translated genomic DNA to PYROXD1 protein sequences from human (Homo), orangutan (Pongo), cattle (Bos), mouse (Mus), rat (Rattus), African clawed frog (Xenopus), zebrafish (Danio), chicken (Gallus), and fruit fly (Drosophila). Exon 12, which contains the guanine (G) to cytosine (C) variant at chr6:47,661,977 as shown in SEQ ID NO:103 (FIG. 22), is indicated below the image of the browser window. The sequence of horse Exon 12 with 10 nucleotides of flanking intron sequence and its coordinates in the current horse assembly is displayed below the image from the UCSC Genome Browser (SEQ ID NO:106).

This disclosure describes methods for detecting the presence or absence of a biomarker in horses associated with a defect of muscle integrity that causes a form of inherited exercise intolerance. This disease condition has been previously described as Polysaccharide Storage Myopathy, type 2 (PSSM2). Another previously described form of exercise intolerance in horses is Polysaccharide Storage Myopathy, type 1 (PSSM1), caused by a semidominant allele of glycogen synthase (GYS1-R309H). The term PSSM2 is commonly used to describe horses that show exercise intolerance, a negative test result for the GYS1-R309H variant of Glycogen Synthase 1 that is associated with Polysaccharide Storage Myopathy, type 1 (PSSM1), and abnormal findings on muscle biopsy, including abnormally shaped muscle fibers, nuclei displaced to the center of muscle fibers rather than the normal position at the edge of fibers, and pools of glycogen granules of normal size in regions of disorganization that give the false appearance of a glycogen storage disease. In one embodiment, the method involves obtaining a physiological sample from a horse and determining whether the biomarker is present in the sample. As used herein, the phrase "physiological sample" refers to a biological sample obtained from a horse that contains nucleic acid. For example, a physiological sample can be a sample collected from an individual horse such as, for example, a cell sample, such as a blood cell, e.g., a lymphocyte, a peripheral blood cell; a sample collected from the spinal cord; a tissue sample such as cardiac tissue or muscle tissue, e.g., cardiac or skeletal muscle; an organ sample, e.g., liver or skin; a hair sample, e.g., a hair sample with roots; and/or a fluid sample, such as blood.

Examples of breeds of affected horse include, but are not limited to, Shires, Clydesdales, Percheron Horses, Belgian Horses, Draft Horses, Quarter Horses, Paint Horses, Warmblood Horses, or related or unrelated breeds. The phrase "related breed" is used herein to refer to breeds that are related to a breed, such as Quarter Horse, Draft Horse, or Warmblood Horse. Such breeds include, but are not limited to stock breeds such as the American Paint horse, the Appaloosa, and the Palomino. The term "Draft Horse" includes many breeds including but not limited to Clydesdale, Belgian, Percheron, and Shire horses. The term "Warmblood" is also a generic term that includes a number of different breeds. "Warmblood" simply distinguishes this type of horse from the "cold bloods" (draft horses) and the "hot bloods" (Thoroughbreds and Arabians). The method described herein also may be performed using a sample obtained from a crossed or mixed breed horse.

The term "biomarker" generally refers herein to a biological indicator, such as a particular molecular feature, that may affect, may be an indicator, and/or be related to diagnosing or predicting an individual's health. For example, in certain embodiments, the biomarker can refer to (1) a mutation in the equine dyferlin (DYSF) coding region (SEQ ID NO:1), such as a polymorphic allele of DYSF that has a substitution of an adenine (A) for a guanine (G) on the forward strand at chr15:31,306,949 of the current horse genome assembly (EquCab2, GCA_000002305.1) as displayed in the UCSC Genome Browser and as shown for the reverse strand in FIG. 1, (2) a mutation in the equine dyferlin (DYSF) coding region (SEQ ID NO:56), a polymorphic allele of DYSF that has a substitution of a thymine (T) for a guanine (G) on the forward strand at chr15:31,225,630 of the current horse genome assembly (EquCab2, GCA_000002305.1) as displayed in the UCSC Genome Browser and as shown for the reverse strand in FIG. 13, (3) a mutation in the equine pyridine nucleotide-disulfide oxidoreductase domain-containing protein 1 (PYROXD1) coding region (SEQ ID NO:103), such as a polymorphic allele of PYROXD1 that has a substitution of a cytosine (C) for a guanine (G) at chr6:47,661,977 on the forward strand of the current horse genome assembly (EquCab2, GCA_000002305.1) as displayed in the UCSC Genome Browser and as shown in FIG. 22, or (4) a mutation in the equine collagen type VI alpha 3 chain (COL6A3) coding region (SEQ ID NO:163), such as a polymorphic allele of COL6A3 that has a substitution of a guanine (G) for a cytosine (C) on the forward strand at chr6:23,480,621 of the current horse genome assembly (EquCab2, GCA_000002305.1) as displayed in the UCSC Genome Browser and as shown for the reverse strand in FIG. 33. The specified nucleotide substitution may be inferred by the detection of the complementary base on the reverse strand.

"Oligonucleotide probe" can refer to a nucleic acid segment, such as a primer, that is useful to amplify a sequence in the DYSF, PYROXD1, or COL6A3 coding regions that is complementary to, and hybridizes specifically to, a particular nucleotide sequence in DYSF, PYROXD1, or COL6A3, or to a nucleic acid region that flanks DYSF, PYROXD1, or COL6A3.

As used herein, the term "nucleic acid" and "polynucleotide" refers to deoxyribonucleotides or ribonucleotides and polymers thereof in either single-stranded or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to DNA or RNA that can be single-stranded or double-stranded, optionally containing synthetic, non-natural, or altered nucleotide bases capable of incorporation into DNA or RNA.

Figure 35:
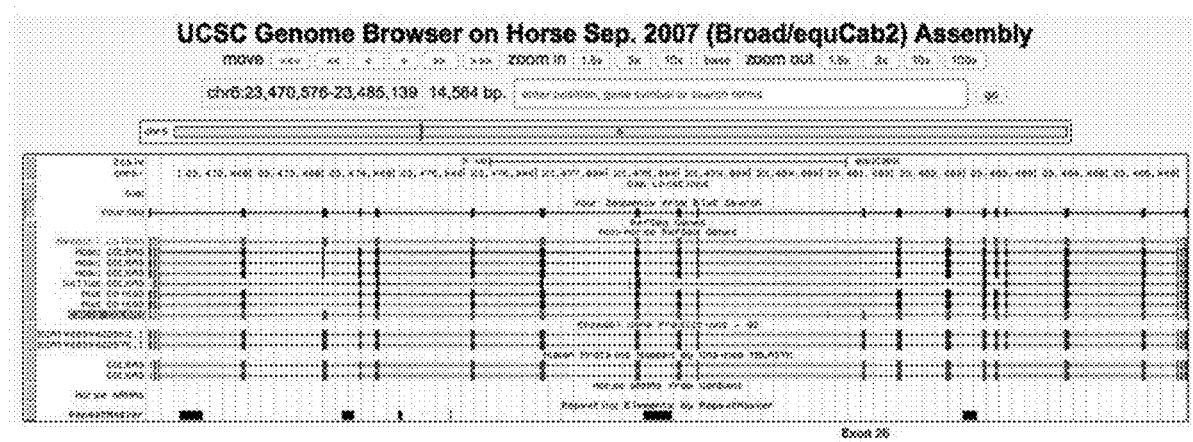
FIG. 35. A view of the current horse genome assembly (EquCab2, GCA_000002305.1) in the UCSC Genome Browser with exon sequences that match the COL6A3 Coding DNA Sequence (SEQ ID NO:164) and the mutant COL6A3 Coding DNA Sequence (SEQ ID NO:165) in a BLAT search. The COL6A3 Coding DNA Sequences in horse correspond to COL6A3 coding sequences in other species as indicated by the regions of sequence similarity of the translated genomic DNA to COL6A3 protein sequences from human (Homo), mouse (Mus), and dog (Canus). Exon 26, which contains the guanine (G) to cytosine (C) variant at chr6:23,480,621 as shown in SEQ ID NO:163 (FIG. 33), is indicated below the image of the browser window. See the text for a discussion of the failure to detect sequence similarity of the translation of Exon 26 to protein sequences from other species. The sequence of horse Exon 26 with 10 nucleotides of flanking intron sequence and its coordinates in the current horse assembly is displayed below the image from the UCSC Genome Browser (SEQ ID NO:166).

In some embodiments, the method can involve contacting the sample with at least one oligonucleotide probe to form a hybridized nucleic acid and then amplifying the hybridized nucleic acid. "Amplifying" utilizes methods such as the polymerase chain reaction (PCR), ligation amplification (or ligase chain reaction, LCR), strand displacement amplification, nucleic acid sequence-based amplification, and amplification methods based on the use of Qβ-replicase. These methods are well known and widely practiced in the art. Reagents and hardware for conducting PCR are commercially available. For example, in certain embodiments, (1) Exon B of the equine dysferlin coding region (also referred to as DYSF) as shown in FIG. 3 or portions thereof, (2) Exon I of the equine dysferlin coding region (also referred to as DYSF) as shown in FIG. 15 or portions thereof, (3) Exon 12 of the equine pyridine nucleotide-disulfide oxidoreductase domain-containing protein 1 coding region (also referred to as PYROXD1) as shown in FIG. 24 or portions thereof, or (4) Exon 26 of the equine collagen type VI alpha 3 chain coding region (also referred to as COL6A3) as shown in FIG. 35 or portions thereof, may be amplified by PCR. In another embodiment, at least one oligonucleotide probe is immobilized on a solid surface or a semisolid surface.

The methods described herein can be used to detect the presence or absence of a biomarker associated with equine Polysaccharide Storage Myopathy type 2 (PSSM2) in a horse (live or dead) regardless of age (e.g., an embryo, a foal, a neonatal foal, aborted foal, a breeding-age adult, or any horse at any stage of life) or sex (e.g., a mare (dam) or stallion (sire)).

As used herein, the term "presence or absence" refers to affirmatively detecting the presence of a biomarker or detecting the absence of the biomarker within the experimental limits of the detection methods used to detect the biomarker.

This disclosure further provides a method for detecting and/or diagnosing Polysaccharide Storage Myopathy type 2 (PSSM2), also referred to as Myofibrillar Myopathy (MFM), in a horse, the method involving obtaining a physiological sample from the horse and detecting the presence or absence of biomarkers in the sample, wherein the presence of the biomarkers is indicative of the disease. One embodiment of the method further involves contacting the sample with at least one oligonucleotide probe to form a hybridized nucleic acid and amplifying the hybridized nucleic acid. For example, in four embodiments, (1) Exon B of equine DYSF as shown in FIG. 3, (2) Exon I of equine DYSF as shown in FIG. 15, (3) Exon 12 of equine PYROXD1 as shown in FIG. 24, or (4) Exon 26 of equine COL6A3 as shown in FIG. 35, are amplified using, for example, polymerase chain reaction, strand displacement amplification, ligase chain reaction, amplification methods based on the use of QP-replicase and/or nucleic acid sequence-based amplification. In these embodiments of the method, the biomarkers can include (1) an equine dysferlin (DYSF) coding region having the specific substitution of an adenine (A) for a guanine (G) on the forward strand at chr15:31,306,949 of the current horse genome assembly (EquCab2, GCA_000002305.1) as displayed in the UCSC Genome Browser and as shown for the reverse strand in FIG. 1, (2) an equine dysferlin (DYSF) coding region having the specific substitution of a thymine (T) for a guanine (G) on the forward strand at chr15:31,225,630 of the current horse genome assembly (EquCab2, GCA_000002305.1) as displayed in the UCSC Genome Browser and as shown for the reverse strand in FIG. 13, (3) an equine pyridine nucleotide-disulfide oxidoreductase domain-containing protein 1 (PYROXD1) coding region having the specific substitution of a cytosine (C) for a guanine (G) on the forward strand at chr6:47,661,977 of the current horse genome assembly (EquCab2, GCA_000002305.1) as displayed in the UCSC Genome Browser and as shown in FIG. 22, or (4) an equine collagen type VI alpha 3 chain (COL6A3) coding region having the specific substitution of a guanine (G) for a cytosine (C) on the forward strand at chr6:23,480,621 of the current horse genome assembly (EquCab2, GCA_000002305.1) as displayed in the UCSC Genome Browser and as shown for the reverse strand in FIG. 33. Biomarkers can also include (1) a coding region that encodes a dysferlin (DYSF) polypeptide (SEQ ID NO:10) having an arginine-to-tryptophan (R to W) substitution at amino acid residue 253 of SEQ ID NO:10, as shown in SEQ ID NO:11, (2) a coding region that encodes a dysferlin (DYSF) polypeptide (SEQ ID NO:60) having an proline-to-threonine (P to T) substitution at amino acid residue 1290 of SEQ ID NO:60, as shown in SEQ ID NO:61, (3) a pyridine nucleotide-disulfide oxidoreductase domain-containing protein 1 (PYROXD1) polypeptide (SEQ ID NO:107) having an aspartate-to-histidine (D to H) substitution at amino acid residue 492 of SEQ ID NO:107, as shown in SEQ ID NO:108, or (4) a collagen type VI alpha 3 chain (COL6A3) polypeptide (SEQ ID NO:167) having an glycine-to-alanine (G to A) substitution at amino acid residue 2182 of SEQ ID NO:167, as shown in SEQ ID NO:168. The method can be used to detect Polysaccharide Storage Myopathy type 2 (PSSM2), also known as Myofibrillar Myopathy (MFM), in a horse.

This disclosure further provides a kit that includes a test for diagnosing and/or detecting the presence of equine Polysaccharide Storage Myopathy type 2 (PSSM2), also known as Myofibrillar Myopathy (MFM), in a horse. The kit generally includes packing material containing, separately packaged, at least one oligonucleotide probe capable of forming hybridized nucleic acids with DYSF, PYROXD1, or COL6A3 and instructions directing the use of the probe in accord with the methods described herein.

Horses affected with Polysaccharide Storage Myopathy type 2 (PSSM2) are either heterozygous or homozygous for the affected DYSF, PYROXD1, or COL6A3 alleles. An "allele" is a variant form of a particular genomic nucleic acid sequence. In the context of the methods described herein, some alleles of the DYSF, PYROXD1, or COL6A3 coding regions cause Polysaccharide Storage Myopathy type 2 (PSSM2) in horses. A "DYSF, PYROXD1, or COL6A3 allele," refers to a normal allele of the DYSF, PYROXD1, or COL6A3 locus as well as an allele carrying one or more variations that predispose a horse to develop Polysaccharide Storage Myopathy type 2 (PSSM2), also known as Myofibrillar Myopathy (MFM). The coexistence of multiple alleles at a locus is known as "genetic polymorphism." Any site at which multiple alleles exist as stable components of the population is by definition "polymorphic." An allele is defined as polymorphic if it is present at a frequency of at least 1% in the population. A "single nucleotide polymorphism (SNP)" is a DNA sequence variation that involves a change in a single nucleotide.

The methods described herein involve the use of isolated or substantially purified nucleic acid molecules. An "isolated" or "purified" nucleic acid molecule is one that, by human intervention, exists apart from its native environment and is therefore not a product of nature. An isolated nucleic acid molecule may exist in a purified form or may exist in a non-native environment. For example, an "isolated" or "purified" nucleic acid molecule, or portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. An isolated or purified nucleic acid molecule can be a fragment and/or variant of a reference nucleotide sequence expressly disclosed herein.

A "fragment" or "portion" of a sequence refers to anything less than full-length of the nucleotide sequence encoding—or the amino acid sequence of—a polypeptide. As it relates to a nucleic acid molecule, sequence, or segment when linked to other sequences for expression, a "portion" or a "fragment" refers to a sequence having, for example, at least 80 nucleotides, at least 150 nucleotides, or at least 400 nucleotides. Alternatively, when not employed for expressing—e.g., in the context of a probe or a primer—a "portion" or a "fragment" means, for example, at least 9, at least 12, at least 15, or at least 20 consecutive nucleotides. Alternatively, a fragment or a portion of a nucleotide sequence that is useful as a hybridization probe generally does not encode fragment proteins retaining biological activity. Thus, fragments or portions of a nucleotide sequence may range from at least about 6 nucleotides, about 9, about 12 nucleotides, about 20 nucleotides, about 50 nucleotides, about 100 nucleotides, or more.

A "variant" of a molecule is a sequence that is substantially similar to the sequence of the reference—e.g., native, naturally-occurring, and/or wild-type—molecule. For nucleotide sequences, a variant includes any nucleotide sequence that, because of the degeneracy of the genetic code, encodes the native amino acid sequence of a protein. Naturally occurring allelic variants such as these can be identified with the use of well-known molecular biology techniques, as, for example, with polymerase chain reaction (PCR) and/or hybridization techniques. A variant nucleotide sequence also can include a synthetically-derived nucleotide sequence such as one generated, for example, by using site-directed mutagenesis that encodes the native protein, as well as variant nucleotide sequences that encode a polypeptide having amino acid substitutions. Generally, a nucleotide sequence variant will have at least 40%, at least 50%, at least 60%, at least 70% (e.g., 71%, 72%, 73%, 74%, 75%, 76%, 77%, 78%, 79%), at least 80% (e.g., 81% 82%, 83%, 84%, 85%, 86%, 87%, 88%, 89%), or at least 90% (e.g., 91%, 92%, 93%, 94%, 95%, 96%, 97%, 98%, 99%) sequence identity to the native (endogenous) nucleotide sequence.

"Synthetic" polynucleotides are those prepared by chemical synthesis.

"Recombinant DNA molecule" is a combination of DNA sequences that are joined together using recombinant DNA technology and procedures that are used to join together DNA sequences as described, for example, in Sambrook and Russell (2001).

"Naturally-occurring," "native," or "wild-type" refers to an amino acid sequence or polynucleotide sequence that can be found in nature, without any known mutation, as distinct from being produced artificially or producing a mutated, non-wild-type phenotype. For example, a nucleotide sequence present in an organism (including a virus) that can be isolated from a source in nature and that has not been intentionally modified in the laboratory is naturally occurring. Furthermore, "wild-type" refers to a coding region or organism as found in nature without any known mutation.

A "mutant" dysferlin (DYSF) is a polypeptide or a fragment thereof that is encoded by a DYSF coding region having a mutation, e.g., such as might occur at the DYSF locus. A mutation in one DYSF allele may lead to an alteration in the ability of the encoded polypeptide to interact with calcium ions, with alpha-actinin-2 (encoded by ACTN2), annexin A1 (encoded by ANXA1), annexin A2 (encoded by ANXA2), voltage-dependent L-type calcium channel subunit alpha-1S (encoded by CACNA1S), caveolin 3 (encoded by CAV3), desmin (encoded by DES), diacylglycerol kinase delta (encoded by DGKD), filamin C (encoded by FLNC), myoferlin (encoded by MYOF), myomesin-1 (encoded by MYOM1), gamma-sarcoglycan (encoded by SGCG), myomesin-2 (encoded by MYOM2), myosin-binding protein C, slow-type (encoded by MYBPC1), nebulin (encoded by NEBU), optineurin (encoded by OPTN), beta-parvin (encoded by PARVB), Rho family-interacting cell polarization regular 2 (encoded by RIPOR2), SNARE-associated protein Snapin (encoded by SNAPN), titin (encoded by TTN), tripartite motif-containing protein 72 (encoded by TRIM72), or other proteins that are involved in repair of the sarcolemma of myofibrils, or other proteins that are expressed in skeletal or cardiac muscle that are required for the integrity of myofibrils, leading to alterations in the integrity of myofibrils in a horse heterozygous or homozygous for the allele. Alterations in the interactions of specific proteins can be determined by methods known to the art. Mutations in DYSF may be disease-causing in a horse heterozygous or homozygous for the mutant DYSF allele, e.g., a horse heterozygous or homozygous for a mutation leading to a mutant DYSF polypeptide such as substitution mutations in Exon B of DYSF as shown in FIG. 3 and FIG. 4, such as that designated herein as DYSF-R253W, or in Exon I of DYSF as shown in FIG. 15 and FIG. 16, such as that designated herein as DYSF-P1290T.

A "mutant" pyridine nucleotide-disulfide oxidoreductase domain-containing protein 1 (PYROXD1) is a polypeptide or a fragment thereof that is encoded by a PYROXD1 coding region having a mutation, e.g., such as might occur at the PYROXD1 locus. A mutation in one PYROXD1 allele may lead to an alteration in the ability of the encoded polypeptide to interact with the cofactors flavin adenine dinucleotide (FAD) or nicotinamide adenine dinucleotide (NAD), with other proteins containing either canonical or non-canonical disulfide (S-S) bonds between cysteine (CVS) residues, such as titin (encoded by TIN), obscurin (encoded by OBSCN), triadin (encoded by TRDN), myosin regulatory light chains (encoded by MYL1, MYL2, MYL3, MYL4, MYL5, MYL6, and others), myosin heavy chains (encoded by MYH1, MYH2, MYH3, MYH4, MYH5, MYH6, and others), the ryanodine receptor (encoded by RYR1), sarcoplasmic reticulum $CA^{2+}$-ATPase (encoded by SERCA), nebulin (encoded by NEB), troponin (encoded by TNNT1, TNNT2, and TNNT3), myosin-binding protein C (encoded by MYBPC1), or other proteins that are involved in repair of the sarcolemma of myofibrils, or other proteins that are expressed in skeletal or cardiac muscle that are required for the integrity of myofibrils, leading to alterations in the integrity of myofibrils in a horse heterozygous or homozygous for the allele. Alterations in the interactions of specific proteins can be determined by methods known to the art. It is also possible that a mutation in one or both PYROXD1 alleles may lead to an alteration in the redox state of the cell, which might interfere with signaling processes that are sensitive to the redox state, or to an increased sensitivity to reactive oxygen species such as superoxide, hydrogen peroxide, or other reactive oxygen or reactive nitrogen species. Alterations in the redox state of the cell, as indicated by the ratio of reduced glutathione (GSH) to oxidized glutathione (GSSG), may lead to the irreversible oxidation of sulfhydryl groups in cysteine residues, causing the affected proteins to be ubiquitinated and destroyed. Turnover of particular muscle proteins may alter the stoichiometry of muscle proteins, causing a temporary decrease in muscle function. Oxidative stress is also known to contribute to muscle fatigue by reducing mitochondrial function through the oxidation of key sulfhydryl groups in sarcoplasmic reticulum CA2+-ATPase (encoded by SERCA) and the ryanodine receptor (encoded by RYR1), which mediate calcium levels. Mutations in PYROXID1 may be disease-causing in a horse heterozygous or homozygous for the mutant PYROXD1 allele, e.g., a horse heterozygous or homozygous for a mutation leading to a mutant PYROXD1 polypeptide such as substitution mutations in Exon 12 of PYROXD1 as shown in FIG. 24 and FIG. 25, such as that designated herein as PYROXD1-D492H.

A "mutant" collagen type VI alpha 3 chain (COL6A3) is a polypeptide or a fragment thereof that is encoded by a COL6A3 coding region having a mutation, e.g., such as might occur at the COL6A3 locus. A mutation in one COL6A3 allele may lead to an alteration in the ability of the encoded polypeptide to interact with the protein encoded by the common or wild-type allele of COL6A3 in a heterozygote, to interact with proteins encoded by COL6A1, COL6A2, COL6A5, or COL6A6, or to assemble into a correctly-configured collagen triple helix. A mutation in one COL6A3 allele may lead to an alteration in the ability of the encoded polypeptide to interact with the protein products of the COL5A1 gene, which encodes one of the collagen type 5 proteins, with dysferlin (encoded by DYSF), or with other proteins known to interact with collagen. Defects caused by mutations in one or both COL6A3 alleles may interfere with the proper posttranslational modification of collagen, for example by interfering with glycosylation, phosphorylation, the modification of proline residues to hydroxyproline residues, the modification of lysine residues to hydroxylysine residues, or the proper formation of interchain disulfide bonds. Such defects may alter the ability of collagen to interact with other components of the extracellular matrix, or alter the mechanical properties of the extracellular matrix. Alterations in the interactions of specific proteins can be determined by methods known to the art. Mutations in COL6A3 may be disease-causing in a horse heterozygous or homozygous for the mutant COL6A3 allele, e.g., a horse heterozygous or homozygous for a mutation leading to a mutant COL6A3 polypeptide such as substitution mutations in Exon 26 of COL6A3 as shown in FIG. 35 and FIG. 36, such as that designated herein as COL6A3-G2182A.

A "somatic mutation" is a mutation that occurs only in certain tissues, e.g., in liver tissue, and are not inherited in the germline. A "germline" mutation can be found in any of a body's tissues and is inherited. The present COL6A3 mutation is a germline mutation.

"Homology" refers to the percent identity between two polynucleotide sequences or two amino acid sequences. Two sequences are "homologous" to each other when the sequences exhibit at least 70% (e.g., 71%, 72%, 73%, 74%, 75%, 76%, 77%, 78%, 79%), at least 80% (e.g., 81% 82%, 83%, 84%, 85%, 86%, 87%, 88%, 89%), or at least 90% (e.g., 91%, 92%, 93%, 94%, 95%, 96%, 97%, 98%, 99%) contiguous sequence identity over a defined length of the sequences.

The following terms are used to describe the sequence relationships between two or more nucleic acids or polynucleotides: "reference sequence," "comparison window," "sequence identity," "percentage of sequence identity," and "substantial identity."

As used herein, "reference sequence" refers to a sequence used as a basis for sequence comparison. A reference sequence may be a subset or the entirety of a specified sequence. For example, a reference sequence may be a segment of a full length cDNA or coding region sequence, or the complete cDNA or coding region sequence.

As used herein, "comparison window" refers to a contiguous and specified segment of a polynucleotide sequence, wherein the polynucleotide sequence in the comparison window may reflect one or more additions and/or deletions (i.e., gaps) compared to the reference sequence (which does not exhibit the additions and/or deletions) for optimal alignment of the two sequences. Generally, the comparison window is at least 20 contiguous nucleotides in length, and optionally can be 30, 40, 50, 100, or longer. To avoid a high similarity to a reference sequence due to inclusion of gaps in the polynucleotide sequence, a gap penalty is typically introduced and is subtracted from the number of matches. Methods of alignment of sequences for comparison are well known in the art. Thus, the determination of percent identity between any two sequences can be accomplished using a mathematical algorithm.

Computer implementations of these mathematical algorithms can be used for comparing sequences to determine sequence identity. Such implementations include, but are not limited to: Clustal Omega (online at EMBL-EBI), COBALT (online at ncbi.nlm.hih.gov), the ALIGN program (Version 2.0), and GAP, BESTFIT, BLAST, FASTA, and TFASTA in the Wisconsin Genetics Software Package, Version 8 (available from the Genetics Computer Group (GCG) Madison, WI, USA). Alignments using these programs can be performed using the default parameters.

Software for performing BLAST analyses is publicly available through the National Center for Biotechnology Information (see the World Wide Web at ncbi.nlm.nih.gov). This algorithm involves first identifying high scoring pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When using BLAST, Gapped BLAST, or PSI-BLAST, the default parameters of the respective programs (e.g., BLASTN for nucleotide sequences, BLASTP for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the World Wide Web at ncbi.nlm.nih.gov. Alignment may also be performed manually by visual inspection. For purposes of the methods described herein, comparison of nucleotide sequences for determination of percent sequence identity to the promoter sequences disclosed herein is preferably made using the BlastN program (version 2.3.0 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by a BLAST program.

As used herein, "sequence identity" or "identity" in the context of two nucleic acid or polypeptide sequences refers to a specified percentage of residues in the two sequences that are the same when aligned for maximum correspondence over a specified comparison window, as measured by sequence comparison algorithms or by visual inspection. When percentage of sequence identity is used in reference to a protein, it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Methods for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, CA).

A used herein, "percentage of sequence identity" refers to the value determined by comparing two optimally aligned sequences over a comparison window, wherein the portion of the polynucleotide sequence in the comparison window may comprise additions or deletions (i.e. gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity," in the context of polynucleotide sequences, means that a polynucleotide sequence possesses at least 70% (e.g., 71%, 72%, 73%, 74%, 75%, 76%, 77%, 78%, 79%), at least 80% (e.g., 81% 82%, 83%, 84%, 85%, 86%, 87%, 88%, 89%), or at least 90% (e.g., 91%, 92%, 93%, 94%, 95%, 96%, 97%, 98%, 99%) sequence identity compared to a reference sequence using one of the alignment programs described using standard parameters. These values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, or at least 80%, 90%, or even at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that the two nucleic acid sequences are substantially identical is when the polypeptide encoded by the first nucleic acid is immunologically cross reactive with the polypeptide encoded by the second nucleic acid.

The term "substantial identity," in the context of a polypeptide, indicates that a polypeptide possesses a sequence with at least 70% (e.g., 71%, 72%, 73%, 74%, 75%, 76%, 77%, 78%, 79%), at least 80% (e.g., 81% 82%, 83%, 84%, 85%, 86%, 87%, 88%, 89%), or at least 90% (e.g., 91%, 92%, 93%, 94%, 95%, 96%, 97%, 98%, 99%) amino acid sequence identity to the reference sequence over a specified comparison window. An indication that two polypeptide sequences are substantially identical is that one polypeptide is immunologically reactive with antibodies raised against the second polypeptide.

Thus, a polypeptide is substantially identical to a second polypeptide when, for example, the two polypeptides differ only by a conservative substitution. For sequence comparison, typically one amino acid sequence acts as a reference sequence to which test amino acid sequences are compared. When using a sequence comparison algorithm, test and reference amino acid sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl:

$$T_m = 81.5° \text{ C.} + 16.6 \, (\log M) + 0.41 \, (\% \text{ GC}) - 0.61 \, (\% \text{ form}) - 500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1° C., 2° C., 3° C., or 4° C. lower than the thermal melting point ($T_m$); moderately stringent conditions can utilize a hybridization and/or wash at 6° C., 7° C., 8° C., 9° C., or 10° C. lower than the thermal melting point ($T_m$); low stringency conditions can utilize a hybridization and/or wash at 11° C., 12° C., 13° C., 14° C., 15° C., or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration (20×SSC=3.0 M NaCl, 0.3 M trisodium citrate) so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for about 15 minutes. Often, a high stringency wash is preceded by a low stringency wash to remove background probe signal. An example medium stringency wash for a duplex of, e.g., more than 100 nucleotides is 4-6×SSC at 40° C. for 15 minutes. For short probes (e.g., about 10 to 50 nucleotides), stringent conditions typically involve salt concentrations of less than about 1.5 M, more preferably about 0.01 M to 1.0 M, Na$^+$ ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code. Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C.; and a wash in 0.1×SSC at 60° C. to 65° C. Exemplary low stringency conditions include hybridization with a buffer solution of 30 to 35% formamide, 1 M NaCl, 1% SDS (sodium dodecyl sulfate) at 37° C., and a wash in 1× to 2×SSC at 50° C. to 55° C. Exemplary moderate stringency conditions include hybridization in 40% to 45% formamide, 1.0 M NaCl, 1% SDS at 37° C., and a wash in 0.5× to 1×SSC at 55° C. to 60° C.

The term "variant" polypeptide refers to a polypeptide derived from the native protein by deletion (so-called truncation) and/or addition of one or more amino acids to the N-terminal and/or C-terminal end of the native protein, deletion and/or addition of one or more amino acids at one or more sites in the native protein, and/or substitution of one or more amino acids at one or more sites in the native protein. Such variants may result from, for example, genetic polymorphism or human manipulation. Methods for such manipulations are generally known in the art. Variant DYSF, PYROXD1, or COL6A3 polypeptides may be altered in various ways including, for example, being altered to exhibit one or more amino acid substitutions, one or more deletions, one or more truncations, and/or one or more insertions. For example, an amino acid sequence can be prepared by one or more mutations in the DNA encoding the DYSF, PYROXD1, or COL6A3 polypeptides. Guidance regarding appropriate amino acid substitutions that do not affect biological activity of the protein of interest is well known in the art. Conservative substitutions, such as exchanging one amino acid with another having similar properties, are preferred.

Thus, the nucleotide sequences used to practice the methods described herein can include both naturally-occurring sequences or mutant forms. Likewise, the polypeptides referred to herein can include naturally-occurring polypeptides as well as variations and modified forms thereof. Such variants may continue to possess the desired activity. The deletions, insertions, or substitutions of the polypeptide sequence encompassed herein are not expected to produce radical changes in the characteristics of the polypeptide. However, when it is difficult to predict the exact effect of the substitution, deletion, or insertion in advance of doing so, the effect can be evaluated by routine screening assays.

An individual substitution, deletion, or addition that alters, adds, or deletes a single amino acid or a small percentage of amino acids (typically less than 5%, more typically less than 1%) in an encoded sequence are "conservatively modified variations."

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance, the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill will recognize that each codon in a nucleic acid (except ATG, which is ordinarily the only codon for methionine, and TGG, which is ordinarily the only codon for tryptophan) can be modified to yield a functionally identical molecule by standard techniques. Accordingly, each "silent variation" of a nucleic acid that encodes a polypeptide is implicit in each described sequence.

Known methods of PCR include, but are not limited to, methods using paired primers, nested primers, single specific primers, degenerate primers, gene-specific primers, vector-specific primers, partially mismatched primers, and the like.

The terms "heterologous DNA sequence," "exogenous DNA segment," or "heterologous nucleic acid" refer to a sequence that originates from a source foreign to the particular host cell or, if from the same source, is modified from its original form. Thus, a heterologous coding region in a host cell includes a coding region that is endogenous to the particular host cell but has been modified through, for example, the use of single-stranded mutagenesis. The terms also include non-naturally-occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments, when expressed, yield exogenous polypeptides.

A "homologous" DNA sequence is a DNA sequence that is naturally associated with a host cell into which it is introduced.

"Genome" refers to the complete genetic material of an organism.

"Coding sequence" refers to a DNA or RNA sequence that codes for a specific amino acid sequence and excludes non-coding (e.g., regulatory) nucleotide sequences. For example, a DNA "coding sequence" or a "sequence encoding" a particular polypeptide is a DNA sequence that is transcribed and translated into a polypeptide in vitro or in vivo when placed under the control of appropriate regulatory elements. The boundaries of the coding sequence are determined by a start codon at the 5'-terminus and a translation stop codon at the 3'-terminus. A coding sequence can include, but is not limited to, prokaryotic sequences, cDNA from eukaryotic mRNA, genomic DNA sequences from eukaryotic (e.g., mammalian) DNA, and/or synthetic DNA sequences. A transcription termination sequence will usually be located 3' to the coding sequence. It may constitute an "uninterrupted coding sequence,"—i.e., lacking an intron, such as in cDNA or it may include one or more introns bounded by appropriate splice junctions. An "intron" is a sequence of RNA that is contained in the primary transcript but that is removed through cleavage and re-ligation of the RNA within the cell to create the mature mRNA that can be translated into a protein.

The terms "open reading frame" and "ORF" refer to the nucleotide sequence between translation initiation and termination codons of a coding sequence. The terms "initiation codon" and "termination codon" refer to a unit of three adjacent nucleotides ("codon") in a coding sequence that specifies initiation and chain termination, respectively, of protein synthesis (mRNA translation).

The term "RNA transcript" refers to the product resulting from RNA polymerase catalyzed transcription of a DNA sequence. When the RNA transcript is a perfect complementary copy of the DNA sequence, it is referred to as a primary transcript or it may be an RNA sequence derived from post transcriptional processing of the primary transcript and is referred to as the mature RNA. "Messenger RNA" (mRNA) refers to the RNA that is without introns and can be translated into protein by the cell. "cDNA" refers to a single- or double-stranded DNA that is complementary to and derived from mRNA.

The term "regulatory sequence" refers to a nucleotide sequence that includes, for example, a promoter, an enhancer, and/or other expression control elements (e.g., polyadenylation signals). Such regulatory sequences are known to those skilled in the art. The design of an expression vector may depend on such factors as the choice of the host cell to be transfected and/or the amount of fusion protein to be expressed.

The term "DNA control elements" refers collectively to promoters, ribosome binding sites, polyadenylation signals, transcription termination sequences, upstream regulatory domains, enhancers, and the like, that collectively provide for the transcription and translation of a coding sequence in a host cell. Not all of these control sequences need always be present in a recombinant vector so long as the desired coding region is capable of being transcribed and translated.

A control element, such as a promoter, "directs the transcription" of a coding sequence in a cell when RNA polymerase binds to the promoter and transcribes the coding sequence into mRNA, which is then translated into the polypeptide encoded by the coding sequence.

A cell has been "transformed" by exogenous DNA when the exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to other eukaryotic cells, a stably transformed cell is one in which the exogenous DNA has become integrated into the chromosome so that it is inherited by daughter cells through chromosome replication. This stability is demonstrated by the ability of the eukaryotic cell to establish cell lines or clones having a population of daughter cells containing the exogenous DNA.

"Operably linked" refers to the association of nucleic acid sequences on single nucleic acid fragments so that the function of one is affected by the other, e.g., an arrangement of elements wherein the components so described are configured so as to perform their usual function. For example, a regulatory DNA sequence is said to be "operably linked to" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably linked to regulatory sequences in sense or antisense orientation. Control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

"Transcription stop fragment" refers to nucleotide sequences that contain one or more regulatory signals, such as polyadenylation signal sequences, capable of terminating transcription. Examples include the 3' non-regulatory regions of the genes dysferlin (DYSF), pyridine nucleotide-disulfide oxidoreductase domain-containing protein 1 (PYROXD1), and collagen type VI alpha 3 chain (COL6A3).

"Translation stop fragment" or "translation stop code" or "stop codon" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. The change of at least one nucleotide in a nucleic acid sequence can result in an interruption of the coding sequence of the gene, e.g., a premature stop codon. Such sequence changes can cause a mutation in the polypeptide encoded by the DYSF, PYROXD1, or COL6A3 gene. For example, if the mutation is a nonsense mutation, the mutation results in the generation of a premature stop codon, causing the generation of a truncated DYSF, PYROXD1, or COL6A3 polypeptide.

Nucleic Acids

Nucleotide sequences that are subjected to the methods described herein can be obtained from any prokaryotic or eukaryotic source. For example, they can be obtained from a mammalian, such as equine, cellular source. Alternatively, nucleic acid molecules can be obtained from a library, such as the CHORI-241 Equine BAC library or a similar resource available elsewhere.

As discussed above, the terms "isolated and/or purified" refer to a nucleic acid—e.g. a DNA or RNA molecule—that has been isolated from its natural cellular environment and from association with other components of the cell, such as nucleic acid or polypeptide, so that it can be sequenced, replicated, and/or expressed. For example, an "isolated nucleic acid" may be a DNA molecule that is complementary or hybridizes to a sequence in a coding region of interest—e.g., a nucleic acid sequence encoding an equine collagen type VI alpha 3 chain protein, and remains stably bound under stringent conditions (as defined by methods well known in the art). Thus, an RNA or a DNA is "isolated" in that it is free from at least one contaminating nucleic acid with which it is normally associated in the natural source of the RNA or DNA and in one embodiment of the invention is substantially free of any other mammalian RNA or DNA. The phrase "free from at least one contaminating source nucleic acid with which it is normally associated" includes the case where nucleic acid is reintroduced into the source or natural cell but is in a different chromosomal location or is otherwise flanked by nucleic acid sequences not normally found in the source cell, e.g., in a vector or plasmid.

As used herein, the term "recombinant nucleic acid," e.g., "recombinant DNA sequence or segment" refers to a nucleic acid, e.g., to DNA that has been derived or isolated from any appropriate cellular source, that may be substantially chemically altered in vitro, so that its sequence is not naturally occurring, or corresponds to naturally occurring sequences that are not positioned as they would be positioned in a genome that has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from the source by chemical means, e.g., by the use of restriction endonucleases, so that it can be further manipulated, e.g. amplified, for use in the methods described herein. Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. Therefore, "recombinant DNA" includes completely synthetic DNA sequences, semi-synthetic DNA sequences, DNA sequences isolated from biological sources, and DNA sequences derived from RNA, as well as mixtures thereof.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or non-variant version of the nucleic acid molecule.

Nucleic Acid Amplification Methods

DNA present in a physiological sample may be amplified by any means known to the art. Examples of suitable amplification techniques include, but are not limited to, polymerase chain reaction (including, for RNA amplification, reverse-transcriptase polymerase chain reaction), ligase chain reaction, strand displacement amplification, transcription-based amplification, self-sustained sequence replication (or "3SR"), the Qβ-replicase system, nucleic acid sequence-based amplification (or "NASBA"), the repair chain reaction (or "RCR"), and boomerang DNA amplification (or "BDA").

The bases incorporated into the amplification product may be natural or modified bases (modified before or after amplification), and the bases may be selected to optimize subsequent electrochemical detection steps.

Polymerase chain reaction (PCR) may be performed according to known techniques. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized that is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe), the probe carrying a detectable label, and then detecting the label in accordance with known techniques. Where the nucleic acid to be amplified is RNA, amplification may be carried out by initial conversion to DNA by reverse transcriptase in accordance with known techniques.

Strand displacement amplification (SDA) may be performed according to known techniques. For example, SDA may be carried out with a single amplification primer or a pair of amplification primers, with exponential amplification being achieved with the latter. In general, SDA amplification primers comprise, in the 5 to 3 direction, a flanking sequence (the DNA sequence of which is noncritical), a restriction site for the restriction enzyme employed in the reaction, and an oligonucleotide sequence (e.g., an oligonucleotide probe) that hybridizes to the target sequence to be amplified and/or detected. The flanking sequence, which serves to facilitate binding of the restriction enzyme to the recognition site and provides a DNA polymerase priming site after the restriction site has been nicked, is about 15 to 20 nucleotides in length in one embodiment. The restriction site is functional in the SDA reaction: the oligonucleotide probe portion is about 13 to 15 nucleotides in length in one embodiment of the invention.

Ligase chain reaction (LCR) also may be performed according to known techniques. In general, the reaction is carried out with two pairs of oligonucleotide probes: one pair binds to one strand of the sequence to be detected; the other pair binds to the other strand of the sequence to be detected; each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

In some embodiments, each exon of the DYSF, PYROXD1, or COL6A3 coding regions is amplified by PCR using primers based on the known sequence. The amplified exons are then sequenced using, for example, an automated sequencer. In this manner, the exons of the DYSF, PYROXD1, or COL6A3 coding regions from horses suspected of having Polysaccharide Storage Myopathy type 2 (PSSM2), also known as Myofibrillar Myopathy (MFM), in their pedigree are then sequenced until a mutation is found. Examples of such mutations include those in Exon B of the DYSF DNA as shown in FIG. 3 and FIG. 4, in Exon I of the DYSF DNA as shown in FIG. 15 and FIG. 16, in Exon 12 of the PYROXD1 DNA as shown in FIG. 24 and FIG. 25, or in Exon 26 of the COL6A3 DNA as shown in FIG. 35 and FIG. 36. For example, mutations in the DYSF, PYROXD1, or COL6A3 genes include (1) the specific substitution of an adenine (A) for a guanine (G) on the forward strand at chr15:31,306,949 of the current horse genome assembly (EquCab2, GCA_000002305.1) as displayed in the UCSC Genome Browser and as shown for the reverse strand in FIG. 1, (2) the specific substitution of an thymine (T) for a guanine (G) on the forward strand at chr15:31,225,630 of the current horse genome assembly (EquCab2, GCA_000002305.1) as displayed in the UCSC Genome Browser and as shown for the reverse strand in FIG. 13, (3) the specific substitution of a cytosine (C) for a guanine (G) on the forward strand at chr6:47,661,977 of the current horse genome assembly (EquCab2, GCA_000002305.1) as displayed in the UCSC Genome Browser and as shown for the reverse strand in FIG. 22, and (4) the specific substitution of a guanine (G) for a cytosine (C) on the forward strand at chr6:23,480,621 of the current horse genome assembly (EquCab2, GCA_000002305.1) as displayed in the UCSC Genome Browser and as shown in FIG. 33. Using this technique, additional mutations causing equine Polysaccharide Storage Myopathy type 2 (PSSM2), also known as Myofibrillar Myopathy, can be identified. Thus, the methods described herein may be used to detect and/or identify an alteration within the wild-type DYSF, PYROXD1, or COL6A3 locus. "Alteration of" a specified locus encompasses all forms of mutations including, for example, a deletion, an insertion, and/or a point mutation in the coding and noncoding regions. A deletion can involve the deletion of all or any portion of the coding region. A point mutation may result in an aberrant stop codon, a frameshift mutation, an amino acid substitution, and/or an alteration in pre-mRNA processing (splicing) that produces a protein with an altered amino acid sequence. Point mutational events may occur in regulatory regions, such as in the promoter of the gene, leading to decreased expression of the mRNA. A point mutation also may interfere with proper RNA processing, leading to decreased expression of the DYSF, PYROXD1, or COL6A3 translation products, decreased mRNA stability, and/or decreased translation efficiency. Polysaccharide Storage Myopathy type 2 (PSSM2), also known as Myofibrillar Myopathy, is a disease caused by point mutations (1) at chr15:31,306,949 of the current horse genome assembly (EquCab2, GCA_000002305.1) as displayed in the UCSC Genome Browser and as shown in FIG. 1, (2) at chr15:31,225,630 of the current horse genome assembly (EquCab2, GCA_000002305.1) as displayed in the UCSC Genome Browser and as shown in FIG. 13, (3) at chr6:47,661,977 of the current horse genome assembly (EquCab2, GCA_000002305.1) as displayed in the UCSC Genome Browser and as shown in FIG. 22, or (4) chr6:23,480,621 of the current horse genome assembly (EquCab2, GCA_000002305.1) as displayed in the UCSC Genome Browser and as shown in FIG. 33. Horses predisposed to or having Polysaccharide Storage Myopathy type 2 (PSSM2) may need only one mutated DYSF, PYROXD1, or COL6A3 allele.

Techniques that are useful in performing the methods described herein include, but are not limited to direct DNA sequencing, PFGE analysis, allele-specific oligonucleotide (ASO), dot blot analysis, and/or denaturing gradient gel electrophoresis.

There are several methods that can be used to detect DNA sequence variation. Direct DNA sequencing, either manual or automated (e.g., fluorescent or semiconductor-based sequencing), can detect sequence variation. Another approach is the single-stranded conformation polymorphism assay (SSCA). This method does not detect all sequence changes, especially if the DNA fragment size is greater than 200 bp, but can be used to detect most DNA sequence variation. SSCA allows for increased throughput compared to direct sequencing for mutation detection on a research basis. The fragments that have shifted mobility on SSCA gels are then sequenced to determine the exact nature of the DNA sequence variation. Other approaches based on the detection of mismatches between the two complementary DNA strands include clamped denaturing gel electrophoresis (CDGE), heteroduplex analysis (HA), and chemical mismatch cleavage (CMC). Once a mutation is known, an allele specific detection approach such as allele specific oligonucleotide (ASO) hybridization can be utilized to rapidly screen large numbers of other samples for that same mutation. Such a technique can utilize probes that are labeled with gold nanoparticles to yield a visual color result.

Detecting point mutations may be accomplished by molecular cloning and then sequencing one or more DYSF, PYROXD1, or COL6A3 alleles. Alternatively, the coding region sequences can be amplified directly from a genomic DNA preparation from equine tissue, using known techniques. The DNA sequence of the amplified sequences can then be determined.

Exemplary methods for a more complete, yet still indirect, test for confirming the presence of a mutant allele include, for example, single stranded conformation analysis (SSCA), denaturing gradient gel electrophoresis (DDGE), an RNase protection assay, allele-specific oligonucleotides (ASOs), the use of a protein that recognizes nucleotide mismatches (e.g., the *E. coli* mutS protein), and allele-specific PCR. For allele-specific PCR, primers are used that hybridize at their 3' ends to a particular DYSF, PYROXD1, or COL6A3 mutation. If the particular mutation is not present, an amplification product is not observed. Allele-specific PCR may also be carried out using quantitative PCR or real-time PCR using a specialized instrument that is capable of detecting and quantifying the appearance of amplification products during each amplification cycle. An Amplification Refractory Mutation System (ARMS) can also be used. Insertions and deletions of genes can also be detected by cloning, sequencing, and amplification. In addition, restriction fragment length polymorphism (RFLP) probes for the target locus or a surrounding marker locus can be used to score alteration of an allele or an insertion in a polymorphic fragment. Other techniques for detecting insertions or deletions as known in the art can also be used.

In the first three methods (i.e., SSCA, DGGE, and RNase protection assay), a new electrophoretic band appears. SSCA detects a band that migrates differently because the sequence change causes a difference in single-strand, intramolecular base pairing. RNase protection involves cleaving the mutant polynucleotide into two or more smaller fragments. DGGE detects differences in migration rates of mutant sequences compared to wild-type sequences using a denaturing gradient gel. In an allele-specific oligonucleotide assay, an oligonucleotide is designed that detects a specific sequence, and the assay is performed by detecting the presence or absence of a hybridization signal. In the mutS assay, the protein binds only to sequences that contain a nucleotide mismatch in a heteroduplex between mutant and wild-type sequence.

As used herein, a "nucleotide mismatch" refers to a hybridized nucleic acid duplex in which the two strands are not 100% complementary. Lack of total homology may be due to a deletion, an insertion, an inversion, and/or a substitution. Mismatch detection can be used to detect point mutation in the coding region or its mRNA product. While these techniques are less sensitive than sequencing, they are simpler to perform on a large number of samples. An example of a mismatch cleavage technique is the RNase protection method. In the context of detecting a DYSF-associated, PYROXD1-associated, or COL6A3-associated mismatch, the method involves the use of a labeled riboprobe that is complementary to the horse wild-type DYSF, PYROXD1, or COL6A3 coding region sequence. The riboprobe and either mRNA or DNA isolated from tissue are annealed (i.e., hybridized) and subsequently digested with the enzyme RNase A, which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen that is smaller than the full length duplex RNA for the riboprobe and the mRNA or DNA. The riboprobe need not be the full length of the DYSF, PYROXD1, or COL6A3 mRNA or coding region but can be a segment of either. If the riboprobe includes only a segment of the DYSF, PYROXD1, or COL6A3 mRNA or DNA, it may be desirable to use a number of probes to screen the whole mRNA sequence for mismatches.

In a similar fashion, DNA probes can be used to detect a mismatch through enzymatic and/or chemical cleavage. Alternatively, a mismatch can be detected by shifts in the electrophoretic mobility of mismatched duplexes relative to matched duplexes. With either riboprobes or DNA probes, the cellular mRNA or DNA that might contain a mutation can be amplified using PCR before hybridization.

Nucleic Acid Analysis via Microchip Technology

A DNA sequence of the DYSF, PYROXD1, or COL6A3 coding regions that has been amplified by PCR may be screened using an allele-specific probe. Allele-specific probes are nucleic acid oligomers, each of which contains a region of the DYSF, PYROXD1, or COL6A3 coding region harboring a known mutation. For example, one oligomer may be about 30 nucleotides in length, corresponding to a portion of the DYSF, PYROXD1, or COL6A3 coding region sequence. Using a battery of such allele-specific probes, a PCR amplification product can be screened to identify the presence of a previously identified mutation in the DYSF, PYROXD1, or COL6A3 coding region. Hybridizing an allele-specific probe with an amplified DYSF, PYROXD1, or COL6A3 sequence can be performed, for example, on a nylon filter. Hybridizing to a particular probe under stringent hybridization conditions indicates the presence of the same mutation in the tissue as in the allele-specific probe.

An alteration of DYSF, PYROXD1, or COL6A3 mRNA expression can be detected by any technique known in the art. Exemplary techniques include, for example, Northern blot analysis, PCR amplification, and/or RNase protection. Decreased mRNA expression indicates an alteration of the wild-type DYSF, PYROXD1, or COL6A3 locus.

Alteration of wild-type DYSF, PYROXD1, or COL6A3 coding region also can be detected by screening for alteration of a wild-type DYSF, PYROXD1, or COL6A3 polypeptide such as, for example, the wild-type DYSF, PYROXD1, or COL6A3 protein or a portion of the wild-type DYSF, PYROXD1, or COL6A3 protein. For example, a monoclonal antibody immunoreactive with wild-type DYSF, PYROXD1, or COL6A3 (or to a specific portion of the DYSF, PYROXD1, or COL6A3 protein) can be used to screen a tissue. Lack of cognate antigen would indicate a mutation. An antibody specific for a product of a mutant allele also can be used to detect a mutation in the DYSF, PYROXD1, or COL6A3 coding region. Such an immunological assay can be performed using conventional methods. Exemplary methods include, for example, Western blot analysis, an immunohistochemical assay, an ELISA assay, and/or any method for detecting an altered DYSF, PYROXD1, or COL6A3 polypeptide. In some embodiments, a functional assay can be used such as, for example, protein binding determination. In addition, an assay can be used that detects DYSF, PYROXD1, or COL6A3 biochemical function. Finding a mutant DYSF, PYROXD1, or COL6A3 polypeptide indicates a mutation at the DYSF, PYROXD1, or COL6A3 locus.

A mutant DYSF, PYROXD1, or COL6A3 coding region or translation product can be detected in a variety of physiological samples collected from a horse. Examples of appropriate samples include a cell sample, such as a blood cell (e.g., a lymphocyte, a peripheral blood cell), a sample collected from the spinal cord, a tissue sample such as cardiac tissue or muscle tissue (e.g. cardiac or skeletal muscle) an organ sample (e.g., liver or skin), a hair sample, especially a hair sample with the hair bulb (roots) attached, and/or a fluid sample (e.g., blood).

The methods described herein are applicable to any equine disease in which DYSF, PYROXD1, or COL6A3 has a role. The method may be particularly useful for, for example, a veterinarian, a Breed Association, and/or individual breeders, so they can decide upon an appropriate course of treatment, and/or to determine if an animal is a suitable candidate as a brood mare or sire.

Oligonucleotide Probes

As described above, the method may be used to detect the presence and/or absence of a polymorphism in equine DNA. In particular, mutations in the DYSF, PYROXD1, or COL6A3 gene include the specific substitution (1) of an adenine (A) for a guanine (G) on the forward strand at chr15:31,306,949 of the current horse genome assembly (EquCab2, GCA_000002305.1) as displayed in the UCSC Genome Browser and as shown for the reverse strand in FIG. 1, (2) of a thymine (T) for a guanine (G) on the forward strand at chr15:31,225,630 of the current horse genome assembly (EquCab2, GCA_000002305.1) as displayed in the UCSC Genome Browser and as shown for the reverse strand in FIG. 13, (3) the specific substitution of a cytosine (C) for a guanine (G) on the forward strand at chr6:47,661,977 of the current horse genome assembly (EquCab2, GCA_000002305.1) as displayed in the UCSC Genome Browser and as shown in FIG. 22, and the specific substitution of a guanine (G) for a cytosine (C) on the forward strand at chr6:23,480,621 of the current horse genome assembly (EquCab2, GCA_000002305.1) as displayed in the UCSC Genome Browser and as shown for the reverse strand in FIG. 33. These substitutions result in (1) an arginine (R) at codon 253 in the dysferlin (DYSF) protein (SEQ ID NO:10) being replaced by a tryptophan (W), as shown in SEQ ID NO: 11, (2) a proline (P) at codon 1290 in the dysferlin (DYSF) protein (SEQ ID NO:57) being replaced by a threonine (T), as shown in SEQ ID NO:58, (3) an aspartate (D) at codon 492 in the pyridine nucleotide-disulfide oxidoreductase domain-containing protein 1 (PYROXD1) protein (SEQ ID NO:104) being replaced by a histidine (H), as shown in SEQ ID NO: 105, and (4) a glycine (G) at codon 2182 in the collagen type VI alpha 3 chain (COL6A3) protein (SEQ ID NO:164) being replaced by an alanine (A), as shown in SEQ ID NO: 165.

A primer pair may be used to determine the nucleotide sequence of a particular DYSF, PYROXD1, or COL6A3 allele using PCR. A pair of single-stranded DNA primers can be annealed to sequences within or surrounding the DYSF, PYROXD1, or COL6A3 coding region in order to prime amplifying DNA synthesis of the DYSF, PYROXD1, or COL6A3 coding region itself. A complete set of primers allows one to synthesize all of the nucleotides of the DYSF, PYROXD1, or COL6A3 coding sequence. In some embodiments, a set of primers can allow synthesis of both intron and exon sequences. In some embodiments, allele-specific primers can be used. Such primers anneal only to particular DYSF, PYROXD1, or COL6A3 mutant alleles, and thus will only amplify product efficiently in the presence of the mutant allele as a template.

The first step of the process involves contacting a physiological sample obtained from a horse, which sample contains nucleic acid, with an oligonucleotide probe to form a hybridized DNA. The oligonucleotide probe can be any probe having from about 4 or 6 bases up to about 80 or 100 bases or more. In one embodiment, the oligonucleotide probe can have between about 10 and about 20 bases.

The primers themselves can be synthesized using conventional techniques and, in some cases, can be made using an automated oligonucleotide synthesizing machine. Given the DYSF, PYROXD1, or COL6A3 genomic sequences as partially set forth in SEQ ID NO:1, SEQ ID NO:56, SEQ ID NO:103, and SEQ ID NO:163, one can design a set of oligonucleotide primers to probe any portion of the DYSF, PYROXD1, or COL6A3 coding sequences. The primers may be designed to hybridize entirely to coding sequence (exons), to noncoding sequence (introns or other noncoding sequences), or to regions spanning the junction of coding and noncoding sequences in genomic DNA.

An oligonucleotide probe may be prepared according to conventional techniques to have any suitable base sequence. Suitable bases for preparing the oligonucleotide probe may be selected from naturally-occurring bases such as adenine, cytosine, guanine, uracil, and thymine. An oligonucleotide probe also can incorporate one or more non-naturally-occurring or "synthetic" nucleotide bases. Exemplary synthetic bases include, for example, 7-deaza-guanine, 8-oxo-guanine, 6-mercaptoguanine, N4-acetylcytidine, 5-(carboxyhydroxyethyl)uridine, 2'-O-methylcytidine, 5-(carboxymethylaminomethyl)-2-thiouridine, 5-carboxymethylaminomethyluridine, dihydrouridine, 2'-O-methylpseudouridine, β,D-galactosylqueuosine, 2"-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, N2-methylguanosine, 3-methylcytidine, 5-methylcytidine, N6-methyl adenosine, 7-methylguanosine, 5-methylaminomethyluridine, 5-methoxyaminomethyl-2-thiouridine, β,D-mannosylqueuosine, 5-methloxycarbonylmethyluridine, 5-methoxyuridine, 2-methylthio-N6-isopentenyladenosine, N-((9-β-D-ribofuranosyl-2-methylthiopurine-6-yl)carbamoyl)threonine, N-((9-β-D-ribofuranosylpurine-6-yl)N-methyl-carbamoyl)threonine, uridine-5-oxyacetic acid methylester, uridine-5-oxyacetic acid, wybutoxosine, pseudouridine, queuosine, 2-thiocytidine, 5-methyl-2-thiouridine, 2-thiouridine, 5-methyluridine, N-((9-beta-D-ribofuranosylpurine-6-yl)carbamoyl) threonine, 2'-O-methyl-5-methyluridine, 2'-O-methyluridine, wybutosine, and/or 3-(3-amino-3-carboxypropyl)uridine. Any oligonucleotide backbone may be employed, including DNA, RNA (although RNA may be less preferred than DNA in certain circumstances), modified sugars such as carbocycles, and sugars containing 2 substitutions (e.g., fluoro or methoxy). The oligonucleotides may be oligonucleotides wherein at least one, or all, of the internucleotide bridging phosphate residues is a modified phosphate such as, for example, a methyl phosphate, a methyl phosphonotlioate, a phosphoroinorpholidate, a phosphoropiperazidate, and/or a phospholioramidate—for example, every other one of the internucleotide bridging phosphate residues may be modified. The oligonucleotide may be a "peptide nucleic acid" such as described in Nielsen et al., Science, 254, 1497-1500 (1991).

The oligonucleotide probe should possess a sequence at least a portion of which is capable of binding to a known portion of the sequence of the nucleic acid in the physiological sample.

In some embodiments, the nucleic acid in the sample may be contacted with a plurality of oligonucleotide probes having different base sequences (e.g., where there are two or more target nucleic acids in the sample, or where a single target nucleic acid is hybridized to two or more probes in a "sandwich" assay).

The oligonucleotide probes provided herein may be useful for a number of purposes. For example, the oligonucleotide probes can be used to detect PCR amplification products and/or to detect mismatches with the DYSF, PYROXD1, or COL6A3 coding region or mRNA.

Hybridization Methodology

The nucleic acid from the physiological sample may be contacted with the oligonucleotide probe in any conventional manner. For example, the sample nucleic acid may be solubilized in solution and contacted with the oligonucleotide probe by solubilizing the oligonucleotide probe in solution with the sample nucleic acid under conditions that permit hybridization. Suitable hybridization conditions are well known to those skilled in the art. Alternatively, the sample nucleic acid may be solubilized in solution with the oligonucleotide probe immobilized on a solid or semisolid support, whereby the sample nucleic acid may be contacted with the oligonucleotide probe by immersing the solid or semisolid support having the oligonucleotide probe immobilized thereon in the solution containing the sample nucleic acid.

Certain embodiments of the methods described herein relate to mutations in the DYSF, PYROXD1, or COL6A3 coding region or the diagnosis of Polysaccharide Storage Myopathy type 2 (PSSM2), also known as Myofibrillar Myopathy (MFM), or the detection of a predisposition for Polysaccharide Storage Myopathy type 2 (PSSM2), also known as Myofibrillar Myopathy (MFM), or to the detection of a mutant DYSF, PYROXD1, or COL6A3 allele in a horse.

Mutations in the equine DYSF, PYROXD1, or COL6A3 coding regions (encoding the dysferlin, pyridine nucleotide-disulfide oxidoreductase domain-containing protein 1, and skeletal muscle protein collagen type VI alpha 3 chain) are present in many populations of horses affected by Polysaccharide Storage Myopathy type 2 (PSSM2), also known as Myofibrillar Myopathy (MFM). The differences in the genomic DNA between horses affected by Polysaccharide Storage Myopathy type 2 (PSSM2), also known as Myofibrillar Myopathy (MFM) include (1) point mutations at nucleic acid chr15:31,306,949 of the current horse genome assembly (EquCab2, GCA_000002305.1) as displayed in the UCSC Genome Browser and as shown in FIG. 1, (2) point mutations at nucleic acid chr15:31,225,630 of the current horse genome assembly (EquCab2, GCA_000002305.1) as displayed in the UCSC Genome Browser and as shown in FIG. 13, (3) chr6:47,661,977 of the current horse genome assembly (EquCab2, GCA_000002305.1) as displayed in the UCSC Genome Browser and as shown in FIG. 22, and (4) chr6:23,480,621 of the current horse genome assembly (EquCab2, GCA_000002305.1) as displayed in the UCSC Genome Browser and as shown in FIG. 33.

Scientific Narrative

Dysferlin (DYSF)

A mutation in the equine DYSF coding region (encoding the membrane protein dysferlin) is present in many populations of horses affected by Polysaccharide Storage Myopathy type 2 (PSSM2), also known as Myofibrillar Myopathy (MFM). The difference in the genomic DNA between horses with PSSM2 and control horses include a G-to-A substitution in DYSF Exon B (as defined in FIG. 3) at nucleotide position chr15:31,306,949.

FIG. 1 shows a portion of the current horse genome assembly (EquCab2, GCA_000002305.1) with coordinates as displayed in the UCSC Genome Browser centered on the chr15:31,306,949 position, the site of a substitution of an adenine (A) for a guanine (G) that results in the substitution of a tryptophan (W) for arginine (R) at amino acid position 253 in dysferlin as shown in FIG. 4 (SEQ ID NO:11). The reverse complement sequence is shown, with the site of a substitution of a thymine (T) for a cytosine (C) as indicated (SEQ ID NO:1). The single nucleotide polymorphism (SNP) defined by this base substitution is identified as rs1145077095 in dbSNP.

There are 21 predicted transcripts of the DYSF coding region in public databases. These models differ somewhat in ways not relevant to the DYSF-R253W mutation. All 21 isoforms share a common segment that includes the chr15:31,306,949 position. This common segment is shown in FIG. 2.

FIG. 2 shows a portion of the normal equine DYSF Coding DNA Sequence (SEQ ID NO:2) and the mutant DYSF Coding DNA Sequence (SEQ ID NO:3) bearing the C to T mutation at nucleotide position 1027 in this figure, corresponding to chr15:31,306,949 as shown in SEQ ID NO:1 (FIG. 1). This sequence is a region of perfect consensus among 21 different experimentally predicted mRNA isoforms. The numbering in FIG. 2 is that of isoform X1 (XM_023618907.1), which for this segment perfectly matches the numbering of isoforms X2 (XM_023618908.1), X3 (XM_023618909.1), X4 (XM_023618910.1), X5 (XM_023618911.1), and X6 (XM_023618912.1). The numbering of the start and end positions for X7 (XM_023618913.1) is 671-1699. The numbering for the start and end positions for X8 (XM_023618914.1) is 763-1791. The numbering for the start and end positions of X9 (XM_023618915.1), X11 (XM_023618917.1), X12 (XM_023618918.1), and X13 (XM_023618919.1) is 670-1698. The numbering for the start and end positions of X10 (XM_023618916.1) is 763-1791. The numbering for the start and end positions of X14 (XM_023618920.1) and X15 (XM_023618921.1) is 1075-2103. The numbering for the start and end positions of X16 (XM_023618922.1) and X18 (XM_023618924.1) is 1074-2102. The numbering for the start and end positions of X17 (XM_023618923.1) and X19 (XM_023618925.1) is 981-2009. The numbering for the start and end positions of X20 (XM_023618926.1) and X21 (XM_023618927.1) is 980-2008. In both sequences, the sequence of Exon B as shown in FIG. 3 is indicated in bold. The site of a C to T mutation site at nucleotide position 1027, corresponding to 31,306,949 in SEQ ID NO:1 (FIG. 1), and to rs1145077095 in dbSNP, is underlined. The region of sequence comprising Exon B as shown in FIG. 3 is displayed as codons in the correct reading frame for both SEQ ID NO:2 and SEQ ID NO: 3 in FIG. 5.

For the sake of simplicity, the amino acid substitution caused by the substitution of an adenine (A) for a guanine (G) at the chr15:31,306,949 position, identified as rs1145077095 in dbSNP, will be referred to as DYSF-R253W, based on SEQ ID NO:11. The amino acid substitution caused by this mutation will remain the same regardless of the numerical position of the affected codon in alternative gene models. The wild-type (e.g., also referred to herein as "normal" or "unaffected") allele of this coding region may be referred to as R253 and the mutant allele R253W.

FIG. 3 shows a view of the current horse genome assembly (EquCab2, GCA_000002305.1) in the UCSC Genome Browser with exon sequences that match the partial DYSF Coding DNA Sequence (SEQ ID NO:2) and the mutant partial DYSF Coding DNA Sequence (SEQ ID NO:3). The DYSF Coding DNA Sequences correspond to Exons A, B, C, D, E, and F as indicated by the regions of sequence similarity of the translated genomic DNA to DYSF protein sequences from human (Homo), cattle (Bos), rat (Rattus), mouse (Mus), and DYSF protein sequences from the more distantly-related zebrafish (Danio) and African claw-toed frog (Xenopus). Partial matches to the paralogous protein myoferlin (MYOF) from human (Homo), cattle (Bos), mouse (Mus), rat (Rattus), and zebrafish (Danio) are also seen. The sequences of Exons A-F with 10 bp of flanking intron sequence and their coordinates in the current horse assembly are displayed below the image from the UCSC Genome Browser. Sequence IDs are Exon A (SEQ ID NO:4), Exon B (SEQ ID NO:5), Exon C (SEQ ID NO:6.), Exon D (SEQ ID NO:7), Exon E (SEQ ID NO:8), and Exon F (SEQ ID NO:9).

FIG. 4 shows a model of part of the normal protein sequence encoded by horse DYSF (XP_023474694.1, presented here as SEQ ID NO:10) corresponding to a translation of SEQ ID NO:2 shown in FIG. 2 and part of the altered protein sequence encoded by horse DYSF with the base substitution at chr15:31,306,949 (based on XP_023474694.1, presented here as SEQ ID NO:11) corresponding to a translation of SEQ ID NO:3 shown in FIG. 2. The portion of the protein encoded by Exon B as shown in FIG. 3 is indicated in bold, while the amino acid position affected by the base substitution of an adenine (A) for a guanine (G) on the forward strand at the chr15:31,306,949 position, corresponding to rs1145077095 in dbSNP as shown in FIG. 1, is underlined. The amino acid positions in XP_023474694.1 are indicated at the beginning and end of the sequence.

FIG. 5 shows horse DYSF Exon B and flanking genomic DNA sequence from which PCR primers to amplify genomic DNA containing the site of the DYSF-R253W mutation would be most appropriately derived. Genomic coordinates are as in FIG. 1. Exon B from chr15:31,307,036 to chr15:31,306,908 is shown broken into codons in the correct reading frame for the wild-type allele (SEQ ID NO:12) and the DYSF-R253W allele (SEQ ID NO:13). Only the reference sequence from the assembly is shown for the flanking sequences. The codon affected by the G to A mutation site at nucleotide position chr15:31,306,949, corresponding to rs1145077095 in dbSNP as shown in FIG. 1 (C to T in the reverse complement as shown), is shown in bold, with the position of the base substitution indicated by underlining. The base substitution changes the bold three base codon from one coding for an arginine (CGG) to one coding for a tryptophan (TGG). Example primers used experimentally to amplify genomic DNA containing the mutation site are shown in lower case

```
                                    (SEQ ID NO: 14)
[5'-CCCGAGATTTCTGGCTTTCT-3'
and
                                    (SEQ ID NO: 15)
5'-CTCGACAAGTTCTGGGGTGT-3'].
```

Genomic DNA obtained from horses can be genotyped by amplifying a region containing a variant in the DYSF gene using Polymerase Chain Reaction (PCR), then sequencing the amplified DNA using Sanger sequencing. The variant allele DYSF-R253W is abbreviated as P5, while the common or wild-type allele is abbreviated as N. The results can be scored as homozygous for the common or wild-type allele (N/N), heterozygous for the nucleotide substitution (N/P5), or homozygous for the nucleotide substitution (P5/P5).

FIG. 6 shows traces from Sanger DNA sequencing of amplified DYSF genomic DNA using primers shown in FIG. 5 (SEQ ID NO:14 and SEQ ID NO:15). The sequence of the reverse strand is shown. The arrows in the figure indicate nucleotide position chr15:31,306,949, the site of a substitution of a thymine (T) for a cytosine (C) in this position, corresponding to rs1145077095 in dbSNP, that creates the DYSF-R253W variant. The traces show, from left to right, results for a horse homozygous for the wild-type or common allele (N/N), results for a horse heterozygous for the substitution (N/P5), and results for a horse homozygous for the substitution (P5/P5).

Dysferlin is a member of a family of genes with a transmembrane domain. The majority of the protein faces the cytoplasm. Dysferlin has seven C2 domains that are implicated in calcium-dependent membrane fusion events. Dysferlin plays an important role in the repair of muscle fibers.

Mice homozygous for targeted mutations in DYSF that are expected to result in a total loss of function display defects in skeletal muscle. These defects include "dystrophic" muscle that exhibits a progressive muscular weakness. Specific defects in limb grasping are observed. The morphology of muscle fibers in mice homozygous for loss-of-function alleles include centrally located nuclei, increased variability of skeletal muscle fiber size, and skeletal muscle fiber degeneration. Increased serum creatine kinase (CK), a sign of muscle damage, is also seen.

The human ortholog of the equine DYSF gene and the human protein that this gene encodes are richly annotated with experimental data derived from genetic and biochemical studies. It is informative to compare the amino acid substitutions in DYSF found in horses to the information on protein domains and clinically significant variation in the human dysferlin (DYSF) protein. In order to do this, the equine protein models used in this disclosure must be compared to the canonical or reference sequence of the human protein in a public database that captures data from the published literature, such as UniProt.

A large number of pathogenic mutations in human DYSF are known. Many pathogenic alleles are nonsense mutations, that is, the mutation of a codon encoding an amino acid to a termination codon, causing the truncation of the encoded dysferlin at the site of the mutation. Other pathogenic alleles are frameshift mutations, that is, the addition or deletion of bases within coding regions where the number of bases is not an integral multiple of three, therefore altering the reading frame downstream of the mutation. The altered reading frame typically reaches a termination codon, causing truncation of the encoded dysferlin downstream of the mutation following a segment of altered amino acid sequence. There are also pathogenic missense alleles of DYSF, in which a point mutation causes the alteration of a single amino acid in the dysferlin protein sequence. A set of such alleles is presented in TABLE 1. Cited sources in this table are Aoki 2001 (Aoki et al. 2001 Neurology 57:271-278), Nguyen 2005 (Nguyen 2005 Hum Mut DOI: 10.1002/humu.9355), Krahn 2008 (Krahn et al. 2009 Hum Mut 30:E345-375 DOI: 10.1002/humu.20910), LMDD (http://www.dmd.nl), and ClinVar (https://www.ncbi.nlm.nih.gov/clinvar/).

Human patients homozygous for missense alleles of DYSF as listed in TABLE 1 may present as cases of Limb-Girdle Muscular Dystrophy 2B or other conditions that overlap this condition clinically, such as Miyoshi Myopathy, Proximodistal Myopathy, Pseudometabolic Myopathy, or Isolated HyperCKemia (a disorder in which serum levels of creatine kinase or CK, a muscle enzyme, are elevated, indicating damage to the sarcolemma).

TABLE 1

Pathogenic missense alleles of the C2B domain of human DYSF.

| Substitution | Domain | Reference |
|---|---|---|
| S209F | C2B | ClinVar |
| Q221H | C2B | ClinVar |
| I227T | C2B | Jin 2016 |
| P233L | C2B | ClinVar |
| G234E | C2B | Krahn 2009, ClinVar |
| R251W | C2B | ClinVar |
| T252M | C2B | Jin 2016, ClinVar |
| R253W | C2B | Nguyen 2005, ClinVar |
| H255P | C2B | ClinVar |
| E264D | C2B | UMD, ClinVar |
| L266R | C2B | UMD, ClinVar |
| I282T | C2B | UMD |
| I284T | C2B | Krahn 2009, ClinVar |

TABLE 1-continued

Pathogenic missense alleles of the C2B domain of human DYSF.

| Substitution | Domain | Reference |
|---|---|---|
| T285M | C2B | ClinVar |
| V286E | C2B | UMD, ClinVar |
| D288V | C2B | Jin 2016, ClinVar |
| S289P | C2B | ClinVar |
| S289F | C2B | ClinVar |
| G299R | C2B | Wenzel 2006, Spuler 2008, Krahn 2009, ClinVar |
| G299E | C2B | UMD, ClinVar |
| G299W | C2B | Spuler 2008, ClinVar, Hofhuis 2017 |

Cited sources in this table are:

ClinVar (https://www.ncbi.nlm.nih.gov/clinvar/), UMD (http://www.umd.be/DYSF/) Davis 2002 (Davis D B et al. 2002 J Biol Chem 277:22883-22888 DOI: 10.1074/jbc.M201858200)

Hofhuis 2017 (Hofhuis J et al. 2017 J Cell Sci 130:841-852 DOI: 10.1242/jcs.198861)

Huang 2007 (Huang Y et al. 2007 FASEB J. 21:732-742. DOI: 10.1096/fj.06-6628com)

Illarioshkin 2000 (Illarioshkin S N et al. 2000 Neurology 55:1931-1933)

Jin 2016 (Jib S-Q et al. 2016 Chin Med J 129:2287-2293 DOI: 10.4103/0366-6999.190671)

Krahn 2009 (Krahn M et al. 2009 Hum Mutat. 30:E345-375 DOI: 10.1002/humu.20910)

Nguyen 2005 (Nguyen K et al. 2005 Hum Mutat. 26:165 DOI: 10.1002/humu.9355),

Spuler 2008 (Spuler S et al. 2008 Ann Neurol. 63:323-328 DOI: 10.1002/ana.21309)

Wenzil 2006 (Wenzil K et al. 2006 Hum Mutat. 27:599-600 DOI: 10.1002/humu.9424)

The C2B domain of dysferlin is highly conserved overall. Comparison to the other two C2 domains with type II topology (C2A and C2E) is helpful in assessing the pathogenicity of missense alleles. TABLE 2 shows pathogenic missense alleles in the other two C2 domains with type II topology.

TABLE 2

Pathogenic missense alleles of the C2A and C2E domains of human DYSF.

| Substitution | Domain | Reference |
|---|---|---|
| M1V | C2A | ClinVar |
| M1T | C2A | ClinVar |
| I6N | C2A | ClinVar |
| W46R | C2A | UMD |
| W52R | C2A | Krahn 2009, ClinVar |
| V67D | C2A | Illarioshkin 2000, Davis 2002, Huang 2007, ClinVar, Hofhuis 2017 |
| V69G | C2A | ClinVar |
| T74M | C2A | ClinVar |
| R1331L | C2E | ClinVar |
| R1331C | C2E | ClinVar |
| L1341P | C2E | Wenzel 2006, ClinVar, Hofhuis 2017 |
| R1342Q | C2E | ClinVar |
| R1342G | C2E | Jin 2016 |
| R1342W | C2E | UMD, ClinVar |
| C1361R | C2E | UMD, Campanaro 2002 |
| P1400R | C2E | UMD, ClinVar |
| G1418D | C2E | ClinVar |

Cited sources in this table are:

ClinVar (https://www.ncbi.nlm.nih.gov/clinvar/), UMD (http://www.umd.be/DYSF/) Davis 2002 (Davis D B et al. 2002 J Biol Chem 277:22883-22888 DOI: 10.1074/jbc.M201858200)

Hofhuis 2017 (Hofhuis J et al. 2017 J Cell Sci 130:841-852 DOI: 10.1242/jcs.198861)

Huang 2007 (Huang Y et al. 2007 FASEB J. 21:732-742. DOI: 10.1096/fj.06-6628com)

Illarioshkin 2000 (Illarioshkin S N et al. 2000 Neurology 55:1931-1933)

Jin 2016 (Jib S-Q et al. 2016 Chin Med J 129:2287-2293 DOI: 10.4103/0366-6999.190671)

Krahn 2009 (Krahn M et al. 2009 Hum Mutat. 30:E345-375 DOI: 10.1002/humu.20910)

Wenzil 2006 (Wenzil K et al. 2006 Hum Mutat. 27:599-600 DOI: 10.1002/humu.9424)

FIG. 7 shows the sequence of the human DYSF coding sequence derived from NM_003494.3 (SEQ ID NO:16). The 5' UTR and 3' UTR have been removed; the sequence begins with the ATG start codon and ends with the TGA stop codon. The numbering of the first and last nucleotides corresponds to that of NM_003494.3. The sequence of the human exon corresponding to Exon B in horse as shown in FIG. 3 is indicated in bold.

FIG. 8 shows the sequence of the human DYSF protein sequence, equivalent to NP_003485.1 (SEQ ID NO:17). The numbering of the first and last amino acids corresponds to that of NP_003485.1. The sequence encoded by the human exon corresponding to Exon B in horse as shown in FIG. 3 is indicated in bold.

Comparison of the equine DYSF-R253W missense allele to the pathogenic human alleles presented in TABLE 1 is informative. FIG. 9 shows a comparison of that portion of the protein sequence of DYSF encoded by horse Exon B as defined in FIG. 3 from wild type (XP_023474694.1, shown here as SEQ ID NO:19) and DYSF-R253W (R253W, shown here as SEQ ID NO:20) to the protein sequence of DYSF encoded by human Exon 7 (NP_003485.1, shown here as SEQ ID NO:18). Between the sequences of the horse and human proteins in the alignment, an asterisk (*) indicates an identical amino acid in that position, while a space ( ) indicates the nonconservative substitution of an arginine (R) in horse for a glycine (G) at human position 247, and a plus sign (+) indicates the conservative substitution of an arginine (R) in horse for a lysine (K) at human position 256. No other amino acid substitutions are seen in comparison of the human sequence (SEQ ID NO:18) and the wild-type horse sequence (SEQ ID NO:19). The sequence from horse bearing the DYSF-R253W mutation (SEQ ID NO:20) has a nonconservative substitution of a tryptophan (W) for an arginine (R) that is found in human (SEQ ID NO:18) and the wild-type horse sequence (SEQ ID NO:19). This position, corresponding to position 253 in horse (SEQ ID NO:19, SEQ ID NO:20) and position 251 in human (SEQ ID NO:18) is indicated by bold and underlining.

FIG. 10 shows features of the dysferlin protein encoded by the human DYSF gene. The protein contains seven C2 calcium-binding domains designated C2A through C2G. The secondary structure of the protein sequence encoded by each of the C2 domains consists of eight segments assembling into beta sheet, with two different topologies described. Domains C2C, C2D, C2F, and C2G are designated as topology type I, while domains C2A, C2B, and C2E are designated as topology type II (C.Therrien et al. 2006 J. Neurological Sciences 250: 71-78). The positions of four additional conserved domains (DysfN, DysfC, annexin binding, and transmembrane) are also indicated (C.Therrien et al. 2006 J. Neurological Sciences 250: 71-78). Positions of pathogenic missense alleles listed in TABLE 1 are shown.

The sequence comparison between human and equine dysferlin proteins shows the high degree of sequence conservation between these two species. It also shows that the human equivalent to the equine DYSF-R253W allele would be DYSF-R251W. This allele has been observed in human patients and has been scored as pathogenic (TABLE 1). The extent of sequence conservation between horse and human is high, and it is of value to examine the extent of sequence conservation among a larger number of species.

FIG. 11 shows amino acid sequences of proteins encoded by the C2B domain of DYSF, including the position of the equine DYSF-R253W substitution. The portion of the human DYSF corresponding to the C2B domain, as identified by UniProt annotation (positions 207-302 of NP_003485.1, identical to O75923) was used as a probe in BLASTP searches of the protein sequence database to identify the corresponding region in the orthologous protein in a set of mammals. Extending this approach to more distantly related organisms (birds, reptile, amphibians, and fish) was not successful; either no match was found, or the top match was to a nonorthologus protein (e.g. myoferlin). In the alignment shown in FIG. 11, sequences that are identical over this range of positions in different species are clustered as a single SEQ ID NO.

The 44 species in the alignment shown in FIG. 11 are presented below with their common names, their scientific names, and the protein database ID from which the amino acid sequence is derived. Amino acid sequences identical over this range in different species have been clustered into single SEQ ID NOs for the alignment. The species associated with the SEQ ID NOs shown in the alignment are: SEQ ID NO:21 [Human (*Homo sapiens*, XP_005264642.1), Chimpanzee (*Pan troglodytes*, XP_016804238.1), Bonobo (*Pan paniscus*, XP_003808226.1), Western lowland gorilla (*Gorilla gorilla gorilla*, XP_004029449.2), Sumatran orangutan (*Pongo abelii*, XP_024097762.1)], SEQ ID NO:22 [Olive baboon (*Papio anubis*, XP_021780640.1), Rhesus macaque (*Macaca mulatta*, XP_014968111.1), Black snub-nosed monkey (*Rhinopithecus bieti*, XP_017733098.1)], SEQ ID NO:23 [Mouse (*Mus musculus*, XP_006506246.1), Brown rat (*Rattus norvegicus*, XP_006236829.1)], SEQ ID NO:24 [Praire vole (*Microtus ochrogaster*, XP_005369881.1), Mongolian gerbil (*Meriones unguiculatus*, XP_021497362.1)], SEQ ID NO:25 [Long-tailed chinchilla (*Chinchilla lanigera*, XP_013370151.1), Damora mole-rat (*Fukomys damarensis*, KF021095.1)], SEQ ID NO:26 [David's myotis (*Myotis davidii*, XP_006775358.1), Brandt's bat (*Myotis brandtii*, XP_005867829.1)], SEQ ID NO:27 [Large flying fox (*Pteropus vampyrus*, XP_023389621.1), Alpaca (*Vicugna pacos*, XP_015092494.1), Dromedary (*Camelus dromedaries*, XP_010992957.1), Bactrian camel (*Camelus bactrianus*, XP_010962007.1)], SEQ ID NO:28 [Horse (*Equus caballus*, XP_023474692.1), Donkey (*Equus asinus*, XP_014692144.1), Przewalski's horse (*Equus przewalskii*, XP_008534159.1)], SEQ ID NO:29 [Cat (*Felis catus*, XP_003984159.2), Leopard (*Panthera pardus*, XP_019297096.1)], SEQ ID NO:30 [Goat (*Capra hircus*, XP_017910544.1), Mouflon (*Ovis aries musimon*, XP_011978930.1)], SEQ ID NO:31 [Panamanian white-throated capuchin (*Cebus capucinus imitator*, XP_017377464.1)], SEQ ID NO:32 [Gray mouse lemur (*Microcebus murinus*, XP_012605526.1)], SEQ ID NO:33 [Philipine tarsier (*Carlito syrichta*, XP_008058745.1)], SEQ ID NO:34 [Northern greater galago (*Otolemur garnettii*, XP_012662868.1)], SEQ ID NO:35 [Coquerel's sifika (*Propithecus coquereli*, XP_012501927.1)], SEQ ID NO:36 [Chinese hamster (*Cricetulus griseus*, ERE66849.1)], SEQ ID NO:37 [Thirteen-lined ground squirrel (*Ictidomys tridecemlineatus*, XP_005322205.1)], SEQ ID NO:38 [Alpine marmot (*Marmota marmota marmota*, XP_015335007.1)], SEQ ID NO:39 [American beaver (*Castor canadensis*, XP_020009964.1)], SEQ ID NO:40 [Ferret (*Mustela putorius furo*, XP_004742226.1)], SEQ ID NO:41 [Great roundleaf bat (*Hipposideros armiger*, XP_019503212.1)], SEQ ID NO:42 [African bush elephant (*Loxodonta africana*, XP_023408298.1)], SEQ ID NO:43 [Wild boar (*Sus scrofa*, XP_013851496.2)], SEQ ID NO:44 [Cattle (*Bos taurus*, NP_001095960.1)], SEQ ID NO:45 [Minke whale (*Balaenoptera acutorostrata scammoni*, XP_007175590.1)], SEQ ID NO:46 [Giant panda (*Ailuropoda melanoleuca*, XP_019650380.1)], SEQ ID NO:47 [Killer whale (*Orcinus orca*, XP_004277106.1)], SEQ ID NO:48 [Koala (*Phascolarctos cinereus*, XP_020856837.1)], SEQ ID NO:49 [Tasmanian devil (*Sarcophilus harrisii*, XP_023351344.1)], SEQ ID NO:50 [Platypus (*Ornithorhynchus anatinus*, XP_007665017.1)].

The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the position of the DYSF-R253W substitution in horse in bold. The position of the DYSF-R253W substitution is indicated in bold in all of the sequences.

The overall sequence conservation of the C2B domain of dysferlin is quite high across mammals. The amino acid alteration seen in the equine DYSF-R253W substitution is not seen in any of the 44 species; all have an arginine (R) at this position. The comparison of dysferlin C2B sequences presented here refutes the hypothesis that the DYSF-R253W substitution is selectively neutral, and supports the claim that the DYSF-R253W mutation found in horses with PSSM2 is pathogenic.

Figure 12:
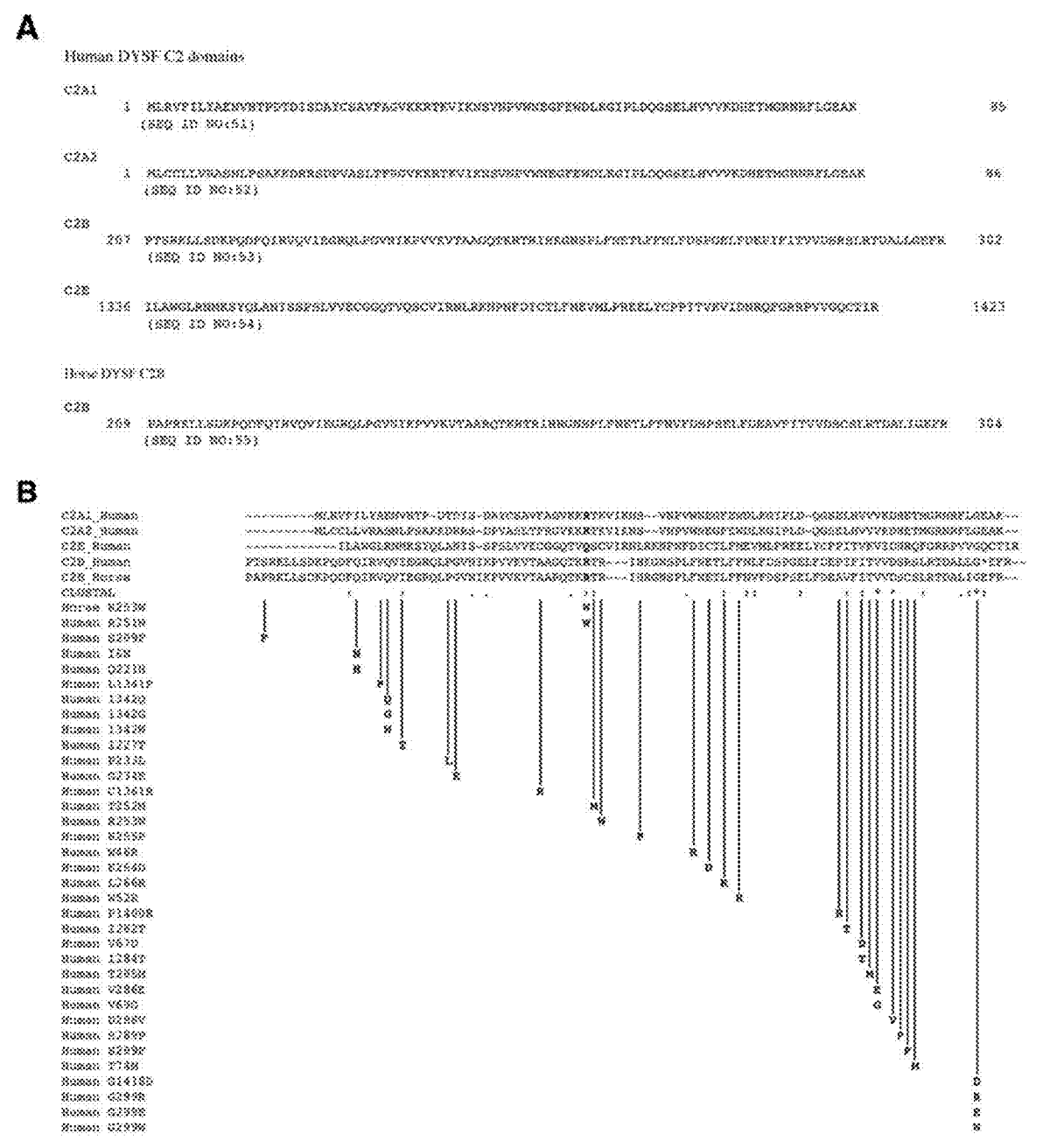

FIG. 12 shows comparison of the C2A, C2B, and C2E domains of dysferlin encoded by human DYSF to the C2B domain of dysferlin encoded by horse DYSF. (A) The amino acid sequences of two isoforms of the C2A domain of human dysferlin (SEQ ID NO:51 and SEQ ID NO:52), the C2B domain of human dysferlin (SEQ ID NO:53), the C2E domain of human dysferlin (SEQ ID NO:54), and the C2B domain of horse dysferlin (SEQ ID NO:55), are shown. (B) Clustal Omega was used to align these four sequences. The fifth line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The remaining lines show the position of the horse DYSF-R253W substitution and various pathogenic human substitutions (presented in TABLE 1 and TABLE 2) aligned to the consensus.

The comparison of C2A, C2B, and C2E domains reveals a much more limited number of highly conserved positions. The position affected by the equine DYSF-R253W mutation is highly conserved, with only arginine (R) and glutamine (Q) seen in this position. In general, there is a good correspondence between positions that are conserved and the positions of substitutions identified in pathogenic human DYSF alleles. This analysis also refutes the hypothesis that the DYSF-R253W substitution is selectively neutral, and supports the claim that the DYSF-R253W mutation found in horses with Polysaccharide Storage Myopathy type 2 (PSSM2), also known as Myofibrillar Myopathy (MFM) is pathogenic.

FIG. 13 shows portion of the current horse genome assembly (EquCab2, GCA_000002305.1) with coordinates as displayed in the UCSC Genome Browser centered on the chr15:31,225,630 position, the site of a substitution of an thymine (T) for a guanine (G) that results in the substitution of a threonine (T) for proline (P) at amino acid position 1290 in dysferlin as shown in FIG. 16 (SEQ ID NO:61). The reverse complement sequence is shown, with the site of a substitution of an adenine (A) for a cytosine (C) as indicated (SEQ ID NO:56). The single nucleotide polymorphism (SNP) defined by this base substitution is identified as rs1136366555 in dbSNP FIG. 14 shows a portion of the normal equine DYSF Coding DNA Sequence (SEQ ID NO:57) and the mutant DYSF Coding DNA Sequence (SEQ ID NO:58) bearing the C to A mutation at nucleotide position 4174 in this figure, corresponding to chr15:31,225,630 as shown in SEQ ID NO:56 (FIG. 13). This sequence is a region of perfect consensus among 21 different experimentally predicted mRNA isoforms. The numbering in FIG. 14 is that of isoform X1 (XM_023618907.1), which for this segment perfectly matches the numbering of isoforms X2 (XM_023618908.1), X4 (XM_023618910.1), and X5 (XM_023618911.1). The numbering of the start and end positions for X3 (XM_023618909.1) and X6 (XM_023618912.1) is 3685-4143. The numbering of the start and end positions for X7 (XM_023618913.1) is 3634-4092. The numbering of the start and end positions for X8 (XM_023618914.1) is 3726-4184. The numbering of the start and end positions for X9 (XM_023618915.1) and X12 (XM_023618918.1) is 3633-4091. The numbering of the start and end positions for X10 (XM_023618916.1) is 3684-4142. The numbering of the start and end positions for X11 (XM_023618917.1) and X13 (XM_023618919.1) is 3591-4049. The numbering of the start and end positions for X14 (XM_023618920.1) is 4038-4496. The numbering of the start and end positions for X15 (XM_023618921.1) is 3996-4454. The numbering of the start and end positions for X16 (XM_023618922.1) is 4037-4495. The numbering of the start and end positions for X17 (XM_023618923.1) is 3944-4402. The numbering of the start and end positions for X18 (XM_023618924.1) is 3995-4453. The numbering of the start and end positions for X19 (XM_023618925.1) is 3902-4360. The numbering of the start and end positions for X20 (XM_023618926.1) is 3943-4401. The numbering of the start and end positions for X21 (XM_023618927.1) is 3901-4359 In both sequences, the sequence of Exon I as shown in FIG. 15 is indicated in bold. The site of a C to A mutation site at nucleotide position 4174, corresponding to chr15:31, 225,630 in SEQ ID NO:56 (FIG. 13), and to to rs1136366555 in dbSNP, is underlined. The region of sequence comprising Exon I as shown in FIG. 15 is displayed as codons in the correct reading frame for both SEQ ID NO:57 and SEQ ID NO:58 in FIG. 17.

FIG. 15 shows a view of the current horse genome assembly (EquCab2, GCA_000002305.1) in the UCSC Genome Browser with exon sequences that match the partial DYSF Coding DNA Sequence (SEQ ID NO:57) and the mutant partial DYSF Coding DNA Sequence (SEQ ID NO:58). The DYSF Coding DNA Sequences correspond to Exons G, H, and I as indicated by the regions of sequence similarity of the translated genomic DNA to DYSF protein sequences from human (Homo), orangutan (Pongo), cattle (Bos), mouse (Mus), rat (Rattus) and DYSF protein sequences from the more distantly-related zebrafish (Danio). The sequence of Exon I with 10 bp of flanking intron sequence and its coordinates in the current horse assembly is displayed below the image from the UCSC Genome Browser (SEQ ID NO: 59).

FIG. 16 shows models of part of the normal protein sequence encoded by horse DYSF (XP_023474694.1, presented here as SEQ ID NO:60) corresponding to a translation of SEQ ID NO:57 shown in FIG. 14 and part of the altered protein sequence encoded by horse DYSF with the base substitution at chr15:31,225,630 (based on XP_023474694.1, presented here as SEQ ID NO:61) corresponding to a translation of SEQ ID NO:58 shown in FIG. 14. The portion of the protein encoded by Exon I as shown in FIG. 15 is indicated in bold, while the amino acid position affected by the base substitution of an adenine (A) for a cytosine (C) at the chr15:31,225,630 position, corresponding to rs1136366555 in dbSNP as shown in FIG. 13, is underlined. The amino acid positions in XP_023474694.1 are indicated at the beginning and end of the sequence.

FIG. 17 shows horse DYSF Exon I and flanking genomic DNA sequence from which PCR primers to amplify genomic DNA containing the site of the DYSF-P1290T mutation would be most appropriately derived. Genomic coordinates are as in FIG. 13. Exon I from chr15:31,225,648 to chr15:31,225,619 is shown broken into codons in the correct reading frame for the wild-type allele (SEQ ID NO:62) and the DYSF-P1290T allele (SEQ ID NO:63). Only the reference sequence from the assembly is shown for the flanking sequences. The codon affected by the G to T mutation site at nucleotide position chr15:31,225,630, corresponding to rs1136366555 in dbSNP as shown in FIG. 13 (C to A in the reverse complement as shown), is shown in bold, with the position of the base substitution indicated by underlining. The base substitution changes the bold three base codon from one coding for a proline (CCT) to one coding for a threonine (ACT). Example primers used experimentally to amplify genomic DNA containing the mutation site are shown in lower case [5"-GGTTGCAAACTCC-CAACTGT-3' (SEQ ID NO:64) and 5'-GATTTTT-CAAGCTGCCGAAG-3' (SEQ ID NO:65)].

Genomic DNA obtained from horses can be genotyped by amplifying a region containing a variant in the DYSF gene using Polymerase Chain Reaction (PCR), then sequencing the amplified DNA using Sanger sequencing. The variant allele DYSF-P1290T is abbreviated as P6, while the common or wild-type allele is abbreviated as N. The results can be scored as homozygous for the common or wild-type allele (N/N), heterozygous for the nucleotide substitution (N/P6), or homozygous for the nucleotide substitution (P6/P6).

FIG. 18 shows traces from Sanger DNA sequencing of amplified DYSF genomic DNA using primers shown in FIG. 17 (SEQ ID NO:64 and SEQ ID NO:65). The sequence of the forward strand is shown. The arrows in the figure indicate nucleotide position chr15:31,225,630, the site of a substitution of a thymine (T) for a guanine (G) in this position, corresponding to rs1136366555 in dbSNP, that creates the DYSF-P1290T variant. The traces show, from left to right, results for a horse homozygous for the wild-type or common allele (N/N), results for a horse heterozygous for the substitution (N/P6), and results for a horse homozygous for the substitution (P6/P6).

The sequence of the human DYSF coding sequence is presented in FIG. 7, while the sequence of the human DYSF protein sequence is presented in FIG. 8, as discussed above.

Comparison of the equine DYSF-P1290T missense allele to the pathogenic human alleles presented in TABLE 3 is informative. FIG. 19 shows a comparison of that portion of the protein sequence of DYSF encoded by horse Exon I from wild type (XP_023474694.1, shown here as SEQ ID NO:67) and DYSF-P1290T (P1290T, shown here as SEQ ID NO:68) to the protein sequence of DYSF encoded by human (NP_003485.1, shown here as SEQ ID NO:66). Between the sequences of the horse and human proteins in the alignment, an asterisk (*) indicates an identical amino acid in that position, while a space ( ) indicates the nonconservative substitution of an glycine (G) in horse for an arginine (R) in human at human position 1297, and a plus sign (+) indicates the conservative substitution of an alanine (A) in horse for a serine (S) in human at human position 1267, a tyrosine (Y) in horse for a histidine (H) in human position 1285, an aspartic acid (D) in horse for a glutamic acid (E) in human position 1294, and a glutamic acid (E) in horse for an aspartic acid (D) in human position 1300. No other amino acid substitutions are seen in comparison of the human sequence (SEQ ID NO:66) and the wild-type horse sequence (SEQ ID NO:67). The sequence from horse bearing the DYSF-P1290T mutation (SEQ ID NO:68) has a nonconservative substitution of a threonine (T) for a proline (P) that is found in human (SEQ ID NO:66) and the wild-type horse sequence (SEQ ID NO:67). This position, corresponding to position 1290 in horse (SEQ ID NO:67, SEQ ID NO:68) and position 1288 in human (SEQ ID NO:66) is indicated by bold and underlining.

Pathogenic and potentially pathogenic missense alleles are spread across the whole of dysferlin. Besides the pathogenic missense alleles described in the C2 calcium-binding domains C2B, C2A, and C2E described earlier and shown in TABLE 1 and TABLE 2, there are pathogenic and potentially pathogenic missense alleles in the interdomain region between C2D and C2E, as shown in TABLE 3.

TABLE 3

Pathogenic missense alleles of the C2D - C2E interdomain region of human DYSF.

| Substitution | Domain | Reference |
| --- | --- | --- |
| P1247L | C2D-C2E Interdomain | ClinVar |
| R1254W | C2D-C2E Interdomain | ClinVar |
| T1261M | C2D-C2E Interdomain | ClinVar |
| G1268E | C2D-C2E Interdomain | ClinVar |
| L1270R | C2D-C2E Interdomain | ClinVar |
| L1270P | C2D-C2E Interdomain | ClinVar |
| L1276P | C2D-C2E Interdomain | Jin 2016 |
| S1302P | C2D-C2E Interdomain | ClinVar |
| T1305K | C2D-C2E Interdomain | ClinVar |
| V1321F | C2D-C2E Interdomain | ClinVar |
| R1331L | C2D-C2E Interdomain | UMD, Hofhuis 2017 |
| E1335G | C2D-C2E Interdomain | UMD |

Cited sources in this table are:
ClinVar (https://www.ncbi.nlm.nih.gov/clinvar/), UMD (http://www.umd.be/DYSF/) Hofhuis 2017 (Hofhuis J et al. 2017 J Cell Sci 130:841-852 DOI: 10.1242/jcs.198861) Jin 2016 (Jib S-Q et al. 2016 Chin Med J 129:2287-2293 DOI: 10.4103/0366-6999.190671)

FIG. 20 shows features of the dysferlin protein encoded by the human DYSF gene. (A) The protein contains seven C2 calcium-binding domains designated C2A through C2G, shaded in gray. The positions of four additional conserved domains (DysfN, DysfC, annexin binding, and transmembrane) are also indicated (C.Therrien et al. 2006 J. Neurological Sciences 250: 71-78), also shaded in gray. The interdomain region between the C2D and C2E domains, affected by the horse DYSF-P1290T mutation, is indicated in light gray. (B) The interdomain region between the C2D and C2E domains is shown expanded, with positions of pathogenic and potentially pathogenic missense alleles listed in TABLE 3 shown. The horse DYSF-P1290T substitution corresponds to a proline at position 1288 in human, with no pathogenic or potentially pathogenic alleles identified at that position in human.

The extent of sequence conservation between horse and human is high, and it is of value to examine the extent of sequence conservation among a larger number of species, in order to assess the likelihood that the horse DYSF-P1290T allele is pathogenic.

FIG. 21 shows amino acid sequences of proteins encoded by part of the C2D-C2E interdomain region of DYSF, including the position of the equine DYSF-P1290T substitution. Part of the portion of the human DYSF corresponding to the C2D-C2E interdomain region, as identified by UniProt annotation (positions 1261-1320 of NP_003485.1, identical to O75923) was used as a probe in BLASTP searches of the protein sequence database to identify the corresponding region in the orthologous protein in a set of mammals. Extending this approach to more distantly related organisms (birds, reptile, amphibians, and fish) was not successful; either no match was found, or the top match was to a nonorthologus protein (e.g. myoferlin). In the alignment shown in FIG. 11, sequences that are identical over this range of positions in different species are clustered as a single SEQ ID NO.

The 46 species in the alignment shown in FIG. 21 are presented below with their common names, their scientific names, and the protein database ID from which the amino acid sequence is derived. Amino acid sequences identical over this range in different species have been clustered into single SEQ ID NOs for the alignment. The species associated with the SEQ ID NOs shown in the alignment are: SEQ ID NO:69 [Human (*Homo sapiens*, XP_520786.2), Chimpanzee (*Pan troglodytes*, XP_016804234.1), Bonobo (*Pan paniscus*, XP_003808233.1), Western lowland gorilla (*Gorilla gorilla gorilla*, XP_004029453.2)], SEQ ID NO:70 [Sumatran orangutan (*Pongo abelii*, XP_024097764.1), Panamanian white-throated capuchin (*Cebus capucinus imitator*, XP_017377462.1)], SEQ ID NO:71 [Mouse (*Mus musculus*, XP_006506242.1), Rat (*Rattus norvegicus*, XP_006236834.1)], SEQ ID NO:72 [David's myotis (*Myotis davidii*, XP_006775352.1), Great roundleaf bat (*Hipposideros armiger*, XP_019503204.1)], SEQ ID NO:73 [Dromedary (*Camelus dromedarius*, XP_010992957.1), Bactrian camel (*Camelus bactrianus*, XP_010962003.1), Alpaca (*Vicugna pacos*, XP_015092494.1)], SEQ ID NO:74 [Cat (*Felis catus*, XP_003984159.2), Leopard (*Panthera pardus*, XP_019297033.1)], SEQ ID NO:75 [Cattle (*Bos taurus*, NP_001095960.1), Goat (*Capra hircus*, XP_017910552.1), Mouflon (*Ovis aries musimon*, XP_011978926.1)], SEQ ID NO:76 [Wild boar (*Sus scrofa*, XP_013851496.2), Sunda pangolin (*Manis javanica*, XP_017524151.1)], SEQ ID NO:77 Olive baboon (*Papio anubis*, XP_021780643.1), SEQ ID NO:78 Rhesus macaque (*Macaca mulatta*, XP_014968113.1), SEQ ID NO:79 Black snub-nosed monkey (*Rhinopithecus bieti*, XP_017733087.1), SEQ ID NO:80 Gray mouse lemur (*Microcebus murinus*, XP_012605531.1), SEQ ID NO:81 Philipine tarsier (*Carlito syrichta*, XP_008058745.1), SEQ ID NO:82 Northern greater galago (*Otolemur garnettii*, XP_012662869.1), SEQ ID NO:83 Coquerel's sifika (*Propithecus coquereli*, XP_012501928.1), SEQ ID NO:84 Chinese hamster (*Cricetulus griseus*, XP_027284348.1), SEQ ID NO:85 Prairie vole (*Microtus ochrogaster*, XP_005369881.1), SEQ ID NO:86 Mongolian gerbil (*Meriones unguiculatus*, XP_021497376.1), SEQ ID NO:87 Thirteen-lined ground squirrel (*Ictidomys tridecemlineatus*, XP_005322200.1), SEQ ID NO:88 Long-tailed chinchilla (*Chinchilla lanigera*, XP_005385648.1), SEQ ID NO:89 Alpine marmot (*Marmota marmota marmota*, XP_015335021.1), SEQ ID NO:90 American beaver (*Castor canadensis*, XP_020009964.1), SEQ ID NO:91 Ferret (*Mustela putorius furo*, XP_004742233.1), SEQ ID NO:92 Damora mole-rat (*Fukomys damarensis*, XP_010607925.1), SEQ ID NO:93 Brandt's bat (*Myotis brandtii*, XP_005867829.1), SEQ ID NO:94 Large flying fox (*Pteropus vampyrus*, XP_023389621.1), SEQ ID NO:95 Horse (*Equus caballus*, XP_023474694.1), SEQ ID NO:96 Donkey (*Equus asinus*, XP_014692152.1), SEQ ID NO:97 African bush elephant (*Loxodonta africana*, XP_023408298.1), SEQ ID NO:98 Minke whale (*Balaenoptera acutorostrata scammoni*, XP_007175594.1), SEQ ID NO:99 Giant panda (*Ailuropoda melanoleuca*, XP_019650381.1), SEQ ID NO:100 Killer whale (*Orcinus orca*, XP_004277100.1), SEQ ID NO:101 Koala (*Phascolarctos cinereus*, XP_020856831.1), SEQ ID NO:102 Platypus (*Ornithorhynchus anatinus*, XP_007665017.1)

The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the position of the DYSF-P1290T substitution in horse in bold. The position of the DYSF-P1290T substitution is indicated in bold in all of the sequences.

The overall sequence conservation of the C2D-C2E interdomain region of dysferlin is quite high across mammals. The amino acid alteration seen in the equine DYSF-P1290T substitution is not seen in any of the 44 species; all have a proline (P) at this position. The comparison of dysferlin C2D-C2E interdomain sequences presented here refutes the hypothesis that the DYSF-P1290T substitution is selectively neutral, and supports the claim that the DYSF-P1290T mutation found in horses with PSSM2 is pathogenic.

Pyridine Nucleotide-Disulfide Oxidoreductase Domain-Containing Protein 1 (PYROXD1)

A mutation in the equine PYROXD1 coding region (encoding the muscle protein pyridine nucleotide-disulfide oxidoreductase domain-containing protein 1) is present in many populations of horses affected by Polysaccharide Storage Myopathy type 2 (PSSM2), also known as Myofibrillar Myopathy (MFM). The difference in the genomic DNA between horses with PSSM2, also known as MFM, and control horses include a G-to-C substitution in PYROXD1 Exon 12 (as defined in FIG. 15) at nucleotide position chr6:47,661,977 of the current horse genome assembly (EquCab2, GCA_000002305.1), as shown in FIG. 13).

FIG. 22 shows a portion of the current horse genome assembly (EquCab2, GCA_000002305.1) with coordinates as displayed in the UCSC Genome Browser centered on the chr6:47,661,977 position, the site of a substitution of a cytosine (C) for a guanine (G) that results in the substitution of a histidine (H) for an aspartate (D) at amino acid position 492 in pyridine nucleotide-disulfide oxidoreductase domain-containing protein 1 (PYROXD1) as shown in FIG. 16 (SEQ ID NO:60). The single nucleotide polymorphism (SNP) defined by this base substitution is identified as rs1136260157 in dbSNP.

There are five predicted transcripts of the PYROXD1 coding region in public databases. These models differ somewhat in ways not relevant to the PYROXD1-D492H mutation. All five isoforms share a common segment that includes the chr6:47,661,977 position. This common segment is shown in FIG. 23.

FIG. 23 shows a portion of the normal equine PYROXD1 Coding DNA Sequence (SEQ ID NO:104) and a portion of the mutant PYROXD1 Coding DNA Sequence (SEQ ID NO:105) bearing the G to C mutation at nucleotide position 1548 in this figure, corresponding to chr6:47,661,977 as shown in SEQ ID NO:103 (FIG. 22). This sequence is a region of perfect consensus among five different experimentally predicted mRNA isoforms. The numbering in FIG. 23 is that of isoform X1 (XM_001502130.5), with the segment from 238 to 1583 shown. The numbering of the start and end positions for X2 (XM_023643216.1) is 148-1493. The numbering of the start and end positions for X3 (XM_023643217.1) is 187-1532. The numbering of the start and end positions for X4 (XM_023643218.1) is 151-1496. The numbering of the start and end positions for X5 (XM_023643219.1) is 191-1536. In both sequences the sequence of Exon 12 as shown in FIG. 24 is indicated in bold. The site of a G to C mutation at nucleotide position 1548, corresponding to 47,661,977 in SEQ ID NO:103 (FIG. 22), and to rs1136260157 in dbSNP, is underlined. The region of sequence comprising Exon 12 as shown in FIG. 24 is displayed as codons in the correct reading frame for both SEQ ID NO:104 and SEQ ID NO:1057 in FIG. 26.

For the sake of simplicity, the amino acid substitution caused by the substitution of an cytosine (C) for a guanine (G) at the chr6:47,661,977 position, identified as rs1136260157 in dbSNP, will be referred to as PYROXD1-D492H, based on SEQ ID NO:108. The amino acid substitution caused by this mutation will remain the same regardless of the numerical position of the affected codon in alternative gene models. The wild-type (e.g., also referred to herein as "normal" or "unaffected") allele of this coding region may be referred to as D492 and the mutant allele D492H.

FIG. 24 shows a view of the current horse genome assembly (EquCab2, GCA_000002305.1) in the UCSC Genome Browser with exon sequences that match the PYROXD1 Coding DNA Sequence (SEQ ID NO:104) and the mutant PYROXD1 Coding DNA Sequence (SEQ ID NO:105) in a BLAT search. The PYROXD1 Coding DNA Sequences in horse correspond to PYROXD1 coding sequences in other species as indicated by the regions of sequence similarity of the translated genomic DNA to PYROXD1 protein sequences from human (Homo), orangutan (Pongo), cattle (Bos), mouse (Mus), rat (Rattus), African clawed frog (Xenopus), zebrafish (Danio), chicken (Gallus), and fruit fly (Drosophila). Exon 12, which contains the guanine (G) to cytosine (C) variant at chr6:47,661,977 as shown in SEQ ID NO:55 (FIG. 13), is indicated below the image of the browser window. The sequence of horse Exon 12 with 10 nucleotides of flanking intron sequence and its coordinates in the current horse assembly is displayed below the image from the UCSC Genome Browser (SEQ ID NO:106).

Conceptual translation of the nucleic acid sequences shown in FIG. 23 (SEQ ID NO:104 and SEQ ID NO:105) yields the amino acid sequences for the proteins shown in FIG. 25. FIG. 25 shows models of part of the normal protein sequence encoded by horse PYROXD1 (XP_001502180.3, presented here as SEQ ID NO:107) corresponding to a translation of SEQ ID NO:104 shown in FIG. 23 and part of the altered protein sequence encoded by mutant horse PYROXD1 (adapted from XP_001502180.3, presented here as SEQ ID NO:108) with the base substitution at chr6:47,661,977 corresponding to a translation of SEQ ID NO:105 shown in FIG. 23. The portion of the protein encoded by Exon 12 is indicated in bold, while the amino acid at position 492 affected by the base substitution of a cytosine (C) for a guanine (G) at the chr6:47,661,977 position as shown in FIG. 23, is underlined. The amino acid positions in XP_001502180.3 are indicated at the beginning and end of the sequence.

FIG. 26 shows horse PYROXD1 Exon 12 and flanking genomic DNA sequence from which PCR primers to amplify genomic DNA containing the site of the PYROXD1-D492H mutation would be most appropriately derived. Genomic coordinates are as in FIG. 22. Exon 12 from chr6:47,661,764 to chr6:47,662,012 is shown broken into codons in the correct reading frame for the wild-type allele (SEQ ID NO:104) and the PYROXD1-D492H allele (SEQ ID NO:105). Only the reference sequence from the assembly is shown for the flanking sequences. The codon affected by the G to C mutation site at nucleotide position chr6:47,661,977, as shown in FIG. 22 is shown in bold, with the position of the base substitution indicated by underlining. The base substitution changes the bold three base codon from one coding for an aspartate (GAT) to one coding for a histidine (CAT). Example primers used experimentally to amplify genomic DNA containing the mutation site [5'-CAGATTTTCTGCTGGCCATT-3' (SEQ ID NO:111) and 5-TGGTCATCATTAAATCAGTGCAA-3' (SEQ ID NO:112)] are shown in lower case in the figure.

Genomic DNA obtained from horses can be genotyped by amplifying a region containing a variant in the PYROXD1 gene using Polymerase Chain Reaction (PCR), then sequencing the amplified DNA using Sanger sequencing. The variant allele PYROXD1-D492H is abbreviated as P8, while the common or wild-type allele is abbreviated as n. The results can be scored as homozygous for the common or wild-type allele (n/n), heterozygous for the nucleotide substitution (n/P8), or homozygous for the nucleotide substitution (P8/P8).

FIG. 27 shows traces from Sanger DNA sequencing of amplified PYROXD1 genomic DNA using primers shown in FIG. 26 (SEQ ID NO:111 and SEQ ID NO:112). The arrows in the figure indicate nucleotide position chr6:47,661,977, the site of a substitution of a cytosine (C) for a guanine (G) in this position that creates the PYROXD1-D492H variant. The traces show, from left to right, results for a horse homozygous for the wild-type or common allele (n/n), results for a horse heterozygous for the substitution (n/P8), and results for a horse homozygous for the substitution (P8/P8).

The human ortholog of the equine PYROXD1 gene encodes pyridine nucleotide-disulfide oxidoreductase domain-containing protein 1, one member of a family of nuclear-cytoplasmic pyridine nucleotide-disulfide reductases (PNDR). These are flavoproteins, bound to flavin adenine dinucleotide (FAD), that catalyze pyridine-nucleotide-dependent (nicotinamide adenine dinucleotide or NAD) reduction of thiol residues in other proteins. PYROXD1 differs from five other human class I PNDRs, dihydrolipoamide dehydrogenase (DLD), glutathione reductase (GSR), thioredoxin 1, 2, and 3 (TXNRD1, TXNRD2, and TXNRD3), in not having a consensus redox active site in the oxidoreductase domain, and in not having a conserved C-terminal dimerization domain found in all other class I PNDRs; instead, it bears a highly conserved C-terminal nitrile reductase domain. Recessive mutations causing a partial loss of function of PYROXD1 are associated with early-onset myopathy in humans (O'Grady et al. 2016 Am J Hum Genet. 99:1086-1105 DOI: 10.1016/j.ajhg.2016.09.005).

Human patients with various mutations in PYROXD1 show progressive weakness, reduction in muscle bulk, and some experience difficulty walking in the second decade of life. Muscle biopsies show central nuclei and disorganized inclusions with positive staining for the Z disc proteins desmin (encoded by DES) and myotilin (encoded by MYOT). Electron microscopy shows sarcomeric disorganization including disorganized Z discs and nemaline rods (a finding associated with several different types of Nemaline Myopathy). The myopathy associated with mutations in PYROXD1 in humans therefore has features associated with several different types of inherited myopathies in humans (Centronuclear Myopathy, Myofibrillar Myopathy, and Nemaline Myopathy).

In mouse, the Knockout Mouse Project (KOMP), a high-throughput gene knockout project, generated a loss-of-function allele of PYROXD1. Mice homozygous for the knockout allele die as embryos prior to organogenesis. Heterozygotes were smaller than normal and had abnormal vertebrae morphology. The muscle phenotype of heterozygotes has not been studied in detail, but it is evident from these results that a reduction in the level of pyridine nucleotide-disulfide oxidoreductase domain-containing protein 1 has phenotypic consequences, that is, the gene is haploinsufficient, and the activity of the pyridine nucleotide-disulfide oxidoreductase domain-containing protein 1 polypeptide is limiting.

In zebrafish, injection of morpholinos (a synthetic molecule containing DNA bases attached to a backbone of methylenemorpholine rings linked through phosphorodiamidate groups) targeting expression of ryroxd1 (the zebrafish ortholog of horse and human PYROXD1) causes reduction of the Ryroxd1 protein. Treated embryos show fragmentation of muscle fibers, loss of Z disc structure, and the formation of nemaline bodies. Treated embryos exhibit impaired swimming performance. These defects can be partially reversed through the injection of human PYROXD1 mRNA. These experiments show that PYROXD1 function is necessary for both normal muscle structure and function in zebrafish (O'Grady et al. 2016 Am J Hum Genet. 99:1086-1105).

In Drosophila, two different lines ubiquitously expressing RNA interference constructs for CG10721 (the Drosophila homolog of horse and human PYROXD1) were developed (Saha et al. 2018 Physiol Genomics doi:10.1152). Flies bearing these constructs failed to complete development, failing to emerge from their pupal cases, demonstrating the importance of PYROXD1 and its homologs in development.

It is therefore informative to compare the horse PYROXD1 gene and the protein that it encodes with the human ortholog. FIG. 28 shows the partial sequence of the human PYROXD1 coding sequence derived from NM_024854.4 (SEQ ID NO:113). This sequence is a region of perfect consensus among three different experimentally predicted mRNA isoforms. The numbering of the first and last nucleotides corresponds to that of NM_024854.4, with the segment from 619 to 1630 shown. The numbering of the start and end positions for transcript variant 2 (NM_001350912.1) is 1032-2043. The numbering of the start and end positions for transcript variant 3 (NM_001350913.1) is 545-1556. The sequence of Exon 12 is indicated in bold. The 3' UTR has been removed; the sequence begins with beginning of the consensus among the three isoforms and ends with the TAA stop codon.

FIG. 29 shows the partial sequence of the human PYROXD1 protein sequence, showing a translation of SEQ ID NO:113, equivalent to NP_079130.2 (SEQ ID NO:114). The numbering of the first and last amino acids corresponds to that of NP_079130.2.

FIG. 30 shows a comparison of that portion of the protein sequence of PYROXD1 encoded by horse Exon 12 from wild type (XP_001502180.3, shown here as SEQ ID NO:116) and PYROXD1-D492H (D492H, derived from XP_001502180.3 and shown here as SEQ ID NO:117) to the protein sequence of PYROXD1 encoded by human Exon 12 (NP_079130.2, shown here as SEQ ID NO:115). Between the sequences of the horse and human proteins in the alignment, an asterisk (*) indicates an identical amino acid in that position, while a plus sign (+) indicates the following conservative substitutions: a glutamine (Q) for an arginine (R) at human position 444, a valine (V) for an isoleucine (I) at human position 447, an alanine (A) for a serine (S) at human position 483, and an aspartate (D) for an asparagine (N) at human position 492. The sequence from horse bearing the PYROXD1-D492H mutation (SEQ ID NO:117) has a nonconservative substitution of a histidine (H) for an aspartate (D) at horse position 492, corresponding to human position 490. This position is indicated in bold for all three sequences. The wild-type horse sequence (SEQ ID NO:116) matches the human sequence (SEQ ID NO:115) at this position.

FIG. 31 shows features of the pyridine nucleotide-disulfide oxidoreductase domain-containing protein 1 protein encoded by the human PYROXD1 gene. The human protein has 500 amino acids and two domains: the pyridine nucleotide-disulfide oxidoreductase domain (amino acids 39-361) and the NADH-dependent nitrite reductase domain (447-494) as described in O'Grady et al. 2016 Am J Hum Genet. 99:1086-1105. Positions of two human pathogenic missense alleles (N155I and Q372H, O'Grady et al. 2016 Am J Hum Genet. 99:1086-1105) are shown, as is the position of the horse D492H mutation described herein.

The sequence comparison between the proteins encoded by horse and human PYROXD1 shows the high degree of sequence conservation between these two species. The extent of sequence conservation is so high that it is difficult to evaluate whether this comparison offers any evidence that the equine PYROXD1-D492H allele would be expected to be pathogenic.

FIG. 32 shows partial amino acid sequences of proteins encoded by PYROXD1, including the position of the equine PYROXD1-D492H substitution. A portion of the human PYROXD1 protein sequence was used as a probe to identify the corresponding region in the orthologous protein across a wide range of species, including mammals, birds, reptiles, amphibians, and fish. In the alignment shown in FIG. 32, sequences that are identical over this range of positions are clustered as a single SEQ ID NO.

The 92 species in the alignment shown in FIG. 32 are presented below with their common names, their scientific names, and the protein database ID from which the amino acid sequence is derived. Amino acid sequences identical over this range in different species have been clustered into single SEQ ID NOs for the alignment. The species associated with the SEQ ID NOs shown in the alignment are: SEQ ID NO:118 [Chimpanzee (*Pan troglodytes*, XP_520786.2), Bonobo (*Pan paniscus*, XP_003828944.1), Western lowland gorilla (*Gorilla gorilla gorilla*, XP_018894407.1), Olive baboon (*Papio anubis*, XP_009178608.1), Rhesus macaque (*Macaca mulatta*, EHH20571.1), Panamanian white-throated capuchin (*Cebus capucinus imitator*, XP_017378442.1), Philipine tarsier (*Carlito syrichta*, XP_008064020.1), Coquerel's sifika (*Propithecus coquereli*, XP_012496437.1)], SEQ ID NO:119 [Sumatran orang-utan (*Pongo abelii*, NP_001127199.1), Gray mouse lemur (*Microcebus murinus*, XP_012640956.1), Large flying fox (*Pteropus vampyrus*, XP_011379886.1), Great roundleaf bat (*Hipposideros armiger*, XP_019485916.1), African bush elephant (*Loxodonta africana*, XP_003405731.1)], SEQ ID NO:120 [Mouse (*Mus musculus*, XP_017177048.1), Mongolian gerbil (*Meriones unguiculatus*, XP_021514531.1), Sunda pangolin (*Manis javanica*, XP_017517789.1)], SEQ ID NO:121 [Black snub-nosed monkey (*Rhinopithecus bieti*, XP_017744103.1), Thirteen-lined ground squirrel (*Ictidomys tridecemlineatus*, XP_021584516.1), Alpine marmot (*Marmota marmota marmota*, XP_015353707.1)], SEQ ID NO:122 [David's myotis (*Myotis davidii*, ELK23147.1), Brandt's bat (*Myotis brandtii*, XP_014397831.1)], SEQ ID NO:123 [Horse (*Equus caballus*, XP_005611026.1), Donkey (*Equus asinus*, XP_014687887.1), Przewalski's horse (*Equus przewalskii*, XP_008533269.1)], SEQ ID NO:124 [Dromedary (*Camelus dromedarius*, XP_010987132.1), Bactrian camel (*Camelus bactrianus*, XP_010944895.1), Wild boar (*Sus scrofa*, XP_020947912.1), Cattle (*Bos taurus*, XP_005206989.1), Goat (*Capra hircus*, XP_017903901.1), Sheep (*Ovis aries*, XP_012030611.1), Mouflon (*Ovis aries musimon*, XP_012018062.1), Central European red deer (*Cervus elaphus hippelaphus*, OWK03976.1), Minke whale (*Balaenoptera acutorostrata scammoni*, XP_007195125.1), Killer whale (*Orcinus orca*, XP_004270982.1)], SEQ ID NO:125 [Cat (*Felis catus*, XP_006933619.1), Leopard (*Panthera pardus*, XP_019307710.1)], SEQ ID NO:126 Human (*Homo sapiens*, NP_079130.2), SEQ ID NO:127 Northern greater galago (*Otolemur garnettii*, XP_003792495.1), SEQ ID NO:128 Rat (*Rattus norvegicus*, EDM01504.1), SEQ ID NO:129 Chinese hamster (*Cricetulus griseus*, ERE65977.1), SEQ ID NO:130 Prairie vole (*Microtus ochrogaster*, XP_005364695.1), SEQ ID NO:131 Long-tailed chinchilla (*Chinchilla lanigera*, XP_005379114.1), SEQ ID NO:132 American beaver (*Castor canadensis*, XP_020016064.1), SEQ ID NO:133 Ferret (*Mustela putorius furo*, XP_004755775.1), SEQ ID NO:134 Damora mole-rat (*Fukomys damarensis*, XP_010613965.1), SEQ ID NO:135 Alpaca (*Vicugna pacos*, XP_015091099.1), SEQ ID NO:136 Giant panda (*Ailuropoda melanoleuca*, XP_002926616.1), SEQ ID NO:137 Koala (*Phascolarctos cinereus*, XP_020849955.1), SEQ ID NO:138 Tasmanian devil (*Sarcophilus harrisii*, XP_003771207.1), SEQ ID NO:139 Gray short-tailed opossum (*Monodelphis domestica*, XP_001365452.2), SEQ ID NO:140 [Bald eagle (*Haliaeetus leucocephalus*, XP_010564402.1), Golden eagle (*Aquila chrysaetos canadensis*, XP_011574851.1), Chicken (*Gallus gallus*, NP_001264205.1), Downy woodpecker (*Picoides pubescens*, XP_009904475.1), Turkey (*Meleagris gallopavo*, XP_003202569.1), Speckled mousebird (*Colius striatus*, XP_010208275.1), Emperor penguin (*Aptenodytes forsteri*, XP_009277280.1), Rock dove (*Columba livia*, XP_021151605.1), Band-tailed pigeon (*Patagioenas fasciata monilis*, OPJ70652.1), Adélie penguin (*Pygoscelis adeliae*, KFW73339.1), Ruff (*Calidris pugnax*, XP_014815036.1), Japanese quail (*Coturnix japonica*, XP_015723825.1), Crested ibis (*Nipponia nippon*, XP_009463403.1), Anna's hummingbird (*Calypte anna*, XP_008500751.1), Little egret (*Egretta garzetta*, KFP11017.1), Chimney swift (*Chaetura pelagica*, KFU93618.1), Scaled quail (*Callipepla squamata*, OXB63337.1), Common cuckoo (*Cuculus canorusz*, XP_009558366.1), Peregrine falcon (*Falco peregrinus*, XP_013156768.1)], SEQ ID NO:141 [Zebra finch (*Taeniopygia guttata*, XP_002200247.1), Society finch (*Lonchura striata domestica*, XP_021407730.1)], SEQ ID NO:142 Northern carmine bee-eater (*Merops nubicus*, KFQ27091.1), SEQ ID NO:143 North Island brown kiwi (*Apteryx australis mantelli*, XP_013802597.1), SEQ ID NO:144 American crow (*Corvus brachyrhynchos*, KF060564.1), SEQ ID NO:145 Hooded crow (*Corvus cornix cornix*, XP_010402574.2), SEQ ID NO:146 Atlantic canary (*Serinus canaria*, XP_009093423.1), SEQ ID NO:147 Common starling (*Sturnus vulgaris*, XP_014735476.1), SEQ ID NO:148 Blue-crowned manakin (*Lepidothrix coronata*, XP_017660339.1), SEQ ID NO:149 Turquoise-fronted amazon (*Amazona aestiva*, KQK78799.1), SEQ ID NO:150 Schlegel's Japanese gecko (*Gekko japonicus*, XP_015277871.1), SEQ ID NO:151 Green anole (*Anolis carolinensis*, XP_003220806.1), SEQ ID NO:152 Burmese python (*Python bivittatus*, XP_007420993.1), SEQ ID NO:153 Central bearded dragon (*Pogona vitticeps*, XP_020669436.1), SEQ ID NO:154 Brown spotted pit viper (*Protobothrops mucrosquamatus*, XP_015682645.1), SEQ ID NO:155 King cobra (*Ophiophagus hannah*, ETE62148.1), SEQ ID NO:156 Common garter snake (*Thamnophis sirtalis*, XP_013928623.1), SEQ ID NO:157 West Indian Ocean coelacanth (*Latimeria chalumnae*, XP_005998922.1), SEQ ID NO:158 Whale shark (*Rhincodon typus*, XP_020373590.1), SEQ ID NO:159 Australian ghostshark (*Callorhinchus milii*, XP_007884060.1), SEQ ID NO:160 Atlantic salmon (*Salmo salar*, XP_014008456.1), SEQ ID NO:161 African clawed frog (*Xenopus laevis*, XP_018107310.1), SEQ ID NO:162 Common carp (*Cyprinus carpio*, KTF74061.1)

The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the position of the PYROXD1-D492H substitution in horse in bold. The position of the PYROXD1-D492H substitution is indicated in bold in all of the aligned sequences.

The overall sequence conservation of this portion of the PYROXD1 protein is quite high. The amino acid alteration seen in the equine PYROXD1-D492H is not seen in any of the 92 species; all have an aspartate (D) or asparagine (N) at this position. The comparison of PYROXD1 sequences presented here refutes the hypothesis that the PYROXD1-D492H substitution is selectively neutral, and supports the claim that the PYROXD1-D492H mutation found in horses with Polysaccharide Storage Myopathy type 2 (PSSM2), also known as Myofibrillar Myopathy (MFM), is pathogenic.

Collagen Type VI Alpha 3 Chain (COL6A3)

A mutation in the equine COL6A3 coding region (encoding the muscle protein collagen type VI alpha 3 chain) is present in many populations of horses affected by Polysaccharide Storage Myopathy type 2 (PSSM2). The difference in the genomic DNA between horses with PSSM2 and control horses include a G-to-C substitution in COL6A3 Exon 26 (as defined in FIG. 33) at nucleotide position chr6:23,480,621 of the current horse genome assembly (EquCab2, GCA_000002305.1), as shown in FIG. 33.

FIG. 33 shows portion of the current horse genome assembly (EquCab2, GCA_000002305.1) with coordinates as displayed in the UCSC Genome Browser centered on the chr6:23,480,621 position, the site of a substitution of a guanine (G) for a cytosine (C) on the forward strand that results in the substitution of an alanine (A) for a glycine (G) at amino acid position 2182 in collagen type VI alpha 3 chain (COL6A3) as shown in FIG. 36 (SEQ ID NO:168). The reverse complement sequence is shown, with the site of a substitution of a cytosine (C) for a guanine (G) on the reverse strand as indicated (SEQ ID NO:163). The single nucleotide polymorphism (SNP) defined by this base substitution is identified as rs1139437410 in dbSNP.

The NCBI database contains five models for the mature horse mRNA containing the coding sequence (CDS) for COL6A3: XM_023642645.1, XM_023642646.1, XM_014740385.2, XM_023642647.1, and XM_023642648.1. There is a complete consensus among the five models for the portion of the coding sequence that encodes the five collagen-like repeats in the middle of the COL6A3 protein (see FIG. 34). For XM_023642645.1 (transcript variant X1), the coordinates are 6356-7363. The other four isoforms have coordinates as follows: XM_023642646.1 (5751-6758), XM_014740385.2 (5733-6740), XM_023642647.1 (5130-6137), and XM_023642648.1 (4530-5537).

FIG. 34 shows a portion of the normal equine COL6A3 Coding DNA Sequence (SEQ ID NO:164) and a portion of the mutant COL6A3 Coding DNA Sequence (SEQ ID NO:165) bearing the G to C mutation at nucleotide position 6792 in this figure, corresponding to chr6:23,480,621 as shown in SEQ ID NO:163 (FIG. 33). The numbering in FIG. 34 is that of the COL6A3 coding sequence (CDS) model XM_023642645.1; the sequence presented comprises the coding sequence for the five collagen-like domains in the middle of the protein. In both sequences the sequence of the third collagen-like domain, partially encoded by Exon 26, as shown in FIG. 35 is indicated in bold. The site of a G to C mutation at nucleotide position 6792, corresponding to 23,480,621 in SEQ ID NO:163 (FIG. 33), and to rs1139437410 in dbSNP, is underlined. The region of sequence comprising Exon 26 is displayed as codons in the correct reading frame for both SEQ ID NO:164 and SEQ ID NO:165 in FIG. 37.

FIG. 35 shows a view of the current horse genome assembly (EquCab2, GCA_000002305.1) in the UCSC Genome Browser with exon sequences that match the COL6A3 Coding DNA Sequence (SEQ ID NO:164) and the mutant COL6A3 Coding DNA Sequence (SEQ ID NO:165) in a BLAT search. The COL6A3 Coding DNA Sequences in horse correspond to COL6A3 coding sequences in other species as indicated by the regions of sequence similarity of the translated genomic DNA to COL6A3 protein sequences from human (Homo), mouse (Mus), and dog (Canus). Exon 26, which contains the guanine (G) to cytosine (C) variant at chr6:23,480,621 on the reverse strand as shown in SEQ ID NO:163 (FIG. 33), is indicated below the image of the browser window. The sequence of horse Exon 26 with 10 nucleotides of flanking intron sequence and its coordinates in the current horse assembly is displayed below the image from the UCSC Genome Browser (SEQ ID NO:166).

The translation of horse COL6A3 CDS does not always produce a significant match to the protein sequences of COL6A3 from other species, as shown in the UCSC Genome Browser window. This is particularly apparent for Exon 26. There are two reasons for this. First, the protein sequence of the collagen-like repeat portion of the protein, as discussed below, is a repeating sequence of Gly-X-Y. With every third residue a glycine, the sequence is of low complexity. Second, Exon 26 is very short. A short sequence with low complexity will not always produce a significant match to orthologous proteins, even if the proteins are truly orthologous.

Conceptual translation of the nucleic acid sequences shown in FIG. 34 (SEQ ID NO:164 and SEQ ID NO:165) yields the amino acid sequences for the proteins shown in FIG. 36. FIG. 36 shows models of part of the normal protein sequence encoded by horse COL6A3 (XP_023498413.1, presented here as SEQ ID NO:167) corresponding to a translation of SEQ ID NO:164 shown in FIG. 34 and part of the altered protein sequence encoded by horse COL6A3 (adapted from XP_023498413.1, presented here as SEQ ID NO:168) with the base substitution at chr6:23,480,621 corresponding to a translation of SEQ ID NO:165 shown in FIG. 34. The portion of the protein corresponding to all five collagen-like domains is shown; the portion corresponding to the third collagen-like domain, partially encoded by Exon 26, is indicated in bold, while the amino acid at position 2182 affected by the base substitution of a cytosine (C) for a guanine (G) at the chr6:23,480,621 position as shown in FIG. 33, is underlined. The amino acid positions in XP_023498413.1 are indicated at the beginning and end of the sequence.

For the sake of simplicity, the amino acid substitution caused by the substitution of an cytosine (C) for a guanine (G) at the chr6:23,480,621 position on the reverse strand as shown in FIG. 33, identified as rs1139437410 in dbSNP, will be referred to as COL6A3-G2182A, based on SEQ ID NO:168. The amino acid substitution caused by this mutation will remain the same regardless of the numerical position of the affected codon in alternative gene models. The wild-type (e.g., also referred to herein as "normal" or "unaffected") allele of this coding region may be referred to as G2182 and the mutant allele G2182A.

FIG. 37 shows horse COL6A3 Exon 26 and flanking genomic DNA sequence from which PCR primers to amplify genomic DNA containing the site of the COL6A3-G2182A mutation would be most appropriately derived. Genomic coordinates are as in FIG. 24. Exon 26 from chr6:23,480,631 to chr6:23,480,578 is shown broken into codons in the correct reading frame for the wild-type allele (SEQ ID NO:169) and the COL6A3-G2182A allele (SEQ ID NO:170). Only the reference sequence from the assembly is shown for the flanking sequences. The codon affected by the G to C mutation site at nucleotide position chr6:23,480,621 on the reverse strand, as shown in FIG. 33, is shown in bold, with the position of the base substitution indicated by underlining. The base substitution changes the bold three base codon from one coding for a glycine (GGG) to one coding for an alanine (GCG). Example primers used experimentally to amplify genomic DNA containing the mutation site [5'-AGATGGGGCACAGATCAAAC-3' (SEQ ID NO:172) and 5'-TTCCCAGACTCTCCTGTGCT-3' (SEQ ID NO:171)] are shown in lower case in the figure.

Genomic DNA obtained from horses can be genotyped by amplifying a region containing a variant in the COL6A3 gene using Polymerase Chain Reaction (PCR), then sequencing the amplified DNA using Sanger sequencing. The variant allele COL6A3-G2182A is abbreviated as K1, while the common or wild-type allele is abbreviated as n. The results can be scored as homozygous for the common or wild-type allele (n/n), heterozygous for the nucleotide substitution (n/K1), or homozygous for the nucleotide substitution (K1/K1).

FIG. 38 shows traces from Sanger DNA sequencing of amplified COL6A3 genomic DNA using primers shown in FIG. 37 (SEQ ID NO:171 and SEQ ID NO:172). The arrows in the figure indicate nucleotide position chr6:23,480,621, the site of a substitution of a cytosine (C) for a guanine (G) in this position on the reverse strand that creates the COL6A3-G2182A variant. The traces show, from left to right, the sequence of the forward strand for a horse homozygous for the wild-type or common allele (n/n), and results for a horse heterozygous for the substitution (n/K1).

Collagen is the main structural protein of the extracellular matrix. Collagens are synthesized with N- and C-terminal extensions that are cleaved off proteolytically upon export from the cell. The N- and C-terminal extensions assist in localization within the extracellular matrix. The core of the collagen protein is the triple helical domain, consisting of Gly-X-Y repeats. The collagen triple helix consists of a right-handed intertwining of three left-handed helices. The glycine residues are critical, because every third residue occupies a position at the center of the triple helix, where there is no room for any other R group besides the hydrogen found in glycine. The collagen triple helix is stiffened by the post-translation modification of proline and lysine residues to hydroxyproline and hydroxylysine. As collagen fibers assemble, each triple helix is joined to its neighbors. In the fully assembled array, each triple helix overlaps with a neighboring triple helix with an offset of about one quarter of its length. The array is stabilized by covalent links through interchain disulfide bonds and post-translationally modified hydroxylysine.

The human ortholog of the equine COL6A3 gene encodes collagen type VI alpha 3 chain, one of a set of collagen type VI genes. The others are COL6A1, COL6A2, COL6A5, and COL6A6 (COL6A4 is a pseudogene). Collagens play important roles in maintaining extracellular matrix structure and function. Members of the collagen VI family, like COL6A3, form distinct networks of microfibrils in connective tissue and interact with other extracellular matrix components. Mutations in the human genes COL6A1, COL6A2, and COL6A3 are associated with Bethlem Myopathy, Ullrich Congenital Muscular Dystrophy, and dystonia. Mutations may be either dominant or recessive, with the age of onset and the severity of the condition varying with the exact mutation.

In mouse, an in-frame intragenic deletion of six Gly-X-Y repeats of COL6A3 (Col6a$^{2tm.2.1Chu}$) is a dominant mutation causing abnormal muscle fiber morphology and myopathy. Targeted mutation of COL6A1 is also a dominant mutation causing myopathy. Electron microscopy of tendons from homozygous mice shows a reduced diameter of collagen fibrils (Pan et al. 2013 J Biol Chem, 288(20):14329-14331).

It is therefore informative to compare the horse COL6A3 gene and the protein that it encodes with the human ortholog. FIG. 39 shows the partial sequence of the human COL6A3 coding sequence derived from NM_004369.3 (SEQ ID NO:173). This sequence is a region of perfect consensus among multiple different experimentally predicted mRNA isoforms. The numbering of the first and last nucleotides corresponds to that of NM_004369.3. The sequence encoding the third collagen-like domain is indicated in bold.

FIG. 40 shows a partial sequence of the human COL6A3 protein, showing a translation of SEQ ID NO:175, equivalent to NP_004360.2 (SEQ ID NO:176). The numbering of the first and last amino acids corresponds to that of NP_004360.2. The sequence of the third collagen-like domain is indicated in bold.

FIG. 41 shows a comparison of the portion of the protein sequence of COL6A3 comprising the five collagen-like repeats from human (NP_079130.2, shown here as SEQ ID NO:175) and horse (XP_001502180.3, shown here as SEQ ID NO:176). The position of the COL6A3-G2182A substitution is shown below the horse sequence. Between the sequences of the horse and human proteins in the alignment, an asterisk (*) indicates an identical amino acid in that position, while a plus sign (+) indicates a conservative substitution, and a space ( ) indicates a nonconservative substitution. The positions of glycine residues that are part of the Gly-X-Y structure of the collagen triple helix are indicated by an asterisk (*) in reverse text (white text on a black background) between the horse and human sequences. All of these glycine residues are conserved between human and horse. The horse G2182A sequence has a nonconservative substitution of an alanine (A) for a glycine (G) at position 2182; the wild-type horse sequence matches the human sequence at this position.

Figure 42:
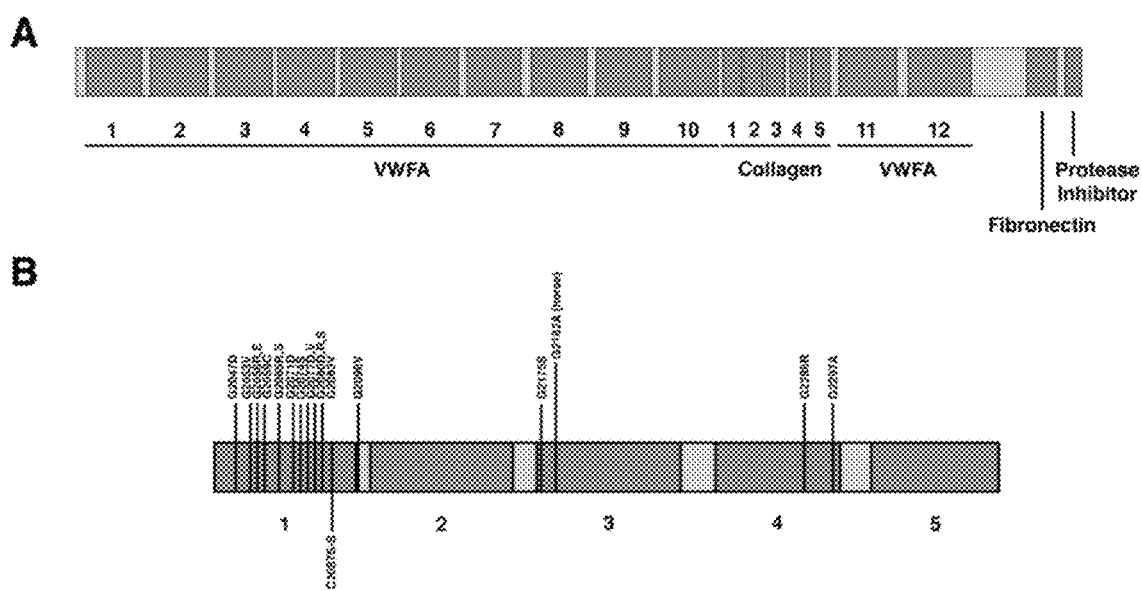
FIG. 42. Features of the collagen type VI alpha 3 chain protein encoded by the human COL6A3 gene. (A) The human protein has 3,177 amino acids. It contains five collagen-like domains consisting of Gly-X-Y repeats, labeled as Collagen 1-5 in the figure. Toward the N-terminus of the collagen-like repeats are 10 Von Willebrand Factor-like repeats, labeled as VWFA 1-10 in the figure. Toward the C-terminus of the collagen-like repeats are two additional Von Willebrand Factor-like repeats, labeled as VWFA 11 and 12 in the figure. Near the C-terminus is a fibronectin-like repeat, labeled as Fibronectin in the figure, and a Protease Inhibitor domain (Pancreatic trypsin inhibitor Kunitz domain). (B) The portion of the protein containing the five collagen-like domains extends from position 2038 to 2373 of the human protein. The five collagen-like domains are numbered. Positions of 19 pathogenic human alleles listed in TABLE 4 are indicated above the segment shown, as is the position of the horse G2182A variant. The position of the cysteine involved in the interchain disulfide bond (C2087S-S) is indicated below the segment shown.

FIG. 42 shows features of the collagen type VI alpha 3 chain protein encoded by the human COL6A3 gene. A) The human protein has 3,162 amino acids. It contains five collagen-like domains consisting of Gly-X-Y repeats, labeled as Collagen 1-5 in the figure. Toward the N-terminus of the collagen-like repeats are 10 Von Willebrand Factor-like repeats, labeled as VWFA 1-10 in the figure. Toward the C-terminus of the collagen-like repeats are two additional Von Willebrand Factor-like repeats, labeled as VWFA 11 and 12 in the figure. Near the C-terminus is a fibronectin-like repeat, labeled as Fibronectin in the figure, and a Protease Inhibitor domain (Pancreatic trypsin inhibitor Kunitz domain). B) The portion of the protein containing the five collagen-like domains extends from position 2038 to 2373 of the human protein. The five collagen-like domains are numbered. Positions of 19 pathogenic human alleles listed in TABLE 2 below are indicated above the segment shown, as is the position of the horse G2182A variant. The position of the cysteine involved in the interchain disulfide bond (C2087S-S) is indicated below the segment shown.

TABLE 4 shows nineteen missense alleles of human COL6A3 shown in FIG. 42. Although pathogenic missense alleles of human COL6A3 outside of the collagen-like repeats in the middle of the protein have been described, we focus on mutations in this region in humans because of the relevance to the COL6A3-G2182A allele in horse. All nineteen mutations are substitutions of other amino acid residues for the glycine residues that are part of the Gly-X-Y repeat structure of the collagen-like region. Human missense alleles of COL6A3 are associated with Bethlem Myopathy and with Ullrich Congenital Muscular Dystrophy. Bethlem Myopathy has also been referred to as Limb-Girdle Muscular Dystrophy D5 (LGMDD5). Both dominant and recessive forms of Bethlem Myopathy, caused by mutations in COL6A1, COL6A2, and COL6A3, are known. Symptoms include progressive muscular weakness with muscle atrophy of the trunk and limbs and joint contractures. Missense alleles affecting the glycine residues of the collagen repeats account for almost one-third of all pathogenic alleles. The symptoms of Ullrich Congenital Muscular Dystrophy overlap those of Bethlem Myopathy. Ullrich Congenital Muscular Dystrophy is caused by mutations in COL6A1, COL6A2, and COL6A3.

TABLE 4

Pathogenic missense alleles of human COL6A3 and associated diseases.

| Substitution | Domain | Disease | Reference |
|---|---|---|---|
| G2047D | Collagen 1 | Bethlem Myopathy | Lampe 2005 |
| G2053V | Collagen 1 | Not provided | ClinVar |
| G2056E | Collagen 1 | Not provided | ClinVar |
| G2056R | Collagen 1 | Bethlem Myopathy | Pepe 1999 |
| G2059C | Collagen 1 | Bethlem Myopathy | ClinVar |
| G2065S | Collagen 1 | Bethlem Myopathy/ Ulrich congenital muscular dystrophy | ClinVar |
| G2055R | Collagen 1 | Bethlem Myopathy/ Ulrich congenital muscular dystrophy | ClinVar |
| G2071D | Collagen 1 | Bethlem Myopathy/ Ulrich congenital muscular dystrophy | ClinVar |
| G2074S | Collagen 1 | Bethlem Myopathy/ Ulrich congenital muscular dystrophy | ClinVar |
| G2077D | Collagen 1 | Bethlem Myopathy/ Ulrich congenital muscular dystrophy | ClinVar |
| G2077V | Collagen 1 | Bethlem Myopathy | ClinVar |
| G2080S | Collagen 1 | Ullrich congenital muscular dystrophy | ClinVar |
| G2080R | Collagen 1 | Not provided | ClinVar |
| G2080D | Collagen 1 | Bethlem Myopathy/ Ulrich congenital muscular dystrophy | ClinVar, Lampe 2005 |
| G2083V | Collagen 1 | Not provided | ClinVar |
| G2098V | Interdomain | Bethlem Myopathy/ Ulrich congenital muscular dystrophy | ClinVar |
| G2174S | Collagen 3 | Bethlem Myopathy | ClinVar |
| G2267S | Collagen 4 | Bethlem Myopathy | ClinVar |
| G2285R | Collagen 4 | Bethlem Myopathy | ClinVar |
| G2297A | Collagen 4 | Bethlem Myopathy/ Ulrich congenital muscular dystrophy | ClinVar |

Cited sources in this table are:
ClinVar (https://www.ncbi.nlm.nih.gov/clinvar/)
Lampe 2005 (Lampe A K et al. 2005 J Med Genet 42:108-120 DOI: 10.1136/jmg.2004.023754)
Pepe 1999 (Pepe G et al. 1999 Neuromuscul Disord 9:264-271)

The glycine substitutions seen in human pathogenic alleles of COL6A3 are clustered in the amino-terminal portion of the collagen-like domain, as shown in FIG. 42 and TABLE 4. This may represent a functional domain within the triple helix (Butterfield et al. Hum Mutat. 2013 34(11):

1558-1567). The most severe cases are caused by glycine substitutions in Gly-X-Y triplets 10 to 15. Glycine substitutions in this region are reported as dominant; the only cases of recessive glycine substitutions are located outside of this region in the C-terminal portion of the triple helix. This generalization applies to glycine substitutions in COL6A1, COL6A2, and COL6A3.

The position of the COL6A3-G2182A mutation in horse is shown in FIG. 42. COL6A3-G2182A affects Gly-X-Y triplet 48, as shown in FIG. 41. The position of the COL6A3-G2182A mutation in horse is closest to the human COL6A3-G2174S allele. The phenotype produced by human pathogenic glycine substitution alleles depends not only on the position of the mutation, but also on the amino acid substitution. There is a published destabilization scale for glycine substitutions in the triple helix (Ala<Ser<Cys<Arg<Val<Glu<Asp<Trp) (Persikov et al. Hum Mutat. 2004 24(4):330-337). The horse COL6A3-G2182A allele is therefore the least damaging substitution in a moderately damaging position in the protein, consistent with the moderate phenotype of affected horses described below.

The sequence comparison between the proteins encoded by horse and human COL6A3 shows the high degree of sequence conservation between these two species. The extent of sequence conservation is so high that it is difficult to evaluate whether this comparison offers any evidence that the equine COL6A3-G2182A allele would be expected to be pathogenic.

Figure 43:
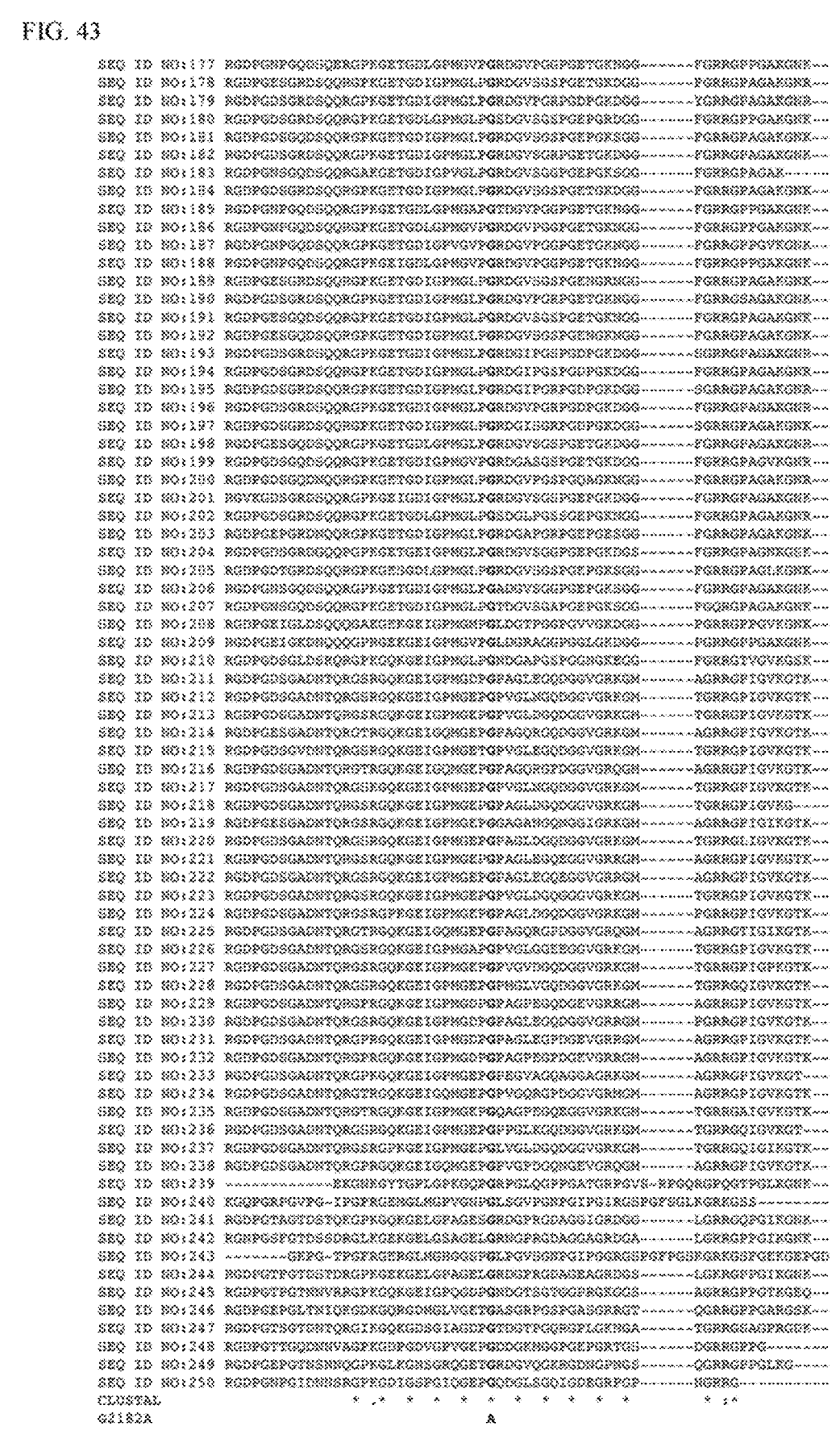

FIG. 43 shows partial amino acid sequences of proteins encoded by COL6A3, including the position of the equine COL6A3-G2182A substitution. A portion of the human COL6A3 protein sequence was used as a probe to identify the corresponding region in the orthologous protein across a wide range of species, including mammals, birds, reptiles, amphibians, and fish. In the alignment shown in FIG. 43, sequences that are identical over this range of positions are clustered as a single SEQ ID NO.

The 89 species in the alignment shown in FIG. 43 are presented below with their common names, their scientific names, and the protein database ID from which the amino acid sequence is derived. Amino acid sequences identical over this range in different species have been clustered into single SEQ ID NOs for the alignment. The species associated with the SEQ ID NOs shown in the alignment are:

SEQ ID NO:177 [Human (*Homo sapiens*, NP_004360.2), Chimpanzee (*Pan troglodytes*, XP_001153544.3), Bonobo (*Pan paniscus*, XP_003813155.1), Western lowland gorilla (*Gorilla gorilla gorilla*, XP_018878003.1), Sumatran orangutan (*Pongo abelii*, XP_009236555.2)], SEQ ID NO:178 [Thirteen-lined ground squirrel (*Ictidomys tridecemlineatus*, XP_013214606.1), Alpine marmot (*Marmota marmota marmota*, XP_015337108.1)], SEQ ID NO:179 [David's myotis (*Myotis davidii*, XP_015417293.1), Brandt's bat (*Myotis brandtii*, XP_014393090.1)], SEQ ID NO:180 [Horse (*Equus caballus*, XP_023498413.1), Donkey (*Equus asinus*, XP_014698264.1), Przewalski's horse (*Equus przewalskii*, XP_008528449.1)], SEQ ID NO:181 [Dromedary (*Camelus dromedarius*, XP_010994640.1), Bactrian camel (*Camelus bactrianus*, XP_010946449.1), Alpaca (*Vicugna pacos*, XP_015098979.1)], SEQ ID NO:182 Ferret [(*Mustela putorius furo*, XP_012907287.1), Cat (*Felis catus*, XP_019694498.2)], SEQ ID NO:183 [Cattle (*Bos taurus*, XP_024846030.1), Goat (*Capra hircus*, XP_017896230.1), Sheep (*Ovis aries*, XP_014947129.1), Mouflon (*Ovis aries musimon*, XP_011989955.1)], SEQ ID NO:184 [Leopard (*Panthera pardus*, XP_019301005.1), Giant panda (*Ailuropoda melanoleuca*, XP_019662500.1)], SEQ ID NO:185 Olive baboon (*Papio anubis*, XP_021779879.1), SEQ ID NO:186 Rhesus macaque (*Macaca mulatta*, XP_014966890.1), SEQ ID NO:187 Panamanian white-throated capuchin (*Cebus capucinus imitator*, XP_017393233.1), SEQ ID NO:188 Black snub-nosed monkey (*Rhinopithecus bieti*, XP_017745835.1), SEQ ID NO:189 Gray mouse lemur (*Microcebus murinus*, XP_012634739.2), SEQ ID NO:190 Philipine tarsier (*Carlito syrichta*, XP_008057564.1), SEQ ID NO:191 Northern greater galago (*Otolemur garnettii*, XP_003798279.2), SEQ ID NO:192 Coquerel's sifika (*Propithecus coquereli*, XP_012504274.1), SEQ ID NO:193 Mouse (*Mus musculus*, NP_001229937.1), SEQ ID NO:194 Rat (*Rattus norvegicus*, XP_008756297.1), SEQ ID NO:195 Chinese hamster (*Cricetulus griseus*, XP_016824341.1), SEQ ID NO:196 Prairie vole (*Microtus ochrogaster*, XP_005361761.1), SEQ ID NO:197 Mongolian gerbil (*Meriones unguiculatus*, XP_021513097.1), SEQ ID NO:198 Long-tailed chinchilla (*Chinchilla lanigera*, XP_005411290.1), SEQ ID NO:199 American beaver (*Castor canadensis*, XP_020043158.1), SEQ ID NO:200 Damora mole-rat (*Fukomys damarensis*, XP_010624430.1), SEQ ID NO:201 Large flying fox (*Pteropus vampyrus*, XP_023380958.1), SEQ ID NO:202 Sunda pangolin (*Manis javanica*, XP_017531172.1), SEQ ID NO:203 Great roundleaf bat (*Hipposideros armiger*, XP_019485542.1), SEQ ID NO:204 African bush elephant (*Loxodonta africana*, XP_010595897.1), SEQ ID NO:205 Wild boar (*Sus scrofa*, XP_020931400.1), SEQ ID NO:206 Minke whale (*Balaenoptera acutorostrata scammoni*, XP_007184961.1), SEQ ID NO:207 Killer whale (*Orcinus orca*, XP_004262601.1), SEQ ID NO:208 Koala (*Phascolarctos cinereus*, XP_020827927.1), SEQ ID NO:209 Tasmanian devil (*Sarcophilus harrisii*, XP_023359576.1), SEQ ID NO:210 Platypus (*Ornithorhynchus anatinus*, XP_007666682.1), SEQ ID NO:211 [American crow (*Corvus brachyrhynchos*, XP_017602594.1), Hooded crow (*Corvus cornix cornix*, XP_019146502.1)], SEQ ID NO:212 Bald eagle (*Haliaeetus leucocephalus*, XP_010576193.1), SEQ ID NO:213 Golden eagle (*Aquila chrysaetos canadensis*, XP_011584187.1), SEQ ID NO:214 Chicken (*Gallus gallus*, NP_990865.2), SEQ ID NO:215 Downy woodpecker (*Picoides pubescens*, XP_009899132.1), SEQ ID NO:216 Turkey (*Meleagris gallopavo*, XP_010711547.1), SEQ ID NO:217 Northern carmine bee-eater (*Merops nubicus*, XP_008936095.1), SEQ ID NO:218 Speckled mousebird (*Colius striatus*, XP_010208169.1), SEQ ID NO:219 North Island brown kiwi (*Apteryx australis mantelli*, XP_013798018.1), SEQ ID NO:220 Emperor penguin (*Aptenodytes forsteri*, XP_019329168.1), SEQ ID NO:221 Rock dove (*Columba livia*, XP_021142382.1), SEQ ID NO:222 Band-tailed pigeon (*Patagioenas fasciata monilis*, OPJ80253.1), SEQ ID NO:223 Adélie penguin (*Pygoscelis adeliae*, XP_009327902.1), SEQ ID NO:224 Ruff (*Calidris pugnax*, XP_014807202.1), SEQ ID NO:225 Japanese quail (*Coturnix japonica*, XP_015723569.1), SEQ ID NO:226 Crested ibis (*Nipponia nippon*, XP_009460310.1), SEQ ID NO:227 Anna's hummingbird (*Calypte anna*, XP_008493236.1), SEQ ID NO:228 Little egret (*Egretta garzetta*, XP_009633772.1), SEQ ID NO:229 Atlantic canary (*Serinus canaria*, XP_009086444.1), SEQ ID NO:230 Common starling (*Sturnus vulgaris*, XP_014737483.1), SEQ ID NO:231 Zebra finch (*Taeniopygia guttata*, XP_004175063.1), SEQ ID NO:232 Society finch (*Lonchura striata domestica*, XP_021391774.1), SEQ ID NO:233 Chimney swift (*Chaetura pelagica*, XP_010003753.1), SEQ ID NO:234 Scaled quail (*Calli-*

*pepla squamata*, OXB61690.1), SEQ ID NO:235 Common cuckoo (*Cuculus canorus*, XP_009568416.1), SEQ ID NO:236 Blue-crowned manakin (*Lepidothrix coronata*, XP_017691139.1), SEQ ID NO:237 Peregrine falcon (*Falco peregrinus*, XP_005244480.1), SEQ ID NO:238 Budgerigar (*Melopsittacus undulatus*, XP_012985362.1), SEQ ID NO:239 Schlegel's Japanese gecko (*Gekko japonicus*, XP_015273310.1), SEQ ID NO:240 Green anole (*Anolis carolinensis*, XP_008104462.1), SEQ ID NO:241 Burmese python (*Python bivittatus*, XP_025027494.1), SEQ ID NO:242 Brown spotted pit viper (*Protobothrops mucrosquamatus*, XP_015676224.1), SEQ ID NO:243 King cobra (*Ophiophagus hannah*, ETE68401.1), SEQ ID NO:244 Common garter snake (*Thamnophis sirtalis*, XP_013925229.1), SEQ ID NO:245 West Indian Ocean coelacanth (*Latimeria chalumnae*, XP_014344739.1), SEQ ID NO:246 Whale shark (*Rhincodon typus*, XP_020391663.1), SEQ ID NO:247 Australian ghostshark (*Callorhinchus milii*, XP_007904071.1), SEQ ID NO:248 Atlantic salmon (*Salmo salar*, XP_014028364.1), SEQ ID NO:249 African clawed frog (*Xenopus laevis*, KTG32498.1), SEQ ID NO:250 Common carp (*Cyprinus carpio*, KTG32498.1).

The next to the last line (labeled CLUSTAL) shows the consensus sequence, where positions with fully conserved amino acids are represented by an asterisk (*), positions with strongly conserved amino acids are indicated by a colon (:), positions with weakly conserved amino acids are indicated are indicated by period (.), and nonconserved positions are indicated by a blank space ( ). The last line shows the position of the COL6A3-G2182A substitution in horse. The position of the COL6A3-G2182A substitution is indicated in bold in all of the aligned sequences.

The strongly conserved positions in the aligned sequences are all glycine (G) residues that are part of the Gly-X-Y repeat structure of the collagen triple helix. The sequences to the N-terminal position of the strongly conserved glycine residues also show a Gly-X-Y repeat structure that is evident from the examination of individual sequences, but a variable number of amino acids between the Gly-X-Y repeats showing sequence conservation and the Gly-X-Y repeats at the N-terminal position prevents this from showing in the multiple alignment. Separation of Gly-X-Y repeats by sequences not conforming to the Gly-X-Y pattern is common among collagens.

The overall sequence conservation of this portion of the COL6A3 protein is quite high. The amino acid alteration seen in the equine COL6A3-G2182A is not seen in any of the 89 species; all have a glycine (G) at this position. The comparison of COL6A3 sequences presented here refutes the hypothesis that the COL6A3-G2182A substitution is selectively neutral, and supports the claim that the COL6A3-G2182A mutation found in horses with PSSM2 is pathogenic.

Phenotypic Effects of the Genetic Variants Associated with PSSM2

This disclosure, together with a prior filing, identifies eight variants associated with PSSM2: MYOT-S232P (P2), FLNC-E753K (P3a), FLNC-A1207T (P3b), MYOZ3-S42L (P4), DYSF-R285W (P5), PYROXD1-D492H (P8), and COL6A3-G2182A (K1). These eight variants correspond to single-base substitutions having the coordinates given as follows on the forward strand in the public horse genome assembly (EquCab 2): chr14:38519183 A/G (P2), chr4:83736244 G/A (P3a), chr4:83738769 G/A (P3b), chr14:27399222 G/A (P4), chr15:31306949 G/A (P5), chr15: 5:31,225,630 T/G (P6), chr6:47,661,977 G/C (P8), and chr6:23,480,621 C/G (K1). The P3a and P3b variants are a haplotype, that is, among hundreds of horses tested, horses with the P3a variant also have the P3b variant and vice versa, whether homozygous or heterozygous. Only two types of chromosomes are seen: those with both P3a and P3b, or those with the wild-type or common alleles of both variants. The haplotype with both variants is therefore abbreviated as P3.

One of the earliest symptoms of PSSM2 is a change in behavior apparently associated with pain. Owners note a difference in temperament, with horses reacting badly to being ridden or even saddled. Common behaviors include biting at the flanks or even at the rider or trainer, and bucking, rearing, and other displays of resistance that trainers often blame on lack of discipline from the owner.

Another early symptom is stifle problems. The stifle is the largest joint in the horse's body, equivalent to the human knee, but in contrast to the human knee, the equine stifle is held at an angle when the horse is standing still. Stifle problems commonly result from injury or arthritis, degenerative joint disease, or injury. In stifle problems resulting from Polysaccharide Storage Myopathy type 2 (PSSM2), there will be no radiographic findings. Stifle problems are one example of shifting lameness. A horse with Polysaccharide Storage Myopathy type 2 (PSSM2) will exhibit lameness that appears first in one limb, then another. There will be no radiographic findings.

Changes in gait are often apparent. These include stiffness in the hindquarters and limited range of motion of the hind legs ("short-gaited"). At canter, disunited canter ("cross-firing") and "bunny hopping" (bringing both hind legs forward at the same time) are seen. "Rope walking" (placing one foot directly in front of the other along the centerline as if walking a tightrope) is sometimes seen in all four legs or in the rear legs only.

Other gait changes resulting from weakness in the hind limbs are described by horse owners as "heavy on the forehand, not able to come from behind." This means that the horse's gait is altered in such a way that it appears to be pulling itself forward with its front hooves instead of pushing from the rear. Farriers note this as a pattern of wear in the front hooves for unshod horses.

There is no evidence of cardiomyopathy.

Phenotypic Effects of the DYSF-R285W and DYSF-P1290T Variants

The DYSF-R253W variant (hereafter abbreviated as P5) was discovered by analysis of whole genome sequencing data from a Shire draft horse (E016) diagnosed via muscle biopsy with Polysaccharide Storage Myopathy type 2 (PSSM2). This horse was homozygous for the P5 allele (P5/P5) and homozygous wild type for six other variants with PSSM2: MYOT-S232P (P2), FLNC-E753K (P3a), FLNC-A1207T (P3b), MYOZ3-S42L (P4), PYROXD1-D492H (P8), and COL6A3-G2182A (K1). The P6 allele of DYSF (DYSF-P1290T) was not present.

We analyzed additional horses using PCR amplification and Sanger sequencing to identify P5/P5 homozygotes. A Shire horse (E799) scored as P5/P5 and homozygous for the wild-type alleles of P2, P3, P4, P5, P8, and K1 was identified at 11 years of age. This horse had been retired from regular work the prior year following an episode of lameness, muscle fasciculation, and profuse sweating during work.

Other individual horses of the Shire breed and the closely related Clydesdale breed that were determined to be normal, that is, not affected by PSSM2, were found to be heterozygous for the P5 allele (N/P5) or homozygous for the wild-type allele (N/N). Therefore, the P5 variant appears to be recessive, as is typical for missense alleles of the human DYSF gene shown in TABLE 1, TABLE 2, and TABLE 3.

The DYSF-P1290T variant (hereafter abbreviated as P6) was discovered by analysis of whole genome sequencing data from a number of horses diagnosed via muscle biopsy with Polysaccharide Storage Myopathy type 2 (PSSM2). Each of these horses had other variants, and all were found to be heterozygous of P6 (N/P6). Because mutations in DYSF analyzed in human patients and mice have all been recessive, we analyzed additional horses using PCR amplification and Sanger sequencing to identify P6/P6 homozygotes.

An Icelandic horse (E885) scored as P6/P6 and homozygous for the wild-type alleles of P2, P3, P4, P5, P8, and K1 was identified at 25 years of age. The horse had been retired from work for at least five years. The owner reported that this horse had gait abnormalities, described by the owner as "tripping." The owner refused an exercise challenge, expected to induce a rise in serum creatine kinase (CK); serum CK measured in this horse in the absence of an exercise challenge was in the normal range, as were the serum CK levels in eight other Icelandics tested at the same time in the same location. All eight of the other Icelandics were also homozygous for the wild-type alleles of P2, P3, P4, P8, and K1; their genotypes with respect to DYSF were N/N (4), N/P6 (3), and N/P5 (1). None of these other eight Icelandics was reported to be symptomatic.

A Thoroughbred (E456) scored as P6/P6, n/P3 and homozygous for the wild-type alleles of P2, P4, P8, and K1 was identified. This horse was also homozygous for the wild-type allele of P5. This Thoroughbred was reported by the owner to have shown frequent tie-ups at the track, was only raced once, and was described by an experienced trainer as "not quite right." The horse died of colic at four years of age.

Two compound heterozygotes scored as P5/P6 and homozygous for the wild-type alleles of P2, P3, P4, P8, and K1 were identified. Both the P5/P6 Percheron (E797) and the P5/P6 Clydesdale (E823) were described by the owners as symptomatic, as were two other P5/P5 Clydesdales (E818 and E820) with the owner of the P5/P6 Clydesdale (E823).

Recombination between the P5 and P6 base substitution can produce a chromosome with both of the mutations in cis. Because both whole-genome sequencing on the Illumina platform and Sanger sequencing of DNA amplified by PCR do not yield phase information, such a chromosome could only be definitively identified in a horse scored as homozygous for P5 and heterozygous for P6, or in a horse scored as homozygous for P6 and heterozygous for P5. No such result has been seen in any sample.

The phenotype of human patients with the various alleles listed in TABLE 1, TABLE 2, and TABLE 3 suggests that horses homozygous for the DYSF-R253W allele (P5) would be expected to show increased serum creatine kinase (CK) and aspartate aminotransferase (AST), especially upon an exercise challenge. Affected horses are also expected to show abnormalities on muscle biopsy, including necrosis and regeneration, which may lead to adipose and fibrotic infiltration of the endomysial space. We do not expect heterozygous horses to be affected.

The novel DYSF-P1290T (P6) allele does not precisely replicate any known human mutation. Nevertheless, the phenotype observed in P6/P6 homozygotes and in P5/P6 compound heterozygotes suggests that these horses would also be expected to show increased serum creatine kinase (CK) and aspartate aminotransferase (AST), especially upon an exercise challenge, as well as defects observable by muscle biopsy, as for horses homozygous for the DYSF-R253W (P5) allele.

Phenotypic Effects of the PYROXD1-D492H Variant

The PYROXD1-D492H variant (hereafter abbreviated as P8) was discovered by analysis of whole genome sequencing data from Icelandic, Arabian, Thoroughbred, and Quarter Horses. Some of these horses were diagnosed via muscle biopsy with Polysaccharide Storage Myopathy type 2 (PSSM2) or Myofibrillar Myopathy (MFM). These horses were heterozygous for the P8 allele (n/P8); some were homozygous wild-type for seven other variants associated with PSSM2: MYOT-S232P (P2), FLNC-E753K (P3a), FLNC-A1207T (P3b), MYOZ3-S42L (P4), DYSF-R285W (P5), DYSF-P1290T (P6) and COL6A3-G2182A (K1).

An Icelandic horse (E013) free of the P2, P3, P4, P5, P6, and K1 variants was diagnosed as having PSSM2 by muscle biopsy. The horse was heterozygous for P8 (n/P8). The symptoms observed in this horse correspond to the general description of the symptoms of PSSM2, and are similar to symptoms produced by homozygosity or heterozygosity for the P2, P3, P4, P5, and K1 variants in various combinations.

An Arabian horse (E361) scored as n/P8 and homozygous for the wild-type alleles of P2, P3, P4, P5, P6, and K1 was diagnosed as having Recurrent Exertional Rhabdomyolysis (RER) from a severe episode of exercise intolerance during which serum creatine kinase (CK) and aspartate aminotransferase (AST) rose to levels above 20,000 units; the baseline is below 500. Myoglobinuria (dark brown urine resulting from the presence of myoglobin) was also observed.

An Arabian horse (E049) scored as n/P8 and homozygous for the wild-type alleles of P2, P3, P4, P5, P6, and K1 was highly symptomatic and was euthanized at 12 years of age. A necropsy showed gluteal muscles affected but normal muscles in the lower limbs, neck, and inner thighs. In the most affected regions, muscle cells were replaced by fat cells. Up to 50% of the muscle cells were replaced by fat in some regions.

Figure 44:
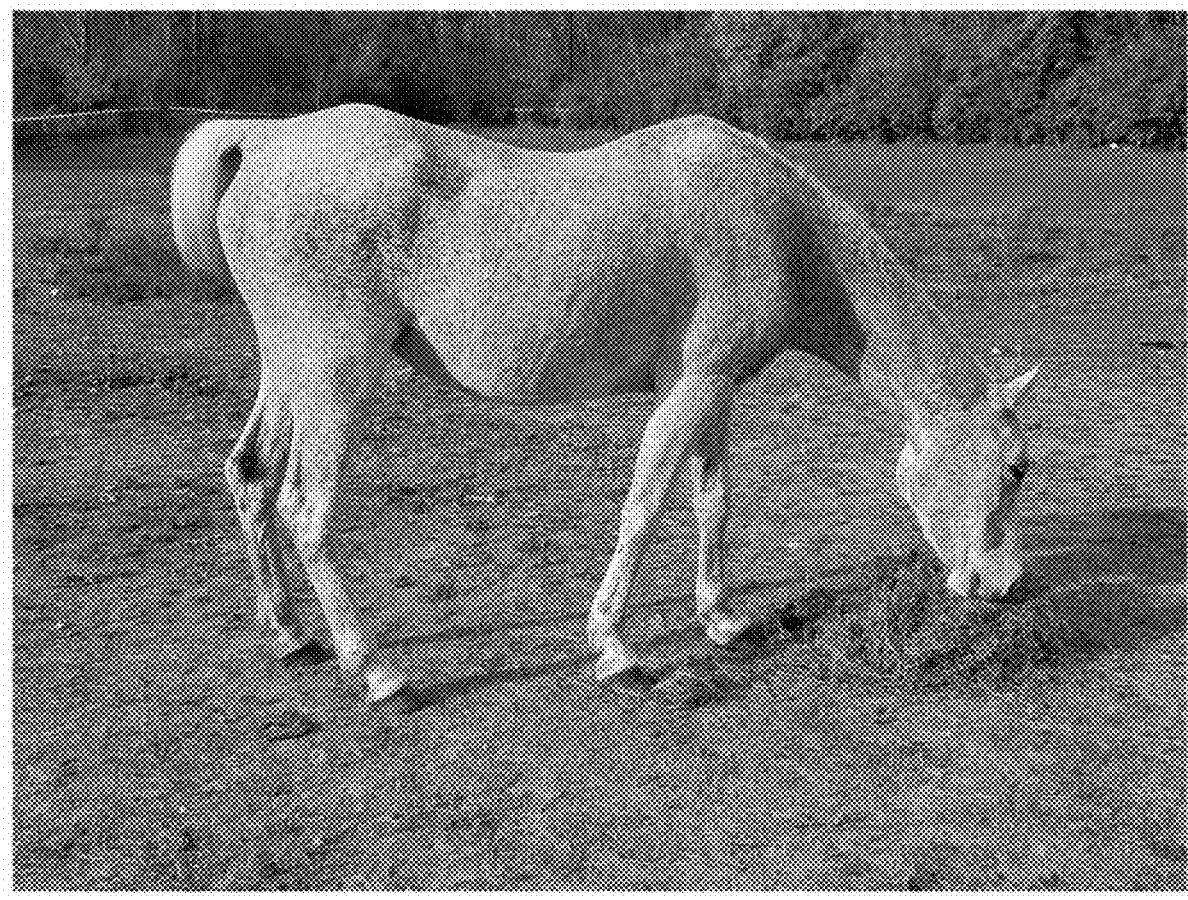
FIG. 44. An Arabian horse (E682) homozygous for the PYROXD1-D492H substitution (P8/P8), heterozygous for MYOT-S232P (n/P2), and homozygous for the wild-type alleles of FLNC-E753K (P3a), FLNC-A1207T (P3b), MYOZ3-S42L (P4), reported in a prior disclosure. Muscle wasting in the pelvic girdle (hindquarters), shoulder girdle (topline), and proximal limbs is evident. The horse is pregnant in the photo. The horse was reported to be symptomatic with gait abnormalities ("rope walking"), and died of a choking incident. Difficulty in swallowing is observed in human patients with Myofibrillar Myopathy 8 (MFM8) due to mutations in PYROXD1 (O'Grady et al. 2016 Am J Hum Genet. 99:1086-1105 DOI: 10.1016/j.ajhg.2016.09.005).

A horse owner who had submitted samples for a number of Arabians received results for P8 several months after submission. One of her Arabian mares (E682) was n/P2 and P8/P8 and homozygous for the wild-type alleles of P3, P4 and not yet scored for P5, P6, and K1. The owner reported that this mare had never been able to keep weight on her, and "looked like a living skeleton no matter what diet was fed." This horse is shown in FIG. 44. Muscle wasting in the pelvic girdle (hindquarters), shoulder girdle (topline), and proximal limbs is evident. The horse is pregnant in the photo. The horse was reported to be symptomatic with gait abnormalities ("rope walking"), and died of a choking incident between the time of submission of the sample and the test results. Difficulty in swallowing is observed in human patients with Myofibrillar Myopathy 8 (MFM8) due to mutations in PYROXD1 (O'Grady et al. 2016 Am J Hum Genet. 99:1086-1105 DOI: 10.1016/j.ajhg.2016.09.005).

The phenotype of human patients with the missense alleles described here suggests that horses heterozygous or homozygous for PYROXD1-D492H (P8) would be expected to show an array of myopathic changes resembling Centronuclear Myopathy, Myofibrillar Myopathy, and Nemaline Myopathy in muscle biopsies. Specifically, we expect to see ectopic aggregates of desmin-positive material outside of the Z disc, Z disc streaming, and other changes seen in Myofibrillar Myopathy.

There is a high incidence of the P8 variant among Arabians (TABLE 7). Arabian horses diagnosed with Myofibrillar Myopathy (MFM) by muscle biopsy and symptoms of exercise intolerance were analyzed in a recent published study (Valberg et al. 2018 Physiol Genomics doi: 10.1152). Samples were taken pre- and post-exercise and analyzed by RNA-Seq and iTRAQ (proteomics). Differential expression was seen for genes involved in pathways for structure morphogenesis, fiber organization, tissue development, and cell differentiation. Proteomic analysis showed lower levels of the antioxidant protein peroxiredoxin 6 in resting muscle; the authors proposed that altered cysteine metabolism and a deficiency of cysteine-containing antioxidants produced oxidative stress during aerobic exercise. Irreversible oxidation of cysteine residues in proteins that are structural components of the contractile apparatus, for example desmin, might induce proteolytic degradation of these proteins, causing Z disc fragmentation and streaming seen in muscle biopsies. While the genotype of the affected horses in this study is unknown, the defect in PYROXD1 described in this disclosure, and the phenotype of PYROXD1 mutants in humans, suggests that the affected horses in this study are n/P8 or P8/P8.

Three Appaloosas kept at the same farm under the same conditions were coincidentally tested for vitamin E levels around the same time that they were genotyped with respect to P8. All three horses were clear for P2, P3, P4, P5, and K1. Two are n/n for P8; one is n/P8.

Vitamin E levels (reference range is 200-1000 ug/dL)

| Horse 1 (n/n) | 255 ug/dL |
| Horse 2 (n/n) | 383 ug/dL |
| Horse 3 (n/P8) | 164 ug/dL |

Vitamin E is an antioxidant that is consumed when it scavenges hyperoxyl radicals in lipid membranes. Increased levels of oxidative stress would be expected to deplete vitamin E.

Prospects for treatment: If the myopathy caused by the defect in PYROXD1 described in this disclosure results from oxidative stress, it is possible that treatments with antioxidants would be effective at preventing symptoms or the progression of the disease. For example, dietary supplementation with vitamin E might be effective. Also, the combination of methylsulfonylmethane (MSM) and vitamin C has been shown to be effective at combatting oxidative stress causes by sustained exercise in horses, leading to an increase in glutathione synthesis and in levels of glutathione transferase (Marñón G et al. 2008 Acta Vet Scand 50:45 DOI: 10.1186/1751-0147-50-45; Williams CA 2016 J Anim Sci 94:4067-4075 DOI: 10.2527/jas.2015-9988). N-acetyl cysteine is a safe, low-cost compound that increases the level of glutathione, and has been shown to protect against muscle damage in mice subjected to oxidative stress through a mutation in CASQ1, the gene encoding calsequestrin (Paolini C et al. Skelet Muscle 5:10 DOI: 10.1186/s13395-015-0035-9).

Phenotypic Effects of the COL6A3-G2182A Variant

The COL6A3-G2182A variant (hereafter abbreviated as K1) was discovered by analysis of whole genome sequencing data from Icelandic, Arabian, Thoroughbred, and Quarter Horses. Some of these horses were diagnosed via muscle biopsy with Polysaccharide Storage Myopathy type 2 (PSSM2). These horses were heterozygous for the K1 allele; some were homozygous wild-type for six other variants previously associated with PSSM2: MYOT-S232P (P2), FLNC-E753K (P3a), FLNC-A1207T (P3b), MYOZ3-S42L (P4), DYSF-R285W (P5), DYSF-P1290T (P6), and PYROXD1-D492H (P8).

A Paint horse (E008) scored as n/K1 and homozygous for the wild-type alleles of P2, P3, P4, P5, P6, and P8 was diagnosed as having PSSM2 by muscle biopsy. The symptoms observed in this horse correspond to the general description of the symptoms of PSSM2, and are similar to symptoms produced by homozygosity or heterozygosity for the P2, P3, P4, P5, and P8 variants in various combinations.

The phenotype of human patients with missense alleles of COL6A3 and of mice with the targeted allele suggests that muscle biopsies from horses bearing the COL6A3-G2182A mutation (K1) will show changes in the connective tissue layer that ensheaths the muscle fiber. The size of the connective tissue layer is expected to increase. In late stages of the disease, replacement of some of this layer with adipose or scar tissue is expected, without evidence of necrosis. This condition has been called skeletal muscle endomysial fibrosis. It has not yet been directly observed in muscle biopsies from n/K1 or K1/K1 horses.

Incidence of Genetic Variants by Breed

The incidence of the previously described genetic variants (P2, P3, and P4) and the genetic variants described in this disclosure (P5, P6, P8, and K1) varies among breeds. It is useful to have a measurement of the allele frequency of different variants among breeds, as this can facilitate a further examination of the phenotype produced by a specific variant by identifying a breed in which it occurs at high incidence, perhaps with other genetic variants at a low incidence.

TABLE 5 shows the observed incidence of P2, P3, P4, P5, P6, P8, and K1 in Quarter Horse-related breeds. For purposes of this tabulation, a "Quarter Horse-related" breed is a Quarter Horse, Appendix Quarter Horse (the result of a cross of a Quarter Horse to a Thoroughbred), Paint Horse, Appaloosa, or a horse resulting from a cross of any two of these types to each other. This sample cannot be considered unselected, as the majority of horse owners volunteering their horses for study did so because their horses had symptoms of some kind. When we attempted to recruit breeding herds, the majority of horse owners did not volunteer; it is possible that those volunteering did so because they observed symptoms of exercise intolerance in their herd.

Quarter Horse-related breeds are of relatively recent origin, with gene flow from other breeds. For example, the American Quarter Horse Association allows the registration of Appendix Quarter Horses that have a Thoroughbred parent. In contrast, Thoroughbreds have a closed breeding book, meaning that a horse can only be registered as a Thoroughbred if both parents are Thoroughbreds. All seven genetic variants are found in Quarter Horse-related breeds. The incidence ranges from an allele frequency of 0.204 for P2 to an allele frequency of 0.007 for K1. Quarter Horse-related breeds are therefore a good choice for the further study of the interaction of all seven genetic variants. It should be noted that P2 (chr14:38519183 A/G) and P4 (chr14:27399222 G/A) are located approximately 11.2 Megabases (Mb) apart on chromosome 14 and are expected to display genetic linkage. Two different genotypes confirm that the chromosome having both P2 and P4 in cis exists in horse populations: P2/P2 n/P4 and n/P2 P4/P4 individuals have been observed in Quarter Horse-related breeds. No horse that is P2/P2 P4/P4, or more properly written, P2 P4/P2 P4, has been observed to date in Quarter Horse-related breeds or in any other breed in a sample of nearly 1,000 horses tested for both variants.

TABLE 6 shows the observed incidence of P2, P3, P4, P5, P6, P8, and K1 in Thoroughbreds. Because as noted above, Thoroughbreds have a closed breeding book, it is possible that Thoroughbreds may be entirely free of one or more of these genetic variants. In the sample of modest size tested to date, P5 and K1 have not yet been observed in Thoroughbreds, while the observed frequency of other variants ranges from 0.028 for P8 to 0.193 for P6. The Thoroughbreds included in this sample are less highly selected for symptomatic horses than is the Quarter Horse-related sample because the method of recruitment of horse owners was different. However, some horse owners were aware of the nature of the research and likely volunteered symptomatic horses. The results show that Thoroughbreds are well suited for the further study of the P6 genetic variant, as it occurs at a reasonably high frequency in the absence of P5, the other allele of DYSF.

TABLE 7 shows the observed incidence of P2, P3, P4, P5, P6, P8, and K1 in Arabians. So far, P3 has not yet been observed in Arabians, nor has P5 or P6. P2, P4, and K1 are observed. P8 is observed at an allele frequency of 0.218. As noted previously in this disclosure, it is possible that the PYROXD1 variant P8 is responsible for the defect in the redox state of cysteine-containing antioxidants seen in Arabians diagnosed with Myofibrillar Myopathy (MFM) in a recent published study (Valberg et al. 2018 Physiol Genomics doi: 10.1152). This shows that Arabians are ideal for the further study of the effects of the PYROXD1 variant P8.

TABLE 8 shows the observed incidence of P2, P3, P4, P5, P6, P8, and K1 in draft breeds, defined for this sample as Shires, Clydesdales, and Percherons, or horses derived from crosses among these breeds. There are many other draft breeds for which we have obtained samples of very modest size, but we initially concentrated on these three breeds because the observed incidence of P5 was very high. The observed frequency of P5 in this modest sample is 0.543. The observed frequency of P6 in this modest sample is 0.136. These frequencies are high enough that compound heterozygotes (P5/P6) can be expected; indeed, two symptomatic compound heterozygotes have been identified. The observed frequency of P4, P8, and K1 in this small sample is zero; P2 and P3 are present. This shows that Shires, Clydesdales, and Percherons are ideal for the further study of the effects of the DYSF variants P5 and P6.

TABLE 5

Incidence of genetic variants in Quarter Horse-related breeds

| | | | | | |
|---|---|---|---|---|---|
| P2 | n/n 390 | n/P2 167 | P2/P2 38 | Total 595 | P2 allele frequency 0.204 |
| P3 | n/n 503 | n/P3 92 | P3/P3 4 | Total 599 | P3 allele frequency 0.083 |
| P4 | n/n 587 | n/P4 81 | P4/P4 4 | Total 587 | P4 allele frequency 0.076 |
| P5 | n/n 35 | n/P5 3 | P5/P5 0 | Total 37 | P5 allele frequency 0.041 |
| P6 | n/n 64 | n/P6 8 | P6/P6 0 | Total 72 | P6 allele frequency 0.056 |
| P8 | n/n 79 | n/P8 7 | P8/P8 0 | Total 86 | P8 allele frequency 0.041 |
| K1 | n/n 145 | n/K1 2 | K1/K1 0 | Total 147 | K1 allele frequency 0.007 |

TABLE 6

Incidence of genetic variants in Thoroughbreds

| | | | | | |
|---|---|---|---|---|---|
| P2 | n/n 149 | n/P2 51 | P2/P2 8 | Total 208 | P2 allele frequency 0.161 |
| P3 | n/n 170 | n/P3 42 | P3/P3 2 | Total 214 | P3 allele frequency 0.107 |
| P4 | n/n 177 | n/P4 34 | P4/P4 1 | Total 212 | P4 allele frequency 0.085 |
| P5 | n/n 102 | n/P5 0 | P5/P5 0 | Total 102 | P5 allele frequency 0.0 |
| P6 | n/n 69 | n/P6 33 | P6/P6 4 | Total 106 | P6 allele frequency 0.193 |
| P8 | n/n 116 | n/P8 7 | P8/P8 0 | Total 123 | P8 allele frequency 0.028 |
| K1 | n/n 121 | n/K1 0 | K1/K1 0 | Total 121 | K1 allele frequency 0.0 |

TABLE 7

Incidence of genetic variants in Arabians

| | | | | | |
|---|---|---|---|---|---|
| P2 | n/n 43 | n/P2 17 | P2/P2 4 | Total 64 | P2 allele frequency 0.195 |
| P3 | n/n 64 | n/P3 0 | P3/P3 0 | Total 64 | P3 allele frequency 0.0 |
| P4 | n/n 58 | n/P4 8 | P4/P4 1 | Total 65 | P4 allele frequency 0.077 |
| P5 | n/n 22 | n/P5 0 | P5/P5 0 | Total 22 | P5 allele frequency 0.0 |
| P6 | n/n 16 | n/P6 0 | P6/P6 0 | Total 16 | P6 allele frequency 0.0 |
| P8 | n/n 38 | n/P8 21 | P8/P8 3 | Total 62 | P8 allele frequency 0.218 |
| K1 | n/n 18 | n/K1 3 | K1/K1 0 | Total 21 | K1 allele frequency 0.071 |

TABLE 8

Incidence of genetic variants in Draft breeds

| | | | | | |
|---|---|---|---|---|---|
| P2 | n/n 15 | n/P2 5 | P2/P2 5 | Total 25 | P2 allele frequency 0.300 |
| P3 | n/n 24 | n/P3 1 | P3/P3 0 | Total 25 | P3 allele frequency 0.020 |
| P4 | n/n 23 | n/P4 0 | P4/P4 0 | Total 23 | P4 allele frequency 0.0 |
| P5 | n/n 6 | n/P5 9 | P5/P5 8 | Total 23 | P5 allele frequency 0.543 |
| P6 | n/n 16 | n/P6 6 | P6/P6 0 | Total 22 | P6 allele frequency 0.136 |
| P8 | n/n 22 | n/P8 0 | P8/P8 0 | Total 22 | P8 allele frequency 0.0 |
| K1 | n/n 23 | n/K1 0 | K1/K1 0 | Total 23 | K1 allele frequency 0.0 |

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

This is illustrated by the following examples. It is to be understood that the particular examples, materials, amounts, and procedures are to be interpreted broadly in accordance with the scope and spirit of the invention as set forth herein.

EXAMPLES

Example 1

Method of Detecting DNA Mutations Associated with Equine Polysaccharide Storage Myopathy Type 2 (PSSM2), Also Known as Myofibrillar Myopathy (MFM)

The complete DNA sequences of the horse DYSF, PYROXD1, and COL6A3 coding regions were obtained from the current version of the public horse genome assembly (EquCab2).

Using the DYSF, PYROXD1, and COL6A3 sequences, PCR primers are developed that can amplify the site of genomic DNA containing the DYSF-R253W, DYSF-P1290T, PYROXD1-D492H, and COL6A3-G2182A mutations. For example, a PCR primer pair that has been successfully and reliably used to amplify the region including DYSF-R253W from isolated horse DNA samples lies in the region around Exon B (FIG. 3). These sequences are

```
                                  (SEQ ID NO: 14)
5'-CCCGAGATTTCTGGCTTTCT-3'
and (SEQ ID NO: 15)
5'-CTCGACAAGTTCTGGGGTGT-3'.
```

A PCR primer pair that has been successfully and reliably used to amplify the region including DYSF-P1290T from isolated horse DNA samples lies in the region around Exon I (FIG. 3). These sequences are

```
                                  (SEQ ID NO: 64)
5'-GGTTGCAAACTCCCAACTGT-3'
and (SEQ ID NO: 65)
5'-GATTTTTCAAGCTGCCGAAG-3'.
```

A PCR primer pair that has been successfully and reliably used to amplify the region including PYROXD1-D492H from isolated horse DNA samples lies in the region around Exon 12 (FIG. 15). These sequences are

```
                                  (SEQ ID NO: 111)
5'-CAGATTTTCTGCTGGCCATT-3'
and (SEQ ID NO: 112)
5'-TGGTCATCATTAAATCAGTGCAA-3']
```

A PCR primer pair that has been successfully and reliably used to amplify the region including COL6A3-G2182A from isolated horse DNA samples lies in the region around Exon 12 (FIG. 26). These sequences are 5'-AG-ATGGGGCACAGATCAAAC-3' (SEQ ID NO:172) and 5'-TTCCCAGACTCTCCTGTGCT-3' (SEQ ID NO:171). Many other primer pairs are also possible.

Using the above PCR primers to amplify the region, the genotype of any horse (G/G, G/A, or A/A) for the DNA sequence of the forward strand at chr15:31,306,949, and R/R, R/W, or W/W for the amino acid sequence of the DYSF-R253W variant can be obtained. In this method, the amplified DNA may be cloned and then sequenced or sequenced directly without cloning. Alternatively, the appearance of amplified product in the presence of primers specific to the wild type or mutant allele may be monitored in real time using a qPCR instrument designed for this purpose. Many other methods of detecting the nucleotides at the positions of the horse DYSF sequence are possible.

Using the above PCR primers to amplify the region, the genotype of any horse (G/G, G/T, or T/T) for the DNA sequence of the forward strand at chr15:31,306,949, and P/P, P/T, or T/T for the amino acid sequence of the DYSF-P1290T variant can be obtained. In this method, the amplified DNA may be cloned and then sequenced or sequenced directly without cloning. Alternatively, the appearance of amplified product in the presence of primers specific to the wild type or mutant allele may be monitored in real time using a qPCR instrument designed for this purpose. Many other methods of detecting the nucleotides at the positions of the horse DYSF sequence are possible.

Using the above PCR primers to amplify the region, the genotype of any horse (G/G, G/C, or C/C) for the DNA sequence of the forward strand at chr6:47,661,977, and D/D, D/H, or H/H for the amino acid sequence of the PYROXD1-D492H variant can be obtained. In this method, the amplified DNA may be cloned and then sequenced or sequenced directly without cloning. Alternatively, the appearance of amplified product in the presence of primers specific to the wild type or mutant allele may be monitored in real time using a qPCR instrument designed for this purpose. Many other methods of detecting the nucleotides at the positions of the horse PYROXD1 sequence are possible.

Using the above PCR primers to amplify the region, the genotype of any horse (G/G, G/C, or C/C) for the DNA sequence of the forward strand at chr6:23,480,621, and G/G, G/A, or A/A for the amino acid sequence of the COL6A3-G2182A variant can be obtained. In this method, the amplified DNA may be cloned and then sequenced or sequenced directly without cloning. Alternatively, the appearance of amplified product in the presence of primers specific to the wild type or mutant allele may be monitored in real time using a qPCR instrument designed for this purpose. Many other methods of detecting the nucleotides at the positions of the horse COL6A3 sequence are possible.

DNA testing now provides veterinarians and veterinary pathologists with a means to more accurately determine if a horse with the clinical signs of Polysaccharide Storage Myopathy type 2 (PSSM2) has the heritable and common form of the disease that can be specifically attributed to the DYSF-R253W, DYSF-P1290T, PYROXD1-D492H, or COL6A3-G2182A coding region mutation. All that is needed is a tissue sample containing the individual's DNA (typically hair root or blood) and appropriate PCR and sequence analysis technology to detect the distinct nucleotide changes. Such PCR primers are based in (1) DYSF Exon B (as shown in FIG. 3) and the flanking intron sequences, as shown in FIG. 3, or in other DNA sequences of this gene, (2) DYSF Exon I (as shown in FIG. 15) and the flanking intron sequences, as shown in FIG. 15, or in other DNA sequences of this gene, (3) PYROXD1 Exon 12 (as shown in FIG. 24) and the flanking intron sequences, as shown in FIG. 24, or in other DNA sequences of this gene, or (4) COL6A3 Exon 26 (as shown in FIG. 35) and the flanking intron sequences, as shown in FIG. 35, or in other DNA sequences of this gene.

Also, DNA testing provides owners and breeders with a means to determine if any horse can be expected to produce offspring with these forms of Polysaccharide Storage Myopathy type 2 (PSSM2). Abbreviating the DYSF-R253W allele as P5, a P5/P5 horse would produce a carrier foal 100% of the time, while an N/P5 horse would produce a carrier foal 50% of the time when mated to an N/N horse. Mating of an N/P5 horse to an N/P5 horse would produce an affected foal 25% of the time and a carrier foal 50% of the time. Abbreviating the DYSF-P1290T allele as P6, a P6/P6 horse would produce a carrier foal 100% of the time, while an N/P6 horse would produce a carrier foal 50% of the time when mated to an N/N horse. Mating of an N/P6 horse to an N/P6 horse would produce an affected foal 25% of the time and a carrier foal 50% of the time. Abbreviating the PYROXD1-D492H allele as P8, a P8/P8 horse would produce a heterozygous foal 100% of the time when mated to an n/n horse, while an n/P8 horse would produce a heterozygous foal 50% of the time when mated to an n/n horse. Mating of an n/P8 horse to an n/P8 horse would produce an affected P8/P8 foal 25% of the time, and an affected n/P8 foal 50% of the time. Abbreviating the COL6A3-G2182A allele as K1, a K1/K1 horse would produce a heterozygous foal 100% of the time when mated to an n/n horse, while an n/K1 horse would produce a heterozygous foal 50% of the time when mated to an n/n horse. Mating of an n/K1 horse to an n/K1 horse would produce an affected K1/K1 foal 25% of the time, and an affected n/K1 foal 50% of the time. Breeding programs could incorporate this information in the selection of parents that could eventually reduce and even eliminate these forms of Polysaccharide Storage Myopathy type 2 (PSSM2) in their herds.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of mating a horse comprising:
   (a) detecting in a biological sample obtained from said horse, said sample comprising nucleic acids that include the coding regions for dysferlin (DYSF), polynucleotide-disulfide oxidoreductase domain-containing protein 1 (PYROXD1) and collagen type VI alpha 3 chain (COL6A3):

(1) a thymine (T) or a cytosine (C) at nucleotide 1001 of SEQ ID NO: 1, wherein detection of the thymine indicates the presence of variant P5;
   (2) an adenine (A) or cytosine (C) at nucleotide 1001 of SEQ ID NO:56, wherein detection of the adenine indicates the presence of variant P6;
   (3) a cytosine (C) or a guanine (G) at nucleotide 1001 of SEQ ID NO:103, wherein detection of the cytosine indicates the presence of variant P8; and (4) a cytosine (C) or a guanine (G) at nucleotide 1001 of SEQ ID NO: 163, wherein detection of the cytosine indicates the presence of variant K1;

wherein in each case the presence of the nucleotide can be inferred from detecting the nucleotide present at the complement thereof;

wherein the presence of any one or more of said variants P5, P6, P8 and K1 in said nucleic acid is indicative of inherited equine myopathy in said horse;

wherein said horse is not homozygous for the presence of P5, P6, P8 or K1;

wherein said horse is heterozygous for at least one of P5, P6, P8 or K1; and (b) mating said horse with a mare or sire.

2. The method according to claim 1 wherein said mare or sire is free of P5, P6, P8 and K1.

3. The method according to claim 1 wherein said mare or sire is heterozygous for variant P5, P6, P8 or K1.

4. The method according to claim 1, further comprising: contacting the nucleic acids of the sample with at least one oligonucleotide probe to form a hybridized nucleic acid; and amplifying the hybridized nucleic acid.

5. The method according to claim 4, wherein:

Exon B of the equine dysferlin coding region (DYSF), as defined in SEQ ID NO: 5, or a portion thereof is amplified;

Exon I of the equine dysferlin coding region (DYSF), as defined in SEQ ID NO: 59, or a portion thereof is amplified;

Exon 12 of the equine pyridine nucleotide-disulfide oxidoreductase domain-containing protein 1 (PYROXD 1), as defined in SEQ ID NO: 106, or a portion thereof is amplified; or Exon 26 of the equine collagen type VI alpha 3 chain coding region (COL6A3), as defined in SEQ ID NO: 166, or a portion thereof is amplified.

6. The method according to claim 4, wherein the hybridized nucleic acid is amplified using polymerase chain reaction, strand displacement amplification, ligase chain reaction, or nucleic acid sequence-based amplification.

7. The method according to claim 4, wherein at least one oligonucleotide probe is immobilized on a solid surface or a semisolid surface.

8. The method according to claim 1, wherein the nucleic acid is genomic DNA.

9. The method according to claim 4, wherein the nucleic acid is genomic DNA.

10. The method according to claim 5, wherein the nucleic acid is genomic DNA.

11. The method according to claim 6, wherein the nucleic acid is genomic DNA.

12. The method according to claim 7, where in the nucleic acid is genomic DNA.

13. The method according to claim 1 wherein the nucleic acid is RNA.

14. The method according to claim 4 wherein the nucleic acid is RNA.

15. The method according to claim 5 wherein the nucleic acid is RNA.

16. The method according to claim 6 wherein the nucleic acid is RNA.

17. The method according to claim 7 wherein the nucleic acid is RNA.

18. The method according to claim 13, wherein the method comprises converting the RNA into DNA by reverse transcriptase.

19. The method according to claim 14, wherein the method comprises converting the RNA into DNA by reverse transcriptase.

20. The method according to claim 15, wherein the method comprises converting the RNA into DNA by reverse transcriptase.

21. The method according to claim 16, wherein the method comprises converting the RNA into DNA by reverse transcriptase.

22. The method according to claim 17, wherein the method comprises converting the RNA into DNA by reverse transcriptase.

23. A method for detecting a biomarker in a horse, the method comprising:

(a) obtaining a biological sample from said horse, the biological sample comprising nucleic acid that includes the coding regions for dysferlin (DYSF) corresponding to SEQ ID NOs: 2 and 57, polynucleotide-disulfide oxidoreductase domain-containing protein 1 (PYROXD1) corresponding to SEQ ID NO: 104 and collagen type VI alpha 3 chain (COL6A3) corresponding to SEQ ID NO: 164; and detecting:

(1) a thymine (T) or a cytosine (C) at nucleotide 264 of SEQ ID NO:2, wherein detection of the thymine indicates the presence of variant P5;

(2) an adenine (A) or cytosine (C) at nucleotide 448 of SEQ ID NO:57, wherein detection of the adenine indicates the presence of variant P6;

(3) a cytosine (C) or a guanine (G) at nucleotide 1311 of SEQ ID NO:104, wherein detection of the cytosine indicates the presence of variant P8; and (4) a cytosine (C) or a guanine (G) at nucleotide 437 of SEQ ID NO: 164, wherein detection of the cytosine indicates the presence of variant K1 wherein in each case the presence of the nucleotide can be inferred from detecting the nucleotide present at the complement thereof;

wherein the presence of any one or more of said variants P5, P6, P8 and K1 in said nucleic acid is indicative of inherited equine myopathy in said horse;

wherein said horse is not homozygous for the presence of P5, P6, P8 or K1;

wherein said horse is heterozygous for at least one of P5, P6, P8 or K1; and (b) mating said horse with a mare or sire.

24. The method according to claim 23 wherein said mare or sire is free from variants P5, P6, P8 and K1.

25. The method according to claim 24 wherein said mare or sire is heterozygous for variant P5, P6, P8 or K1.

26. The method of claim 23, further comprising: contacting the nucleic acid with at least one oligonucleotide probe to form a hybridized nucleic acid; and amplifying the hybridized nucleic acid.

27. The method of claim 26, wherein the hybridized nucleic acid is amplified using polymerase chain reaction, strand displacement amplification, ligase chain reaction, or nucleic acid sequence-based amplification.

28. The method of claim 26, wherein at least one oligonucleotide probe is immobilized on a solid surface or semisolid surface.

* * * * *

SEQUENCE LISTING

```
<160> NUMBER OF SEQ ID NOS: 264

<210> SEQ ID NO 1
<211> LENGTH: 2001
<212> TYPE: DNA
<213> ORGANISM: Equus caballus

<400> SEQUENCE: 1
ttcagttcta aatcatgata atttaaggaa aagtgccagc tataaccact atgtttaccc       60
gaaagacaaa attctaattt attgttatta ttattattcc caaggcatgt ttttattgtc      120
tttttcctcc ttagaaaatt aatatatatt tattgtagaa aacttggaaa atacagcaca      180
atgaagagaa taaaaatcac tcacccacct tccgattgtt attaacaaaa taacattctt      240
ctattttagt atgctgtttt ttttaaaaag agttaatcca taaagaaata actgttgatt      300
agaaattaga accagtaaat atcttttttc catgaaactt gttttaatat ttttaaattt      360
catcttttta aaaatatttt gcctacattt aagaagcaca gatatttacg aaacttcatt      420
tacttaaagt tcaatggaga aaagtcttaa tttatttctc agaatgtgag aaatccttac      480
atcttataaa gaataaagtg gggtcatgtc gccacgtaag tttgacctct gagggaattg      540
ttagtaaaga atgttcgagc cacttcaaaa cgtcagcctc cagggtccga ggtggggatt      600
gtgccaacgg ctgcatgaag tgaaccgggc tgcatccttg gcccagctct gggatctaac      660
```

```
actggtggct tatttggggc agcctggcag ctcttttgca gaactgtggg attttacagc    720
tgcaaggtac cttgatggga aaatatgact gttcttacaa tgctcctcct aattcttttt    780
taatttcctt cccaagaagc cagcagggag ggtggtcccc gagatttctg gctttctttg    840
tggcgaggtc gggggaggtg ggtgcctgac tgttttcccc ttcctcctgc tcatgcccct    900
tcctggcttt cagatcaggg tccaggtgat cgaggggcgc cagctgccag ggtgaacat     960
caagcctgtg gtcaaggtca ccgcggccag gcagaccaag yggactcgga ttcacagggg   1020
aaacagcccg ctcttcaacg aggtgggaga catggcgttt tagggctggt agcttggtgg   1080
gccttccaga ttgggagcac ccggcagata cctggcaatt ctttcagttt ttgttcatgg   1140
cgctaacttt ggtttgagag gtgtgccagg tcctgagtac gttatctgag gaactggaga   1200
gagggttcta gttcttattc ctgtcccggg ctcctggtgc tccacatccc tgtcttcctg   1260
tggggccagc cacccatgct gtcctggaga tgacaacctc tgagaggtca ggggtggaac   1320
accccagaac ttgtcgagtc ctcagagctc agggccgggc agagctcact ctgtgctttc   1380
cgtgtggacc agacctgaag gctgtgggtg tggccgaccc tcttcccagc ctgggggtca   1440
acaggctctc gtttatcttc ctttcgccct gaaccaacag actctcttct tcaacgtgtt   1500
tgactctccc tcggagctgt ttgacgaggc cgtctttatc acggtacgtc tcagggatca   1560
aggcgtgctc tgtgggccgt gtgtacacac atgcattcag tgtgcatgtg tgtgtatgca   1620
cgtaggggtg tgagtgtgag agtgtgtagg agaagcctta gggcccgggg cctgggtgat   1680
gtggggagct cgctgctaag ctctgctggt cacaaaagtg ccttcagcag ctcagatgag   1740
gcagcagccc agtggggaga ccccccgctg ctcagcaccc ccaggtgcct caggccaggt   1800
cctgatatca ttcctgcagg ggatactttg attttcctct ttttttcttt gtccacttgc   1860
ctgcttctgg ccaagattgc ctctctctga gcctcagctc tttgtttttc ttccctctga   1920
aaggcagtat agtttggtga aaagcgtggg ctttggagcc aaactgtctg gattctagtc   1980
ctgcctgtgc catgtagggg c                                             2001
```

<210> SEQ ID NO 2
<211> LENGTH: 1029
<212> TYPE: DNA
<213> ORGANISM: Equus caballus

<400> SEQUENCE: 2

```
atacaggagg agaggaggac accgaggacc aggggctcac gggagatgag gcagagccat     60
tcttggatca gaacggagcc ccaggccccg gggctcccac caccctgaag aagccacctt    120
cccatcctcc cccctaccat cctgggggga aaaggaagag aagcacgcct gcgcccagaa    180
agctgctttc ggataaacca caggacttcc agatcagggt ccaggtgatc gaggggcgcc    240
agctgccagg ggtgaacatc aagcctgtgg tcaaggtcac cgcggccagg cagaccaagc    300
ggactcggat tcacagggga aacagcccgc tcttcaacga gactctcttc ttcaacgtgt    360
ttgactctcc ctcggagctg tttgacgagg ccgtctttat cacggtggta gactcctgtt    420
cgctccggac agatgccctc atcggggagt tccggatgga tgtgggtacc atctacagag    480
agccccgaca cgcctatctc aggaagtggc tgctgctctc ggaccctgac gatttctctg    540
ctgggcccaa aggctacctg aaagcaagcc tttgtgtgct ggggcctgga gacgaagctc    600
cgctggagag aaaggacccc tctgaagaca aggaggacat tgaaagcaat ctgctcaggc    660
caactggcat ggcccttcga ggagcgcact tctgtctgaa ggtcttcagg gctgaggact    720
```

```
taccacagat ggacgatgcc gtggtggaca gcgtgaagca gatcttcggc tttgacagta      780
acaagaagaa cctggtggat cccttcgtcg aggtcagctt tgcggggaaa atgctctgca      840
gcaagatcct ggagaagatg gccaaccctc agtggaacca gagcatcacg ctgcctgtca      900
tgtttccctc catgtctgaa aaaatgagga ttcgtgtcat agactgggac cgcctcaccc      960
acaatgacat cgtggccacc acctacctga atatgtcgaa aatctctgcc cctggaggag     1020
aaatagcag                                                             1029

<210> SEQ ID NO 3
<211> LENGTH: 1029
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atacaggagg agaggaggac accgaggacc aggggctcac gggagatgag gcagagccat       60
tcttggatca gaacggagcc ccaggccccg ggctcccac caccctgaag aagccacctt      120
cccatcctcc cccctaccat cctgggggga aaggaagag aagcacgcct gcgcccagaa      180
agctgctttc ggataaacca caggacttcc agatcagggt ccaggtgatc gagggggcgcc     240 agctgccagg ggtgaacatc aagtctgtgg tcaaggtcac cgcggccagg cagaccaagc      300
ggactcggat tcacagggga aacagcccgc tcttcaacga gactctcttc ttcaacgtgt      360
ttgactctcc ctcggagctg tttgacgagg ccgtctttat cacggtggta gactcctgtt      420
cgctccggac agatgccctc atcggggagt tccggatgga tgtgggtacc atctacagag      480
agccccgaca cgcctatctc aggaagtggc tgctgctctc ggaccctgac gatttctctg      540
ctgggcccaa aggctacctg aaagcaagcc tttgtgtgct ggggcctgga gacgaagctc      600
cgctggagag aaaggacccc tctgaagaca aggaggacat tgaaagcaat ctgctcaggc      660
caactggcat ggcccttcga ggagcgcact tctgtctgaa ggtcttcagg gctgaggact      720
taccacagat ggacgatgcc gtggtggaca gcgtgaagca gatcttcggc tttgacagta      780
acaagaagaa cctggtggat cccttcgtcg aggtcagctt tgcggggaaa atgctctgca      840
gcaagatcct ggagaagatg gccaaccctc agtggaacca gagcatcacg ctgcctgtca      900
tgtttccctc catgtctgaa aaaatgagga ttcgtgtcat agactgggac cgcctcaccc      960
acaatgacat cgtggccacc acctacctga atatgtcgaa aatctctgcc cctggaggag     1020
aaatagcag                                                             1029

<210> SEQ ID NO 4
<211> LENGTH: 232
<212> TYPE: DNA
<213> ORGANISM: Equus caballus

<400> SEQUENCE: 4
ctcctcccag atacaggagg agaggaggac accgaggacc aggggctcac gggagatgag       60
gcagagccat tcttggatca gaacggagcc ccaggccccg ggctcccac caccctgaag      120 aagccacctt cccatcctcc cccctaccat cctgggggga aaggaagag aagcacgcct      180 gcgcccagaa agctgctttc ggataaacca caggacttcc aggtgatgca cc             232

<210> SEQ ID NO 5
<211> LENGTH: 149
<212> TYPE: DNA
```

<213> ORGANISM: Equus caballus

<400> SEQUENCE: 5

```
tggctttcag atcagggtcc aggtgatcga ggggcgccag ctgccagggg tgaacatcaa    60
gcctgtggtc aaggtcaccg cggccaggca gaccaagcgg actcggattc acaggggaaa   120
cagcccgctc ttcaacgagg tgggagaca                                     149
```

<210> SEQ ID NO 6
<211> LENGTH: 83
<212> TYPE: DNA
<213> ORGANISM: Equus caballus

<400> SEQUENCE: 6

```
gaaccaacag actctcttct tcaacgtgtt tgactctccc tcggagctgt ttgacgaggc    60
cgtctttatc acggtacgtc tca                                            83
```

<210> SEQ ID NO 7
<211> LENGTH: 71
<212> TYPE: DNA
<213> ORGANISM: Equus caballus

<400> SEQUENCE: 7

```
ttccctccag gtggtagact cctgttcgct ccggacagat gccctcatcg gggagttccg    60
ggtaattagt t                                                          71
```

<210> SEQ ID NO 8
<211> LENGTH: 53
<212> TYPE: DNA
<213> ORGANISM: Equus caballus

<400> SEQUENCE: 8

```
ctgattgcag atggatgtgg gtaccatcta cagagagccc cgtgagtcat att           53
```

<210> SEQ ID NO 9
<211> LENGTH: 136
<212> TYPE: DNA
<213> ORGANISM: Equus caballus

<400> SEQUENCE: 9

```
tctctcttag dacacgccta tctcaggaag tggctgctgc tctcggaccc tgacgatttc    60
tctgctgggc ccaaaggcta cctgaaagca agcctttgtg tgctggggcc tggagacgaa   120
gctccggtga gtcatt                                                   136
```

<210> SEQ ID NO 10
<211> LENGTH: 342
<212> TYPE: PRT
<213> ORGANISM: Equus caballus

<400> SEQUENCE: 10

Thr Gly Gly Glu Glu Asp Thr Glu Asp Gln Leu Thr Gly Asp Glu
1               5                   10                  15

Ala Glu Pro Phe Leu Asp Gln Asn Gly Ala Pro Gly Pro Gly Ala Pro
            20                  25                  30

Thr Thr Leu Lys Lys Pro Pro Ser His Pro Pro Tyr His Pro Gly
        35                  40                  45

Gly Lys Arg Lys Arg Ser Thr Pro Ala Pro Arg Lys Leu Leu Ser Asp
    50                  55                  60

Lys Pro Gln Asp Phe Gln Ile Arg Val Gln Val Ile Glu Gly Arg Gln

```
            65                  70                  75                  80

Leu Pro Gly Val Asn Ile Lys Pro Val Val Lys Val Thr Ala Ala Arg
                    85                  90                  95

Gln Thr Lys Arg Thr Arg Ile His Arg Gly Asn Ser Pro Leu Phe Asn
                100                 105                 110

Glu Thr Leu Phe Phe Asn Val Phe Asp Ser Pro Ser Glu Leu Phe Asp
                115                 120                 125

Glu Ala Val Phe Ile Thr Val Val Asp Ser Cys Ser Leu Arg Thr Asp
                130                 135                 140

Ala Leu Ile Gly Glu Phe Arg Met Asp Val Gly Thr Ile Tyr Arg Glu
145                 150                 155                 160

Pro Arg His Ala Tyr Leu Arg Lys Trp Leu Leu Ser Asp Pro Asp
                165                 170                 175

Asp Phe Ser Ala Gly Pro Lys Gly Tyr Leu Lys Ala Ser Leu Cys Val
                180                 185                 190

Leu Gly Pro Gly Asp Glu Ala Pro Leu Glu Arg Lys Asp Pro Ser Glu
                195                 200                 205

Asp Lys Glu Asp Ile Glu Ser Asn Leu Leu Arg Pro Thr Gly Met Ala
                210                 215                 220

Leu Arg Gly Ala His Phe Cys Leu Lys Val Phe Arg Ala Glu Asp Leu
225                 230                 235                 240

Pro Gln Met Asp Asp Ala Val Val Asp Ser Val Lys Gln Ile Phe Gly
                245                 250                 255

Phe Asp Ser Asn Lys Lys Asn Leu Val Asp Pro Phe Val Glu Val Ser
                260                 265                 270

Phe Ala Gly Lys Met Leu Cys Ser Lys Ile Leu Glu Lys Met Ala Asn
                275                 280                 285

Pro Gln Trp Asn Gln Ser Ile Thr Leu Pro Val Met Phe Pro Ser Met
                290                 295                 300

Ser Glu Lys Met Arg Ile Arg Val Ile Asp Trp Asp Arg Leu Thr His
305                 310                 315                 320

Asn Asp Ile Val Ala Thr Thr Tyr Leu Asn Met Ser Lys Ile Ser Ala
                325                 330                 335

Pro Gly Gly Glu Ile Ala
                340

<210> SEQ ID NO 11
<211> LENGTH: 342
<212> TYPE: PRT
<213> ORGANISM: Equus caballus

<400> SEQUENCE: 11

Thr Gly Gly Glu Glu Asp Thr Glu Asp Gln Gly Leu Thr Gly Asp Glu
1               5                   10                  15

Ala Glu Pro Phe Leu Asp Gln Asn Gly Ala Pro Gly Pro Gly Ala Pro
                20                  25                  30

Thr Thr Leu Lys Lys Pro Pro Ser His Pro Pro Tyr His Pro Gly
                35                  40                  45

Gly Lys Arg Lys Arg Ser Thr Pro Ala Pro Arg Lys Leu Leu Ser Asp
            50                  55                  60

Lys Pro Gln Asp Phe Gln Ile Arg Val Gln Val Ile Glu Gly Arg Gln
65                  70                  75                  80

Leu Pro Gly Val Asn Ile Lys Pro Val Val Lys Val Thr Ala Ala Arg
                    85                  90                  95
```

```
Gln Thr Lys Trp Thr Arg Ile His Arg Gly Asn Ser Pro Leu Phe Asn
            100                 105                 110
Glu Thr Leu Phe Phe Asn Val Phe Asp Ser Pro Ser Glu Leu Phe Asp
        115                 120                 125
Glu Ala Val Phe Ile Thr Val Val Asp Ser Cys Ser Leu Arg Thr Asp
    130                 135                 140
Ala Leu Ile Gly Glu Phe Arg Met Asp Val Gly Thr Ile Tyr Arg Glu
145                 150                 155                 160
Pro Arg His Ala Tyr Leu Arg Lys Trp Leu Leu Ser Asp Pro Asp
                165                 170                 175
Asp Phe Ser Ala Gly Pro Lys Gly Tyr Leu Lys Ala Ser Leu Cys Val
            180                 185                 190
Leu Gly Pro Gly Asp Glu Ala Pro Leu Glu Arg Lys Asp Pro Ser Glu
        195                 200                 205
Asp Lys Glu Asp Ile Glu Ser Asn Leu Leu Arg Pro Thr Gly Met Ala
    210                 215                 220
Leu Arg Gly Ala His Phe Cys Leu Lys Val Phe Arg Ala Glu Asp Leu
225                 230                 235                 240
Pro Gln Met Asp Asp Ala Val Val Asp Ser Val Lys Gln Ile Phe Gly
                245                 250                 255
Phe Asp Ser Asn Lys Lys Asn Leu Val Asp Pro Phe Val Glu Val Ser
            260                 265                 270
Phe Ala Gly Lys Met Leu Cys Ser Lys Ile Leu Glu Lys Met Ala Asn
        275                 280                 285
Pro Gln Trp Asn Gln Ser Ile Thr Leu Pro Val Met Phe Pro Ser Met
    290                 295                 300
Ser Glu Lys Met Arg Ile Arg Val Ile Asp Trp Asp Arg Leu Thr His
305                 310                 315                 320
Asn Asp Ile Val Ala Thr Thr Tyr Leu Asn Met Ser Lys Ile Ser Ala
                325                 330                 335
Pro Gly Gly Glu Ile Ala
            340

<210> SEQ ID NO 12
<211> LENGTH: 129
<212> TYPE: DNA
<213> ORGANISM: Equus caballus

<400> SEQUENCE: 12
atcagggtcc aggtgatcga ggggcgccag ctgccagggg tgaacatcaa gcctgtggtc      60
aaggtcaccg cggccaggca gaccaagcgg actcggattc acaggggaaa cagcccgctc     120
ttcaacgag                                                             129

<210> SEQ ID NO 13
<211> LENGTH: 129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
atcagggtcc aggtgatcga ggggcgccag ctgccagggg tgaacatcaa gcctgtggtc      60
aaggtcaccg cggccaggca gaccaagtgg actcggattc acaggggaaa cagcccgctc     120
ttcaacgag                                                             129
```

-continued

```
<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccgagattt ctggctttct                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctcgacaagt tctgggtgt                                                    20

<210> SEQ ID NO 16
<211> LENGTH: 6243
<212> TYPE: DNA
<213> ORGANISM: Homo sapiens

<400> SEQUENCE: 16
atgctgaggg tcttcatcct ctatgccgag aacgtccaca caccccgacac cgacatcagc      60 gatgcctact gctccgcggt gtttgcaggg gtgaagaaga gaaccaaagt catcaagaac      120
agcgtgaacc ctgtatggaa tgagggattt gaatgggacc tcaagggcat ccccctggac     180
cagggctctg agcttcatgt ggtggtcaaa gaccatgaga cgatggggag gaacaggttc     240 ctggggggaag ccaaggtccc actccgagag gtcctcgcca cccctagtct gtccgccagc   300
ttcaatgccc cctgctgga caccaagaag cagcccacag gggcctcgct ggtcctgcag     360
gtgtcctaca caccgctgcc tggagctgtg cccctgttcc cgccccctac tcctctggag   420
ccctccccga ctctgcctga cctggatgta gtggcagaca caggaggaga ggaagacaca     480
gaggaccagg gactcactgg agatgaggcg gagccattcc tggatcaaag cggaggcccg   540
ggggctccca ccaccccaag gaaactacct tcacgtcctc cgccccacta ccccgggatc     600
aaaagaaagc gaagtgcgcc tacatctaga aagctgctgt cagacaaacc gcaggatttc     660
cagatcaggg tccaggtgat cgaggggcgc cagctgccgg gggtgaacat caagcctgtg   720
gtcaaggtta ccgctgcagg gcagaccaag cggacgcgga tccacaaggg aaacagccca   780
ctcttcaatg agactctttt cttcaacttg tttgactctc ctgggagct gtttgatgag     840 cccatctta tcacggtggt agactctcgt tctctcagga cagatgctct cctcggggag   900
ttccggatgg acgtgggcac catttacaga gagccccggc acgcctatct caggaagtgg   960
ctgctgctct cagaccctga tgacttctct gctggggcca gaggctacct gaaaacaagc    1020
ctttgtgtgc tggggcctgg gacgaagcg cctctggaga gaaaagaccc ctctgaagac    1080
aaggaggaca ttgaaagcaa cctgctccgg cccacaggcg tagccctgcg aggagcccac   1140
ttctgcctga aggtcttccg ggccgaggac ttgccgcaga tggacgatgc cgtgatggac  1200
aacgtgaaac agatctttgg cttcgagagt aacaagaaga acttggtgga ccccttgtg     1260 gaggtcagct tgcggggaa aatgctgtgc agcaagatct ggagaagac ggccaaccct   1320 cagtggaacc agaacatcac actgcctgcc atgtttccct ccatgtgcga aaaatgagg   1380
```

```
attcgtatca tagactggga ccgcctgact cacaatgaca tcgtggctac cacctacctg   1440
agtatgtcga aaatctctgc ccctggagga gaaatagaag aggagcctgc aggtgctgtc   1500
aagccttcga aagcctcaga cttggatgac tacctgggct tcctcccccac ttttgggccc  1560
tgctacatca acctctatgg cagtcccaga gagttcacag gcttcccaga ccctacaca    1620
gagctcaaca caggcaaggg ggaaggtgtg gcttatcgtg gccggcttct gctctccctg   1680
gagaccaagc tggtggagca cagtgaacag aaggtggagg accttcctgc ggatgacatc   1740
ctccgggtgg agaagtacct taggaggcgc aagtactccc tgtttgcggc cttctactca   1800
gccaccatgc tgcaggatgt ggatgatgcc atccagtttg aggtcagcat cgggaactac   1860
gggaacaagt tcgacatgac ctgcctgccg ctggcctcca ccactcagta cagccgtgca   1920
gtctttgacg ggtgccacta ctactaccta ccctgggggta acgtgaaacc tgtggtggtg  1980
ctgtcatcct actgggagga catcagccat agaatcgaga ctcagaacca gctgcttggg   2040
attgctgacc ggctggaagc tggcctggag caggtccacc tggccctgaa ggcgcagtgc   2100
tccacggagg acgtggactc gctggtggct cagctgacgg atgagctcat cgcaggctgc   2160
agccagcctc tgggtgacat ccatgagaca ccctctgcca cccacctgga ccagtacctg   2220
taccagctgc gcacccatca cctgagccaa atcactgagg ctgccctggc cctgaagctc   2280
ggccacagtg agctccctgc agctctggag caggcggagg actggctcct gcgtctgcgt   2340
gccctggcag aggagcccca gaacagcctg ccggacatcg tcatctggat gctgcaggga   2400
gacaagcgtg tggcatacca gcgggtgccc gcccaccaag tcctcttctc ccggcggggt   2460
gccaactact gtggcaagaa ttgtgggaag ctacagacaa tctttctgaa atatccgatg   2520
gagaaggtgc ctggcgcccg gatgccagtg cagatacggg tcaagctgtg gtttgggctc   2580
tcagtggatg agaaggagtt caaccagttt gctgagggga agtgtctgt ctttgctgaa    2640
acctatgaga acgagactaa gttggccctt gttgggaact ggggcacaac gggcctcacc   2700
taccccaagt tttctgacgt cacgggcaag atcaagctac ccaaggacag cttccgcccc   2760
tcggccggct ggacctgggc tggagattgg ttcgtgtgtc cggagaagac tctgctccat   2820
gacatggacg ccggtcacct gagcttcgtg aagaggtgt tgagaacca gacccggctt     2880
cccggaggcc agtggatcta catgagtgac aactacaccg atgtgaacgg ggagaaggtg   2940
cttcccaagg atgacattga gtgcccactg gctggaagt gggaagatga ggaatggtcc    3000
acagacctca accgggctgt cgatgagcaa ggctgggagt atagcatcac catcccccccg  3060
gagcggaagc cgaagcactg gtccctgct gagaagatgt actacacaca ccgacggcgg    3120
cgctgggtgc gcctgcgcag gagggatctc agccaaatgg aagcactgaa aaggcacagg   3180
caggcggagg cggagggcga gggctggag tacgcctctc tttttggctg gaagttccac     3240
ctcgagtacc gcaagacaga tgccttccgc cgccgccgct ggcgccgtcg catggagcca   3300
ctggagaaga cggggcctgc agctgtgttt gcccttgagg gggccctggg cggcgtgatg   3360
gatgacaaga gtgaagattc catgtccgtc tccaccttga gcttcggtgt gaacagaccc   3420
acgatttcct gcatattcga ctatgggaac cgctaccatc tacgctgcta catgtaccag   3480
gccccgggacc tggctgcgat ggacaaggac tcttttttctg atcccctatgc catcgtctcc  3540
ttcctgcacc agagccagaa gacggtggtg gtgaagaaca cccttaaccc cacctgggac   3600
cagacgctca tcttctacga gatcgagatc tttggcgagc cggccacagt tgctgagcaa   3660
ccgcccagca ttgtggtgga gctgtacgac catgacactt atggtgcaga cgagtttatg   3720
```

```
ggtcgctgca tctgtcaacc gagtctggaa cggatgccac ggctggcctg gttcccactg    3780
acgaggggca gccagccgtc gggggagctg ctggcctctt ttgagctcat ccagagagag    3840
aagccggcca tccaccatat tcctggtttt gaggtgcagg agacatcaag gatcctggat    3900
gagtctgagg acacagacct gccctaccca ccaccccaga gggaggccaa catctacatg    3960
gttcctcaga acatcaagcc agcgctccag cgtaccgcca tcgagatcct ggcatggggc    4020
ctgcggaaca tgaagagtta ccagctggcc aacatctcct cccccagcct cgtggtagag    4080
tgtgggggcc agacggtgca gtcctgtgtc atcaggaacc tccggaagaa ccccaacttt    4140
gacatctgca ccctcttcat ggaagtgatg ctgcccaggg aggagctcta ctgccccccc    4200
atcaccgtca aggtcatcga taaccgccag tttggccgcc ggcctgtggt gggccagtgt    4260
accatccgct ccctggagag cttcctgtgt gaccccact cggcggagag tccatcccca    4320
cagggtggcc cagacgatgt gagcctactc agtcctgggg aagacgtgct catcgacatt    4380
gatgacaagg agcccctcat ccccatccag gaggaagagt tcatcgattg gtggagcaaa    4440
ttctttgcct ccataggggga gagggaaaag tgcggctcct acctggagaa ggattttgac    4500
accctgaagg tctatgacac acagctggag aatgtggagg cctttgaggg cctgtctgac    4560
ttttgtaaca ccttcaagct gtaccggggc aagacgcagg aggagacaga agatccatct    4620
gtgattggtg aatttaaggg cctcttcaaa atttatcccc tcccagaaga cccagccatc    4680
cccatgcccc caagacagtt ccaccagctg gccgcccagg accccaggag gtgcttggtc    4740
cgtatctaca ttgtccgagc atttggcctg cagcccaagg accccaatgg aaagtgtgat    4800
ccttacatca agatctccat agggaagaaa tcagtgagtg accaggataa ctacatcccc    4860
tgcacgctgg agcccgtatt tggaaagatg ttcgagctga cctgcactct gcctctggag    4920
aaggacctaa agatcactct ctatgactat gacctcctct ccaaggacga aaagatcggt    4980
gagacggtcg tcgacctgga gaacaggctg ctgtccaagt ttggggctcg ctgtggactc    5040
ccacagacct actgtgtctc tggaccgaac cagtggcggg accagctccg cccctcccag    5100
ctcctccacc tcttctgcca gcagcataga gtcaaggcac ctgtgtaccg gacagaccgt    5160
gtaatgtttc aggataaaga atattccatt gaagagatag aggctggcag gatcccaaac    5220
ccacacctgg gcccagtgga ggagcgtctg gctctgcatg tgcttcagca gcagggcctg    5280
gtcccggagc acgtggagtc acggcccctc tacagccccc tgcagccaga catcgagcag    5340
gggaagctgc agatgtgggt cgacctattt ccgaaggccc tggggcggcc tggacctccc    5400
ttcaacatca ccccacggag agccagaagg ttttttcctgc gttgtattat ctggaatacc    5460
agagatgtga tcctggatga cctgagcctc acggggggaga agatgagcga catttatgtg    5520
aaaggttgga tgattggctt tgaagaacac aagcaaaaga cagacgtgca ttatcgttcc    5580
ctgggaggtg aaggcaactt caactggagg ttcattttcc ccttcgacta cctgccagct    5640
gagcaagtct gtaccattgc caagaaggat gccttctgga ggctggacaa gactgagagc    5700
aaaatcccag cacgagtggt gttccagatc tgggacaatg acaagttctc ctttgatgat    5760
tttctgggct ccctgcagct cgatctcaac cgcatgccca gccagccaa gacagccaag    5820 aagtgctcct ggaccagct ggatgatgct ttccacccag aatggtttgt gtccctttt    5880 gagcagaaaa cagtgaaggg ctggtggccc tgtgtagcag aagagggtga aagaaaata    5940 ctggcgggca gctggaaat gaccttggag attgtagcag agagtgagca tgaggagcgg    6000
cctgctggca gggccggga tgagcccaac atgaaccta agcttgagga cccaaggcgc    6060
cccgacacct ccttcctgtg gtttaccctcc ccatacaaga ccatgaagtt catcctgtgg    6120
```

```
cggcgtttcc ggtgggccat catcctcttc atcatcctct tcatcctgct gctgttcctg    6180
gccatcttca tctacgcctt cccgaactat gctgccatga agctggtgaa gcccttcagc    6240
tga                                                                  6243
```

<210> SEQ ID NO 17
<211> LENGTH: 2080
<212> TYPE: PRT
<213> ORGANISM: Homo sapiens

<400> SEQUENCE: 17

```
Met Leu Arg Val Phe Ile Leu Tyr Ala Glu Asn Val His Thr Pro Asp
1               5                   10                  15

Thr Asp Ile Ser Asp Ala Tyr Cys Ser Ala Val Phe Ala Gly Val Lys
            20                  25                  30

Lys Arg Thr Lys Val Ile Lys Asn Ser Val Asn Pro Val Trp Asn Glu
        35                  40                  45

Gly Phe Glu Trp Asp Leu Lys Gly Ile Pro Leu Asp Gln Gly Ser Glu
    50                  55                  60

Leu His Val Val Lys Asp His Glu Thr Met Gly Arg Asn Arg Phe
65                  70                  75                  80

Leu Gly Glu Ala Lys Val Pro Leu Arg Glu Val Leu Ala Thr Pro Ser
                85                  90                  95

Leu Ser Ala Ser Phe Asn Ala Pro Leu Leu Asp Thr Lys Lys Gln Pro
            100                 105                 110

Thr Gly Ala Ser Leu Val Leu Gln Val Ser Tyr Thr Pro Leu Pro Gly
        115                 120                 125

Ala Val Pro Leu Phe Pro Pro Thr Pro Leu Glu Pro Ser Pro Thr
    130                 135                 140

Leu Pro Asp Leu Asp Val Val Ala Asp Thr Gly Gly Glu Glu Asp Thr
145                 150                 155                 160

Glu Asp Gln Gly Leu Thr Gly Asp Glu Ala Glu Pro Phe Leu Asp Gln
                165                 170                 175

Ser Gly Gly Pro Gly Ala Pro Thr Thr Pro Arg Lys Leu Pro Ser Arg
            180                 185                 190

Pro Pro Pro His Tyr Pro Gly Ile Lys Arg Lys Arg Ser Ala Pro Thr
        195                 200                 205

Ser Arg Lys Leu Leu Ser Asp Lys Pro Gln Asp Phe Gln Ile Arg Val
    210                 215                 220

Gln Val Ile Glu Gly Arg Gln Leu Pro Gly Val Asn Ile Lys Pro Val
225                 230                 235                 240

Val Lys Val Thr Ala Ala Gly Gln Thr Lys Arg Thr Arg Ile His Lys
                245                 250                 255

Gly Asn Ser Pro Leu Phe Asn Glu Thr Leu Phe Phe Asn Leu Phe Asp
            260                 265                 270

Ser Pro Gly Glu Leu Phe Asp Glu Pro Ile Phe Ile Thr Val Val Asp
        275                 280                 285

Ser Arg Ser Leu Arg Thr Asp Ala Leu Leu Gly Glu Phe Arg Met Asp
    290                 295                 300

Val Gly Thr Ile Tyr Arg Glu Pro Arg His Ala Tyr Leu Arg Lys Trp
305                 310                 315                 320

Leu Leu Leu Ser Asp Pro Asp Asp Phe Ser Ala Gly Ala Arg Gly Tyr
                325                 330                 335

Leu Lys Thr Ser Leu Cys Val Leu Gly Pro Gly Asp Glu Ala Pro Leu
```

```
                    340                 345                 350
Glu Arg Lys Asp Pro Ser Glu Asp Lys Glu Asp Ile Glu Ser Asn Leu
            355                 360                 365

Leu Arg Pro Thr Gly Val Ala Leu Arg Gly Ala His Phe Cys Leu Lys
370                 375                 380

Val Phe Arg Ala Glu Asp Leu Pro Gln Met Asp Asp Ala Val Met Asp
385                 390                 395                 400

Asn Val Lys Gln Ile Phe Gly Phe Glu Ser Asn Lys Lys Asn Leu Val
            405                 410                 415

Asp Pro Phe Val Glu Val Ser Phe Ala Gly Lys Met Leu Cys Ser Lys
                420                 425                 430

Ile Leu Glu Lys Thr Ala Asn Pro Gln Trp Asn Gln Asn Ile Thr Leu
            435                 440                 445

Pro Ala Met Phe Pro Ser Met Cys Glu Lys Met Arg Ile Arg Ile Ile
            450                 455                 460

Asp Trp Asp Arg Leu Thr His Asn Asp Ile Val Ala Thr Thr Tyr Leu
465                 470                 475                 480

Ser Met Ser Lys Ile Ser Ala Pro Gly Gly Glu Ile Glu Glu Glu Pro
            485                 490                 495

Ala Gly Ala Val Lys Pro Ser Lys Ala Ser Asp Leu Asp Asp Tyr Leu
            500                 505                 510

Gly Phe Leu Pro Thr Phe Gly Pro Cys Tyr Ile Asn Leu Tyr Gly Ser
            515                 520                 525

Pro Arg Glu Phe Thr Gly Phe Pro Asp Pro Tyr Thr Glu Leu Asn Thr
            530                 535                 540

Gly Lys Gly Glu Gly Val Ala Tyr Arg Gly Arg Leu Leu Leu Ser Leu
545                 550                 555                 560

Glu Thr Lys Leu Val Glu His Ser Glu Gln Lys Val Glu Asp Leu Pro
            565                 570                 575

Ala Asp Asp Ile Leu Arg Val Glu Lys Tyr Leu Arg Arg Lys Tyr
            580                 585                 590

Ser Leu Phe Ala Ala Phe Tyr Ser Ala Thr Met Leu Gln Asp Val Asp
            595                 600                 605

Asp Ala Ile Gln Phe Glu Val Ser Ile Gly Asn Tyr Gly Asn Lys Phe
            610                 615                 620

Asp Met Thr Cys Leu Pro Leu Ala Ser Thr Thr Gln Tyr Ser Arg Ala
625                 630                 635                 640

Val Phe Asp Gly Cys His Tyr Tyr Leu Pro Trp Gly Asn Val Lys
            645                 650                 655

Pro Val Val Val Leu Ser Ser Tyr Trp Glu Asp Ile Ser His Arg Ile
            660                 665                 670

Glu Thr Gln Asn Gln Leu Leu Gly Ile Ala Asp Arg Leu Glu Ala Gly
            675                 680                 685

Leu Glu Gln Val His Leu Ala Leu Lys Ala Gln Cys Ser Thr Glu Asp
            690                 695                 700

Val Asp Ser Leu Val Ala Gln Leu Thr Asp Glu Leu Ile Ala Gly Cys
705                 710                 715                 720

Ser Gln Pro Leu Gly Asp Ile His Glu Thr Pro Ser Ala Thr His Leu
            725                 730                 735

Asp Gln Tyr Leu Tyr Gln Leu Arg Thr His His Leu Ser Gln Ile Thr
            740                 745                 750

Glu Ala Ala Leu Ala Leu Lys Leu Gly His Ser Glu Leu Pro Ala Ala
            755                 760                 765
```

```
Leu Glu Gln Ala Glu Asp Trp Leu Arg Leu Arg Ala Leu Ala Glu
    770             775             780

Glu Pro Gln Asn Ser Leu Pro Asp Ile Val Ile Trp Met Leu Gln Gly
785             790             795                 800

Asp Lys Arg Val Ala Tyr Gln Arg Val Pro Ala His Gln Val Leu Phe
            805                 810                 815

Ser Arg Arg Gly Ala Asn Tyr Cys Gly Lys Asn Cys Gly Lys Leu Gln
            820                 825                 830

Thr Ile Phe Leu Lys Tyr Pro Met Glu Lys Val Pro Gly Ala Arg Met
        835                 840                 845

Pro Val Gln Ile Arg Val Lys Leu Trp Phe Gly Leu Ser Val Asp Glu
    850                 855                 860

Lys Glu Phe Asn Gln Phe Ala Glu Gly Lys Leu Ser Val Phe Ala Glu
865             870                 875                 880

Thr Tyr Glu Asn Glu Thr Lys Leu Ala Leu Val Gly Asn Trp Gly Thr
                885                 890                 895

Thr Gly Leu Thr Tyr Pro Lys Phe Ser Asp Val Thr Gly Lys Ile Lys
            900                 905                 910

Leu Pro Lys Asp Ser Phe Arg Pro Ser Ala Gly Trp Thr Trp Ala Gly
        915                 920                 925

Asp Trp Phe Val Cys Pro Glu Lys Thr Leu Leu His Asp Met Asp Ala
    930                 935                 940

Gly His Leu Ser Phe Val Glu Glu Val Phe Glu Asn Gln Thr Arg Leu
945             950                 955                 960

Pro Gly Gly Gln Trp Ile Tyr Met Ser Asp Asn Tyr Thr Asp Val Asn
                965                 970                 975

Gly Glu Lys Val Leu Pro Lys Asp Ile Glu Cys Pro Leu Gly Trp
            980                 985                 990

Lys Trp Glu Asp Glu Glu Trp Ser  Thr Asp Leu Asn Arg  Ala Val Asp
        995                 1000                1005

Glu Gln  Gly Trp Glu Tyr Ser  Ile Thr Ile Pro  Glu Arg Lys
    1010            1015                1020

Pro Lys  His Trp Val Pro Ala  Glu Lys Met Tyr Tyr  Thr His Arg
    1025            1030                1035

Arg Arg  Arg Trp Val Arg Leu  Arg Arg Arg Asp Leu  Ser Gln Met
    1040            1045                1050

Glu Ala  Leu Lys Arg His Arg  Gln Ala Glu Ala Glu  Gly Glu Gly
    1055            1060                1065

Trp Glu  Tyr Ala Ser Leu Phe  Gly Trp Lys Phe His  Leu Glu Tyr
    1070            1075                1080

Arg Lys  Thr Asp Ala Phe Arg  Arg Arg Arg Trp Arg  Arg Arg Met
    1085            1090                1095

Glu Pro  Leu Glu Lys Thr Gly  Pro Ala Ala Val Phe  Ala Leu Glu
    1100            1105                1110

Gly Ala  Leu Gly Gly Val Met  Asp Asp Lys Ser Glu  Asp Ser Met
    1115            1120                1125

Ser Val  Ser Thr Leu Ser Phe  Gly Val Asn Arg Pro  Thr Ile Ser
    1130            1135                1140

Cys Ile  Phe Asp Tyr Gly Asn  Arg Tyr His Leu Arg  Cys Tyr Met
    1145            1150                1155

Tyr Gln  Ala Arg Asp Leu Ala  Ala Met Asp Lys Asp  Ser Phe Ser
    1160            1165                1170
```

```
Asp Pro Tyr Ala Ile Val Ser Phe Leu His Gln Ser Gln Lys Thr
    1175                1180                1185
Val Val Val Lys Asn Thr Leu Asn Pro Thr Trp Asp Gln Thr Leu
    1190                1195                1200
Ile Phe Tyr Glu Ile Glu Ile Phe Gly Glu Pro Ala Thr Val Ala
    1205                1210                1215
Glu Gln Pro Pro Ser Ile Val Val Glu Leu Tyr Asp His Asp Thr
    1220                1225                1230
Tyr Gly Ala Asp Glu Phe Met Gly Arg Cys Ile Cys Gln Pro Ser
    1235                1240                1245
Leu Glu Arg Met Pro Arg Leu Ala Trp Phe Pro Leu Thr Arg Gly
    1250                1255                1260
Ser Gln Pro Ser Gly Glu Leu Leu Ala Ser Phe Glu Leu Ile Gln
    1265                1270                1275
Arg Glu Lys Pro Ala Ile His His Ile Pro Gly Phe Glu Val Gln
    1280                1285                1290
Glu Thr Ser Arg Ile Leu Asp Glu Ser Glu Asp Thr Asp Leu Pro
    1295                1300                1305
Tyr Pro Pro Pro Gln Arg Glu Ala Asn Ile Tyr Met Val Pro Gln
    1310                1315                1320
Asn Ile Lys Pro Ala Leu Gln Arg Thr Ala Ile Glu Ile Leu Ala
    1325                1330                1335
Trp Gly Leu Arg Asn Met Lys Ser Tyr Gln Leu Ala Asn Ile Ser
    1340                1345                1350
Ser Pro Ser Leu Val Val Glu Cys Gly Gly Gln Thr Val Gln Ser
    1355                1360                1365
Cys Val Ile Arg Asn Leu Arg Lys Asn Pro Asn Phe Asp Ile Cys
    1370                1375                1380
Thr Leu Phe Met Glu Val Met Leu Pro Arg Glu Glu Leu Tyr Cys
    1385                1390                1395
Pro Pro Ile Thr Val Lys Val Ile Asp Asn Arg Gln Phe Gly Arg
    1400                1405                1410
Arg Pro Val Val Gly Gln Cys Thr Ile Arg Ser Leu Glu Ser Phe
    1415                1420                1425
Leu Cys Asp Pro Tyr Ser Ala Glu Ser Pro Ser Pro Gln Gly Gly
    1430                1435                1440
Pro Asp Asp Val Ser Leu Leu Ser Pro Gly Glu Asp Val Leu Ile
    1445                1450                1455
Asp Ile Asp Asp Lys Glu Pro Leu Ile Pro Ile Gln Glu Glu Glu
    1460                1465                1470
Phe Ile Asp Trp Trp Ser Lys Phe Phe Ala Ser Ile Gly Glu Arg
    1475                1480                1485
Glu Lys Cys Gly Ser Tyr Leu Glu Lys Asp Phe Asp Thr Leu Lys
    1490                1495                1500
Val Tyr Asp Thr Gln Leu Glu Asn Val Glu Ala Phe Glu Gly Leu
    1505                1510                1515
Ser Asp Phe Cys Asn Thr Phe Lys Leu Tyr Arg Gly Lys Thr Gln
    1520                1525                1530
Glu Glu Thr Glu Asp Pro Ser Val Ile Gly Glu Phe Lys Gly Leu
    1535                1540                1545
Phe Lys Ile Tyr Pro Leu Pro Glu Asp Pro Ala Ile Pro Met Pro
    1550                1555                1560
Pro Arg Gln Phe His Gln Leu Ala Ala Gln Gly Pro Gln Glu Cys
```

```
              1565                1570                1575
Leu Val Arg Ile Tyr Ile Val Arg Ala Phe Gly Leu Gln Pro Lys
    1580                1585                1590

Asp Pro Asn Gly Lys Cys Asp Pro Tyr Ile Lys Ile Ser Ile Gly
    1595                1600                1605

Lys Lys Ser Val Ser Asp Gln Asp Asn Tyr Ile Pro Cys Thr Leu
    1610                1615                1620

Glu Pro Val Phe Gly Lys Met Phe Glu Leu Thr Cys Thr Leu Pro
    1625                1630                1635

Leu Glu Lys Asp Leu Lys Ile Thr Leu Tyr Asp Tyr Asp Leu Leu
    1640                1645                1650

Ser Lys Asp Glu Lys Ile Gly Glu Thr Val Val Asp Leu Glu Asn
    1655                1660                1665

Arg Leu Leu Ser Lys Phe Gly Ala Arg Cys Gly Leu Pro Gln Thr
    1670                1675                1680

Tyr Cys Val Ser Gly Pro Asn Gln Trp Arg Asp Gln Leu Arg Pro
    1685                1690                1695

Ser Gln Leu Leu His Leu Phe Cys Gln Gln His Arg Val Lys Ala
    1700                1705                1710

Pro Val Tyr Arg Thr Asp Arg Val Met Phe Gln Asp Lys Glu Tyr
    1715                1720                1725

Ser Ile Glu Glu Ile Glu Ala Gly Arg Ile Pro Asn Pro His Leu
    1730                1735                1740

Gly Pro Val Glu Glu Arg Leu Ala Leu His Val Leu Gln Gln Gln
    1745                1750                1755

Gly Leu Val Pro Glu His Val Glu Ser Arg Pro Leu Tyr Ser Pro
    1760                1765                1770

Leu Gln Pro Asp Ile Glu Gln Gly Lys Leu Gln Met Trp Val Asp
    1775                1780                1785

Leu Phe Pro Lys Ala Leu Gly Arg Pro Gly Pro Phe Asn Ile
    1790                1795                1800

Thr Pro Arg Arg Ala Arg Arg Phe Phe Leu Arg Cys Ile Ile Trp
    1805                1810                1815

Asn Thr Arg Asp Val Ile Leu Asp Asp Leu Ser Leu Thr Gly Glu
    1820                1825                1830

Lys Met Ser Asp Ile Tyr Val Lys Gly Trp Met Ile Gly Phe Glu
    1835                1840                1845

Glu His Lys Gln Lys Thr Asp Val His Tyr Arg Ser Leu Gly Gly
    1850                1855                1860

Glu Gly Asn Phe Asn Trp Arg Phe Ile Phe Pro Phe Asp Tyr Leu
    1865                1870                1875

Pro Ala Glu Gln Val Cys Thr Ile Ala Lys Lys Asp Ala Phe Trp
    1880                1885                1890

Arg Leu Asp Lys Thr Glu Ser Lys Ile Pro Ala Arg Val Val Phe
    1895                1900                1905

Gln Ile Trp Asp Asn Asp Lys Phe Ser Phe Asp Asp Phe Leu Gly
    1910                1915                1920

Ser Leu Gln Leu Asp Leu Asn Arg Met Pro Lys Pro Ala Lys Thr
    1925                1930                1935

Ala Lys Lys Cys Ser Leu Asp Gln Leu Asp Asp Ala Phe His Pro
    1940                1945                1950

Glu Trp Phe Val Ser Leu Phe Glu Gln Lys Thr Val Lys Gly Trp
    1955                1960                1965
```

```
Trp Pro Cys Val Ala Glu Glu Gly Lys Lys Ile Leu Ala Gly
    1970            1975                1980

Lys Leu Glu Met Thr Leu Glu Ile Val Ala Glu Ser Glu His Glu
    1985                1990                1995

Glu Arg Pro Ala Gly Gln Gly Arg Asp Glu Pro Asn Met Asn Pro
    2000                2005                2010

Lys Leu Glu Asp Pro Arg Arg Pro Asp Thr Ser Phe Leu Trp Phe
    2015                2020                2025

Thr Ser Pro Tyr Lys Thr Met Lys Phe Ile Leu Trp Arg Arg Phe
    2030                2035                2040

Arg Trp Ala Ile Ile Leu Phe Ile Ile Leu Phe Ile Leu Leu Leu
    2045                2050                2055

Phe Leu Ala Ile Phe Ile Tyr Ala Phe Pro Asn Tyr Ala Ala Met
    2060                2065                2070

Lys Leu Val Lys Pro Phe Ser
    2075            2080

<210> SEQ ID NO 18
<211> LENGTH: 45
<212> TYPE: PRT
<213> ORGANISM: Homo sapiens

<400> SEQUENCE: 18

Phe Gln Ile Arg Val Gln Val Ile Glu Gly Arg Gln Leu Pro Gly
1               5                   10                  15

Asn Ile Lys Pro Val Val Lys Val Thr Ala Ala Gly Gln Thr Lys Arg
            20                  25                  30

Thr Arg Ile His Lys Gly Asn Ser Pro Leu Phe Asn Glu
        35                  40                  45

<210> SEQ ID NO 19
<211> LENGTH: 45
<212> TYPE: PRT
<213> ORGANISM: Equus caballus

<400> SEQUENCE: 19

Phe Gln Ile Arg Val Gln Val Ile Glu Gly Arg Gln Leu Pro Gly
1               5                   10                  15

Asn Ile Lys Pro Val Val Lys Val Thr Ala Ala Arg Gln Thr Lys Arg
            20                  25                  30

Thr Arg Ile His Arg Gly Asn Ser Pro Leu Phe Asn Glu
        35                  40                  45

<210> SEQ ID NO 20
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Phe Gln Ile Arg Val Gln Val Ile Glu Gly Arg Gln Leu Pro Gly
1               5                   10                  15

Asn Ile Lys Pro Val Val Lys Val Thr Ala Ala Arg Gln Thr Lys Trp
            20                  25                  30

Thr Arg Ile His Arg Gly Asn Ser Pro Leu Phe Asn Glu
        35                  40                  45
```

<210> SEQ ID NO 21
<211> LENGTH: 96
<212> TYPE: PRT
<213> ORGANISM: Unknown
<220> FEATURE:
<223> OTHER INFORMATION: Description of Unknown:
    DYSF sequence

<400> SEQUENCE: 21

Pro Thr Ser Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Lys
            20                  25                  30

Pro Val Val Lys Val Thr Ala Ala Gly Gln Thr Lys Arg Thr Arg Ile
        35                  40                  45

His Lys Gly Asn Ser Pro Leu Phe Asn Glu Thr Leu Phe Phe Asn Leu
    50                  55                  60

Phe Asp Ser Pro Gly Glu Leu Phe Asp Glu Pro Ile Phe Ile Thr Val
65                  70                  75                  80

Val Asp Ser Arg Ser Leu Arg Thr Asp Ala Leu Leu Gly Glu Phe Arg
                85                  90                  95

<210> SEQ ID NO 22
<211> LENGTH: 96
<212> TYPE: PRT
<213> ORGANISM: Unknown
<220> FEATURE:
<223> OTHER INFORMATION: Description of Unknown:
    DYSF sequence

<400> SEQUENCE: 22

Pro Thr Ser Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Lys
            20                  25                  30

Pro Val Val Lys Val Thr Ala Ala Gly Gln Thr Lys Arg Thr Arg Ile
        35                  40                  45

His Lys Gly Asn Ser Pro Leu Phe Asn Glu Thr Leu Phe Phe Asn Leu
    50                  55                  60

Phe Asp Cys Pro Ala Glu Leu Phe Asp Glu Pro Ile Phe Ile Thr Val
65                  70                  75                  80

Val Asp Ser Arg Ser Leu Arg Thr Asp Ala Leu Leu Gly Glu Phe Arg
                85                  90                  95

<210> SEQ ID NO 23
<211> LENGTH: 93
<212> TYPE: PRT
<213> ORGANISM: Unknown
<220> FEATURE:
<223> OTHER INFORMATION: Description of Unknown:
    DYSF sequence

<400> SEQUENCE: 23

Arg Lys Leu Leu Ser Asp Lys Pro Gln Asp Phe Gln Ile Arg Val Gln
1               5                   10                  15

Val Ile Glu Gly Arg Gln Leu Pro Gly Val Asn Ile Lys Pro Val Val
            20                  25                  30

Lys Val Thr Ala Ala Gly Gln Thr Lys Arg Thr Arg Ile Gln Lys Gly
        35                  40                  45

Asn Ser Pro Leu Phe Asn Glu Thr Leu Phe Phe Asn Val Phe Asp Ser

```
                  50                  55                  60

Pro Leu Glu Leu Phe Asp Glu Pro Ile Phe Ile Thr Val Val Asp Ser
 65                  70                  75                  80

Arg Ser Leu Arg Thr Asp Ala Leu Leu Gly Glu Phe Arg
                 85                  90
```

<210> SEQ ID NO 24
<211> LENGTH: 93
<212> TYPE: PRT
<213> ORGANISM: Unknown
<220> FEATURE:
<223> OTHER INFORMATION: Description of Unknown:
      DYSF sequence

<400> SEQUENCE: 24

```
Arg Lys Leu Leu Ser Asp Lys Pro Gln Asp Phe Gln Ile Arg Val Gln
  1               5                  10                  15

Val Ile Glu Gly Arg Gln Leu Pro Gly Val Asn Ile Lys Pro Val Val
                 20                  25                  30

Lys Val Thr Ala Ala Gly Gln Thr Lys Arg Thr Arg Ile Gln Lys Gly
                 35                  40                  45

Asn Ser Pro Leu Phe Asn Glu Thr Leu Phe Phe Asn Val Phe Asp Ser
 50                  55                  60

Pro Ser Glu Leu Phe Asp Glu Pro Ile Phe Ile Thr Val Val Asp Ser
 65                  70                  75                  80

Arg Ser Leu Arg Thr Asp Ala Leu Leu Gly Glu Phe Arg
                 85                  90
```

<210> SEQ ID NO 25
<211> LENGTH: 96
<212> TYPE: PRT
<213> ORGANISM: Unknown
<220> FEATURE:
<223> OTHER INFORMATION: Description of Unknown:
      DYSF sequence

<400> SEQUENCE: 25

```
Pro Pro Pro Arg Lys Leu Leu Ser Asp Lys Pro Gln Asp Phe Gln Ile
  1               5                  10                  15

Arg Val Gln Val Ile Glu Gly Arg Gln Leu Pro Gly Val Asn Ile Lys
                 20                  25                  30

Pro Val Val Lys Val Thr Ala Ala Gly Gln Thr Lys Arg Thr Arg Ile
                 35                  40                  45

His Lys Gly Asn Ser Pro Leu Phe Asn Glu Thr Leu Phe Phe Asn Leu
 50                  55                  60

Phe Asp Ser Pro Ser Glu Leu Phe Asp Glu Pro Ile Phe Ile Thr Val
 65                  70                  75                  80

Val Asp Ser Arg Ser Leu Arg Thr Asp Ala Leu Ile Gly Glu Phe Arg
                 85                  90                  95
```

<210> SEQ ID NO 26
<211> LENGTH: 96
<212> TYPE: PRT
<213> ORGANISM: Unknown
<220> FEATURE:
<223> OTHER INFORMATION: Description of Unknown:
      DYSF sequence

<400> SEQUENCE: 26

```
Pro Ala Pro Arg Lys Val Leu Ser Asp Lys Pro Gln Asp Phe Gln Ile
  1               5                  10                  15
```

```
Arg Val Gln Val Ile Glu Gly Arg Gln Leu Pro Gly Val Asn Ile Lys
            20                  25                  30

Pro Val Val Lys Val Thr Ala Ala Gly Gln Thr Arg Thr Arg Ile
            35                  40                  45

His Lys Gly Asn Ser Pro Leu Phe Asn Glu Thr Leu Phe Phe Asn Val
        50                  55                  60

Phe Asp Ser Pro Ala Glu Leu Phe Asp Glu Pro Ile Phe Ile Thr Val
65                  70                  75                  80

Val Asp Ser Arg Ser Arg Arg Thr Asp Ala Leu Ile Gly Glu Phe Arg
                85                  90                  95
```

<210> SEQ ID NO 27
<211> LENGTH: 96
<212> TYPE: PRT
<213> ORGANISM: Unknown
<220> FEATURE:
<223> OTHER INFORMATION: Description of Unknown:
      DYSF sequence

<400> SEQUENCE: 27

```
Pro Thr Pro Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Lys
            20                  25                  30

Pro Val Val Lys Val Thr Ala Ala Gly Gln Thr Lys Arg Thr Arg Ile
            35                  40                  45

His Lys Gly Asn Ser Pro Leu Phe Asn Glu Thr Leu Phe Phe Asn Val
        50                  55                  60

Phe Asp Ser Pro Ala Glu Leu Phe Asp Glu Pro Ile Phe Ile Thr Val
65                  70                  75                  80

Val Asp Ser Arg Ser Leu Arg Thr Asp Ala Leu Ile Gly Glu Phe Arg
                85                  90                  95
```

<210> SEQ ID NO 28
<211> LENGTH: 96
<212> TYPE: PRT
<213> ORGANISM: Unknown
<220> FEATURE:
<223> OTHER INFORMATION: Description of Unknown:
      DYSF sequence

<400> SEQUENCE: 28

```
Pro Ala Pro Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Lys
            20                  25                  30

Pro Val Val Lys Val Thr Ala Ala Arg Gln Thr Lys Arg Thr Arg Ile
            35                  40                  45

His Arg Gly Asn Ser Pro Leu Phe Asn Glu Thr Leu Phe Phe Asn Val
        50                  55                  60

Phe Asp Ser Pro Ser Glu Leu Phe Asp Glu Ala Val Phe Ile Thr Val
65                  70                  75                  80

Val Asp Ser Cys Ser Leu Arg Thr Asp Ala Leu Ile Gly Glu Phe Arg
                85                  90                  95
```

<210> SEQ ID NO 29
<211> LENGTH: 96
<212> TYPE: PRT
<213> ORGANISM: Unknown

```
<220> FEATURE:
<223> OTHER INFORMATION: Description of Unknown:
      DYSF sequence

<400> SEQUENCE: 29

Pro Thr Ser Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Lys
            20                  25                  30

Pro Val Val Lys Val Thr Ala Ala Gly Gln Thr Lys Arg Thr Arg Ile
        35                  40                  45

Gln Lys Gly Asn Ser Pro Leu Phe Asn Glu Thr Leu Phe Phe Asn Val
50                  55                  60

Phe Asp Ser Pro Ser Glu Leu Phe Asp Glu Pro Ile Phe Ile Thr Val
65                  70                  75                  80

Val Asp Ser Arg Ser Leu Arg Thr Asp Ala Leu Ile Gly Glu Phe Arg
                85                  90                  95

<210> SEQ ID NO 30
<211> LENGTH: 96
<212> TYPE: PRT
<213> ORGANISM: Unknown
<220> FEATURE:
<223> OTHER INFORMATION: Description of Unknown:
      DYSF sequence

<400> SEQUENCE: 30

Pro Ala Pro Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Lys
            20                  25                  30

Pro Val Val Lys Val Thr Ala Ala Gly Gln Thr Lys Arg Thr Arg Ile
        35                  40                  45

His Lys Gly Asn Ser Pro Phe Phe Asn Glu Thr Leu Phe Phe Asn Val
50                  55                  60

Phe Asp Ser Pro Ala Glu Leu Phe Asn Glu Pro Ile Phe Ile Thr Val
65                  70                  75                  80

Val Asp Ser Arg Ser Leu Arg Thr Asp Ala Leu Ile Gly Glu Phe Arg
                85                  90                  95

<210> SEQ ID NO 31
<211> LENGTH: 96
<212> TYPE: PRT
<213> ORGANISM: Cebus capucinus imitator

<400> SEQUENCE: 31

Pro Thr Pro Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Lys
            20                  25                  30

Pro Val Val Lys Val Thr Ala Ala Gly Gln Thr Lys Arg Thr Arg Ile
        35                  40                  45

His Lys Gly Asn Ser Pro Leu Phe Asn Glu Thr Leu Phe Phe Asn Leu
50                  55                  60

Phe Asp Ser Pro Ala Glu Leu Phe Asp Glu Pro Ile Phe Ile Thr Val
65                  70                  75                  80

Val Asp Ser Arg Ser Leu Arg Thr Asp Ala Leu Leu Gly Glu Phe Arg
                85                  90                  95
```

<210> SEQ ID NO 32
<211> LENGTH: 96
<212> TYPE: PRT
<213> ORGANISM: Microcebus murinus

<400> SEQUENCE: 32

Pro Pro Ser Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Lys
            20                  25                  30

Pro Val Val Lys Val Thr Ala Ala Gly Gln Thr Lys Arg Thr Arg Ile
        35                  40                  45

His Lys Gly Asn Ser Pro Leu Phe Ser Glu Thr Leu Phe Asn Leu
    50                  55                  60

Phe Glu Ser Pro Ala Glu Leu Phe Asp Glu Pro Ile Phe Ile Thr Val
65                  70                  75                  80

Val Asp Ser Arg Ser Leu Arg Thr Asp Ala Leu Leu Gly Glu Phe Arg
                85                  90                  95

<210> SEQ ID NO 33
<211> LENGTH: 96
<212> TYPE: PRT
<213> ORGANISM: Carlito syrichta

<400> SEQUENCE: 33

Pro Thr Ser Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Lys
            20                  25                  30

Pro Val Val Lys Val Thr Ala Ala Gly His Thr Lys Arg Thr Arg Ile
        35                  40                  45

Gln Lys Gly Asn Asn Pro Leu Phe Ser Glu Thr Leu Phe Asn Leu
    50                  55                  60

Phe Asp Ser Pro Ala Glu Leu Phe Asp Glu Pro Ile Phe Ile Thr Val
65                  70                  75                  80

Val Asp Ser Arg Ser Leu Arg Thr Asp Ala Leu Leu Gly Glu Phe Arg
                85                  90                  95

<210> SEQ ID NO 34
<211> LENGTH: 93
<212> TYPE: PRT
<213> ORGANISM: Otolemur garnettii

<400> SEQUENCE: 34

Arg Lys Leu Leu Ser Asp Lys Pro Gln Asp Phe Gln Ile Arg Val Gln
1               5                   10                  15

Val Ile Glu Gly Arg Gln Leu Pro Gly Val Asn Ile Lys Pro Val Val
            20                  25                  30

Lys Val Thr Ala Ala Gly His Thr Lys Arg Thr Arg Ile His Lys Gly
        35                  40                  45

Asn Ser Pro Leu Phe Asn Glu Thr Leu Phe Asn Leu Val Glu Ser
    50                  55                  60

Pro Ala Glu Leu Phe Asp Glu Pro Ile Phe Ile Thr Val Val Asp Ser
65                  70                  75                  80

Arg Ser Leu Arg Thr Asp Ala Leu Leu Gly Glu Phe Arg
                85                  90

-continued

<210> SEQ ID NO 35
<211> LENGTH: 96
<212> TYPE: PRT
<213> ORGANISM: Propithecus coquereli

<400> SEQUENCE: 35

Pro Thr Ser Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Lys
            20                  25                  30

Pro Val Val Lys Val Thr Ala Ala Gly His Thr Lys Arg Thr Arg Ile
        35                  40                  45

Gln Lys Gly Asn Asn Pro Leu Phe Asn Glu Thr Leu Phe Phe Asn Leu
    50                  55                  60

Phe Asp Ser Pro Ala Glu Leu Phe Asp Glu Pro Ile Phe Ile Thr Val
65                  70                  75                  80

Val Asp Ser Arg Ser Leu Arg Thr Asp Ala Leu Leu Gly Glu Phe Arg
                85                  90                  95

<210> SEQ ID NO 36
<211> LENGTH: 93
<212> TYPE: PRT
<213> ORGANISM: Cricetulus griseus

<400> SEQUENCE: 36

Arg Lys Leu Leu Ser Asp Lys Pro Gln Asp Phe Gln Ile Arg Val Gln
1               5                   10                  15

Val Ile Glu Gly Arg Gln Leu Pro Gly Val Asn Ile Lys Pro Val Val
            20                  25                  30

Lys Val Thr Ala Ala Gly Gln Thr Lys Arg Thr Arg Ile Gln Lys Gly
        35                  40                  45

Asn Ser Pro Val Phe Asn Glu Thr Leu Phe Phe Asn Val Phe Asp Ser
    50                  55                  60

Pro Ser Glu Leu Phe Asp Glu Pro Ile Phe Ile Thr Val Val Asp Ser
65                  70                  75                  80

Arg Ser Leu Arg Thr Asp Ala Leu Leu Gly Glu Phe Arg
                85                  90

<210> SEQ ID NO 37
<211> LENGTH: 96
<212> TYPE: PRT
<213> ORGANISM: Ictidomys tridecemlineatus

<400> SEQUENCE: 37

Pro Pro Ser Arg Lys Pro Leu Ser Asp Lys Gln Asp Phe Gln Ile
1               5                   10                  15

Arg Val Gln Val Ile Glu Gly Arg Gln Leu Pro Gly Val Asn Ile Arg
            20                  25                  30

Pro Val Val Lys Val Thr Ala Ala Gly Gln Thr Lys Arg Thr Arg Ile
        35                  40                  45

His Lys Gly Asn Ser Pro Phe Phe Asn Glu Thr Leu Phe Phe Asn Val
    50                  55                  60

Phe Asp Ser Pro Leu Glu Leu Phe Asp Glu Pro Ile Phe Ile Thr Val
65                  70                  75                  80

Val Asp Ser Cys Ser Leu Arg Thr Asp Ala Leu Ile Gly Glu Phe Arg
                85                  90                  95

<210> SEQ ID NO 38

```
<211> LENGTH: 96
<212> TYPE: PRT
<213> ORGANISM: Marmota marmota marmota

<400> SEQUENCE: 38

Pro Pro Ser Arg Lys Pro Leu Ser Asp Lys Gln Gln Asp Phe Gln Ile
1               5                   10                  15

Arg Val Gln Val Ile Glu Gly Arg Gln Leu Pro Gly Val Asn Ile Arg
            20                  25                  30

Pro Val Val Lys Val Thr Ala Ala Gly Gln Thr Lys Arg Thr Arg Ile
        35                  40                  45

His Lys Gly Asn Ser Pro Leu Phe Asn Glu Thr Leu Phe Phe Asn Val
50                  55                  60

Phe Asp Ser Pro Leu Glu Leu Phe Asp Glu Pro Ile Phe Ile Thr Val
65                  70                  75                  80

Val Asp Ser Cys Ser Leu Arg Thr Asp Ala Leu Ile Gly Glu Phe Arg
                85                  90                  95

<210> SEQ ID NO 39
<211> LENGTH: 96
<212> TYPE: PRT
<213> ORGANISM: Castor canadensis

<400> SEQUENCE: 39

Pro Thr Ser Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Arg
            20                  25                  30

Pro Val Val Lys Val Thr Ala Ala Gly Gln Thr Lys Arg Thr Arg Ile
        35                  40                  45

His Lys Gly Asn Ser Pro Val Phe Asn Glu Thr Leu Phe Phe Asn Met
50                  55                  60

Phe Glu Ser Pro Ala Glu Leu Phe Asp Glu Pro Ile Phe Ile Thr Val
65                  70                  75                  80

Val Asp Ser Arg Ser Leu Arg Thr Asp Ala Leu Ile Gly Glu Phe Arg
                85                  90                  95

<210> SEQ ID NO 40
<211> LENGTH: 96
<212> TYPE: PRT
<213> ORGANISM: Mustela putorius furo

<400> SEQUENCE: 40

Pro Thr Pro Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Lys
            20                  25                  30

Pro Val Val Lys Val Thr Ala Ala Gly Gln Thr Lys Arg Thr Arg Ile
        35                  40                  45

His Lys Gly Asn Ser Pro Leu Phe Asn Glu Thr Leu Phe Phe Asn Val
50                  55                  60

Phe Asp Ser Pro Ser Glu Leu Phe Glu Glu Pro Ile Phe Ile Thr Val
65                  70                  75                  80

Val Asp Ser Arg Ser Leu Arg Thr Asp Ala Leu Ile Gly Glu Phe Arg
                85                  90                  95

<210> SEQ ID NO 41
<211> LENGTH: 96
```

```
<212> TYPE: PRT
<213> ORGANISM: Hipposideros armiger

<400> SEQUENCE: 41

Pro Lys Ala Arg Thr Leu Leu Ser Glu Lys Pro Gln Asp Phe Gln Ile
1               5                   10                  15

Arg Val Gln Val Ile Glu Gly Arg Gln Leu Pro Gly Leu Asn Ile Lys
            20                  25                  30

Pro Val Val Lys Val Thr Ala Ala Gly Gln Thr Lys Arg Thr Arg Ile
        35                  40                  45

His Lys Gly Asn Ser Pro Leu Phe Ser Glu Thr Leu Phe Phe Asn Val
    50                  55                  60

Phe Asp Ser Pro Ala Glu Leu Phe Asp Glu Pro Ile Phe Ile Thr Val
65                  70                  75                  80

Val Asp Ser Arg Ser Leu Arg Thr Asp Ala Leu Ile Gly Glu Phe Arg
                85                  90                  95

<210> SEQ ID NO 42
<211> LENGTH: 90
<212> TYPE: PRT
<213> ORGANISM: Loxodonta africana

<400> SEQUENCE: 42

Leu Ser Asp Lys Pro Gln Asp Phe Gln Ile Arg Val Gln Val Ile Glu
1               5                   10                  15

Gly Arg Gln Leu Pro Gly Val Asn Ile Lys Pro Val Val Lys Val Thr
            20                  25                  30

Ala Ala Gly Gln Thr Lys Arg Thr Arg Ile His Lys Gly Asn Ser Pro
        35                  40                  45

Leu Phe Asn Glu Thr Leu Phe Phe Asn Val Cys Glu Ser Pro Ala Gln
    50                  55                  60

Leu Phe Asp Glu Pro Ile Phe Ile Thr Val Val Asp Ser Arg Ser Leu
65                  70                  75                  80

Arg Thr Asp Ala Leu Ile Gly Glu Phe Arg
                85                  90

<210> SEQ ID NO 43
<211> LENGTH: 96
<212> TYPE: PRT
<213> ORGANISM: Sus scrofa

<400> SEQUENCE: 43

Pro Ala Pro Arg Lys Pro Leu Ser Asp Lys Pro Gln Asp Phe Gln Ile
1               5                   10                  15

Arg Val Gln Val Ile Glu Gly Arg Gln Leu Pro Gly Val Asn Ile Lys
            20                  25                  30

Pro Val Val Lys Val Thr Ala Ala Gly Gln Thr Lys Arg Thr Arg Ile
        35                  40                  45

His Lys Gly Asn Ser Pro Leu Phe Asn Glu Thr Leu Phe Phe Asn Val
    50                  55                  60

Phe Asp Ser Pro Ala Glu Leu Phe Asn Glu Pro Ile Phe Ile Thr Val
65                  70                  75                  80

Val Asp Ser Arg Ser Leu Arg Thr Asp Ala Leu Ile Gly Glu Phe Arg
                85                  90                  95

<210> SEQ ID NO 44
<211> LENGTH: 96
<212> TYPE: PRT
```

<213> ORGANISM: Bos taurus

<400> SEQUENCE: 44

Pro Ala Pro Ser Lys Pro Leu Ser Asp Lys Pro Gln Asp Phe Gln Ile
1               5                   10                  15

Arg Val Gln Val Ile Lys Gly Arg Gln Leu Pro Gly Val Asn Ile Lys
                20                  25                  30

Pro Val Val Lys Val Thr Ala Ala Gly Gln Thr Lys Arg Thr Arg Ile
            35                  40                  45

His Lys Gly Asn Ser Pro Val Phe Asn Glu Thr Leu Phe Phe Asn Val
        50                  55                  60

Phe Asp Ser Pro Ala Glu Leu Phe Asn Glu Pro Ile Phe Ile Thr Val
65                  70                  75                  80

Val Asp Ser Arg Ser Leu Arg Thr Asp Ala Leu Ile Gly Glu Phe Arg
                85                  90                  95

<210> SEQ ID NO 45
<211> LENGTH: 96
<212> TYPE: PRT
<213> ORGANISM: Balaenoptera acutorostrata scammoni

<400> SEQUENCE: 45

Pro Ala Pro Arg Lys Leu Leu Ser Asp Lys Ser Gln Asp Phe Gln Ile
1               5                   10                  15

Arg Val Gln Val Ile Glu Gly Arg Gln Leu Pro Gly Val Asn Ile Lys
                20                  25                  30

Pro Val Val Lys Val Thr Ala Ala Gly Gln Thr Lys Arg Thr Arg Ile
            35                  40                  45

His Lys Gly Asn Ser Pro Leu Phe Asn Glu Thr Leu Phe Phe Asn Val
        50                  55                  60

Phe Asp Ser Pro Ala Glu Leu Phe Asp Glu Pro Ile Phe Ile Thr Val
65                  70                  75                  80

Val Asp Ser Cys Ser Leu Arg Thr Asp Ala Phe Leu Gly Glu Phe Arg
                85                  90                  95

<210> SEQ ID NO 46
<211> LENGTH: 96
<212> TYPE: PRT
<213> ORGANISM: Ailuropoda melanoleuca

<400> SEQUENCE: 46

Pro Thr Pro Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Lys
                20                  25                  30

Pro Val Val Lys Val Thr Ala Ala Gly Gln Thr Lys Arg Thr Arg Ile
            35                  40                  45

His Lys Gly Asn Ser Pro Leu Phe Asn Glu Thr Leu Phe Phe Asn Val
        50                  55                  60

Phe Asp Ser Pro Ser Glu Leu Phe Asp Glu Pro Ile Phe Ile Thr Val
65                  70                  75                  80

Val Asp Ser Arg Ser Leu Arg Thr Asp Ala Leu Ile Gly Glu Phe Arg
                85                  90                  95

<210> SEQ ID NO 47
<211> LENGTH: 96
<212> TYPE: PRT
<213> ORGANISM: Orcinus orca

<400> SEQUENCE: 47

Pro Ala Pro Arg Lys Pro Leu Ser Asp Lys Ser Gln Asp Phe Gln Ile
1               5                   10                  15

Arg Val Gln Val Ile Glu Gly Arg Gln Leu Pro Gly Val Asn Ile Lys
                20                  25                  30

Pro Val Val Lys Val Thr Ala Ala Gly Gln Thr Lys Arg Thr Arg Ile
            35                  40                  45

His Lys Gly Asn Ser Pro Leu Phe Asn Glu Thr Leu Phe Phe Asn Val
        50                  55                  60

Phe Asp Ser Pro Ala Glu Leu Phe Asp Glu Pro Ile Phe Ile Thr Val
65                  70                  75                  80

Val Asp Ser Cys Ser Leu Arg Thr Asp Ala Leu Ile Gly Glu Phe Arg
                85                  90                  95

<210> SEQ ID NO 48
<211> LENGTH: 95
<212> TYPE: PRT
<213> ORGANISM: Phascolarctos cinereus

<400> SEQUENCE: 48

Ser Ser Lys Lys Leu Leu Ser Asp Lys Pro Gln Asp Phe Gln Val Arg
1               5                   10                  15

Val Gln Val Ile Glu Gly Arg Gln Leu Pro Gly Leu Asn Ile Arg Pro
                20                  25                  30

Val Val Lys Val Met Ala Cys Gly Gln Thr Lys Arg Thr Arg Ile Arg
            35                  40                  45

Lys Gly Asn Gly Pro Val Phe Asp Glu Thr Leu Phe Phe Asn Val Phe
        50                  55                  60

Asp Ser Pro Val Glu Leu Phe Asp Glu Val Ile Cys Ile Thr Val Val
65                  70                  75                  80

Asp Ser Arg Ser Leu Arg Thr Asp Ala Leu Leu Gly Glu Phe Arg
                85                  90                  95

<210> SEQ ID NO 49
<211> LENGTH: 89
<212> TYPE: PRT
<213> ORGANISM: Sarcophilus harrisii

<400> SEQUENCE: 49

Ser Asp Leu Ser Leu Cys Leu Gln Ile Arg Val Gln Val Val Glu Gly
1               5                   10                  15

Arg Gln Leu Pro Gly Val Asn Ile Arg Pro Val Val Lys Val Thr Ala
                20                  25                  30

Ala Gly Gln Thr Lys Arg Thr Arg Ile Arg Lys Gly Asn Ser Pro Val
            35                  40                  45

Phe Asp Glu Thr Leu Phe Phe Asn Val Phe Asp Ser Pro Leu Glu Leu
        50                  55                  60

Phe Asp Glu Pro Ile Phe Ile Thr Val Val Asp Ser Arg Ser Leu Arg
65                  70                  75                  80

Thr Asp Ala Leu Ile Gly Glu Phe Arg
                85

<210> SEQ ID NO 50
<211> LENGTH: 78
<212> TYPE: PRT
<213> ORGANISM: Ornithorhynchus anatinus

```
<400> SEQUENCE: 50

Lys Ile Arg Val Arg Val Ile Glu Gly Arg Gln Leu Pro Gly Ala Ser
1               5                   10                  15

Ile Arg Pro Val Val Lys Val Thr Ala Ala Gly Lys Thr Lys Arg Thr
                20                  25                  30

Arg Ile Cys Lys Gly Asn Ser Pro Phe Phe Asp Glu Thr Leu Phe Phe
            35                  40                  45

Asn Val Phe Glu Ser Pro Val Glu Leu Phe Glu Asp Pro Ile Phe Ile
        50                  55                  60

Thr Val Arg Thr Asn Ala Ser Cys Arg Ser Pro Ser Pro Leu
65                  70                  75

<210> SEQ ID NO 51
<211> LENGTH: 85
<212> TYPE: PRT
<213> ORGANISM: Homo sapiens

<400> SEQUENCE: 51

Met Leu Arg Val Phe Ile Leu Tyr Ala Glu Asn Val His Thr Pro Asp
1               5                   10                  15

Thr Asp Ile Ser Asp Ala Tyr Cys Ser Ala Val Phe Ala Gly Val Lys
                20                  25                  30

Lys Arg Thr Lys Val Ile Lys Asn Ser Val Asn Pro Val Trp Asn Glu
            35                  40                  45

Gly Phe Glu Trp Asp Leu Lys Gly Ile Pro Leu Asp Gln Gly Ser Glu
        50                  55                  60

Leu His Val Val Lys Asp His Glu Thr Met Gly Arg Asn Arg Phe
65                  70                  75                  80

Leu Gly Glu Ala Lys
                85

<210> SEQ ID NO 52
<211> LENGTH: 86
<212> TYPE: PRT
<213> ORGANISM: Homo sapiens

<400> SEQUENCE: 52

Met Leu Cys Cys Leu Leu Val Arg Ala Ser Asn Leu Pro Ser Ala Lys
1               5                   10                  15

Lys Asp Arg Arg Ser Asp Pro Val Ala Ser Leu Thr Phe Arg Gly Val
                20                  25                  30

Lys Lys Arg Thr Lys Val Ile Lys Asn Ser Val Asn Pro Val Trp Asn
            35                  40                  45

Glu Gly Phe Glu Trp Asp Leu Lys Gly Ile Pro Leu Asp Gln Gly Ser
        50                  55                  60

Glu Leu His Val Val Lys Asp His Glu Thr Met Gly Arg Asn Arg
65                  70                  75                  80

Phe Leu Gly Glu Ala Lys
                85

<210> SEQ ID NO 53
<211> LENGTH: 96
<212> TYPE: PRT
<213> ORGANISM: Homo sapiens

<400> SEQUENCE: 53

Pro Thr Ser Arg Lys Leu Leu Ser Asp Lys Pro Gln Asp Phe Gln Ile
1               5                   10                  15
```

```
Arg Val Gln Val Ile Glu Gly Arg Gln Leu Pro Gly Val Asn Ile Lys
            20                  25                  30

Pro Val Val Lys Val Thr Ala Ala Gly Gln Thr Lys Arg Thr Arg Ile
        35                  40                  45

His Lys Gly Asn Ser Pro Leu Phe Asn Glu Thr Leu Phe Phe Asn Leu
50                  55                  60

Phe Asp Ser Pro Gly Glu Leu Phe Asp Glu Pro Ile Phe Ile Thr Val
65                  70                  75                  80

Val Asp Ser Arg Ser Leu Arg Thr Asp Ala Leu Leu Gly Glu Phe Arg
                85                  90                  95
```

<210> SEQ ID NO 54
<211> LENGTH: 88
<212> TYPE: PRT
<213> ORGANISM: Homo sapiens

<400> SEQUENCE: 54

```
Ile Leu Ala Trp Gly Leu Arg Asn Met Lys Ser Tyr Gln Leu Ala Asn
1               5                   10                  15

Ile Ser Ser Pro Ser Leu Val Val Glu Cys Gly Gly Gln Thr Val Gln
            20                  25                  30

Ser Cys Val Ile Arg Asn Leu Arg Lys Asn Pro Asn Phe Asp Ile Cys
        35                  40                  45

Thr Leu Phe Met Glu Val Met Leu Pro Arg Glu Glu Leu Tyr Cys Pro
50                  55                  60

Pro Ile Thr Val Lys Val Ile Asp Asn Arg Gln Phe Gly Arg Arg Pro
65                  70                  75                  80

Val Val Gly Gln Cys Thr Ile Arg
                85
```

<210> SEQ ID NO 55
<211> LENGTH: 96
<212> TYPE: PRT
<213> ORGANISM: Equus caballus

<400> SEQUENCE: 55

```
Pro Ala Pro Arg Lys Leu Leu Ser Asp Lys Pro Gln Asp Phe Gln Ile
1               5                   10                  15

Arg Val Gln Val Ile Glu Gly Arg Gln Leu Pro Gly Val Asn Ile Lys
            20                  25                  30

Pro Val Val Lys Val Thr Ala Ala Arg Gln Thr Lys Arg Thr Arg Ile
        35                  40                  45

His Arg Gly Asn Ser Pro Leu Phe Asn Glu Thr Leu Phe Phe Asn Val
50                  55                  60

Phe Asp Ser Pro Ser Glu Leu Phe Asp Glu Ala Val Phe Ile Thr Val
65                  70                  75                  80

Val Asp Ser Cys Ser Leu Arg Thr Asp Ala Leu Ile Gly Glu Phe Arg
                85                  90                  95
```

<210> SEQ ID NO 56
<211> LENGTH: 2001
<212> TYPE: DNA
<213> ORGANISM: Equus caballus

<400> SEQUENCE: 56

```
gactctttt  tctccacgtc gggtctaggg tgcagatgag tttatgggac gctgcatctg    60
tcagccgact ctggaacgga tgccccggct gacctggttc ccactgacta ggggcagcca   120
```

| | |
|---|---|
| gccggcgggc gagctgctgg cctcttttga gctcatccag agagagaagg tgaggctggt | 180 |
| ccccatcctg atccaggaag cccagacagg gagtacatgg taggagaggg taggggggcac | 240 |
| aggcagggat gccccgaagg aggggagggg ctgccgatac atccttctcc ccccaccagg | 300 |
| cctgctcagt ggggagcact gaaccgccac ctctggaatt caggcttcct gctgagactg | 360 |
| gttttgcccc tcttttctga accccaagtt aggctactgt ctaaacattg gggtagaatg | 420 |
| ttggaatctg gctgtgctg gaatgtctga gtcctctggc cattggatgt attttccct | 480 |
| gggtcatatc ctgacgtggt ttctgagagg aggacctccg tgatctggtc ggggagactt | 540 |
| aattgtgatg gtggcaccca gggacaggta aggtcaggac ctccggtgta gtgttggctc | 600 |
| tgccatggcc tggctgtgcg accctgggcc aggcacttcc ctgctgtgaa atagggggtt | 660 |
| tgggttagaa ccatatcttc agctttgctc ttagagtgat gtgaaccca ggtgtaagct | 720 |
| ggatggaagt caggctactc tgggtcaagt gtctggaggg ggcacacagt atgctgcaac | 780 |
| ctggcttccc ctggcacctg gctgccaact cccgggcacc tccaaggagt ccctaggttg | 840 |
| caaactccca actgtgatca ctgacatatt ccatgagtgt cattttgtgg ctgaaggtgt | 900 |
| gtttgcctgg ccccggacaga aaggagggtg atggggcctt gggtgacagg cactgaccaa | 960 |
| agctcttttt tctaccccgc agccggccat ctaccacatt mctggttttg aggtaagtct | 1020 |
| tgctcttccc tcttcttctt caaactcatg gcccgcctct gtgtgtttgc agcccccctat | 1080 |
| gagctaggaa gggcagtcag gtgtatacca ccaccggccc gccttcaggg atggggtggg | 1140 |
| tgagggccgg ggtccctggc cagctcaggc ctttcccgcc cttcttccct gagactcaga | 1200 |
| ctgtagggac ctcatggtca tccagcccac gggctctcag ctgggctgca tgttagaatc | 1260 |
| ccttcggcag cttgaaaaat caccagtgct caggccccac cccagaccag atggaacaca | 1320 |
| gtctctgggg atgtggccca ggcattggta tctttcagag cttcccaggg gatttttaatg | 1380 |
| tgctgctagg gctgagcacc atcgacttag cccagtggtt ctcagtgtga tatcacctgg | 1440 |
| gatgttgtta gaaatgccga ttcttggctc ctgcttcaca cctactgaag caaactctga | 1500 |
| ggggcagtgc agcaacctgc aaattaacaa gcctccaggg gattctgatg cccactcgag | 1560 |
| tttcagaagc tctggcttag accatcttcc ccaactcatt gttcccccca tgaccggttt | 1620 |
| ttcctcctct actagtgatg ggggctctgt tcccttctcc ctgctctcct tccttctcct | 1680 |
| gggggcatgg tagaaaatgc agacccttc ctggtaccca ggctaatttg attcaggaga | 1740 |
| tactgttctc agtcaggttc agctgcatct tggaggagcg gtcatccggt ctgtcgttgg | 1800 |
| atgccttccc ccttacaagg cagtccacgc aatctgcaga cagttttac catgcaggcc | 1860 |
| ttccttcacc cctgtctctg ctccaccccc ggcatccctc agcccctct ctctcctgct | 1920 |
| ccctctcctg tccagcccaa gctcccgctc tcaggtctgc cagcccctgg ggatccagat | 1980 |
| tctttctccc tggctctcca a | 2001 |

<210> SEQ ID NO 57
<211> LENGTH: 459
<212> TYPE: DNA
<213> ORGANISM: Equus caballus

<400> SEQUENCE: 57

| | |
|---|---|
| agacccacga tttcctgcat cttcgactac gggaaccgct accatctacg ctgctacatg | 60 |
| taccaggccc gggacctgcc cgccatggac aaggactctt tttctgatcc ctacgcaatc | 120 |
| gtctccttcc tgcaccagag ccagaagaca gtggtggtga agaacaccct gaaccccacc | 180 |

```
tgggaccaga cactcatctt ctatgagatc gagatctttg gtgagccgcc cagcatcgcc    240
gagcagccgc ccagcatcgt ggtggagcta tacgaccatg acacctacgg tgcagatgag    300
tttatgggac gctgcatctg tcagccgact ctggaacgga tgccccggct gacctggttc    360
ccactgacta ggggcagcca gccggcgggc gagctgctgg cctcttttga gctcatccag    420
agagagaagc cggccatcta ccacattcct ggttttgag                           459
```

<210> SEQ ID NO 58
<211> LENGTH: 459
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
agacccacga tttcctgcat cttcgactac gggaaccgct accatctacg ctgctacatg    60
taccaggccc gggacctgcc cgccatggac aaggactctt tttctgatcc ctacgcaatc    120
gtctccttcc tgcaccagag ccagaagaca gtggtggtga agaacaccct gaaccccacc    180
tgggaccaga cactcatctt ctatgagatc gagatctttg gtgagccgcc cagcatcgcc    240
gagcagccgc ccagcatcgt ggtggagcta tacgaccatg acacctacgg tgcagatgag    300
tttatgggac gctgcatctg tcagccgact ctggaacgga tgccccggct gacctggttc    360
ccactgacta ggggcagcca gccggcgggc gagctgctgg cctcttttga gctcatccag    420
agagagaagc cggccatcta ccacattact ggttttgag                           459
```

<210> SEQ ID NO 59
<211> LENGTH: 50
<212> TYPE: DNA
<213> ORGANISM: Equus caballus

<400> SEQUENCE: 59

```
taccccgcag ccggccatct accacattcc tggttttgag gtaagtcttg               50
```

<210> SEQ ID NO 60
<211> LENGTH: 153
<212> TYPE: PRT
<213> ORGANISM: Equus caballus

<400> SEQUENCE: 60

```
Arg Pro Thr Ile Ser Cys Ile Phe Asp Tyr Gly Asn Arg Tyr His Leu
1               5                   10                  15

Arg Cys Tyr Met Tyr Gln Ala Arg Asp Leu Pro Ala Met Asp Lys Asp
            20                  25                  30

Ser Phe Ser Asp Pro Tyr Ala Ile Val Ser Phe Leu His Gln Ser Gln
        35                  40                  45

Lys Thr Val Val Lys Asn Thr Leu Asn Pro Thr Trp Asp Gln Thr
    50                  55                  60

Leu Ile Phe Tyr Glu Ile Glu Ile Phe Gly Glu Pro Pro Ser Ile Ala
65                  70                  75                  80

Glu Gln Pro Pro Ser Ile Val Val Glu Leu Tyr Asp His Asp Thr Tyr
                85                  90                  95

Gly Ala Asp Glu Phe Met Gly Arg Cys Ile Cys Gln Pro Thr Leu Glu
            100                 105                 110

Arg Met Pro Arg Leu Thr Trp Phe Pro Leu Thr Arg Gly Ser Gln Pro
        115                 120                 125
```

```
Ala Gly Glu Leu Leu Ala Ser Phe Glu Leu Ile Gln Arg Glu Lys Pro
    130                 135                 140

Ala Ile Tyr His Ile Pro Gly Phe Glu
145                 150

<210> SEQ ID NO 61
<211> LENGTH: 153
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Arg Pro Thr Ile Ser Cys Ile Phe Asp Tyr Gly Asn Arg Tyr His Leu
1               5                   10                  15

Arg Cys Tyr Met Tyr Gln Ala Arg Asp Leu Pro Ala Met Asp Lys Asp
            20                  25                  30

Ser Phe Ser Asp Pro Tyr Ala Ile Val Ser Phe Leu His Gln Ser Gln
        35                  40                  45

Lys Thr Val Val Lys Asn Thr Leu Asn Pro Thr Trp Asp Gln Thr
    50                  55                  60

Leu Ile Phe Tyr Glu Ile Glu Ile Phe Gly Glu Pro Pro Ser Ile Ala
65                  70                  75                  80

Glu Gln Pro Pro Ser Ile Val Val Glu Leu Tyr Asp His Asp Thr Tyr
                85                  90                  95

Gly Ala Asp Glu Phe Met Gly Arg Cys Ile Cys Gln Pro Thr Leu Glu
            100                 105                 110

Arg Met Pro Arg Leu Thr Trp Phe Pro Leu Thr Arg Gly Ser Gln Pro
        115                 120                 125

Ala Gly Glu Leu Leu Ala Ser Phe Glu Leu Ile Gln Arg Glu Lys Pro
    130                 135                 140

Ala Ile Tyr His Ile Thr Gly Phe Glu
145                 150

<210> SEQ ID NO 62
<211> LENGTH: 30
<212> TYPE: DNA
<213> ORGANISM: Equus caballus

<400> SEQUENCE: 62
ccggccatct accacattcc tggttttgag                                          30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ccggccatct accacattac tggttttgag                                          30

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 64
ggttgcaaac tcccaactgt                                               20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gatttttcaa gctgccgaag                                               20

<210> SEQ ID NO 66
<211> LENGTH: 60
<212> TYPE: PRT
<213> ORGANISM: Homo sapiens

<400> SEQUENCE: 66

Thr Arg Gly Ser Gln Pro Ser Gly Glu Leu Leu Ala Ser Phe Glu Leu
1               5                   10                  15

Ile Gln Arg Glu Lys Pro Ala Ile His His Ile Pro Gly Phe Glu Val
            20                  25                  30

Gln Glu Thr Ser Arg Ile Leu Asp Glu Ser Glu Asp Thr Asp Leu Pro
        35                  40                  45

Tyr Pro Pro Pro Gln Arg Glu Ala Asn Ile Tyr Met
    50                  55                  60

<210> SEQ ID NO 67
<211> LENGTH: 60
<212> TYPE: PRT
<213> ORGANISM: Equus caballus

<400> SEQUENCE: 67

Thr Arg Gly Ser Gln Pro Ala Gly Glu Leu Leu Ala Ser Phe Glu Leu
1               5                   10                  15

Ile Gln Arg Glu Lys Pro Ala Ile Tyr His Ile Pro Gly Phe Glu Val
            20                  25                  30

Gln Asp Thr Ser Gly Ile Leu Glu Glu Ser Glu Asp Thr Asp Leu Pro
        35                  40                  45

Tyr Pro Pro Pro Gln Arg Glu Ala Asn Ile Tyr Met
    50                  55                  60

<210> SEQ ID NO 68
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Thr Arg Gly Ser Gln Pro Ala Gly Glu Leu Leu Ala Ser Phe Glu Leu
1               5                   10                  15

Ile Gln Arg Glu Lys Pro Ala Ile Tyr His Ile Thr Gly Phe Glu Val
            20                  25                  30

Gln Asp Thr Ser Gly Ile Leu Glu Glu Ser Glu Asp Thr Asp Leu Pro
        35                  40                  45

Tyr Pro Pro Pro Gln Arg Glu Ala Asn Ile Tyr Met
    50                  55                  60
```

<210> SEQ ID NO 69
<211> LENGTH: 60
<212> TYPE: PRT
<213> ORGANISM: Unknown
<220> FEATURE:
<223> OTHER INFORMATION: Description of Unknown:
    DYSF sequence

<400> SEQUENCE: 69

Thr Arg Gly Ser Gln Pro Ser Gly Glu Leu Leu Ala Ser Phe Glu Leu
1               5                   10                  15

Ile Gln Arg Glu Lys Pro Ala Ile His His Ile Pro Gly Phe Glu Val
            20                  25                  30

Gln Glu Thr Ser Arg Ile Leu Asp Glu Ser Glu Asp Thr Asp Leu Pro
        35                  40                  45

Tyr Pro Pro Gln Arg Glu Ala Asn Ile Tyr Met
    50                  55                  60

<210> SEQ ID NO 70
<211> LENGTH: 59
<212> TYPE: PRT
<213> ORGANISM: Unknown
<220> FEATURE:
<223> OTHER INFORMATION: Description of Unknown:
    DYSF sequence

<400> SEQUENCE: 70

Arg Gly Ser Gln Pro Ser Gly Glu Leu Leu Ala Ser Phe Glu Leu Ile
1               5                   10                  15

Gln Arg Glu Lys Pro Ala Ile His His Ile Pro Gly Phe Glu Val Gln
            20                  25                  30

Glu Thr Ser Arg Ile Leu Asp Glu Ser Glu Asp Thr Asp Leu Pro Tyr
        35                  40                  45

Pro Pro Pro Gln Arg Glu Ala Asn Ile Tyr Met
    50                  55

<210> SEQ ID NO 71
<211> LENGTH: 60
<212> TYPE: PRT
<213> ORGANISM: Unknown
<220> FEATURE:
<223> OTHER INFORMATION: Description of Unknown:
    DYSF sequence

<400> SEQUENCE: 71

Thr Arg Gly Ser Gln Pro Ala Gly Glu Leu Leu Ala Ala Phe Glu Leu
1               5                   10                  15

Ile Gln Arg Glu Lys Pro Ala Ile His His Ile Pro Gly Phe Glu Met
            20                  25                  30

His Glu Thr Ser Arg Ile Leu Asp Glu Thr Glu Asp Thr Asp Leu Pro
        35                  40                  45

Tyr Pro Pro Gln Arg Glu Ala Asn Ile Tyr Met
    50                  55                  60

<210> SEQ ID NO 72
<211> LENGTH: 60
<212> TYPE: PRT
<213> ORGANISM: Unknown
<220> FEATURE:
<223> OTHER INFORMATION: Description of Unknown:
    DYSF sequence

```
<400> SEQUENCE: 72

Thr Arg Gly Ser Gln Pro Ala Gly Glu Leu Leu Ala Ser Phe Glu Leu
1               5                   10                  15

Ile Gln Arg Glu Lys Pro Ala Ile His His Ile Pro Gly Phe Glu Val
                20                  25                  30

Gln Asp Thr Ser Arg Ile Leu Glu Glu Ser Glu Asp Thr Asp Leu Pro
            35                  40                  45

Tyr Pro Pro Pro Gln Arg Glu Ala Asn Ile Tyr Met
        50                  55                  60

<210> SEQ ID NO 73
<211> LENGTH: 60
<212> TYPE: PRT
<213> ORGANISM: Unknown
<220> FEATURE:
<223> OTHER INFORMATION: Description of Unknown:
      DYSF sequence

<400> SEQUENCE: 73

Thr Arg Gly Asn Gln Pro Ala Gly Glu Leu Leu Ala Ser Phe Glu Leu
1               5                   10                  15

Ile Gln Arg Glu Lys Pro Ala Ile His His Ile Pro Gly Phe Glu Val
                20                  25                  30

Gln Asp Thr Ala Gly Ile Leu Glu Glu Ser Glu Asp Thr Asp Leu Pro
            35                  40                  45

Tyr Pro Pro Pro Gln Arg Glu Ala Asn Ile Tyr Met
        50                  55                  60

<210> SEQ ID NO 74
<211> LENGTH: 59
<212> TYPE: PRT
<213> ORGANISM: Unknown
<220> FEATURE:
<223> OTHER INFORMATION: Description of Unknown:
      DYSF sequence

<400> SEQUENCE: 74

Arg Gly Ser Gln Pro Ala Gly Glu Leu Leu Ala Ser Phe Glu Leu Ile
1               5                   10                  15

Gln Arg Glu Lys Pro Ala Ile His His Ile Pro Gly Phe Glu Val Gln
                20                  25                  30

Asp Thr Ser Gly Ile Leu Glu Glu Ser Glu Asp Thr Asp Leu Pro Tyr
            35                  40                  45

Pro Pro Pro Gln Arg Glu Ala Asn Ile Tyr Met
        50                  55

<210> SEQ ID NO 75
<211> LENGTH: 60
<212> TYPE: PRT
<213> ORGANISM: Unknown
<220> FEATURE:
<223> OTHER INFORMATION: Description of Unknown:
      DYSF sequence

<400> SEQUENCE: 75

Thr Arg Gly Ser Gln Pro Ala Gly Glu Leu Leu Ala Ser Phe Glu Leu
1               5                   10                  15

Ile Gln Arg Glu Lys Pro Ala Ile His His Ile Pro Gly Phe Glu Val
                20                  25                  30

Gln Asp Thr Thr Gly Ile Leu Glu Glu Ser Glu Asp Thr Asp Leu Pro
            35                  40                  45
```

Tyr Pro Pro Pro Gln Arg Glu Ala Asn Ile Tyr Met
    50                  55                  60

<210> SEQ ID NO 76
<211> LENGTH: 60
<212> TYPE: PRT
<213> ORGANISM: Unknown
<220> FEATURE:
<223> OTHER INFORMATION: Description of Unknown:
      DYSF sequence

<400> SEQUENCE: 76

Thr Arg Gly Ser Gln Pro Ala Gly Glu Leu Leu Ala Ser Phe Glu Leu
1               5                   10                  15

Ile Gln Arg Glu Lys Pro Ala Ile His His Ile Pro Gly Phe Glu Val
            20                  25                  30

Gln Asp Thr Ser Gly Ile Leu Glu Glu Ser Glu Asp Thr Asp Leu Pro
        35                  40                  45

Tyr Pro Pro Pro Gln Arg Glu Ala Asn Ile Tyr Met
    50                  55                  60

<210> SEQ ID NO 77
<211> LENGTH: 60
<212> TYPE: PRT
<213> ORGANISM: Papio anubis

<400> SEQUENCE: 77

Thr Lys Gly Ser Gln Pro Thr Gly Glu Leu Leu Ala Ser Phe Glu Leu
1               5                   10                  15

Ile Gln Arg Glu Lys Pro Ala Ile His His Ile Pro Gly Phe Glu Val
            20                  25                  30

Gln Glu Thr Ser Arg Ile Leu Asp Glu Ser Glu Asp Thr Asp Leu Pro
        35                  40                  45

Tyr Pro Pro Pro Gln Arg Glu Ala Asn Ile Tyr Met
    50                  55                  60

<210> SEQ ID NO 78
<211> LENGTH: 60
<212> TYPE: PRT
<213> ORGANISM: Macaca mulatta

<400> SEQUENCE: 78

Thr Arg Gly Ser Gln Pro Thr Gly Glu Leu Leu Ala Ser Phe Glu Leu
1               5                   10                  15

Ile Gln Arg Glu Lys Pro Ala Ile His His Ile Pro Gly Phe Glu Val
            20                  25                  30

Gln Glu Thr Ser Arg Ile Leu Asp Glu Ser Glu Asp Thr Asp Leu Pro
        35                  40                  45

Tyr Pro Pro Pro Gln Arg Glu Ala Asn Ile Tyr Met
    50                  55                  60

<210> SEQ ID NO 79
<211> LENGTH: 60
<212> TYPE: PRT
<213> ORGANISM: Rhinopithecus bieti

<400> SEQUENCE: 79

Thr Arg Gly Ser Gln Pro Met Gly Glu Leu Leu Ala Ser Phe Glu Leu
1               5                   10                  15

Ile Gln Arg Glu Lys Pro Ala Ile His His Ile Pro Gly Phe Glu Val

-continued

```
                    20                  25                  30

Gln Glu Thr Ser Arg Ile Leu Asp Glu Ser Glu Asp Thr Asp Leu Pro
             35                  40                  45

Tyr Pro Pro Pro Gln Arg Glu Ala Asn Ile Tyr Met
         50                  55                  60

<210> SEQ ID NO 80
<211> LENGTH: 59
<212> TYPE: PRT
<213> ORGANISM: Microcebus murinus

<400> SEQUENCE: 80

Arg Gly Ser Gln Pro Ser Gly Glu Leu Leu Ala Ser Phe Glu Leu Ile
1               5                   10                  15

Gln Arg Glu Lys Pro Ala Ile Tyr His Ile Pro Gly Phe Glu Val Gln
             20                  25                  30

Asp Thr Ser Arg Ile Leu Asp Glu Ser Glu Asp Thr Asp Leu Pro Tyr
             35                  40                  45

Pro Pro Pro Gln Arg Glu Ala Asn Val Tyr Met
         50                  55

<210> SEQ ID NO 81
<211> LENGTH: 59
<212> TYPE: PRT
<213> ORGANISM: Carlito syrichta

<400> SEQUENCE: 81

Arg Gly Gly Gln Pro Ser Gly Glu Leu Leu Ala Ala Phe Glu Leu Ile
1               5                   10                  15

Gln Arg Glu Lys Pro Ala Ile His His Ile Pro Gly Phe Glu Val Gln
             20                  25                  30

Asp Ala Ser Arg Ile Leu Asp Glu Ala Glu Asp Thr Asp Leu Pro Tyr
             35                  40                  45

Pro Pro Pro Gln Arg Glu Ala Asn Val His Met
         50                  55

<210> SEQ ID NO 82
<211> LENGTH: 59
<212> TYPE: PRT
<213> ORGANISM: Otolemur garnettii

<400> SEQUENCE: 82

Arg Gly Ser Gln Pro Ser Gly Glu Leu Leu Ala Ser Phe Glu Leu Ile
1               5                   10                  15

Gln Arg Glu Lys Pro Ala Ile His His Ile Pro Gly Phe Glu Val Gln
             20                  25                  30

Asp Thr Ala Arg Ile Leu Asp Glu Ser Glu Asp Thr Asp Leu Pro Tyr
             35                  40                  45

Pro Pro Pro Gln Arg Glu Ala Asn Ile Tyr Val
         50                  55

<210> SEQ ID NO 83
<211> LENGTH: 59
<212> TYPE: PRT
<213> ORGANISM: Propithecus coquereli

<400> SEQUENCE: 83

Arg Gly Ser Gln Ala Ser Gly Glu Leu Leu Ala Ser Phe Glu Leu Ile
1               5                   10                  15
```

Gln Arg Glu Lys Pro Ala Ile Tyr His Ile Pro Gly Phe Glu Val Gln
            20                  25                  30

Asp Thr Ser Arg Ile Leu Asp Glu Ser Glu Asp Thr Asp Leu Pro Tyr
        35                  40                  45

Pro Pro Pro Gln Arg Glu Ala Asn Val Tyr Met
    50                  55

<210> SEQ ID NO 84
<211> LENGTH: 60
<212> TYPE: PRT
<213> ORGANISM: Cricetulus griseus

<400> SEQUENCE: 84

Thr Arg Gly Gly Gln Pro Ala Gly Glu Leu Leu Ala Ala Phe Glu Leu
1               5                   10                  15

Ile Gln Arg Glu Lys Pro Ala Ile His His Ile Pro Gly Phe Glu Met
            20                  25                  30

His Glu Thr Ser Arg Ile Leu Asp Glu Thr Glu Asp Thr Asp Leu Pro
        35                  40                  45

Tyr Pro Pro Pro Gln Arg Glu Ala Asn Ile Tyr Met
    50                  55                  60

<210> SEQ ID NO 85
<211> LENGTH: 60
<212> TYPE: PRT
<213> ORGANISM: Microtus ochrogaster

<400> SEQUENCE: 85

Thr Arg Gly Ser Gln Pro Ala Gly Glu Leu Leu Ala Ala Phe Glu Leu
1               5                   10                  15

Ile Gln Arg Glu Lys Pro Ala Ile His His Ile Pro Gly Phe Glu Met
            20                  25                  30

His Glu Thr Ser Ser Ile Leu Glu Glu Thr Glu Asp Thr Asp Leu Pro
        35                  40                  45

Tyr Pro Pro Pro Gln Arg Glu Ala Asn Ile Tyr Met
    50                  55                  60

<210> SEQ ID NO 86
<211> LENGTH: 60
<212> TYPE: PRT
<213> ORGANISM: Meriones unguiculatus

<400> SEQUENCE: 86

Thr Arg Gly Ser Gln Pro Ala Gly Glu Leu Leu Ala Ala Phe Glu Leu
1               5                   10                  15

Ile Gln Arg Glu Lys Pro Ala Ile His His Ile Pro Gly Phe Glu Val
            20                  25                  30

Gln Glu Thr Ser Arg Thr Leu Asp Glu Thr Glu Asp Thr Asp Leu Pro
        35                  40                  45

Tyr Pro Pro Pro Gln Arg Glu Ala Asn Ile Tyr Met
    50                  55                  60

<210> SEQ ID NO 87
<211> LENGTH: 59
<212> TYPE: PRT
<213> ORGANISM: Ictidomys tridecemlineatus

<400> SEQUENCE: 87

Arg Gly Ser Gln Pro Ala Gly Glu Leu Leu Ala Ser Phe Glu Leu Ile
1               5                   10                  15

Gln Arg Glu Lys Pro Ala Ile Tyr His Ile Pro Gly Phe Glu Val Gln
            20                  25                  30

Asp Thr Ser Arg Ile Leu Asp Glu Ser Glu Asp Thr Asp Leu Pro Tyr
        35                  40                  45

Pro Pro Pro Gln Arg Glu Ala Asn Ile Tyr Val
    50                  55

<210> SEQ ID NO 88
<211> LENGTH: 60
<212> TYPE: PRT
<213> ORGANISM: Chinchilla lanigera

<400> SEQUENCE: 88

Thr Arg Gly Asn Gln Pro Ala Gly Glu Leu Leu Ala Ser Phe Glu Leu
1               5                   10                  15

Ile Gln Arg Glu Lys Pro Ala Ile His His Ile Pro Gly Phe Glu Val
            20                  25                  30

Gln Asp Thr Ser Arg Ile Leu Asp Glu Ser Glu Asp Thr Asp Leu Pro
        35                  40                  45

Tyr Pro Pro Pro Gln Arg Glu Ala Asn Ile Tyr Met
    50                  55                  60

<210> SEQ ID NO 89
<211> LENGTH: 59
<212> TYPE: PRT
<213> ORGANISM: Marmota marmota marmota

<400> SEQUENCE: 89

Arg Gly Ser Gln Pro Ala Gly Glu Leu Leu Ala Ser Phe Glu Leu Ile
1               5                   10                  15

Gln Arg Glu Lys Pro Ala Ile Tyr His Ile Pro Gly Phe Glu Val Gln
            20                  25                  30

Asp Thr Ser Arg Ile Leu Asp Glu Ser Glu Asp Thr Asp Leu Pro Tyr
        35                  40                  45

Pro Pro Pro Gln Arg Glu Ala Asn Val Tyr Val
    50                  55

<210> SEQ ID NO 90
<211> LENGTH: 59
<212> TYPE: PRT
<213> ORGANISM: Castor canadensis

<400> SEQUENCE: 90

Arg Ser Ser Gln Pro Ala Gly Glu Leu Leu Ala Ser Phe Glu Leu Ile
1               5                   10                  15

Gln Arg Glu Lys Pro Ala Ile His His Ile Pro Gly Phe Glu Val Gln
            20                  25                  30

Asp Thr Ser Arg Ile Leu Asp Glu Ser Glu Asp Ala Asp Leu Pro Tyr
        35                  40                  45

Pro Pro Pro Gln Arg Glu Val Asn Ile Tyr Met
    50                  55

<210> SEQ ID NO 91
<211> LENGTH: 59
<212> TYPE: PRT
<213> ORGANISM: Mustela putorius furo

<400> SEQUENCE: 91

Arg Gly Ser Gln Pro Ala Gly Glu Leu Leu Ala Ser Phe Glu Leu Ile

```
                1               5                  10                 15
             Gln Arg Glu Lys Pro Ala Ile His His Ile Pro Gly Phe Glu Val His
                            20                  25                 30

Asp Thr Ser Gly Ile Leu Asp Glu Ser Glu Asp Thr Asp Leu Pro Tyr
                            35                  40                 45

Pro Pro Pro Gln Arg Glu Ala Asn Ile Tyr Met
                            50                  55
```

<210> SEQ ID NO 92
<211> LENGTH: 60
<212> TYPE: PRT
<213> ORGANISM: Fukomys damarensis

<400> SEQUENCE: 92

```
             Thr Arg Gly Ser Gln Pro Ala Gly Glu Leu Leu Ala Ser Phe Glu Leu
             1               5                  10                 15

Ile Gln Arg Glu Lys Pro Ala Ile His His Ile Pro Gly Phe Glu Val
                            20                  25                 30

Gln Asp Thr Ser Arg Ile Leu Asp Glu Ser Glu Asp Thr Asp Leu Pro
                            35                  40                 45

Tyr Pro Pro Pro Gln Arg Glu Ala Asn Ile Tyr Met
                            50                  55                 60
```

<210> SEQ ID NO 93
<211> LENGTH: 60
<212> TYPE: PRT
<213> ORGANISM: Myotis brandtii

<400> SEQUENCE: 93

```
             Thr Arg Gly Ser Gln Pro Ala Gly Glu Leu Leu Ala Ser Phe Glu Leu
             1               5                  10                 15

Ile Gln Arg Glu Lys Pro Ala Ile His His Ile Pro Gly Phe Glu Val
                            20                  25                 30

Gln Asp Ala Ser Arg Ile Leu Glu Glu Ser Glu Asp Thr Asp Leu Pro
                            35                  40                 45

Tyr Pro Pro Pro Gln Arg Glu Ala Asn Ile Tyr Met
                            50                  55                 60
```

<210> SEQ ID NO 94
<211> LENGTH: 60
<212> TYPE: PRT
<213> ORGANISM: Pteropus vampyrus

<400> SEQUENCE: 94

```
             Thr Arg Gly Ser Gln Pro Ala Gly Glu Leu Leu Ala Ser Phe Glu Leu
             1               5                  10                 15

Ile Gln Arg Glu Lys Pro Ala Ile Tyr His Ile Pro Gly Phe Glu Val
                            20                  25                 30

Gln Asp Thr Ser Arg Ile Leu Glu Glu Ser Glu Asp Thr Asp Leu Pro
                            35                  40                 45

Tyr Pro Pro Pro Gln Arg Glu Ala Asn Ile Tyr Ile
                            50                  55                 60
```

<210> SEQ ID NO 95
<211> LENGTH: 60
<212> TYPE: PRT
<213> ORGANISM: Equus caballus

<400> SEQUENCE: 95

Thr Arg Gly Ser Gln Pro Ala Gly Glu Leu Leu Ala Ser Phe Glu Leu
1               5                   10                  15

Ile Gln Arg Glu Lys Pro Ala Ile Tyr His Ile Pro Gly Phe Glu Val
            20                  25                  30

Gln Asp Thr Ser Gly Ile Leu Glu Glu Ser Glu Asp Thr Asp Leu Pro
        35                  40                  45

Tyr Pro Pro Pro Gln Arg Glu Ala Asn Ile Tyr Met
    50                  55                  60

<210> SEQ ID NO 96
<211> LENGTH: 60
<212> TYPE: PRT
<213> ORGANISM: Equus asinus

<400> SEQUENCE: 96

Thr Arg Gly Ser Gln Leu Ala Gly Glu Leu Leu Ala Ser Phe Glu Leu
1               5                   10                  15

Ile Gln Arg Glu Lys Pro Ala Ile Tyr His Leu Pro Gly Phe Glu Val
            20                  25                  30

Gln Asp Thr Ser Gly Ile Leu Glu Glu Ser Glu Asp Thr Asp Leu Pro
        35                  40                  45

Tyr Pro Pro Pro Gln Arg Glu Ala Asn Ile Tyr Met
    50                  55                  60

<210> SEQ ID NO 97
<211> LENGTH: 60
<212> TYPE: PRT
<213> ORGANISM: Loxodonta africana

<400> SEQUENCE: 97

Thr Arg Gly Ser Gln Ala Ala Gly Glu Leu Leu Ala Ser Phe Glu Leu
1               5                   10                  15

Ile Gln Arg Glu Lys Pro Ala Ile His His Ile Pro Gly Phe Glu Val
            20                  25                  30

Gln Asp Thr Ser Arg Ile Leu Glu Glu Ser Glu Asp Thr Asp Leu Pro
        35                  40                  45

Tyr Pro Pro Pro Gln Arg Glu Ala Asn Ile Tyr Met
    50                  55                  60

<210> SEQ ID NO 98
<211> LENGTH: 60
<212> TYPE: PRT
<213> ORGANISM: Balaenoptera acutorostrata scammoni

<400> SEQUENCE: 98

Thr Arg Gly Asn Gln Pro Ala Gly Glu Leu Leu Ala Ser Phe Glu Leu
1               5                   10                  15

Ile Gln Arg Glu Lys Pro Ala Ile His His Ile Pro Gly Phe Glu Val
            20                  25                  30

Gln Asp Thr Ser Gly Ile Leu Glu Glu Ser Glu Asp Thr Asp Leu Pro
        35                  40                  45

Tyr Pro Pro Pro Gln Arg Glu Ala Asn Ile Tyr Met
    50                  55                  60

<210> SEQ ID NO 99
<211> LENGTH: 60
<212> TYPE: PRT
<213> ORGANISM: Ailuropoda melanoleuca

<400> SEQUENCE: 99

-continued

```
Val Arg Gly Ser Gln Pro Ala Gly Glu Leu Leu Ala Ser Phe Glu Leu
1               5                   10                  15

Ile Gln Arg Glu Lys Pro Ala Ile His His Ile Pro Gly Phe Glu Val
            20                  25                  30

Gln Asp Thr Ser Gly Ile Leu Asp Glu Ser Glu Asp Thr Asp Leu Pro
        35                  40                  45

Tyr Pro Pro Gln Arg Glu Ala Asn Ile Tyr Met
    50                  55                  60

<210> SEQ ID NO 100
<211> LENGTH: 60
<212> TYPE: PRT
<213> ORGANISM: Orcinus orca

<400> SEQUENCE: 100

Thr Arg Gly Asn Gln Pro Ala Gly Glu Leu Leu Ala Ser Phe Glu Leu
1               5                   10                  15

Ile Gln Arg Glu Lys Pro Ala Ile Tyr His Ile Pro Gly Phe Glu Val
            20                  25                  30

Gln Asp Thr Ser Gly Ile Leu Glu Ser Glu Asp Thr Asp Leu Pro
        35                  40                  45

Tyr Pro Pro Gln Arg Glu Ala Asn Ile Tyr Met
    50                  55                  60

<210> SEQ ID NO 101
<211> LENGTH: 60
<212> TYPE: PRT
<213> ORGANISM: Phascolarctos cinereus

<400> SEQUENCE: 101

Val Arg Gly Ser Arg Pro Ala Gly Glu Leu Leu Ala Ala Phe Glu Leu
1               5                   10                  15

Ile Met Arg Glu Lys Pro Ala Thr His His Ile Pro Gly Phe Glu Pro
            20                  25                  30

Glu Glu Ile Ser Gly Val Ala Asp Glu Ile Gly Asp Thr Asp Leu Pro
        35                  40                  45

Tyr Pro Pro Gln Arg Glu Ala Asn Ile Tyr Val
    50                  55                  60

<210> SEQ ID NO 102
<211> LENGTH: 60
<212> TYPE: PRT
<213> ORGANISM: Ornithorhynchus anatinus

<400> SEQUENCE: 102

Thr Lys Lys Asn Lys Pro Ala Gly Asp Leu Leu Ala Ala Phe Glu Leu
1               5                   10                  15

Ile Gln Arg Glu Lys Pro Ser Thr His His Ser Asp Pro Gly Phe Asp
            20                  25                  30

Pro Ala Val Arg Thr Ser Arg Pro Leu Gly Lys Ala Gly Asp Ser Asp
        35                  40                  45

Leu Pro Tyr Pro Pro Pro Gln Arg Glu Pro Asn Val
    50                  55                  60

<210> SEQ ID NO 103
<211> LENGTH: 2001
<212> TYPE: DNA
<213> ORGANISM: Equus caballus
```

<400> SEQUENCE: 103

```
cttccagatt tgctccctgt tactgcattt ctaaatttta cttgagattc attctttcct      60
tgtgagggca actatcagct atcatactca agaatgaagc aagtgctttc ccacatgtat     120
tatcttaatc ctctactttg aggcaagtat tttctccctt atttactgat aagtagaaac     180
acacacatac aaacacgtgc acaaggttca aggagagtaa ataatttgcc catgaaagat     240
ctaactcagt tccttattaa atctttaaat catgactcca ggctaatgta gtctacatcc     300
tacatctaca tatttgtata tgccttatat ttttttttt tttttgagga agattgtgag     360
ctgacgtcta ttgccaatct tcctcttttt gcttaaggaa gacctgagct aacatctgtg     420
ccatcttcct gtattttgta tgtgggccac tgccacagca ttacttgatg accggtgtgt     480
aggtctgtgc ctgggatccg aaccccaggc caccaaagcg gagcgtgtga acttaaccac     540
tacgccacca ggccggcccc tccttagata ttttaatgt tcatatagat tatgtggtat     600
tatcatctgt aggataaatg tatgccattc aaatgttttc tttggaactc tctccagtga     660
cactttagc tgtaaaattt tgtgaacaga ttttctgctg ccattctaa ataacacaaa      720
ataactatat attgtgtttc cttttatac tcactagaat aacttcttta tcgcctttta     780
tatataggtt gtattgctgg gaaaatacaa tgcacagggc ttaggttcag atcatgaatt     840
aatgctgaga tgtaccaaag gacaagaata cgtcaaagtc gtcatgcaaa atgggcgaat     900
gatgggagct gtcttaattg gtgaaaccga tttagaagaa acatttgaaa acttgatttt     960
aaaccagatg aatctttcag catacggaga agatctgctg satccagata ttgacataga    1020
agattatttt gactaaaaag gtcattccaa gaaccacata aagttccaaa taagacaaaa    1080
aagtcacaca tcaataaagt aaatgattgc actgatttaa tgatgaccac attgaagtta    1140
aaagtacaga agtgataatg atttcagtgg aaaaatatta aaaataaat tctaaagata    1200
aaatcaattc aagtaactta tttacagatt ttttcctaa cacaaaattg accaattatg    1260
taagaattct caagttattc atttctgtgt tttaaacgta cacacattca tttgtgattt    1320
tagctttgga gcacatttag ctaggctgtt atctgctcag cccacaactt ggtcttggtt    1380
agtagaccag agccattctt tgattggaaa acgtcaagaa gcttgtaatt ttattttact    1440
tagagatgcc gcaatatctt cttgctaata ttatttgtat tgataccttta ttccttttt    1500
gtttgaattc tacagctatt attttaacct gaaatcattc actttctgtc atgagcctgt    1560
gacttttcag tacaataaca ctaccatcaa aagagagtta tgtgaaaaga aaaaatatag    1620
ctaggtatat cacggcataa agagcttaag acagttatgt gaacttactc ttttaaggag    1680
tttacataaa aaagattta ttttcccttg tttcatactg taaatttata caattcatgc    1740
tctcaaattt tcaaaagatc tcaaattctc agtcctcaa ttctttagag ataagttctt     1800
aaaatatagc tccatttgta taaaacatta atgaaattgt cttaaaaatt aaactttgat    1860
taactacaaa aataatggtg taaacatgca taaactgttc tgttcttgga aaatttagat    1920
acactcatgc atcatcaatt tttcttttct tagcccctgt gttcttagcc tcagattgct    1980
gaagcatgtt tgcagacttc t                                              2001
```

<210> SEQ ID NO 104
<211> LENGTH: 1346
<212> TYPE: DNA
<213> ORGANISM: Equus caballus

<400> SEQUENCE: 104

```
aggtttccag agtattggaa gaatttgatg ttgaagaaca gccaaatacc atgttagaaa      60
```

```
atcgctttcc caacattaag gttatagaat ctggagtaaa gcaactgaag agtgaagaac      120
actgcatttt aacagaagat ggcaatcagc atgtatataa gaaactctgt ctgtgtgctg      180
gagctaaacc aaagttgata tgtgaaggaa atccttatgt attaggaatc cgtgacacag      240
acagtgctca ggaatttcag aaacagctta ctaaggctaa agaataatg atcataggca       300 atggtgggat cgcacttgaa ttagtgtatg aaattgaagg ctgtgaagtc atttgggtca      360
ttaaagacaa agctattggg aatacgttct tcgatgcagg agcagctgaa ttcttgactt      420
caaagctcat cgctgaaaaa ccagagggta aaattgcaca tagaagaacc agatatacaa      480
ctgaaggaag gaaaaaggaa gcacgaacca aggtgatgc tgctaatgta ggcagtgccc       540
tgggacctga ctggcatgaa ggcttgaatc ttaaaggaac aaaagagttt tctcataaga      600
ttcacattga aactatgtgt gaagtaaaga aaatctacct tcaggaagaa tttagaattt      660
ccaagaaaaa gtccttgact tttccaagag accataataa tcagtcagtt tcaactgata      720
aagagatatg gcctgtatat gtggaattga ccaatgaaaa gatatatggc tgcgatttca      780
ttgtcagtgc tacaggagtt acaccaaata tagaaccttt cctctgtggc aacaattttg      840
atctaggaga agatggtggc ctgaaagtga ataatcatat gcacacgtcc cttcctgaca      900
tctatgctgc aggtgacatc tgcactgcct cctgggaacc cagcccagtg tggcagcaga      960
tgaggctgtg gacgcaggct agacagatgg gatggtatgc agccaagtgc atggctgcag     1020
ctactttagg agactccatt gacatggatt tcagcttcga actgtttgct catgtaacaa     1080 aatttttaa ctataaggtt gtattgctgg gaaaatacaa tgcacagggc ttaggttcag      1140
atcatgaatt aatgctgaga tgtaccaaag gacaagaata cgtcaaagtc gtcatgcaaa     1200
atgggcgaat gatgggagct gtcttaattg gtgaaaccga tttagaagaa acatttgaaa     1260
acttgatttt aaaccagatg aatctttcag catatggaga agatctgctg gatccagata     1320
ttgacataga agattatttt gactaa                                          1346
```

<210> SEQ ID NO 105  
<211> LENGTH: 1346  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 105

```
aggtttccag agtattggaa gaatttgatg ttgaagaaca gccaaatacc atgttagaaa       60
atcgctttcc caacattaag gttatagaat ctggagtaaa gcaactgaag agtgaagaac      120
actgcatttt aacagaagat ggcaatcagc atgtatataa gaaactctgt ctgtgtgctg      180
gagctaaacc aaagttgata tgtgaaggaa atccttatgt attaggaatc cgtgacacag      240
acagtgctca ggaatttcag aaacagctta ctaaggctaa agaataatg atcataggca       300 atggtgggat cgcacttgaa ttagtgtatg aaattgaagg ctgtgaagtc atttgggtca      360
ttaaagacaa agctattggg aatacgttct tcgatgcagg agcagctgaa ttcttgactt      420
caaagctcat cgctgaaaaa ccagagggta aaattgcaca tagaagaacc agatatacaa      480
ctgaaggaag gaaaaaggaa gcacgaacca aggtgatgc tgctaatgta ggcagtgccc       540
tgggacctga ctggcatgaa ggcttgaatc ttaaaggaac aaaagagttt tctcataaga      600
ttcacattga aactatgtgt gaagtaaaga aaatctacct tcaggaagaa tttagaattt      660
ccaagaaaaa gtccttgact tttccaagag accataataa tcagtcagtt tcaactgata      720
```

```
aagagatatg gcctgtatat gtggaattga ccaatgaaaa gatatatggc tgcgatttca     780
ttgtcagtgc tacaggagtt acaccaaata tagaaccttt cctctgtggc aacaattttg     840
atctaggaga agatggtggc ctgaaagtga ataatcatat gcacacgtcc cttcctgaca     900
tctatgctgc aggtgacatc tgcactgcct cctgggaacc cagcccagtg tggcagcaga     960
tgaggctgtg gacgcaggct agacagatgg gatggtatgc agccaagtgc atggctgcag    1020
ctactttagg agactccatt gacatggatt tcagcttcga actgtttgct catgtaacaa    1080 aatttttttaa ctataaggtt gtattgctgg gaaaatacaa tgcacagggc ttaggttcag    1140
atcatgaatt aatgctgaga tgtaccaaag gacaagaata cgtcaaagtc gtcatgcaaa    1200
atgggcgaat gatgggagct gtcttaattg gtgaaaccga tttagaagaa acatttgaaa    1260
acttgatttt aaaccagatg aatctttcag catatggaga agatctgctg catccagata    1320
ttgacataga agattatttt gactaa                                          1346
```

<210> SEQ ID NO 106
<211> LENGTH: 269
<212> TYPE: DNA
<213> ORGANISM: Equus caballus

<400> SEQUENCE: 106

```
ttatatatag gttgtattgc tgggaaaata caatgcacag ggcttaggtt cagatcatga      60
attaatgctg agatgtacca aggacaaga atacgtcaaa gtcgtcatgc aaaatgggcg     120
aatgatggga gctgtcttaa ttggtgaaac cgatttagaa gaaacatttg aaaacttgat    180
tttaaaccag atgaatcttt cagcatacgg agaagatctg ctggatccag atattgacat    240
agaagattat tttgactaaa aaggtcatt                                       269
```

<210> SEQ ID NO 107
<211> LENGTH: 447
<212> TYPE: PRT
<213> ORGANISM: Equus caballus

<400> SEQUENCE: 107

```
Val Ser Arg Val Leu Glu Glu Phe Asp Val Glu Glu Gln Pro Asn Thr
 1               5                  10                  15

Met Leu Glu Asn Arg Phe Pro Asn Ile Lys Val Ile Glu Ser Gly Val
            20                  25                  30

Lys Gln Leu Lys Ser Glu Glu His Cys Ile Leu Thr Glu Asp Gly Asn
        35                  40                  45

Gln His Val Tyr Lys Lys Leu Cys Leu Cys Ala Gly Ala Lys Pro Lys
    50                  55                  60

Leu Ile Cys Glu Gly Asn Pro Tyr Val Leu Gly Ile Arg Asp Thr Asp
65                  70                  75                  80

Ser Ala Gln Glu Phe Gln Lys Gln Leu Thr Lys Ala Lys Arg Ile Met
                85                  90                  95

Ile Ile Gly Asn Gly Gly Ile Ala Leu Glu Leu Val Tyr Glu Ile Glu
            100                 105                 110

Gly Cys Glu Val Ile Trp Val Ile Lys Asp Lys Ala Ile Gly Asn Thr
        115                 120                 125

Phe Phe Asp Ala Gly Ala Ala Glu Phe Leu Thr Ser Lys Leu Ile Ala
    130                 135                 140

Glu Lys Pro Glu Gly Lys Ile Ala His Arg Arg Thr Arg Tyr Thr Thr
145                 150                 155                 160
```

```
Glu Gly Arg Lys Lys Glu Ala Arg Thr Lys Gly Asp Ala Ala Asn Val
                165                 170                 175
Gly Ser Ala Leu Gly Pro Asp Trp His Glu Gly Leu Asn Leu Lys Gly
            180                 185                 190
Thr Lys Glu Phe Ser His Lys Ile His Ile Glu Thr Met Cys Glu Val
                195                 200                 205
Lys Lys Ile Tyr Leu Gln Glu Glu Phe Arg Ile Ser Lys Lys Lys Ser
            210                 215                 220
Leu Thr Phe Pro Arg Asp His Asn Asn Gln Ser Val Ser Thr Asp Lys
225                 230                 235                 240
Glu Ile Trp Pro Val Tyr Val Glu Leu Thr Asn Glu Lys Ile Tyr Gly
                245                 250                 255
Cys Asp Phe Ile Val Ser Ala Thr Gly Val Thr Pro Asn Ile Glu Pro
                260                 265                 270
Phe Leu Cys Gly Asn Asn Phe Asp Leu Gly Glu Asp Gly Gly Leu Lys
            275                 280                 285
Val Asn Asn His Met His Thr Ser Leu Pro Asp Ile Tyr Ala Ala Gly
            290                 295                 300
Asp Ile Cys Thr Ala Ser Trp Glu Pro Ser Pro Val Trp Gln Gln Met
305                 310                 315                 320
Arg Leu Trp Thr Gln Ala Arg Gln Met Gly Trp Tyr Ala Ala Lys Cys
                325                 330                 335
Met Ala Ala Thr Leu Gly Asp Ser Ile Asp Met Asp Phe Ser Phe
                340                 345                 350
Glu Leu Phe Ala His Val Thr Lys Phe Phe Asn Tyr Lys Val Val Leu
            355                 360                 365
Leu Gly Lys Tyr Asn Ala Gln Gly Leu Gly Ser Asp His Glu Leu Met
            370                 375                 380
Leu Arg Cys Thr Lys Gly Gln Glu Tyr Val Lys Val Met Gln Asn
385                 390                 395                 400
Gly Arg Met Met Gly Ala Val Leu Ile Gly Glu Thr Asp Leu Glu Glu
                405                 410                 415
Thr Phe Glu Asn Leu Ile Leu Asn Gln Met Asn Leu Ser Ala Tyr Gly
                420                 425                 430
Glu Asp Leu Leu Asp Pro Asp Ile Asp Ile Glu Asp Tyr Phe Asp
            435                 440                 445

<210> SEQ ID NO 108
<211> LENGTH: 447
<212> TYPE: PRT
<213> ORGANISM: Equus caballus

<400> SEQUENCE: 108

Val Ser Arg Val Leu Glu Glu Phe Asp Val Glu Gln Pro Asn Thr
1               5                   10                  15
Met Leu Glu Asn Arg Phe Pro Asn Ile Lys Val Ile Glu Ser Gly Val
                20                  25                  30
Lys Gln Leu Lys Ser Glu Glu His Cys Ile Leu Thr Glu Asp Gly Asn
            35                  40                  45
Gln His Val Tyr Lys Lys Leu Cys Leu Cys Ala Gly Ala Lys Pro Lys
            50                  55                  60
Leu Ile Cys Glu Gly Asn Pro Tyr Val Leu Gly Ile Arg Asp Thr Asp
65                  70                  75                  80
Ser Ala Gln Glu Phe Gln Lys Gln Leu Thr Lys Ala Lys Arg Ile Met
                85                  90                  95
```

Ile Ile Gly Asn Gly Gly Ile Ala Leu Glu Leu Val Tyr Glu Ile Glu
            100                 105                 110

Gly Cys Glu Val Ile Trp Val Ile Lys Asp Lys Ala Ile Gly Asn Thr
        115                 120                 125

Phe Phe Asp Ala Gly Ala Ala Glu Phe Leu Thr Ser Lys Leu Ile Ala
    130                 135                 140

Glu Lys Pro Glu Gly Lys Ile Ala His Arg Arg Thr Arg Tyr Thr Thr
145                 150                 155                 160

Glu Gly Arg Lys Lys Glu Ala Arg Thr Lys Gly Asp Ala Ala Asn Val
                165                 170                 175

Gly Ser Ala Leu Gly Pro Asp Trp His Glu Gly Leu Asn Leu Lys Gly
            180                 185                 190

Thr Lys Glu Phe Ser His Lys Ile His Ile Glu Thr Met Cys Glu Val
        195                 200                 205

Lys Lys Ile Tyr Leu Gln Glu Glu Phe Arg Ile Ser Lys Lys Ser
    210                 215                 220

Leu Thr Phe Pro Arg Asp His Asn Asn Gln Ser Val Ser Thr Asp Lys
225                 230                 235                 240

Glu Ile Trp Pro Val Tyr Val Glu Leu Thr Asn Glu Lys Ile Tyr Gly
                245                 250                 255

Cys Asp Phe Ile Val Ser Ala Thr Gly Val Thr Pro Asn Ile Glu Pro
            260                 265                 270

Phe Leu Cys Gly Asn Asn Phe Asp Leu Gly Glu Asp Gly Gly Leu Lys
        275                 280                 285

Val Asn Asn His Met His Thr Ser Leu Pro Asp Ile Tyr Ala Ala Gly
    290                 295                 300

Asp Ile Cys Thr Ala Ser Trp Glu Pro Ser Pro Val Trp Gln Gln Met
305                 310                 315                 320

Arg Leu Trp Thr Gln Ala Arg Gln Met Gly Trp Tyr Ala Ala Lys Cys
                325                 330                 335

Met Ala Ala Thr Leu Gly Asp Ser Ile Asp Met Asp Phe Ser Phe
            340                 345                 350

Glu Leu Phe Ala His Val Thr Lys Phe Phe Asn Tyr Lys Val Val Leu
        355                 360                 365

Leu Gly Lys Tyr Asn Ala Gln Gly Leu Gly Ser Asp His Glu Leu Met
    370                 375                 380

Leu Arg Cys Thr Lys Gly Gln Glu Tyr Val Lys Val Val Met Gln Asn
385                 390                 395                 400

Gly Arg Met Met Gly Ala Val Leu Ile Gly Glu Thr Asp Leu Glu Glu
                405                 410                 415

Thr Phe Glu Asn Leu Ile Leu Asn Gln Met Asn Leu Ser Ala Tyr Gly
            420                 425                 430

Glu Asp Leu Leu His Pro Asp Ile Asp Ile Glu Asp Tyr Phe Asp
        435                 440                 445

<210> SEQ ID NO 109
<211> LENGTH: 249
<212> TYPE: DNA
<213> ORGANISM: Equus caballus

<400> SEQUENCE: 109
gttgtattgc tgggaaaata caatgcacag ggcttaggtt cagatcatga attaatgctg    60
agatgtacca aaggacaaga atacgtcaaa gtcgtcatgc aaaatgggcg aatgatggga   120

```
gctgtcttaa ttggtgaaac cgatttagaa gaaacatttg aaaacttgat tttaaaccag      180
atgaatcttt cagcatatgg agaagatctg ctggatccag atattgacat agaagattat      240
tttgactaa                                                              249

<210> SEQ ID NO 110
<211> LENGTH: 249
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
gttgtattgc tgggaaaata caatgcacag ggcttaggtt cagatcatga attaatgctg       60
agatgtacca aaggacaaga atacgtcaaa gtcgtcatgc aaaatgggcg aatgatggga      120
gctgtcttaa ttggtgaaac cgatttagaa gaaacatttg aaaacttgat tttaaaccag      180
atgaatcttt cagcatatgg agaagatctg ctgcatccag atattgacat agaagattat      240
tttgactaa                                                              249

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cagattttct gctggccatt                                                   20

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
tggtcatcat taaatcagtg caa                                               23

<210> SEQ ID NO 113
<211> LENGTH: 1012
<212> TYPE: DNA
<213> ORGANISM: Homo sapiens

<400> SEQUENCE: 113
tgaaattgaa ggctgtgaag tgatttgggc cattaaagat aaagctatag ggaatacttt       60
cttcgatgca ggagcagctg aattcttgac ttcaaagctc attgctgaaa aatcagaggc      120
taaaattgca cataaaagaa ccagatatac aactgaagga aggaaaaagg aagctagaag      180
caaatctaaa gcagataatg taggaagtgc attgggacca gattggcatg aaggcttgaa      240
tcttaaagga acaaaagagt tttctcataa gattcaccct gaaactatgt gtgaagtaaa      300
gaaaatctac cttcaggatg agtttagaat tttgaagaaa aagtccttca cttttccaag      360
agaccataag tcagttacag ctgatacaga gatgtggcct gtctatgtgg aattgaccaa      420
tgaaaagata tatggctgcg atttcattgt cagtgctaca ggagttacac caaatgtaga      480
accttttctc catggtaaca gttttgatct aggagaagat ggtggcctga agtggatga       540
```

```
tcatatgcac acatcccttc ctgatatcta tgctgccggt gacatctgta ctacatcctg    600
gcagctgagc ccagtctggc agcagatgag gctgtggacc caggctagac agatgggatg    660
gtatgcagca aagtgcatgg ctgcagcgag ttcaggagac tctattgaca tggatttcag    720
ctttgaactg tttgctcatg tgacaaaatt ttttaactat aaggttgtac tgctgggaaa    780
atacaatgca cagggcttag gttcagatca tgaattaatg ctgagatgta ccaaaggacg    840
agaatacatc aaagtcgtca tgcaaaatgg acgaatgatg ggagctgtct taattggtga    900
aaccgattta gaagaaacat tgaaaacct aatcttaaac caaatgaatc tttcatcata    960
tggagaagat ctgctagatc caaatattga tatagaagat tattttgact aa            1012
```

<210> SEQ ID NO 114
<211> LENGTH: 445
<212> TYPE: PRT
<213> ORGANISM: Homo sapiens

<400> SEQUENCE: 114

```
Ile Ser Lys Ile Leu Glu Glu Phe Asp Val Glu Glu Gln Ser Ser Thr
1               5                   10                  15

Met Leu Gly Lys Arg Phe Pro Asn Ile Lys Val Ile Glu Ser Gly Val
            20                  25                  30

Lys Gln Leu Lys Ser Glu Glu His Cys Ile Val Thr Glu Asp Gly Asn
        35                  40                  45

Gln His Val Tyr Lys Lys Leu Cys Leu Cys Ala Gly Ala Lys Pro Lys
    50                  55                  60

Leu Ile Cys Glu Gly Asn Pro Tyr Val Leu Gly Ile Arg Asp Thr Asp
65                  70                  75                  80

Ser Ala Gln Glu Phe Gln Lys Gln Leu Thr Lys Ala Lys Arg Ile Met
                85                  90                  95

Ile Ile Gly Asn Gly Gly Ile Ala Leu Glu Leu Val Tyr Glu Ile Glu
            100                 105                 110

Gly Cys Glu Val Ile Trp Ala Ile Lys Asp Lys Ala Ile Gly Asn Thr
        115                 120                 125

Phe Phe Asp Ala Gly Ala Ala Glu Phe Leu Thr Ser Lys Leu Ile Ala
    130                 135                 140

Glu Lys Ser Glu Ala Lys Ile Ala His Lys Arg Thr Arg Tyr Thr Thr
145                 150                 155                 160

Glu Gly Arg Lys Lys Glu Ala Arg Ser Lys Ser Lys Ala Asp Asn Val
                165                 170                 175

Gly Ser Ala Leu Gly Pro Asp Trp His Glu Gly Leu Asn Leu Lys Gly
            180                 185                 190

Thr Lys Glu Phe Ser His Lys Ile His Leu Glu Thr Met Cys Glu Val
        195                 200                 205

Lys Lys Ile Tyr Leu Gln Asp Glu Phe Arg Ile Leu Lys Lys Lys Ser
    210                 215                 220

Phe Thr Phe Pro Arg Asp His Lys Ser Val Thr Ala Asp Thr Glu Met
225                 230                 235                 240

Trp Pro Val Tyr Val Glu Leu Thr Asn Glu Lys Ile Tyr Gly Cys Asp
                245                 250                 255

Phe Ile Val Ser Ala Thr Gly Val Thr Pro Asn Val Glu Pro Phe Leu
            260                 265                 270

His Gly Asn Ser Phe Asp Leu Gly Glu Asp Gly Gly Leu Lys Val Asp
        275                 280                 285

Asp His Met His Thr Ser Leu Pro Asp Ile Tyr Ala Ala Gly Asp Ile
```

```
                290                 295                 300
Cys Thr Thr Ser Trp Gln Leu Ser Pro Val Trp Gln Gln Met Arg Leu
305                 310                 315                 320

Trp Thr Gln Ala Arg Gln Met Gly Trp Tyr Ala Ala Lys Cys Met Ala
                325                 330                 335

Ala Ala Ser Ser Gly Asp Ser Ile Asp Met Asp Phe Ser Phe Glu Leu
                340                 345                 350

Phe Ala His Val Thr Lys Phe Phe Asn Tyr Lys Val Val Leu Leu Gly
                355                 360                 365

Lys Tyr Asn Ala Gln Gly Leu Gly Ser Asp His Glu Leu Met Leu Arg
                370                 375                 380

Cys Thr Lys Gly Arg Glu Tyr Ile Lys Val Val Met Gln Asn Gly Arg
385                 390                 395                 400

Met Met Gly Ala Val Leu Ile Gly Glu Thr Asp Leu Glu Glu Thr Phe
                405                 410                 415

Glu Asn Leu Ile Leu Asn Gln Met Asn Leu Ser Ser Tyr Gly Glu Asp
                420                 425                 430

Leu Leu Asp Pro Asn Ile Asp Ile Glu Asp Tyr Phe Asp
                435                 440                 445

<210> SEQ ID NO 115
<211> LENGTH: 82
<212> TYPE: PRT
<213> ORGANISM: Homo sapiens

<400> SEQUENCE: 115

Val Val Leu Leu Gly Lys Tyr Asn Ala Gln Gly Leu Gly Ser Asp His
1               5                   10                  15

Glu Leu Met Leu Arg Cys Thr Lys Gly Arg Glu Tyr Ile Lys Val Val
                20                  25                  30

Met Gln Asn Gly Arg Met Met Gly Ala Val Leu Ile Gly Glu Thr Asp
                35                  40                  45

Leu Glu Glu Thr Phe Glu Asn Leu Ile Leu Asn Gln Met Asn Leu Ser
            50                  55                  60

Ser Tyr Gly Glu Asp Leu Leu Asp Pro Asn Ile Asp Ile Glu Asp Tyr
65                  70                  75                  80

Phe Asp

<210> SEQ ID NO 116
<211> LENGTH: 82
<212> TYPE: PRT
<213> ORGANISM: Equus caballus

<400> SEQUENCE: 116

Val Val Leu Leu Gly Lys Tyr Asn Ala Gln Gly Leu Gly Ser Asp His
1               5                   10                  15

Glu Leu Met Leu Arg Cys Thr Lys Gly Gln Glu Tyr Val Lys Val Val
                20                  25                  30

Met Gln Asn Gly Arg Met Met Gly Ala Val Leu Ile Gly Glu Thr Asp
                35                  40                  45

Leu Glu Glu Thr Phe Glu Asn Leu Ile Leu Asn Gln Met Asn Leu Ser
            50                  55                  60

Ala Tyr Gly Glu Asp Leu Leu Asp Pro Asp Ile Asp Ile Glu Asp Tyr
65                  70                  75                  80

Phe Asp
```

<210> SEQ ID NO 117
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Val Val Leu Leu Gly Lys Tyr Asn Ala Gln Gly Leu Gly Ser Asp His
1               5                   10                  15

Glu Leu Met Leu Arg Cys Thr Lys Gly Gln Glu Tyr Val Lys Val Val
            20                  25                  30

Met Gln Asn Gly Arg Met Met Gly Ala Val Leu Ile Gly Glu Thr Asp
        35                  40                  45

Leu Glu Glu Thr Phe Glu Asn Leu Ile Leu Asn Gln Met Asn Leu Ser
    50                  55                  60

Ala Tyr Gly Glu Asp Leu Leu His Pro Asp Ile Asp Ile Glu Asp Tyr
65                  70                  75                  80

Phe Asp

<210> SEQ ID NO 118
<211> LENGTH: 60
<212> TYPE: PRT
<213> ORGANISM: Unknown
<220> FEATURE:
<223> OTHER INFORMATION: Description of Unknown:
      PYROXD1 sequence

<400> SEQUENCE: 118

Thr Lys Gly Gln Glu Tyr Ile Lys Val Val Met Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Gln Met Asn Leu Ser Ser Tyr Gly Glu Asp Leu
        35                  40                  45

Leu Asp Pro Asn Ile Asp Ile Glu Asp Tyr Phe Asp
    50                  55                  60

<210> SEQ ID NO 119
<211> LENGTH: 60
<212> TYPE: PRT
<213> ORGANISM: Unknown
<220> FEATURE:
<223> OTHER INFORMATION: Description of Unknown:
      PYROXD1 sequence

<400> SEQUENCE: 119

Thr Lys Gly Gln Glu Tyr Val Lys Val Val Met Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Gln Met Asn Leu Ser Ser Tyr Gly Glu Asp Leu
        35                  40                  45

Leu Asp Pro Asn Ile Asp Ile Glu Asp Tyr Phe Asp
    50                  55                  60

<210> SEQ ID NO 120
<211> LENGTH: 60
<212> TYPE: PRT
<213> ORGANISM: Unknown

<220> FEATURE:
<223> OTHER INFORMATION: Description of Unknown:
      PYROXD1 sequence

<400> SEQUENCE: 120

Thr Arg Gly Gln Glu Tyr Val Lys Val Val Met Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Gln Met Asp Leu Ser Ser Tyr Gly Glu Asp Leu
        35                  40                  45

Leu Asp Pro Asn Ile Asp Ile Glu Asp Tyr Phe Asp
    50                  55                  60

<210> SEQ ID NO 121
<211> LENGTH: 60
<212> TYPE: PRT
<213> ORGANISM: Unknown
<220> FEATURE:
<223> OTHER INFORMATION: Description of Unknown:
      PYROXD1 sequence

<400> SEQUENCE: 121

Thr Lys Gly Gln Glu Tyr Val Lys Val Val Met Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Gln Met Asp Leu Ser Ser Tyr Gly Glu Asp Leu
        35                  40                  45

Leu Asp Pro Asn Ile Asp Ile Glu Asp Tyr Phe Asp
    50                  55                  60

<210> SEQ ID NO 122
<211> LENGTH: 60
<212> TYPE: PRT
<213> ORGANISM: Unknown
<220> FEATURE:
<223> OTHER INFORMATION: Description of Unknown:
      PYROXD1 sequence

<400> SEQUENCE: 122

Thr Lys Gly Gln Glu Tyr Ile Lys Val Val Met Gln Asn Gly Arg Met
1               5                   10                  15

Met Gly Ala Val Leu Ile Gly Glu Thr Asn Leu Glu Glu Thr Phe Glu
            20                  25                  30

Asn Leu Ile Leu Asn Gln Met Asn Leu Ser Ser Tyr Gly Glu Asp Leu
        35                  40                  45

Leu Asp Pro Asn Ile Asp Ile Glu Asp Tyr Phe Asp
    50                  55                  60

<210> SEQ ID NO 123
<211> LENGTH: 60
<212> TYPE: PRT
<213> ORGANISM: Unknown
<220> FEATURE:
<223> OTHER INFORMATION: Description of Unknown:
      PYROXD1 sequence

<400> SEQUENCE: 123

Thr Lys Gly Gln Glu Tyr Val Lys Val Val Met Gln Asn Gly Arg Met
1               5                   10                  15

Met Gly Ala Val Leu Ile Gly Glu Thr Asp Leu Glu Glu Thr Phe Glu

-continued

```
                 20                  25                  30
Asn Leu Ile Leu Asn Gln Met Asn Leu Ser Ala Tyr Gly Glu Asp Leu
         35                  40                  45
Leu Asp Pro Asp Ile Asp Ile Glu Asp Tyr Phe Asp
     50                  55                  60

<210> SEQ ID NO 124
<211> LENGTH: 60
<212> TYPE: PRT
<213> ORGANISM: Unknown
<220> FEATURE:
<223> OTHER INFORMATION: Description of Unknown:
      PYROXD1 sequence

<400> SEQUENCE: 124

Thr Lys Gly Gln Glu Tyr Ile Lys Ala Val Leu Gln Asn Gly Arg Met
1               5                   10                  15
Met Gly Ala Val Leu Ile Gly Glu Thr Asp Leu Glu Glu Thr Phe Glu
                 20                  25                  30
Asn Leu Ile Leu Asn Gln Met Asn Leu Ser Ala Tyr Gly Glu Asp Leu
         35                  40                  45
Leu Asp Pro Asn Ile Asp Ile Glu Asp Tyr Phe Asp
     50                  55                  60

<210> SEQ ID NO 125
<211> LENGTH: 60
<212> TYPE: PRT
<213> ORGANISM: Unknown
<220> FEATURE:
<223> OTHER INFORMATION: Description of Unknown:
      PYROXD1 sequence

<400> SEQUENCE: 125

Thr Lys Gly Gln Glu Tyr Val Lys Val Val Met Gln Asn Gly Arg Met
1               5                   10                  15
Met Gly Ala Val Leu Ile Gly Glu Thr Asp Leu Glu Glu Thr Phe Glu
                 20                  25                  30
Asn Leu Ile Leu Asn Gln Met Asp Leu Ser Ser Tyr Gly Glu Asp Leu
         35                  40                  45
Leu Asp Pro Asn Ile Asp Leu Glu Asp Tyr Phe Asp
     50                  55                  60

<210> SEQ ID NO 126
<211> LENGTH: 60
<212> TYPE: PRT
<213> ORGANISM: Homo sapiens

<400> SEQUENCE: 126

Thr Lys Gly Arg Glu Tyr Ile Lys Val Val Met Gln Asn Gly Arg Met
1               5                   10                  15
Met Gly Ala Val Leu Ile Gly Glu Thr Asp Leu Glu Glu Thr Phe Glu
                 20                  25                  30
Asn Leu Ile Leu Asn Gln Met Asn Leu Ser Ser Tyr Gly Glu Asp Leu
         35                  40                  45
Leu Asp Pro Asn Ile Asp Ile Glu Asp Tyr Phe Asp
     50                  55                  60

<210> SEQ ID NO 127
<211> LENGTH: 60
<212> TYPE: PRT
<213> ORGANISM: Otolemur garnettii
```

<400> SEQUENCE: 127

Thr Lys Gly Gln Glu Tyr Ile Lys Val Val Met Gln Asn Gly Arg Met
1               5                   10                  15

Met Gly Ala Val Leu Ile Gly Glu Thr Asp Leu Glu Glu Thr Phe Glu
                20                  25                  30

Asn Leu Ile Leu Asn Gln Met Asn Leu Ser Gln Tyr Gly Glu Asp Leu
            35                  40                  45

Leu Asp Pro Asn Ile Asp Ile Glu Asp Tyr Phe Asp
        50                  55                  60

<210> SEQ ID NO 128
<211> LENGTH: 60
<212> TYPE: PRT
<213> ORGANISM: Rattus norvegicus

<400> SEQUENCE: 128

Thr Arg Gly Gln Glu Tyr Ile Lys Val Val Met His Asn Gly Arg Met
1               5                   10                  15

Met Gly Ala Val Leu Ile Gly Glu Thr Asp Leu Glu Glu Thr Phe Glu
                20                  25                  30

Asn Leu Ile Leu Asn Gln Met Asp Leu Ser Ser Tyr Gly Glu Asp Leu
            35                  40                  45

Leu Asn Pro Asp Ile Asp Ile Glu Asp Tyr Phe Asp
        50                  55                  60

<210> SEQ ID NO 129
<211> LENGTH: 60
<212> TYPE: PRT
<213> ORGANISM: Cricetulus griseus

<400> SEQUENCE: 129

Thr Arg Gly Gln Glu Tyr Ile Lys Val Val Met Gln Asn Gly Arg Met
1               5                   10                  15

Met Gly Ala Val Leu Ile Gly Glu Thr Asp Leu Glu Glu Thr Phe Glu
                20                  25                  30

Asn Leu Ile Leu Asn Gln Met Asp Leu Ser Ser Tyr Gly Glu Asp Leu
            35                  40                  45

Leu Asp Pro Asn Ile Asp Ile Glu Asp Tyr Phe Asp
        50                  55                  60

<210> SEQ ID NO 130
<211> LENGTH: 60
<212> TYPE: PRT
<213> ORGANISM: Microtus ochrogaster

<400> SEQUENCE: 130

Thr Arg Gly Gln Glu Tyr Val Lys Val Val Met Gln Asn Gly Arg Met
1               5                   10                  15

Met Gly Ala Val Leu Ile Gly Thr Asp Leu Glu Glu Thr Phe Glu
                20                  25                  30

Asn Leu Ile Leu Asn Gln Met Asp Leu Ser Ser Tyr Gly Glu Asp Leu
            35                  40                  45

Leu Asp Pro Asp Ile Asp Ile Glu Asp Tyr Phe Asp
        50                  55                  60

<210> SEQ ID NO 131
<211> LENGTH: 60
<212> TYPE: PRT

<213> ORGANISM: Chinchilla lanigera

<400> SEQUENCE: 131

Thr Lys Gly Gln Glu Tyr Val Lys Val Val Met Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Gln Met Asp Leu Ser Pro Tyr Gly Glu Glu Leu
        35                  40                  45

Leu Asp Pro Asn Ile Asp Ile Glu Asp Tyr Phe Asp
    50                  55                  60

<210> SEQ ID NO 132
<211> LENGTH: 60
<212> TYPE: PRT
<213> ORGANISM: Castor canadensis

<400> SEQUENCE: 132

Thr Lys Gly Gln Glu Tyr Ile Lys Val Ile Met Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Gln Met Asp Leu Ser Ser Tyr Gly Glu Asp Leu
        35                  40                  45

Leu Asp Pro Asn Ile Asp Ile Glu Asp Tyr Phe Asp
    50                  55                  60

<210> SEQ ID NO 133
<211> LENGTH: 60
<212> TYPE: PRT
<213> ORGANISM: Mustela putorius furo

<400> SEQUENCE: 133

Thr Lys Gly Gln Glu Tyr Val Lys Val Val Met Gln His Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Gln Thr Asp Leu Ser Ser Tyr Gly Glu Asp Leu
        35                  40                  45

Leu Asp Pro Asn Ile Asp Leu Glu Asp Tyr Phe Asp
    50                  55                  60

<210> SEQ ID NO 134
<211> LENGTH: 60
<212> TYPE: PRT
<213> ORGANISM: Fukomys damarensis

<400> SEQUENCE: 134

Thr Lys Gly Gln Glu Tyr Ile Lys Val Val Met Gln Asn Gly His Met
1               5                   10                  15

Met Gly Ala Val Leu Ile Gly Glu Thr Asp Leu Glu Glu Thr Phe Glu
            20                  25                  30

Asn Leu Ile Leu Asn Gln Met Asp Leu Ser Pro Tyr Gly Glu Asp Leu
        35                  40                  45

Leu Asp Pro Asn Ile Asp Ile Glu Asp Tyr Phe Asp
    50                  55                  60

<210> SEQ ID NO 135
<211> LENGTH: 60

```
<212> TYPE: PRT
<213> ORGANISM: Vicugna pacos

<400> SEQUENCE: 135

Thr Lys Gly Gln Glu Tyr Val Lys Ala Val Leu Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Gln Met Asn Leu Ser Ala Tyr Gly Glu Asp Leu
        35                  40                  45

Leu Asp Pro Asn Ile Asp Ile Glu Asp Tyr Phe Asp
    50                  55                  60

<210> SEQ ID NO 136
<211> LENGTH: 60
<212> TYPE: PRT
<213> ORGANISM: Ailuropoda melanoleuca

<400> SEQUENCE: 136

Thr Lys Gly Gln Glu Tyr Val Lys Val Val Met Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Gln Thr Asp Leu Ser Ser Tyr Gly Glu Asp Leu
        35                  40                  45

Leu Asp Pro Asn Ile Asp Leu Glu Asp Tyr Phe Asp
    50                  55                  60

<210> SEQ ID NO 137
<211> LENGTH: 60
<212> TYPE: PRT
<213> ORGANISM: Phascolarctos cinereus

<400> SEQUENCE: 137

Thr Lys Gly Gln Glu Tyr Val Lys Val Val Met Gln Asn Gly Arg Met
1               5                   10                  15

Met Gly Ala Ile Leu Ile Gly Glu Thr Asp Leu Glu Glu Thr Phe Glu
            20                  25                  30

Asn Leu Ile Leu Asn Gln Met Asn Leu Ser Ala Tyr Gly Glu Asp Leu
        35                  40                  45

Leu Asp Pro Asp Ile Asp Ile Glu Asp Tyr Phe Asp
    50                  55                  60

<210> SEQ ID NO 138
<211> LENGTH: 60
<212> TYPE: PRT
<213> ORGANISM: Sarcophilus harrisii

<400> SEQUENCE: 138

Thr Lys Gly Gln Glu Tyr Val Lys Val Val Met Gln Asn Gly Arg Met
1               5                   10                  15

Met Gly Ala Ile Leu Ile Gly Glu Thr Asp Leu Glu Glu Thr Phe Glu
            20                  25                  30

Asn Leu Ile Leu Asn Gln Met Asn Leu Ser Ala Tyr Gly Glu Asp Leu
        35                  40                  45

Leu Asp Pro Asn Ile Asp Ile Glu Asp Tyr Phe Asp
    50                  55                  60

<210> SEQ ID NO 139
```

```
<211> LENGTH: 60
<212> TYPE: PRT
<213> ORGANISM: Monodelphis domestica

<400> SEQUENCE: 139

Thr Lys Gly Gln Glu Tyr Val Lys Val Val Met Gln Asn Gly Arg Met
1               5                   10                  15

Met Gly Ala Ile Leu Ile Gly Glu Thr Asn Leu Glu Glu Thr Phe Glu
            20                  25                  30

Asn Leu Ile Leu Asn Gln Met Asn Leu Ser Ala Tyr Gly Glu Asp Leu
        35                  40                  45

Leu Asp Pro Ser Ile Asp Ile Glu Asp Tyr Phe Asp
    50                  55                  60

<210> SEQ ID NO 140
<211> LENGTH: 60
<212> TYPE: PRT
<213> ORGANISM: Unknown
<220> FEATURE:
<223> OTHER INFORMATION: Description of Unknown:
      PYROXD1 sequence

<400> SEQUENCE: 140

Thr Lys Gly Gln Glu Tyr Val Lys Val Val Met Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Gln Met Asp Leu Ser Ala Tyr Gly Glu Asp Leu
        35                  40                  45

Leu Asn Pro Asp Ile Asp Ile Glu Asp Tyr Phe Asp
    50                  55                  60

<210> SEQ ID NO 141
<211> LENGTH: 60
<212> TYPE: PRT
<213> ORGANISM: Unknown
<220> FEATURE:
<223> OTHER INFORMATION: Description of Unknown:
      PYROXD1 sequence

<400> SEQUENCE: 141

Thr Lys Gly His Glu Tyr Val Lys Val Val Met Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Gln Met Asp Leu Ser Ala Tyr Gly Glu Asp Leu
        35                  40                  45

Leu Asn Pro Asp Ile Asp Ile Glu Asp Tyr Phe Asp
    50                  55                  60

<210> SEQ ID NO 142
<211> LENGTH: 60
<212> TYPE: PRT
<213> ORGANISM: Merops nubicus

<400> SEQUENCE: 142

Thr Lys Gly Gln Glu Tyr Val Lys Val Val Met Gln Asn Gly Arg Met
1               5                   10                  15

Val Gly Ala Val Leu Ile Gly Glu Thr Asp Leu Glu Glu Thr Phe Glu
            20                  25                  30

Asn Leu Ile Leu Asn Gln Met Asp Leu Ser Ala Tyr Gly Glu Asp Leu
```

35                  40                  45

Leu Asn Pro Asp Ile Asp Ile Glu Asp Tyr Phe Asp
        50                  55                  60

<210> SEQ ID NO 143
<211> LENGTH: 60
<212> TYPE: PRT
<213> ORGANISM: Apteryx australis mantelli

<400> SEQUENCE: 143

Thr Lys Gly Gln Glu Tyr Val Lys Val Val Met Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Gln Met Asp Leu Ser Ala Tyr Gly Glu Asp Leu
        35                  40                  45

Leu Asn Pro Asn Ile Asp Ile Glu Asp Tyr Phe Asp
        50                  55                  60

<210> SEQ ID NO 144
<211> LENGTH: 60
<212> TYPE: PRT
<213> ORGANISM: Corvus brachyrhynchos

<400> SEQUENCE: 144

Thr Lys Gly His Glu Tyr Val Lys Val Val Met Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Arg Met Asp Leu Ser Ala Tyr Gly Glu Asp Leu
        35                  40                  45

Leu Asn Pro Asp Ile Asp Ile Glu Asp Tyr Phe Asp
        50                  55                  60

<210> SEQ ID NO 145
<211> LENGTH: 60
<212> TYPE: PRT
<213> ORGANISM: Corvus cornix cornix

<400> SEQUENCE: 145

Thr Lys Gly His Glu Tyr Val Lys Val Val Met Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Arg Met Asp Leu Ser Ala Tyr Gly Glu Asp Leu
        35                  40                  45

Leu Asn Pro Asp Ile Asp Ile Glu Asp Tyr Phe Asp
        50                  55                  60

<210> SEQ ID NO 146
<211> LENGTH: 60
<212> TYPE: PRT
<213> ORGANISM: Serinus canaria

<400> SEQUENCE: 146

Thr Lys Gly His Glu Tyr Ile Lys Val Val Met Gln Asn Gly Arg Met
1               5                   10                  15

Met Gly Ala Val Leu Ile Gly Glu Thr Asp Leu Glu Glu Thr Phe Glu
            20                  25                  30

```
Asn Leu Ile Leu Asn Gln Met Asp Leu Ser Ala Tyr Gly Glu Asp Leu
             35                  40                  45

Leu Asn Pro Asp Ile Asp Ile Glu Asp Tyr Phe Asp
     50                  55                  60

<210> SEQ ID NO 147
<211> LENGTH: 60
<212> TYPE: PRT
<213> ORGANISM: Sturnus vulgaris

<400> SEQUENCE: 147

Thr Lys Gly His Glu Tyr Val Lys Val Val Met Gln Asn Gly Arg Met
1               5                   10                  15

Met Gly Ala Val Leu Ile Gly Glu Thr Asp Leu Glu Glu Thr Phe Glu
            20                  25                  30

Asn Leu Ile Leu Asn Gln Ile Asp Leu Ser Ala Tyr Gly Glu Asp Leu
             35                  40                  45

Leu Asn Pro Asp Ile Asp Leu Glu Asp Tyr Phe Asp
     50                  55                  60

<210> SEQ ID NO 148
<211> LENGTH: 60
<212> TYPE: PRT
<213> ORGANISM: Lepidothrix coronata

<400> SEQUENCE: 148

Thr Lys Gly Gln Glu Tyr Val Lys Ala Val Met Gln Asn Gly Arg Met
1               5                   10                  15

Val Gly Ala Val Leu Ile Gly Glu Thr Asp Leu Glu Glu Thr Phe Glu
            20                  25                  30

Asn Leu Ile Leu Asn Gln Met Asp Leu Ser Ala Tyr Gly Glu Asp Leu
             35                  40                  45

Leu Asn Pro Asp Ile Asp Ile Glu Asp Tyr Phe Asp
     50                  55                  60

<210> SEQ ID NO 149
<211> LENGTH: 60
<212> TYPE: PRT
<213> ORGANISM: Amazona aestiva

<400> SEQUENCE: 149

Thr Lys Gly Gln Glu Tyr Val Lys Val Val Met Gln Ser Gly Arg Met
1               5                   10                  15

Val Gly Ala Val Leu Ile Gly Asp Thr Asp Leu Glu Glu Thr Phe Glu
            20                  25                  30

Asn Leu Ile Leu Asn Gln Met Asp Leu Ser Ala Tyr Gly Glu Asp Leu
             35                  40                  45

Leu Asn Pro Asp Val Asp Ile Glu Asp Tyr Phe Asp
     50                  55                  60

<210> SEQ ID NO 150
<211> LENGTH: 60
<212> TYPE: PRT
<213> ORGANISM: Gekko japonicus

<400> SEQUENCE: 150

Thr Lys Gly Gln Glu Tyr Val Lys Val Val Met Gln Asn Gly Arg Met
1               5                   10                  15

Met Gly Ala Val Leu Ile Gly Glu Thr Asp Leu Glu Glu Thr Phe Glu
            20                  25                  30
```

Asn Leu Ile Leu Asn Gln Met Asp Leu Ser Arg Tyr Gly Glu Asp Leu
            35                  40                  45

Leu Asp Pro Asn Ile Asp Ile Glu Asp Tyr Phe Asp
    50                  55                  60

<210> SEQ ID NO 151
<211> LENGTH: 60
<212> TYPE: PRT
<213> ORGANISM: Anolis carolinensis

<400> SEQUENCE: 151

Thr Lys Gly Leu Glu Tyr Val Lys Val Val Met Gln Asn Gly Arg Met
1               5                   10                  15

Leu Gly Ala Val Leu Ile Gly Glu Thr Asp Leu Glu Glu Thr Phe Glu
            20                  25                  30

Asn Leu Ile Leu Asn Gln Met Asp Leu Ser Arg Tyr Gly Glu Asp Leu
            35                  40                  45

Leu Asp Pro Asn Ile Asp Ile Glu Asp Tyr Phe Asp
    50                  55                  60

<210> SEQ ID NO 152
<211> LENGTH: 60
<212> TYPE: PRT
<213> ORGANISM: Python bivittatus

<400> SEQUENCE: 152

Thr Lys Gly Gln Glu Tyr Val Lys Val Val Met Gln Asn Gly Arg Met
1               5                   10                  15

Leu Gly Ala Val Leu Ile Gly Glu Thr Asp Leu Glu Glu Thr Phe Glu
            20                  25                  30

Asn Leu Ile Leu Asn Gln Met Asp Leu Ser Arg Tyr Gly Glu Asp Leu
            35                  40                  45

Leu Asp Pro Asn Ile Asp Ile Glu Asp Tyr Phe Asp
    50                  55                  60

<210> SEQ ID NO 153
<211> LENGTH: 60
<212> TYPE: PRT
<213> ORGANISM: Pogona vitticeps

<400> SEQUENCE: 153

Thr Lys Gly Gln Glu Tyr Ile Lys Val Val Met Gln Asn Gly Arg Met
1               5                   10                  15

Leu Gly Ala Val Leu Ile Gly Glu Thr Asp Leu Glu Glu Thr Phe Glu
            20                  25                  30

Asn Leu Ile Leu Asn Gln Met Asp Leu Ser Arg Tyr Gly Glu Asn Leu
            35                  40                  45

Leu Asp Pro Asn Ile Asp Ile Glu Asp Tyr Phe Asp
    50                  55                  60

<210> SEQ ID NO 154
<211> LENGTH: 60
<212> TYPE: PRT
<213> ORGANISM: Protobothrops mucrosquamatus

<400> SEQUENCE: 154

Thr Lys Gly Gln Glu Tyr Ile Lys Val Val Met Gln Asn Gly Arg Met
1               5                   10                  15

Leu Gly Ala Val Leu Ile Gly Glu Thr Asp Leu Glu Glu Thr Phe Glu

```
                    20                  25                  30

Asn Leu Ile Leu Asn Gln Met Asp Leu Ser Arg Tyr Gly Glu Asp Leu
            35                  40                  45

Leu Asp Pro Asn Ile Asp Ile Glu Asp Tyr Phe Asp
        50                  55                  60

<210> SEQ ID NO 155
<211> LENGTH: 60
<212> TYPE: PRT
<213> ORGANISM: Ophiophagus hannah

<400> SEQUENCE: 155

Thr Lys Gly Gln Glu Tyr Ile Lys Val Val Met Gln His Gly Arg Met
1               5                  10                  15

Leu Gly Ala Val Leu Ile Gly Glu Thr Asp Leu Glu Glu Thr Phe Glu
            20                  25                  30

Asn Leu Ile Leu Asn Gln Met Asp Leu Ser Arg Tyr Gly Glu Asp Leu
            35                  40                  45

Leu Asp Pro Asn Ile Asp Ile Glu Asp Tyr Phe Asp
        50                  55                  60

<210> SEQ ID NO 156
<211> LENGTH: 60
<212> TYPE: PRT
<213> ORGANISM: Thamnophis sirtalis

<400> SEQUENCE: 156

Thr Lys Gly Gln Glu Tyr Ile Lys Val Val Met Gln Asn Gly Arg Met
1               5                  10                  15

Leu Gly Ala Val Leu Ile Gly Glu Thr Asp Leu Glu Glu Thr Phe Glu
            20                  25                  30

Asn Ile Leu Asn Gln Met Asp Leu Ser Arg Tyr Gly Lys Asp Leu
            35                  40                  45

Leu Asp Pro Asn Ile Asp Ile Glu Asp Tyr Phe Asp
        50                  55                  60

<210> SEQ ID NO 157
<211> LENGTH: 60
<212> TYPE: PRT
<213> ORGANISM: Latimeria chalumnae

<400> SEQUENCE: 157

Thr Lys Gly Gln Glu Tyr Val Lys Val Leu Gln Asn Gly Arg Met
1               5                  10                  15

Met Gly Ala Ile Leu Ile Gly Glu Thr Asp Leu Glu Glu Thr Phe Glu
            20                  25                  30

Asn Leu Met Leu Asn Gln Met Asp Leu Ser Ala Tyr Gly Glu Glu Leu
            35                  40                  45

Leu Asn Pro Asp Ile Asp Ile Glu Asp Tyr Phe Asp
        50                  55                  60

<210> SEQ ID NO 158
<211> LENGTH: 60
<212> TYPE: PRT
<213> ORGANISM: Rhincodon typus

<400> SEQUENCE: 158

Thr Thr Gly Gln Glu Tyr Val Lys Val Thr Val Met Gln Asn Gly Arg Met
1               5                  10                  15
```

-continued

```
Lys Gly Ala Val Leu Ile Gly Glu Thr Asp Leu Glu Glu Thr Phe Glu
            20                  25                  30

Asn Leu Ile Leu Asn Gln Met Asp Leu Ser Ala Tyr Gly Glu Asp Leu
            35                  40                  45

Leu Asn Pro Asn Ile Asp Ile Glu Asp Tyr Phe Asp
    50                  55                  60

<210> SEQ ID NO 159
<211> LENGTH: 60
<212> TYPE: PRT
<213> ORGANISM: Callorhinchus milii

<400> SEQUENCE: 159

Thr Lys Gly His Glu Tyr Val Lys Ala Val Met Gln Asn Gly Arg Met
1               5                   10                  15

Met Gly Ala Val Leu Ile Gly Glu Thr Asn Leu Glu Glu Thr Phe Glu
            20                  25                  30

Asn Leu Ile Leu Asn Gln Met Asp Leu Ser Ser Tyr Gly Glu Glu Leu
            35                  40                  45

Leu Asn Pro Asn Ile Asp Ile Glu Asp Tyr Phe Asp
    50                  55                  60

<210> SEQ ID NO 160
<211> LENGTH: 60
<212> TYPE: PRT
<213> ORGANISM: Salmo salar

<400> SEQUENCE: 160

Thr Lys Gly His Glu Tyr Val Lys Val Val Leu Ser Gly Gly Arg Met
1               5                   10                  15

Leu Gly Ala Val Leu Ile Gly Glu Thr Asp Leu Glu Glu Thr Phe Glu
            20                  25                  30

Asn Leu Ile Leu Asn Gln Met Asp Leu Thr Pro Tyr Gly Glu Glu Leu
            35                  40                  45

Leu Asn Pro Asn Ile Asp Ile Glu Asp Tyr Phe Asp
    50                  55                  60

<210> SEQ ID NO 161
<211> LENGTH: 60
<212> TYPE: PRT
<213> ORGANISM: Xenopus laevis

<400> SEQUENCE: 161

Thr Arg Gly His Glu Tyr Val Lys Leu Val Met Gln Gly Gly Arg Met
1               5                   10                  15

Val Gly Ala Leu Leu Ile Gly Asp Thr Asp Leu Glu Glu Thr Phe Glu
            20                  25                  30

Asn Leu Ile Leu Asn Gln Thr Asp Leu Ser Ser Tyr Gly Glu Arg Leu
            35                  40                  45

Leu Asp Pro Asn Ile Asp Ile Glu Asp Tyr Phe Asp
    50                  55                  60

<210> SEQ ID NO 162
<211> LENGTH: 60
<212> TYPE: PRT
<213> ORGANISM: Cyprinus carpio

<400> SEQUENCE: 162

Thr Lys Gly Gln Glu Tyr Val Lys Val Val Leu Thr Gly Gly Arg Met
1               5                   10                  15
```

```
Val Gly Ala Val Leu Ile Gly Glu Thr Asp Leu Glu Glu Thr Phe Glu
         20                  25                  30

Asn Leu Ile Leu Asn Gln Met Asp Leu Ser Arg Tyr Gly Glu Glu Leu
         35                  40                  45

Leu Asn Pro Asn Ile Asp Ile Glu Asp Tyr Phe Asp
         50                  55                  60

<210> SEQ ID NO 163
<211> LENGTH: 2001
<212> TYPE: DNA
<213> ORGANISM: Equus caballus

<400> SEQUENCE: 163
ttagaattct ggggtggctg gaggtgtgtt tgctctctag ctgcaaagat aaacgtttgc      60
aagacctgtc atacgaagac ctgagaagtt tccctaaaat gtggtctcag ggtactttaa     120
gtttgtttta agaaaagaga agagttcgta gcttttcttg tttcaggctc tataaaacct     180
gtaagttttt gtaggtgacc attgcgggga ccggcctctt cttgtccatg aggccagagt     240
agcctggggc atcgtgcttc ctggggagga agaagcattg ccccctgtt ggggcagaga      300 gtgggtgctg accgcatggt cagggtctgt cagaggcagg tggacgttct gtggatggga     360
tgtgactgaa gggacccgtc tcttgagcct cacattcata tcatcacgaa tatttttctg     420
agcacctgat cctgcggcgg tggctttcct cgcacatgtg gctcatttcc ctgacttgtg     480
ttgttttcag ggtgactcag ggcgggacag ccagcagaga ggacccaaag gagaaaccgg     540
agacctcggg cccatggtac gatgctcctt gttcccagac tctcctgtgc tggaggccag     600
agaaacaaag ctcacactgg ctcgccaggg gccgaaggac catggaagtg gtctttgagg     660
ctggggagca tatgccggtca ggaacagagg gccccgtgaa gcccaccctg tgtgcccatg    720
aaggacgttt ccattgtgga acagaagcaa gccctaccga gaggagcttc ttctgggcag    780
aagttgtgct ctttagatat ttacgaaagc gcttgtcaag ccaaaggctg tggggcgggg    840
cacgtaccta agtctagcgc acctcacgac agagtaccga ccttcctctg cctatccatc     900 cctttcctg tagtgtctcg tgcaatattc cagagttcct gctcttcttt gcagatgaaa      960
atcttacacc aattttcttc cccacgccag ggtctgcctg sgagtgatgg tgtctcggga    1020
agtcctggag aaccagggag ggacgtgagt gtctcttaca gctttggagg gaggtggcgg    1080
ggcctctgtg ctggtattta gcaggtgccc tccagatctt ccagacactg cctgggcgt    1140 tgttacccag caactctttg tttaaagaat ttaaagagat ttctgaaacc tttgtcaccc    1200
aaatcttgat gcttatggaa acattcgtc cttattgttt gatctgtgcc ccatctgtgc     1260
ccgtctcttc tcccacccc agtcccgctt actcccctcc ccaaaactca ccgaacagac    1320 acttttaaa gtattgtctt cccagctttc aagtatctgg ccaggtttta tcccactaaa    1380
tgtttaaaaa aatcccaaca gaaacacgaa aacgggggcg gggggggggg atgagggaat    1440
atggggcagg gaggctgctg gggttgtata tttgtggttg cttttagaat tgttttcgt    1500 gtgctgctgt agctcaagca aggaaacgag actcagtttt ctagtgaatc gcttttgaa    1560 atcgctttcc caaggcattt cagaaatgcc ctttgtagat tagctgattg catgcctagt    1620
ctttgagtct ttctggaaga gctgctaaag ccaaagggat aaagatcgtc tttaggaagc    1680
cagtggaatg cttccagggc ccaggggcaa gatggtctgg aagctcatac atcctctggg    1740
gtgcgtcagg atgctggggg cgggtgccca ggcaggtct ctgctcagaa gctgcctggg    1800
actatgcagc cttgaacggg gcccctcag ctgtctcccc agtggcagcg acacatttag    1860
```

```
ggatcagcag ctggacaatc ggggggtgt atgctgaggt gagcgctctg aaaagaagta    1920
actctcacct gtaatcagat gatatatcat gggccaaagt ttgcttttaa aattcagaag    1980
aagacttaaa atttgaaaat g                                              2001
```

<210> SEQ ID NO 164
<211> LENGTH: 1008
<212> TYPE: DNA
<213> ORGANISM: Equus caballus

<400> SEQUENCE: 164

```
ggacaaaggg gagaccgagg gcccatcggc agcatcgggc caaagggtgt tcccggagaa      60
gacggctacc gagggtaccc cggtgatgag ggtgggcccg gtgatcgggg tccaccgggt     120
gtgaacggca ctcaaggttt ccagggctgc cccgggcaga gaggaataaa gggctctcgt     180
ggattcccag gagagaaggg tgaattagga gaaatcggac ttgatggtct tgacggtgaa     240
gatggagaca aaggattgcc tgggtcttct ggagagaaag ggaatcctgg aaggaggggt     300
gacaaaggac ctaaaggaga ccaagggaa agaggagatg ttggaattag ggcgacccg      360 ggtgactcag ggcgggacag ccagcagaga ggacccaaag gagaaaccgg agacctcggg     420
cccatgggtc tgcctgggag tgatggtgtc tcgggaagtc ctggagaacc agggagggac     480
ggtggctttg gccgaagggg accaccagga gctaagggca caagggcgg tcctggccag     540 cagggcaccg tgggagagca ggggaccaga ggtgcacagg gtccacctgg ttccaccggt     600
cctccagggc tgatcggcga acaaggcatt cctggacctc ggggaagcgg aggtgctgtg     660
ggcgtccctg gagaacgcgg ccgaaccggt cccttgggaa gaaagggcga gcctggagag     720 ccggagcga agggaggact cgggccccgg ggccccgtg gggaaacggg agatgacggg       780
cgagacggag ttggcagtga aggacaaaaa ggcaaaaag gagaaagagg attccctgga     840
tacccaggtc caaagggtac ccgtggtgag ccagggacag acggaacact aggacccaaa     900
ggcgtcagag gccgaagggg agactcagga cctccagggg cagctggaca aagggagac     960 cctggttacc cgggaccatc tggtctcaaa ggcaacagag gcgactcg                1008
```

<210> SEQ ID NO 165
<211> LENGTH: 1008
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 165

```
ggacaaaggg gagaccgagg gcccatcggc agcatcgggc caaagggtgt tcccggagaa      60
gacggctacc gagggtaccc cggtgatgag ggtgggcccg gtgatcgggg tccaccgggt     120
gtgaacggca ctcaaggttt ccagggctgc cccgggcaga gaggaataaa gggctctcgt     180
ggattcccag gagagaaggg tgaattagga gaaatcggac ttgatggtct tgacggtgaa     240
gatggagaca aaggattgcc tgggtcttct ggagagaaag ggaatcctgg aaggaggggt     300
gacaaaggac ctaaaggaga ccaagggaa agaggagatg ttggaattag ggcgacccg      360 ggtgactcag ggcgggacag ccagcagaga ggacccaaag gagaaaccgg agacctcggg     420
cccatgggtc tgcctgcgag tgatggtgtc tcgggaagtc ctggagaacc agggagggac     480
ggtggctttg gccgaagggg accaccagga gctaagggca caagggcgg tcctggccag     540 cagggcaccg tgggagagca ggggaccaga ggtgcacagg gtccacctgg ttccaccggt     600
```

```
cctccagggc tgatcggcga acaaggcatt cctggacctc ggggaagcgg aggtgctgtg        660
ggcgtccctg gagaacgcgg ccgaaccggt cccttgggaa gaaagggcga gcctggagag        720
ccgggagcga agggaggact cgggccccgg ggccccgtg gggaaacggg agatgacggg         780
cgagacggag ttggcagtga aggacaaaaa ggcaaaaaag gagaaagagg attccctgga        840
tacccaggtc caaagggtac ccgtggtgag ccagggacag acggaacact aggacccaaa        900
ggcgtcagag gccgaagggg agactcagga cctccagggg cagctggaca gaagggagac        960
cctggttacc cgggaccatc tggtctcaaa ggcaacagag gcgactcg                    1008
```

<210> SEQ ID NO 166
<211> LENGTH: 82
<212> TYPE: DNA
<213> ORGANISM: Equus caballus

<400> SEQUENCE: 166

```
cccacgccag ggtctgccgg tctgcctggg agtgatggtg tctcgggaag tcctggagaa         60
ccagggaggg acgtgagtgt ct                                                  82
```

<210> SEQ ID NO 167
<211> LENGTH: 336
<212> TYPE: PRT
<213> ORGANISM: Equus caballus

<400> SEQUENCE: 167

```
Gly Gln Arg Gly Asp Arg Gly Pro Ile Gly Ser Ile Gly Pro Lys Gly
1               5                   10                  15

Val Pro Gly Glu Asp Gly Tyr Arg Gly Tyr Pro Gly Asp Glu Gly Gly
            20                  25                  30

Pro Gly Asp Arg Gly Pro Pro Gly Val Asn Gly Thr Gln Gly Phe Gln
        35                  40                  45

Gly Cys Pro Gly Gln Arg Gly Ile Lys Gly Ser Arg Gly Phe Pro Gly
    50                  55                  60

Glu Lys Gly Glu Leu Gly Glu Ile Gly Leu Asp Gly Leu Asp Gly Glu
65                  70                  75                  80

Asp Gly Asp Lys Gly Leu Pro Gly Ser Ser Gly Glu Lys Gly Asn Pro
                85                  90                  95

Gly Arg Arg Gly Asp Lys Gly Pro Lys Gly Asp Gln Gly Glu Arg Gly
            100                 105                 110

Asp Val Gly Ile Arg Gly Asp Pro Gly Asp Ser Gly Arg Asp Ser Gln
        115                 120                 125

Gln Arg Gly Pro Lys Gly Glu Thr Gly Asp Leu Gly Pro Met Gly Leu
    130                 135                 140

Pro Gly Ser Asp Gly Val Ser Gly Ser Pro Gly Glu Pro Gly Arg Asp
145                 150                 155                 160

Gly Gly Phe Gly Arg Arg Gly Pro Pro Gly Ala Lys Gly Asn Lys Gly
                165                 170                 175

Gly Pro Gly Gln Gln Gly Thr Val Gly Glu Gln Gly Thr Arg Gly Ala
            180                 185                 190

Gln Gly Pro Pro Gly Ser Thr Gly Pro Pro Gly Leu Ile Gly Glu Gln
        195                 200                 205

Gly Ile Pro Gly Pro Arg Gly Ser Gly Gly Ala Val Gly Val Pro Gly
    210                 215                 220

Glu Arg Gly Arg Thr Gly Pro Leu Gly Arg Lys Gly Glu Pro Gly Glu
225                 230                 235                 240
```

```
Pro Gly Ala Lys Gly Gly Leu Gly Pro Arg Gly Pro Arg Gly Glu Thr
                245                 250                 255

Gly Asp Asp Gly Arg Asp Gly Val Gly Ser Glu Gly Gln Lys Gly Lys
            260                 265                 270

Lys Gly Glu Arg Gly Phe Pro Gly Tyr Pro Gly Pro Lys Gly Thr Arg
        275                 280                 285

Gly Glu Pro Gly Thr Asp Gly Thr Leu Gly Pro Lys Gly Val Arg Gly
    290                 295                 300

Arg Arg Gly Asp Ser Gly Pro Pro Gly Ala Ala Gly Gln Lys Gly Asp
305                 310                 315                 320

Pro Gly Tyr Pro Gly Pro Ser Gly Leu Lys Gly Asn Arg Gly Asp Ser
                325                 330                 335

<210> SEQ ID NO 168
<211> LENGTH: 336
<212> TYPE: PRT
<213> ORGANISM: Equus caballus

<400> SEQUENCE: 168

Gly Gln Arg Gly Asp Arg Gly Pro Ile Gly Ser Ile Gly Pro Lys Gly
1               5                   10                  15

Val Pro Gly Glu Asp Gly Tyr Arg Gly Tyr Pro Gly Asp Glu Gly Gly
            20                  25                  30

Pro Gly Asp Arg Gly Pro Pro Gly Val Asn Gly Thr Gln Gly Phe Gln
        35                  40                  45

Gly Cys Pro Gly Gln Arg Gly Ile Lys Gly Ser Arg Gly Phe Pro Gly
    50                  55                  60

Glu Lys Gly Glu Leu Gly Glu Ile Gly Leu Asp Gly Leu Asp Gly Glu
65                  70                  75                  80

Asp Gly Asp Lys Gly Leu Pro Gly Ser Ser Gly Glu Lys Gly Asn Pro
                85                  90                  95

Gly Arg Arg Gly Asp Lys Gly Pro Lys Gly Asp Gln Gly Glu Arg Gly
            100                 105                 110

Asp Val Gly Ile Arg Gly Asp Pro Gly Asp Ser Gly Arg Asp Ser Gln
        115                 120                 125

Gln Arg Gly Pro Lys Gly Glu Thr Gly Asp Leu Gly Pro Met Gly Leu
    130                 135                 140

Pro Ala Ser Asp Gly Val Ser Gly Ser Pro Gly Glu Pro Gly Arg Asp
145                 150                 155                 160

Gly Gly Phe Gly Arg Arg Gly Pro Pro Gly Ala Lys Gly Asn Lys Gly
                165                 170                 175

Gly Pro Gly Gln Gln Gly Thr Val Gly Glu Gln Gly Thr Arg Gly Ala
            180                 185                 190

Gln Gly Pro Pro Gly Ser Thr Gly Pro Pro Gly Leu Ile Gly Glu Gln
        195                 200                 205

Gly Ile Pro Gly Pro Arg Gly Ser Gly Gly Ala Val Gly Val Pro Gly
    210                 215                 220

Glu Arg Gly Arg Thr Gly Pro Leu Gly Arg Lys Gly Glu Pro Gly Glu
225                 230                 235                 240

Pro Gly Ala Lys Gly Gly Leu Gly Pro Arg Gly Pro Arg Gly Glu Thr
                245                 250                 255

Gly Asp Asp Gly Arg Asp Gly Val Gly Ser Glu Gly Gln Lys Gly Lys
            260                 265                 270

Lys Gly Glu Arg Gly Phe Pro Gly Tyr Pro Gly Pro Lys Gly Thr Arg
```

```
                275                 280                 285
Gly Glu Pro Gly Thr Asp Gly Thr Leu Gly Pro Lys Gly Val Arg Gly
        290                 295                 300

Arg Arg Gly Asp Ser Gly Pro Pro Gly Ala Ala Gly Gln Lys Gly Asp
305                 310                 315                 320

Pro Gly Tyr Pro Gly Pro Ser Gly Leu Lys Gly Asn Arg Gly Asp Ser
                325                 330                 335

<210> SEQ ID NO 169
<211> LENGTH: 54
<212> TYPE: DNA
<213> ORGANISM: Equus caballus

<400> SEQUENCE: 169
ggtctgcctg ggagtgatgg tgtctcggga agtcctggag aaccagggag ggac        54

<210> SEQ ID NO 170
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ggtctgcctg cgagtgatgg tgtctcggga agtcctggag aaccagggag ggac        54

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
ttcccagact ctcctgtgct                                              20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
agatggggca cagatcaaac                                              20

<210> SEQ ID NO 173
<211> LENGTH: 1008
<212> TYPE: DNA
<213> ORGANISM: Homo sapiens

<400> SEQUENCE: 173
gggcagaggg gagaccgcgg gcccatcggc agcatcgggc caaagggtat tcctggagaa    60
gacggctacc gaggctatcc tggtgatgag ggtggacccg gtgagcgtgg tccgcctggt   120
gtgaacggca ctcaaggttt ccagggctgc ccgggccaga gaggagtaaa gggctctcgg   180
ggattcccag agagaagggc gaagtaggag gaaattggac tggatggtct ggatggtgaa   240
gatggagaca aaggattgcc tggttcttct ggagagaaag ggatcctgg aagaaggggt   300 gataaaggac ctcgaggaga gaaaggagaa agaggagatg ttgggattcg agggacccg   360
```

```
ggtaacccag gacaagacag ccaggagaga ggacccaaag gagaaaccgg tgacctcggc    420
cccatgggtg tcccagggag agatggagta cctggaggac ctggagaaac tgggaagaat    480
ggtggctttg ccgaaggggg accccccgga gctaagggca acaagggcgg tcctggccag    540
ccgggctttg agggagagca ggggaccaga ggtgcacagg gcccagctgg tcctgctggt    600
cctccagggc tgataggaga acaaggcatt tctggacctc ggggaagcgg aggtgccgct    660
ggtgctcctg gagaacgagg cagaaccggt ccactgggaa gaaagggtga gcccggagag    720
ccaggaccaa aaggaggaat cgggaaccgg ggccctcgtg gggagacggg agatgacggg    780
agagacggag ttggcagtga aggacgcaga ggcaaaaaag gagaagagg  attccctgga    840 tacccaggac caaagggtaa cccaggtgaa cctgggctaa atggaacaac aggacccaaa    900
ggcatcagag gccgaagggg aaattcggga cctccaggga tagttggaca gaagggagac    960
cctggctacc caggaccagc tggtcccaag ggcaacaggg gcgactcc               1008
```

<210> SEQ ID NO 174
<211> LENGTH: 336
<212> TYPE: PRT
<213> ORGANISM: Homo sapiens

<400> SEQUENCE: 174

```
Gly Gln Arg Gly Asp Arg Gly Pro Ile Gly Ser Ile Gly Pro Lys Gly
1               5                   10                  15

Ile Pro Gly Glu Asp Gly Tyr Arg Gly Tyr Pro Gly Asp Glu Gly Gly
            20                  25                  30

Pro Gly Glu Arg Gly Pro Pro Gly Val Asn Gly Thr Gln Gly Phe Gln
        35                  40                  45

Gly Cys Pro Gly Gln Arg Gly Val Lys Gly Ser Arg Gly Phe Pro Gly
    50                  55                  60

Glu Lys Gly Glu Val Gly Glu Ile Gly Leu Asp Gly Leu Asp Gly Glu
65                  70                  75                  80

Asp Gly Asp Lys Gly Leu Pro Gly Ser Ser Gly Glu Lys Gly Asn Pro
                85                  90                  95

Gly Arg Arg Gly Asp Lys Gly Pro Arg Gly Glu Lys Gly Glu Arg Gly
            100                 105                 110

Asp Val Gly Ile Arg Gly Asp Pro Gly Asn Pro Gly Gln Asp Ser Gln
        115                 120                 125

Glu Arg Gly Pro Lys Gly Glu Thr Gly Asp Leu Gly Pro Met Gly Val
    130                 135                 140

Pro Gly Arg Asp Gly Val Pro Gly Gly Pro Gly Glu Thr Gly Lys Asn
145                 150                 155                 160

Gly Gly Phe Gly Arg Arg Gly Pro Pro Gly Ala Lys Gly Asn Lys Gly
                165                 170                 175

Gly Pro Gly Gln Pro Gly Phe Glu Gly Glu Gln Gly Thr Arg Gly Ala
            180                 185                 190

Gln Gly Pro Ala Gly Pro Ala Gly Pro Gly Leu Ile Gly Glu Gln
        195                 200                 205

Gly Ile Ser Gly Pro Arg Gly Ser Gly Gly Ala Ala Gly Ala Pro Gly
    210                 215                 220

Glu Arg Gly Arg Thr Gly Pro Leu Gly Arg Lys Gly Glu Pro Gly Glu
225                 230                 235                 240

Pro Gly Pro Lys Gly Gly Ile Gly Asn Arg Gly Pro Arg Gly Glu Thr
                245                 250                 255
```

Gly Asp Asp Gly Arg Asp Gly Val Gly Ser Glu Gly Arg Arg Gly Lys
            260                 265                 270

Lys Gly Glu Arg Gly Phe Pro Gly Tyr Pro Gly Pro Lys Gly Asn Pro
        275                 280                 285

Gly Glu Pro Gly Leu Asn Gly Thr Thr Gly Pro Lys Gly Ile Arg Gly
    290                 295                 300

Arg Arg Gly Asn Ser Gly Pro Pro Gly Ile Val Gly Gln Lys Gly Asp
305                 310                 315                 320

Pro Gly Tyr Pro Gly Pro Ala Gly Pro Lys Gly Asn Arg Gly Asp Ser
                325                 330                 335

<210> SEQ ID NO 175
<211> LENGTH: 336
<212> TYPE: PRT
<213> ORGANISM: Homo sapiens

<400> SEQUENCE: 175

Gly Gln Arg Gly Asp Arg Gly Pro Ile Gly Ser Ile Gly Pro Lys Gly
1               5                   10                  15

Ile Pro Gly Glu Asp Gly Tyr Arg Gly Tyr Pro Gly Asp Glu Gly Gly
            20                  25                  30

Pro Gly Glu Arg Gly Pro Pro Gly Val Asn Gly Thr Gln Gly Phe Gln
        35                  40                  45

Gly Cys Pro Gly Gln Arg Gly Val Lys Gly Ser Arg Gly Phe Pro Gly
    50                  55                  60

Glu Lys Gly Glu Val Gly Glu Ile Gly Leu Asp Gly Leu Asp Gly Glu
65                  70                  75                  80

Asp Gly Asp Lys Gly Leu Pro Gly Ser Ser Gly Glu Lys Gly Asn Pro
                85                  90                  95

Gly Arg Arg Gly Asp Lys Gly Pro Arg Gly Glu Lys Gly Glu Arg Gly
            100                 105                 110

Asp Val Gly Ile Arg Gly Asp Pro Gly Asn Pro Gly Gln Asp Ser Gln
        115                 120                 125

Glu Arg Gly Pro Lys Gly Glu Thr Gly Asp Leu Gly Pro Met Gly Val
    130                 135                 140

Pro Gly Arg Asp Gly Val Pro Gly Gly Pro Gly Glu Thr Gly Lys Asn
145                 150                 155                 160

Gly Gly Phe Gly Arg Arg Gly Pro Pro Gly Ala Lys Gly Asn Lys Gly
                165                 170                 175

Gly Pro Gly Gln Pro Gly Phe Glu Gly Glu Gln Gly Thr Arg Gly Ala
            180                 185                 190

Gln Gly Pro Ala Gly Pro Ala Gly Pro Pro Gly Leu Ile Gly Glu Gln
        195                 200                 205

Gly Ile Ser Gly Pro Arg Gly Ser Gly Gly Ala Ala Gly Ala Pro Gly
    210                 215                 220

Glu Arg Gly Arg Thr Gly Pro Leu Gly Arg Lys Gly Glu Pro Gly Glu
225                 230                 235                 240

Pro Gly Pro Lys Gly Gly Ile Gly Asn Arg Gly Pro Arg Gly Glu Thr
                245                 250                 255

Gly Asp Asp Gly Arg Asp Gly Val Gly Ser Glu Gly Arg Arg Gly Lys
            260                 265                 270

Lys Gly Glu Arg Gly Phe Pro Gly Tyr Pro Gly Pro Lys Gly Asn Pro
        275                 280                 285

Gly Glu Pro Gly Leu Asn Gly Thr Thr Gly Pro Lys Gly Ile Arg Gly
    290                 295                 300

Arg Arg Gly Asn Ser Gly Pro Pro Gly Ile Val Gly Gln Lys Gly Asp
305                 310                 315                 320

Pro Gly Tyr Pro Gly Pro Ala Gly Pro Lys Gly Asn Arg Gly Asp Ser
                325                 330                 335

<210> SEQ ID NO 176
<211> LENGTH: 336
<212> TYPE: PRT
<213> ORGANISM: Equus caballus

<400> SEQUENCE: 176

Gly Gln Arg Gly Asp Arg Gly Pro Ile Gly Ser Ile Gly Pro Lys Gly
1               5                   10                  15

Val Pro Gly Glu Asp Gly Tyr Arg Gly Tyr Pro Gly Asp Glu Gly Gly
            20                  25                  30

Pro Gly Asp Arg Gly Pro Pro Gly Val Asn Gly Thr Gln Gly Phe Gln
        35                  40                  45

Gly Cys Pro Gly Gln Arg Gly Ile Lys Gly Ser Arg Gly Phe Pro Gly
    50                  55                  60

Glu Lys Gly Glu Leu Gly Glu Ile Gly Leu Asp Gly Leu Asp Gly Glu
65                  70                  75                  80

Asp Gly Asp Lys Gly Leu Pro Gly Ser Ser Gly Glu Lys Gly Asn Pro
                85                  90                  95

Gly Arg Arg Gly Asp Lys Gly Pro Lys Gly Asp Gln Gly Glu Arg Gly
            100                 105                 110

Asp Val Gly Ile Arg Gly Asp Pro Gly Asp Ser Gly Arg Asp Ser Gln
        115                 120                 125

Gln Arg Gly Pro Lys Gly Glu Thr Gly Asp Leu Gly Pro Met Gly Leu
130                 135                 140

Pro Gly Ser Asp Gly Val Ser Gly Ser Pro Gly Glu Pro Gly Arg Asp
145                 150                 155                 160

Gly Gly Phe Gly Arg Arg Gly Pro Pro Gly Ala Lys Gly Asn Lys Gly
            165                 170                 175

Gly Pro Gly Gln Gln Gly Thr Val Gly Glu Gln Gly Thr Arg Gly Ala
            180                 185                 190

Gln Gly Pro Pro Gly Ser Thr Gly Pro Pro Gly Leu Ile Gly Glu Gln
        195                 200                 205

Gly Ile Pro Gly Pro Arg Gly Ser Gly Gly Ala Val Gly Val Pro Gly
210                 215                 220

Glu Arg Gly Arg Thr Gly Pro Leu Gly Arg Lys Gly Glu Pro Gly Glu
225                 230                 235                 240

Pro Gly Ala Lys Gly Gly Leu Gly Pro Arg Gly Pro Arg Gly Glu Thr
            245                 250                 255

Gly Asp Asp Gly Arg Asp Gly Val Gly Ser Glu Gly Gln Lys Gly Lys
            260                 265                 270

Lys Gly Glu Arg Gly Phe Pro Gly Tyr Pro Gly Pro Lys Gly Thr Arg
        275                 280                 285

Gly Glu Pro Gly Thr Asp Gly Thr Leu Gly Pro Lys Gly Val Arg Gly
    290                 295                 300

Arg Arg Gly Asp Ser Gly Pro Pro Gly Ala Ala Gly Gln Lys Gly Asp
305                 310                 315                 320

Pro Gly Tyr Pro Gly Pro Ser Gly Leu Lys Gly Asn Arg Gly Asp Ser
                325                 330                 335

-continued

```
<210> SEQ ID NO 177
<211> LENGTH: 59
<212> TYPE: PRT
<213> ORGANISM: Unknown
<220> FEATURE:
<223> OTHER INFORMATION: Description of Unknown:
      COL6A3 sequence

<400> SEQUENCE: 177

Arg Gly Asp Pro Gly Asn Pro Gly Gln Asp Ser Gln Glu Arg Gly Pro
1               5                   10                  15

Lys Gly Glu Thr Gly Asp Leu Gly Pro Met Gly Val Pro Gly Arg Asp
            20                  25                  30

Gly Val Pro Gly Gly Pro Gly Glu Thr Gly Lys Asn Gly Gly Phe Gly
        35                  40                  45

Arg Arg Gly Pro Pro Gly Ala Lys Gly Asn Lys
    50                  55

<210> SEQ ID NO 178
<211> LENGTH: 59
<212> TYPE: PRT
<213> ORGANISM: Unknown
<220> FEATURE:
<223> OTHER INFORMATION: Description of Unknown:
      COL6A3 sequence

<400> SEQUENCE: 178

Arg Gly Asp Pro Gly Glu Ser Gly Arg Asp Ser Gln Gln Arg Gly Pro
1               5                   10                  15

Lys Gly Glu Thr Gly Asp Ile Gly Pro Met Gly Leu Pro Gly Arg Asp
            20                  25                  30

Gly Val Ser Gly Ser Pro Gly Glu Thr Gly Lys Asp Gly Gly Phe Gly
        35                  40                  45

Arg Arg Gly Pro Ala Gly Ala Lys Gly Asn Arg
    50                  55

<210> SEQ ID NO 179
<211> LENGTH: 59
<212> TYPE: PRT
<213> ORGANISM: Unknown
<220> FEATURE:
<223> OTHER INFORMATION: Description of Unknown:
      COL6A3 sequence

<400> SEQUENCE: 179

Arg Gly Asp Pro Gly Asp Ser Gly Arg Asp Ser Gln Gln Arg Gly Pro
1               5                   10                  15

Lys Gly Glu Thr Gly Asp Ile Gly Pro Met Gly Leu Pro Gly Arg Asp
            20                  25                  30

Gly Val Pro Gly Arg Pro Gly Asp Pro Gly Lys Asp Gly Gly Tyr Gly
        35                  40                  45

Arg Arg Gly Pro Ala Gly Ala Lys Gly Asn Arg
    50                  55

<210> SEQ ID NO 180
<211> LENGTH: 59
<212> TYPE: PRT
<213> ORGANISM: Unknown
<220> FEATURE:
<223> OTHER INFORMATION: Description of Unknown:
      COL6A3 sequence

<400> SEQUENCE: 180
```

Arg Gly Asp Pro Gly Asp Ser Gly Arg Asp Ser Gln Gln Arg Gly Pro
1               5                   10                  15

Lys Gly Glu Thr Gly Asp Leu Gly Pro Met Gly Leu Pro Gly Ser Asp
            20                  25                  30

Gly Val Ser Gly Ser Pro Gly Glu Pro Gly Arg Asp Gly Gly Phe Gly
            35                  40                  45

Arg Arg Gly Pro Pro Gly Ala Lys Gly Asn Lys
            50                  55

<210> SEQ ID NO 181
<211> LENGTH: 59
<212> TYPE: PRT
<213> ORGANISM: Unknown
<220> FEATURE:
<223> OTHER INFORMATION: Description of Unknown:
      COL6A3 sequence

<400> SEQUENCE: 181

Arg Gly Asp Pro Gly Asp Ser Gly Gln Asp Ser Gln Gln Arg Gly Pro
1               5                   10                  15

Lys Gly Glu Thr Gly Asp Ile Gly Pro Met Gly Leu Pro Gly Arg Asp
            20                  25                  30

Gly Val Ser Gly Ser Pro Gly Glu Pro Gly Lys Ser Gly Gly Phe Gly
            35                  40                  45

Arg Arg Gly Pro Ala Gly Ala Lys Gly Asn Lys
            50                  55

<210> SEQ ID NO 182
<211> LENGTH: 59
<212> TYPE: PRT
<213> ORGANISM: Unknown
<220> FEATURE:
<223> OTHER INFORMATION: Description of Unknown:
      COL6A3 sequence

<400> SEQUENCE: 182

Arg Gly Asp Pro Gly Asp Ser Gly Arg Asp Ser Gln Gln Arg Gly Pro
1               5                   10                  15

Lys Gly Glu Thr Gly Asp Ile Gly Pro Met Gly Leu Pro Gly Arg Asp
            20                  25                  30

Gly Val Ser Gly Arg Pro Gly Glu Thr Gly Lys Asp Gly Gly Phe Gly
            35                  40                  45

Arg Arg Gly Pro Ala Gly Ala Lys Gly Asn Lys
            50                  55

<210> SEQ ID NO 183
<211> LENGTH: 56
<212> TYPE: PRT
<213> ORGANISM: Unknown
<220> FEATURE:
<223> OTHER INFORMATION: Description of Unknown:
      COL6A3 sequence

<400> SEQUENCE: 183

Arg Gly Asp Pro Gly Asn Ser Gly Gln Asp Ser Gln Gln Arg Gly Ala
1               5                   10                  15

Lys Gly Glu Thr Gly Asp Ile Gly Pro Val Gly Leu Pro Gly Arg Asp
            20                  25                  30

Gly Val Ser Gly Gly Pro Gly Glu Pro Gly Lys Ser Gly Gly Phe Gly
            35                  40                  45

Arg Arg Gly Pro Ala Gly Ala Lys

<210> SEQ ID NO 184
<211> LENGTH: 59
<212> TYPE: PRT
<213> ORGANISM: Unknown
<220> FEATURE:
<223> OTHER INFORMATION: Description of Unknown:
      COL6A3 sequence

<400> SEQUENCE: 184

Arg Gly Asp Pro Gly Asp Ser Gly Arg Asp Ser Gln Gln Arg Gly Pro
1               5                   10                  15
Lys Gly Glu Thr Gly Asp Ile Gly Pro Met Gly Leu Pro Gly Arg Asp
            20                  25                  30
Gly Val Ser Gly Ser Pro Gly Glu Thr Gly Lys Asp Gly Gly Phe Gly
        35                  40                  45
Arg Arg Gly Pro Ala Gly Ala Lys Gly Asn Lys
    50                  55

<210> SEQ ID NO 185
<211> LENGTH: 59
<212> TYPE: PRT
<213> ORGANISM: Papio anubis

<400> SEQUENCE: 185

Arg Gly Asp Pro Gly Asn Pro Gly Gln Asp Ser Gln Gln Arg Gly Pro
1               5                   10                  15
Lys Gly Glu Thr Gly Asp Leu Gly Pro Met Gly Ala Pro Gly Thr Asp
            20                  25                  30
Gly Val Pro Gly Gly Pro Gly Glu Thr Gly Lys Asn Gly Gly Phe Gly
        35                  40                  45
Arg Arg Gly Pro Pro Gly Ala Lys Gly Asn Lys
    50                  55

<210> SEQ ID NO 186
<211> LENGTH: 59
<212> TYPE: PRT
<213> ORGANISM: Macaca mulatta

<400> SEQUENCE: 186

Arg Gly Asp Pro Gly Asn Pro Gly Gln Asp Ser Gln Gln Arg Gly Pro
1               5                   10                  15
Lys Gly Glu Thr Gly Asp Leu Gly Pro Met Gly Val Pro Gly Arg Asp
            20                  25                  30
Gly Val Pro Gly Gly Pro Gly Glu Thr Gly Lys Asn Gly Gly Phe Gly
        35                  40                  45
Arg Arg Gly Pro Pro Gly Ala Lys Gly Asn Lys
    50                  55

<210> SEQ ID NO 187
<211> LENGTH: 59
<212> TYPE: PRT
<213> ORGANISM: Cebus capucinus imitator

<400> SEQUENCE: 187

Arg Gly Asp Pro Gly Asn Pro Gly Gln Asp Ser Gln Gln Arg Gly Pro
1               5                   10                  15
Lys Gly Glu Thr Gly Asp Ile Gly Pro Val Gly Val Pro Gly Arg Asp
            20                  25                  30

```
Gly Val Pro Gly Pro Gly Glu Thr Gly Lys Asn Gly Gly Phe Gly
            35                  40                  45

Arg Arg Gly Pro Pro Gly Val Lys Gly Asn Lys
 50                  55
```

<210> SEQ ID NO 188
<211> LENGTH: 59
<212> TYPE: PRT
<213> ORGANISM: Rhinopithecus bieti

<400> SEQUENCE: 188

```
Arg Gly Asp Pro Gly Asn Pro Gly Gln Asp Ser Gln Gln Arg Gly Pro
 1               5                  10                  15

Lys Gly Glu Ile Gly Asp Leu Gly Pro Met Gly Val Pro Gly Arg Asp
            20                  25                  30

Gly Val Pro Gly Pro Gly Glu Thr Gly Lys Asn Gly Gly Phe Gly
            35                  40                  45

Arg Arg Gly Pro Pro Gly Ala Lys Gly Asn Lys
 50                  55
```

<210> SEQ ID NO 189
<211> LENGTH: 59
<212> TYPE: PRT
<213> ORGANISM: Microcebus murinus

<400> SEQUENCE: 189

```
Arg Gly Asp Pro Gly Glu Ser Gly Arg Asp Ser Gln Gln Arg Gly Pro
 1               5                  10                  15

Lys Gly Glu Thr Gly Asp Ile Gly Pro Met Gly Leu Pro Gly Arg Asp
            20                  25                  30

Gly Val Ser Gly Ser Pro Gly Glu Asn Gly Arg Asn Gly Gly Phe Gly
            35                  40                  45

Arg Arg Gly Pro Ala Gly Ala Lys Gly Asn Lys
 50                  55
```

<210> SEQ ID NO 190
<211> LENGTH: 59
<212> TYPE: PRT
<213> ORGANISM: Carlito syrichta

<400> SEQUENCE: 190

```
Arg Gly Asp Pro Gly Asp Ser Gly Arg Asp Ser Gln Gln Arg Gly Pro
 1               5                  10                  15

Lys Gly Glu Thr Gly Asp Ile Gly Pro Met Gly Leu Pro Gly Arg Asp
            20                  25                  30

Gly Val Pro Gly Arg Pro Gly Glu Thr Gly Lys Asn Gly Gly Phe Gly
            35                  40                  45

Arg Arg Gly Ser Ala Gly Ala Lys Gly Asn Lys
 50                  55
```

<210> SEQ ID NO 191
<211> LENGTH: 59
<212> TYPE: PRT
<213> ORGANISM: Otolemur garnettii

<400> SEQUENCE: 191

```
Arg Gly Asp Pro Gly Glu Ser Gly Gln Asp Ser Gln Gln Arg Gly Pro
 1               5                  10                  15

Lys Gly Glu Thr Gly Asp Ile Gly Pro Met Gly Leu Pro Gly Arg Asp
            20                  25                  30
```

-continued

Gly Val Ser Gly Ser Pro Gly Glu Thr Gly Lys Asn Gly Gly Phe Gly
            35                  40                  45

Arg Arg Gly Pro Ala Gly Ala Lys Gly Asn Lys
    50                  55

<210> SEQ ID NO 192
<211> LENGTH: 59
<212> TYPE: PRT
<213> ORGANISM: Propithecus coquereli

<400> SEQUENCE: 192

Arg Gly Asp Pro Gly Glu Ser Gly Gln Asp Ser Gln Gln Arg Gly Pro
1               5                   10                  15

Lys Gly Glu Thr Gly Asp Ile Gly Pro Met Gly Leu Pro Gly Arg Asp
            20                  25                  30

Gly Val Ser Gly Ser Pro Gly Glu Asn Gly Lys Asn Gly Gly Phe Gly
            35                  40                  45

Arg Arg Gly Pro Ala Gly Ala Lys Gly Asn Lys
    50                  55

<210> SEQ ID NO 193
<211> LENGTH: 59
<212> TYPE: PRT
<213> ORGANISM: Mus musculus

<400> SEQUENCE: 193

Arg Gly Asp Pro Gly Asp Ser Gly Arg Asp Ser Gln Gln Arg Gly Pro
1               5                   10                  15

Lys Gly Glu Thr Gly Asp Ile Gly Pro Met Gly Leu Pro Gly Arg Asp
            20                  25                  30

Gly Ile Pro Gly Ser Pro Gly Asp Pro Gly Lys Asp Gly Gly Ser Gly
            35                  40                  45

Arg Arg Gly Pro Ala Gly Ala Lys Gly Asn Arg
    50                  55

<210> SEQ ID NO 194
<211> LENGTH: 59
<212> TYPE: PRT
<213> ORGANISM: Rattus norvegicus

<400> SEQUENCE: 194

Arg Gly Asp Pro Gly Asp Ser Gly Arg Asp Ser Gln Gln Arg Gly Pro
1               5                   10                  15

Lys Gly Glu Thr Gly Asp Ile Gly Pro Met Gly Leu Pro Gly Arg Asp
            20                  25                  30

Gly Ile Pro Gly Ser Pro Gly Asp Pro Gly Lys Asp Gly Gly Phe Gly
            35                  40                  45

Arg Arg Gly Pro Ala Gly Ala Lys Gly Asn Arg
    50                  55

<210> SEQ ID NO 195
<211> LENGTH: 59
<212> TYPE: PRT
<213> ORGANISM: Cricetulus griseus

<400> SEQUENCE: 195

Arg Gly Asp Pro Gly Asp Ser Gly Arg Asp Ser Gln Gln Arg Gly Pro
1               5                   10                  15

Lys Gly Glu Thr Gly Asp Ile Gly Pro Met Gly Leu Pro Gly Arg Asp 20                  25                  30

Gly Ile Pro Gly Arg Pro Gly Asp Pro Gly Lys Asp Gly Gly Ser Gly
                35                  40                  45

Arg Arg Gly Pro Ala Gly Ala Lys Gly Asn Arg
    50                  55

<210> SEQ ID NO 196
<211> LENGTH: 59
<212> TYPE: PRT
<213> ORGANISM: Microtus ochrogaster

<400> SEQUENCE: 196

Arg Gly Asp Pro Gly Asp Ser Gly Arg Asp Ser Gln Gln Arg Gly Pro
1               5                   10                  15

Lys Gly Glu Thr Gly Asp Ile Gly Pro Met Gly Leu Pro Gly Arg Asp
                20                  25                  30

Gly Val Pro Gly Arg Pro Gly Asp Pro Gly Lys Asp Gly Gly Phe Gly
                35                  40                  45

Arg Arg Gly Pro Ala Gly Ala Lys Gly Asn Arg
    50                  55

<210> SEQ ID NO 197
<211> LENGTH: 59
<212> TYPE: PRT
<213> ORGANISM: Meriones unguiculatus

<400> SEQUENCE: 197

Arg Gly Asp Pro Gly Asp Ser Gly Arg Asp Ser Gln Gln Arg Gly Pro
1               5                   10                  15

Lys Gly Glu Thr Gly Asp Ile Gly Pro Met Gly Leu Pro Gly Arg Asp
                20                  25                  30

Gly Ile Ser Gly Arg Pro Gly Asp Pro Gly Lys Asp Gly Gly Ser Gly
                35                  40                  45

Arg Arg Gly Pro Ala Gly Ala Lys Gly Asn Lys
    50                  55

<210> SEQ ID NO 198
<211> LENGTH: 59
<212> TYPE: PRT
<213> ORGANISM: Chinchilla lanigera

<400> SEQUENCE: 198

Arg Gly Asp Pro Gly Glu Ser Gly Gln Asp Ser Gln Gln Arg Gly Pro
1               5                   10                  15

Lys Gly Glu Thr Gly Asp Leu Gly Pro Met Gly Leu Pro Gly Arg Asp
                20                  25                  30

Gly Val Ser Gly Ser Pro Gly Glu Thr Gly Lys Asp Gly Gly Phe Gly
                35                  40                  45

Arg Arg Gly Pro Ala Gly Ala Lys Gly Asn Arg
    50                  55

<210> SEQ ID NO 199
<211> LENGTH: 59
<212> TYPE: PRT
<213> ORGANISM: Castor canadensis

<400> SEQUENCE: 199

Arg Gly Asp Pro Gly Asp Ser Gly Gln Asp Ser Gln Gln Arg Gly Pro
1               5                   10                  15

Lys Gly Glu Thr Gly Asp Ile Gly Pro Met Gly Val Pro Gly Arg Asp
            20                  25                  30

Gly Ala Ser Gly Ser Pro Gly Glu Thr Gly Lys Asp Gly Gly Phe Gly
        35                  40                  45

Arg Arg Gly Pro Ala Gly Val Lys Gly Asn Arg
    50                  55

<210> SEQ ID NO 200
<211> LENGTH: 59
<212> TYPE: PRT
<213> ORGANISM: Fukomys damarensis

<400> SEQUENCE: 200

Arg Gly Asp Pro Gly Asp Ser Gly Gln Asp Asn Gln Gln Arg Gly Pro
1               5                   10                  15

Lys Gly Glu Thr Gly Asp Ile Gly Pro Met Gly Leu Pro Gly Arg Asp
            20                  25                  30

Gly Val Pro Gly Ser Pro Gly Gln Ala Gly Lys Asn Gly Gly Phe Gly
        35                  40                  45

Arg Arg Gly Pro Ala Gly Ala Lys Gly Asn Arg
    50                  55

<210> SEQ ID NO 201
<211> LENGTH: 59
<212> TYPE: PRT
<213> ORGANISM: Pteropus vampyrus

<400> SEQUENCE: 201

Arg Gly Val Lys Gly Asp Ser Gly Arg Asp Ser Gln Gln Arg Gly Pro
1               5                   10                  15

Lys Gly Glu Ile Gly Asp Ile Gly Pro Met Gly Leu Pro Gly Arg Asp
            20                  25                  30

Gly Val Ser Gly Ser Pro Gly Glu Pro Gly Lys Asp Gly Gly Phe Gly
        35                  40                  45

Arg Arg Gly Pro Ala Gly Ala Lys Gly Asn Lys
    50                  55

<210> SEQ ID NO 202
<211> LENGTH: 59
<212> TYPE: PRT
<213> ORGANISM: Manis javanica

<400> SEQUENCE: 202

Arg Gly Asp Pro Gly Asp Ser Gly Arg Asp Ser Gln Gln Arg Gly Pro
1               5                   10                  15

Lys Gly Glu Thr Gly Asp Leu Gly Pro Met Gly Leu Pro Gly Ser Asp
            20                  25                  30

Gly Leu Pro Gly Ser Ser Gly Glu Pro Gly Lys Asn Gly Gly Phe Gly
        35                  40                  45

Arg Arg Gly Pro Ala Gly Ala Lys Gly Asn Arg
    50                  55

<210> SEQ ID NO 203
<211> LENGTH: 59
<212> TYPE: PRT
<213> ORGANISM: Hipposideros armiger

<400> SEQUENCE: 203

Arg Gly Asp Pro Gly Glu Pro Gly Arg Asp Asn Gln Gln Arg Gly Pro
1               5                   10                  15

Lys Gly Glu Thr Gly Asp Ile Gly Pro Met Gly Leu Pro Gly Arg Asp
            20                  25                  30

Gly Ala Pro Gly Arg Pro Gly Glu Pro Gly Glu Ser Gly Gly Phe Gly
            35                  40                  45

Arg Arg Gly Pro Ala Gly Ala Lys Gly Asn Lys
            50                  55

<210> SEQ ID NO 204
<211> LENGTH: 59
<212> TYPE: PRT
<213> ORGANISM: Loxodonta africana

<400> SEQUENCE: 204

Arg Gly Asp Pro Gly Asp Ser Gly Arg Asp Gly Gln Gln Pro Gly Pro
1               5                   10                  15

Lys Gly Glu Thr Gly Glu Ile Gly Pro Met Gly Leu Pro Gly Arg Asp
            20                  25                  30

Gly Val Ser Gly Gly Pro Gly Glu Pro Gly Lys Asp Gly Ser Phe Gly
            35                  40                  45

Arg Arg Gly Pro Ala Gly Asn Lys Gly Ser Lys
            50                  55

<210> SEQ ID NO 205
<211> LENGTH: 59
<212> TYPE: PRT
<213> ORGANISM: Sus scrofa

<400> SEQUENCE: 205

Arg Gly Asp Pro Gly Asp Thr Gly Arg Asp Ser Gln Gln Arg Gly Pro
1               5                   10                  15

Lys Gly Glu Ser Gly Asp Leu Gly Pro Met Gly Leu Pro Gly Arg Asp
            20                  25                  30

Gly Val Ser Gly Ser Pro Gly Glu Pro Gly Lys Ser Gly Gly Phe Gly
            35                  40                  45

Arg Arg Gly Pro Ala Gly Leu Lys Gly Asn Lys
            50                  55

<210> SEQ ID NO 206
<211> LENGTH: 59
<212> TYPE: PRT
<213> ORGANISM: Balaenoptera acutorostrata scammoni

<400> SEQUENCE: 206

Arg Gly Asp Pro Gly Asn Ser Gly Gln Asp Ser Gln Gln Arg Gly Pro
1               5                   10                  15

Lys Gly Glu Thr Gly Asp Ile Gly Pro Met Gly Leu Pro Gly Ala Asp
            20                  25                  30

Gly Val Ser Gly Gly Pro Gly Glu Pro Gly Lys Ser Gly Gly Phe Gly
            35                  40                  45

Arg Arg Gly Pro Ala Gly Ala Lys Gly Asn Lys
            50                  55

<210> SEQ ID NO 207
<211> LENGTH: 59
<212> TYPE: PRT
<213> ORGANISM: Orcinus orca

<400> SEQUENCE: 207

Arg Gly Asp Pro Gly Asn Ser Gly Gln Asp Ser Gln Gln Arg Gly Pro

```
                1               5                  10                 15
Lys Gly Glu Thr Gly Asp Ile Gly Pro Met Gly Leu Pro Gly Thr Asp
                20                 25                 30

Gly Val Ser Gly Ala Pro Gly Glu Pro Gly Lys Ser Gly Gly Phe Gly
        35                 40                 45

Gln Arg Gly Pro Ala Gly Ala Lys Gly Asn Lys
    50                  55
```

<210> SEQ ID NO 208
<211> LENGTH: 59
<212> TYPE: PRT
<213> ORGANISM: Phascolarctos cinereus

<400> SEQUENCE: 208

```
Arg Gly Asp Pro Gly Glu Ile Gly Leu Asp Ser Gln Gln Gln Gly Ala
1               5                  10                 15

Glu Gly Glu Lys Gly Glu Ile Gly Pro Met Gly Met Pro Gly Leu Asp
                20                 25                 30

Gly Thr Pro Gly Gly Pro Gly Val Val Gly Lys Asp Gly Gly Pro Gly
        35                 40                 45

Arg Arg Gly Pro Pro Gly Val Lys Gly Asn Lys
    50                  55
```

<210> SEQ ID NO 209
<211> LENGTH: 59
<212> TYPE: PRT
<213> ORGANISM: Sarcophilus harrisii

<400> SEQUENCE: 209

```
Arg Gly Asp Pro Gly Glu Ile Gly Lys Asp Asn Gln Gln Gln Gly Pro
1               5                  10                 15

Arg Gly Glu Lys Gly Glu Ile Gly Pro Met Gly Val Pro Gly Leu Asp
                20                 25                 30

Gly Arg Ala Gly Gly Pro Gly Gly Leu Gly Lys Asp Gly Gly Pro Gly
        35                 40                 45

Arg Arg Gly Pro Pro Gly Ala Lys Gly Asn Lys
    50                  55
```

<210> SEQ ID NO 210
<211> LENGTH: 59
<212> TYPE: PRT
<213> ORGANISM: Ornithorhynchus anatinus

<400> SEQUENCE: 210

```
Arg Gly Asp Pro Gly Asp Ser Gly Leu Asp Ser Arg Gln Arg Gly Pro
1               5                  10                 15

Lys Gly Gln Lys Gly Glu Ile Gly Pro Met Gly Leu Pro Gly Asn Asp
                20                 25                 30

Gly Ala Pro Gly Ser Pro Gly Gly Asn Gly Lys Glu Gly Gly Phe Gly
        35                 40                 45

Arg Arg Gly Thr Val Gly Val Lys Gly Ser Lys
    50                  55
```

<210> SEQ ID NO 211
<211> LENGTH: 59
<212> TYPE: PRT
<213> ORGANISM: Unknown
<220> FEATURE:
<223> OTHER INFORMATION: Description of Unknown:
      COL6A3 sequence

<400> SEQUENCE: 211

Arg Gly Asp Pro Gly Asp Ser Gly Ala Asp Asn Thr Gln Arg Gly Ser
1               5                   10                  15

Arg Gly Gln Lys Gly Glu Ile Gly Pro Met Gly Asp Pro Gly Pro Ala
            20                  25                  30

Gly Leu Glu Gly Gln Asp Gly Gly Val Gly Arg Lys Gly Met Ala Gly
        35                  40                  45

Arg Arg Gly Pro Ile Gly Val Lys Gly Thr Lys
    50                  55

<210> SEQ ID NO 212
<211> LENGTH: 59
<212> TYPE: PRT
<213> ORGANISM: Haliaeetus leucocephalus

<400> SEQUENCE: 212

Arg Gly Asp Pro Gly Asp Ser Gly Ala Asp Asn Thr Gln Arg Gly Ser
1               5                   10                  15

Arg Gly Gln Lys Gly Glu Ile Gly Pro Met Gly Glu Pro Gly Pro Val
            20                  25                  30

Gly Leu Asn Gly Gln Asp Gly Gly Val Gly Arg Lys Gly Met Thr Gly
        35                  40                  45

Arg Arg Gly Pro Ile Gly Val Lys Gly Thr Lys
    50                  55

<210> SEQ ID NO 213
<211> LENGTH: 59
<212> TYPE: PRT
<213> ORGANISM: Aquila chrysaetos canadensis

<400> SEQUENCE: 213

Arg Gly Asp Pro Gly Asp Ser Gly Ala Asp Asn Thr Gln Arg Gly Ser
1               5                   10                  15

Arg Gly Gln Lys Gly Glu Ile Gly Pro Met Gly Glu Pro Gly Pro Val
            20                  25                  30

Gly Leu Asp Gly Gln Asp Gly Gly Val Gly Arg Lys Gly Met Thr Gly
        35                  40                  45

Arg Arg Gly Pro Ile Gly Val Lys Gly Thr Lys
    50                  55

<210> SEQ ID NO 214
<211> LENGTH: 59
<212> TYPE: PRT
<213> ORGANISM: Gallus gallus

<400> SEQUENCE: 214

Arg Gly Asp Pro Gly Glu Ser Gly Ala Asp Asn Thr Gln Arg Gly Thr
1               5                   10                  15

Arg Gly Gln Lys Gly Glu Ile Gly Gln Met Gly Glu Pro Gly Pro Ala
            20                  25                  30

Gly Gln Arg Gly Gln Asp Gly Gly Val Gly Arg Lys Gly Met Ala Gly
        35                  40                  45

Arg Arg Gly Pro Ile Gly Val Lys Gly Thr Lys
    50                  55

<210> SEQ ID NO 215
<211> LENGTH: 59
<212> TYPE: PRT

<213> ORGANISM: Picoides pubescens

<400> SEQUENCE: 215

Arg Gly Asp Pro Gly Asp Ser Gly Val Asp Asn Thr Gln Arg Gly Ser
1               5                   10                  15

Arg Gly Gln Lys Gly Glu Ile Gly Pro Met Gly Glu Thr Gly Pro Val
            20                  25                  30

Gly Leu Glu Gly Gln Asp Gly Gly Val Gly Arg Lys Gly Met Thr Gly
        35                  40                  45

Arg Arg Gly Pro Ile Gly Val Lys Gly Thr Lys
    50                  55

<210> SEQ ID NO 216
<211> LENGTH: 59
<212> TYPE: PRT
<213> ORGANISM: Meleagris gallopavo

<400> SEQUENCE: 216

Arg Gly Asp Pro Gly Asp Ser Gly Ala Asp Asn Thr Gln Arg Gly Thr
1               5                   10                  15

Arg Gly Gln Lys Gly Glu Ile Gly Gln Met Gly Glu Pro Gly Pro Ala
            20                  25                  30

Gly Gln Arg Gly Pro Asp Gly Gly Val Gly Arg Gln Gly Met Ala Gly
        35                  40                  45

Arg Arg Gly Pro Ile Gly Val Lys Gly Thr Lys
    50                  55

<210> SEQ ID NO 217
<211> LENGTH: 59
<212> TYPE: PRT
<213> ORGANISM: Merops nubicus

<400> SEQUENCE: 217

Arg Gly Asp Pro Gly Asp Ser Gly Ala Asp Asn Thr Gln Arg Gly Ser
1               5                   10                  15

Lys Gly Gln Lys Gly Glu Ile Gly Pro Met Gly Glu Pro Gly Pro Val
            20                  25                  30

Gly Leu Asn Gly Gln Asp Gly Gly Val Gly Arg Lys Gly Met Thr Gly
        35                  40                  45

Arg Arg Gly Pro Ile Gly Val Lys Gly Thr Lys
    50                  55

<210> SEQ ID NO 218
<211> LENGTH: 57
<212> TYPE: PRT
<213> ORGANISM: Colius striatus

<400> SEQUENCE: 218

Arg Gly Asp Pro Gly Asp Ser Gly Ala Asp Asn Thr Gln Arg Gly Ser
1               5                   10                  15

Arg Gly Gln Lys Gly Glu Ile Gly Pro Met Gly Glu Pro Gly Pro Ala
            20                  25                  30

Gly Leu Asp Gly Gln Asp Gly Gly Val Gly Arg Lys Gly Met Thr Gly
        35                  40                  45

Arg Arg Gly Pro Ile Gly Val Lys Gly
    50                  55

<210> SEQ ID NO 219
<211> LENGTH: 59

```
<212> TYPE: PRT
<213> ORGANISM: Apteryx australis mantelli

<400> SEQUENCE: 219

Arg Gly Asp Pro Gly Glu Ser Gly Ala Asp Asn Thr Gln Arg Gly Ser
1               5                   10                  15

Arg Gly Gln Lys Gly Glu Ile Gly Pro Met Gly Glu Pro Gly Gly Ala
            20                  25                  30

Gly Ala Asn Gly Gln Asn Gly Gly Ile Gly Arg Lys Gly Met Ala Gly
        35                  40                  45

Arg Arg Gly Pro Ile Gly Ile Lys Gly Thr Lys
    50                  55

<210> SEQ ID NO 220
<211> LENGTH: 59
<212> TYPE: PRT
<213> ORGANISM: Aptenodytes forsteri

<400> SEQUENCE: 220

Arg Gly Asp Pro Gly Asp Ser Gly Ala Asp Asn Thr Gln Arg Gly Ser
1               5                   10                  15

Arg Gly Gln Lys Gly Glu Ile Gly Pro Met Gly Glu Pro Gly Pro Ala
            20                  25                  30

Gly Leu Asp Gly Gln Asp Gly Gly Val Gly Arg Lys Gly Met Thr Gly
        35                  40                  45

Arg Arg Gly Leu Ile Gly Val Lys Gly Thr Lys
    50                  55

<210> SEQ ID NO 221
<211> LENGTH: 59
<212> TYPE: PRT
<213> ORGANISM: Columba livia

<400> SEQUENCE: 221

Arg Gly Asp Pro Gly Asp Ser Gly Ala Asp Asn Thr Gln Arg Gly Ser
1               5                   10                  15

Arg Gly Gln Lys Gly Glu Ile Gly Pro Met Gly Glu Pro Gly Pro Ala
            20                  25                  30

Gly Leu Glu Gly Gln Glu Gly Gly Val Gly Arg Arg Gly Met Ala Gly
        35                  40                  45

Arg Arg Gly Pro Ile Gly Val Lys Gly Thr Lys
    50                  55

<210> SEQ ID NO 222
<211> LENGTH: 59
<212> TYPE: PRT
<213> ORGANISM: Patagioenas fasciata monilis

<400> SEQUENCE: 222

Arg Gly Asp Pro Gly Asp Ser Gly Ala Asp Asn Thr Gln Arg Gly Ser
1               5                   10                  15

Arg Gly Gln Lys Gly Glu Ile Gly Pro Met Gly Glu Pro Gly Pro Ala
            20                  25                  30

Gly Leu Glu Gly Gln Glu Gly Gly Val Gly Arg Arg Gly Met Ala Gly
        35                  40                  45

Arg Arg Gly Pro Ile Gly Val Lys Gly Thr Lys
    50                  55

<210> SEQ ID NO 223
```

```
<211> LENGTH: 59
<212> TYPE: PRT
<213> ORGANISM: Pygoscelis adeliae

<400> SEQUENCE: 223

Arg Gly Asp Pro Gly Asp Ser Gly Ala Asp Asn Thr Gln Arg Gly Ser
1               5                   10                  15

Arg Gly Gln Lys Gly Glu Ile Gly Pro Met Gly Glu Pro Gly Pro Val
            20                  25                  30

Gly Leu Asp Gly Gln Gly Gly Val Gly Arg Lys Gly Met Thr Gly
        35                  40                  45

Arg Arg Gly Pro Ile Gly Val Lys Gly Thr Lys
    50                  55

<210> SEQ ID NO 224
<211> LENGTH: 59
<212> TYPE: PRT
<213> ORGANISM: Calidris pugnax

<400> SEQUENCE: 224

Arg Gly Asp Pro Gly Asp Ser Gly Ala Asp Asn Thr Gln Arg Gly Ser
1               5                   10                  15

Arg Gly Pro Lys Gly Glu Ile Gly Pro Met Gly Glu Pro Gly Pro Ala
            20                  25                  30

Gly Leu Asp Gly Gln Asp Gly Gly Val Gly Arg Lys Gly Met Pro Gly
        35                  40                  45

Arg Arg Gly Pro Ile Gly Val Lys Gly Thr Lys
    50                  55

<210> SEQ ID NO 225
<211> LENGTH: 59
<212> TYPE: PRT
<213> ORGANISM: Coturnix japonica

<400> SEQUENCE: 225

Arg Gly Asp Pro Gly Asp Ser Gly Ala Asp Asn Thr Gln Arg Gly Thr
1               5                   10                  15

Arg Gly Gln Lys Gly Glu Ile Gly Gln Met Gly Glu Pro Gly Pro Ala
            20                  25                  30

Gly Gln Arg Gly Pro Asp Gly Gly Val Gly Arg Gln Gly Met Ala Gly
        35                  40                  45

Arg Arg Gly Thr Ile Gly Ile Lys Gly Thr Lys
    50                  55

<210> SEQ ID NO 226
<211> LENGTH: 59
<212> TYPE: PRT
<213> ORGANISM: Nipponia nippon

<400> SEQUENCE: 226

Arg Gly Asp Pro Gly Asp Ser Gly Ala Asp Asn Thr Gln Arg Gly Ser
1               5                   10                  15

Arg Gly Gln Lys Gly Glu Ile Gly Pro Met Gly Ala Pro Gly Pro Val
            20                  25                  30

Gly Leu Gly Gly Glu Glu Gly Val Gly Arg Lys Gly Met Thr Gly
        35                  40                  45

Arg Arg Gly Pro Ile Gly Val Lys Gly Thr Lys
    50                  55
```

```
<210> SEQ ID NO 227
<211> LENGTH: 59
<212> TYPE: PRT
<213> ORGANISM: Calypte anna

<400> SEQUENCE: 227

Arg Gly Asp Pro Gly Asp Ser Gly Ala Asp Asn Thr Gln Arg Gly Ser
1               5                   10                  15

Arg Gly Gln Lys Gly Glu Ile Gly Pro Met Gly Glu Pro Gly Pro Val
            20                  25                  30

Gly Val Asp Gly Gln Asp Gly Gly Val Gly Arg Lys Gly Met Thr Gly
        35                  40                  45

Arg Arg Gly Pro Ile Gly Pro Lys Gly Thr Lys
    50                  55

<210> SEQ ID NO 228
<211> LENGTH: 59
<212> TYPE: PRT
<213> ORGANISM: Egretta garzetta

<400> SEQUENCE: 228

Arg Gly Asp Pro Gly Asp Ser Gly Ala Asp Asn Thr Gln Arg Gly Ser
1               5                   10                  15

Arg Gly Gln Lys Gly Glu Ile Gly Pro Met Gly Glu Pro Gly Pro Met
            20                  25                  30

Gly Leu Val Gly Gln Asp Gly Gly Val Gly Arg Lys Gly Met Thr Gly
        35                  40                  45

Arg Arg Gly Gln Ile Gly Val Lys Gly Thr Lys
    50                  55

<210> SEQ ID NO 229
<211> LENGTH: 59
<212> TYPE: PRT
<213> ORGANISM: Serinus canaria

<400> SEQUENCE: 229

Arg Gly Asp Pro Gly Asp Ser Gly Ala Asp Asn Thr Gln Arg Gly Pro
1               5                   10                  15

Arg Gly Gln Lys Gly Glu Ile Gly Pro Met Gly Asp Pro Gly Pro Ala
            20                  25                  30

Gly Pro Glu Gly Gln Asp Gly Glu Val Gly Arg Arg Gly Met Ala Gly
        35                  40                  45

Arg Arg Gly Pro Ile Gly Val Lys Gly Thr Lys
    50                  55

<210> SEQ ID NO 230
<211> LENGTH: 59
<212> TYPE: PRT
<213> ORGANISM: Sturnus vulgaris

<400> SEQUENCE: 230

Arg Gly Asp Pro Gly Asp Ser Gly Ala Asp Asn Thr Gln Arg Gly Ser
1               5                   10                  15

Arg Gly Gln Lys Gly Glu Ile Gly Pro Met Gly Asp Pro Gly Pro Ala
            20                  25                  30

Gly Leu Glu Gly Gln Asp Gly Gly Val Gly Arg Arg Gly Met Pro Gly
        35                  40                  45

Arg Arg Gly Pro Ile Gly Val Lys Gly Thr Lys
    50                  55
```

<210> SEQ ID NO 231
<211> LENGTH: 59
<212> TYPE: PRT
<213> ORGANISM: Taeniopygia guttata

<400> SEQUENCE: 231

Arg Gly Asp Pro Gly Asp Ser Gly Ala Asp Asn Thr Gln Arg Gly Pro
1               5                   10                  15

Arg Gly Gln Lys Gly Glu Ile Gly Pro Met Gly Asp Pro Gly Pro Ala
            20                  25                  30

Gly Leu Glu Gly Pro Asp Gly Glu Val Gly Arg Arg Gly Met Ala Gly
        35                  40                  45

Arg Arg Gly Pro Ile Gly Val Lys Gly Thr Lys
    50                  55

<210> SEQ ID NO 232
<211> LENGTH: 59
<212> TYPE: PRT
<213> ORGANISM: Lonchura striata domestica

<400> SEQUENCE: 232

Arg Gly Asp Pro Gly Asp Ser Gly Ala Asp Asn Thr Gln Arg Gly Pro
1               5                   10                  15

Arg Gly Gln Lys Gly Glu Ile Gly Pro Met Gly Asp Pro Gly Pro Ala
            20                  25                  30

Gly Pro Glu Gly Pro Asp Gly Glu Val Gly Arg Arg Gly Met Ala Gly
        35                  40                  45

Arg Arg Gly Pro Ile Gly Val Lys Gly Thr Lys
    50                  55

<210> SEQ ID NO 233
<211> LENGTH: 58
<212> TYPE: PRT
<213> ORGANISM: Chaetura pelagica

<400> SEQUENCE: 233

Arg Gly Asp Pro Gly Asp Ser Gly Ala Asp Asn Thr Gln Arg Gly Pro
1               5                   10                  15

Lys Gly Gln Lys Gly Glu Ile Gly Pro Met Gly Glu Pro Gly Pro Glu
            20                  25                  30

Gly Val Ala Gly Gln Ala Gly Ala Gly Arg Lys Gly Met Ala Gly
        35                  40                  45

Arg Arg Gly Pro Ile Gly Val Lys Gly Thr
    50                  55

<210> SEQ ID NO 234
<211> LENGTH: 59
<212> TYPE: PRT
<213> ORGANISM: Callipepla squamata

<400> SEQUENCE: 234

Arg Gly Asp Pro Gly Asp Ser Gly Ala Asp Asn Thr Gln Arg Gly Thr
1               5                   10                  15

Arg Gly Gln Lys Gly Glu Ile Gly Gln Met Gly Glu Pro Gly Pro Val
            20                  25                  30

Gly Gln Arg Gly Pro Asp Gly Val Gly Arg Met Gly Met Ala Gly
        35                  40                  45

Arg Arg Gly Pro Ile Gly Val Lys Gly Thr Lys
    50                  55

<210> SEQ ID NO 235
<211> LENGTH: 59
<212> TYPE: PRT
<213> ORGANISM: Cuculus canorus

<400> SEQUENCE: 235

Arg Gly Asp Pro Gly Asp Ser Gly Ala Asp Asn Thr Gln Arg Gly Thr
1               5                   10                  15

Arg Gly Gln Lys Gly Glu Ile Gly Pro Met Gly Glu Pro Gly Gln Ala
            20                  25                  30

Gly Pro Glu Gly Gln Glu Gly Val Gly Arg Lys Gly Met Thr Gly
        35                  40                  45

Arg Arg Gly Ala Ile Gly Val Lys Gly Thr Lys
    50                  55

<210> SEQ ID NO 236
<211> LENGTH: 58
<212> TYPE: PRT
<213> ORGANISM: Lepidothrix coronata

<400> SEQUENCE: 236

Arg Gly Asp Pro Gly Asp Ser Gly Ala Asp Asn Thr Gln Arg Gly Ser
1               5                   10                  15

Arg Gly Gln Lys Gly Glu Ile Gly Pro Met Gly Glu Pro Gly Pro Pro
            20                  25                  30

Gly Leu Lys Gly Gln Asp Gly Gly Val Gly Arg Lys Gly Met Thr Gly
        35                  40                  45

Arg Arg Gly Gln Ile Gly Val Lys Gly Thr
    50                  55

<210> SEQ ID NO 237
<211> LENGTH: 59
<212> TYPE: PRT
<213> ORGANISM: Falco peregrinus

<400> SEQUENCE: 237

Arg Gly Asp Pro Gly Asp Ser Gly Ala Asp Asn Thr Gln Arg Gly Ser
1               5                   10                  15

Arg Gly Pro Lys Gly Glu Ile Gly Pro Met Gly Glu Pro Gly Leu Val
            20                  25                  30

Gly Leu Asp Gly Gln Asp Gly Gly Val Gly Arg Lys Gly Met Thr Gly
        35                  40                  45

Arg Arg Gly Gln Ile Gly Ile Lys Gly Thr Lys
    50                  55

<210> SEQ ID NO 238
<211> LENGTH: 59
<212> TYPE: PRT
<213> ORGANISM: Melopsittacus undulatus

<400> SEQUENCE: 238

Arg Gly Asp Pro Gly Asp Ser Gly Ala Asp Asn Thr Gln Arg Gly Pro
1               5                   10                  15

Arg Gly Gln Lys Gly Glu Ile Gly Gln Met Gly Glu Pro Gly Pro Val
            20                  25                  30

Gly Pro Asp Gly Gln Asn Gly Glu Val Gly Arg Gln Gly Met Ala Gly
        35                  40                  45

Arg Arg Gly Pro Ile Gly Val Lys Gly Thr Lys

<210> SEQ ID NO 239
<211> LENGTH: 52
<212> TYPE: PRT
<213> ORGANISM: Gekko japonicus

<400> SEQUENCE: 239

Glu Lys Gly Asn Lys Gly Tyr Thr Gly Pro Leu Gly Pro Lys Gly Gln
1               5                   10                  15

Pro Gly Arg Pro Gly Leu Gln Gly Pro Pro Gly Ala Thr Gly Arg Pro
            20                  25                  30

Gly Val Ser Arg Pro Gly Gln Arg Gly Pro Gln Gly Thr Pro Gly Leu
        35                  40                  45

Lys Gly Asn Lys
    50

<210> SEQ ID NO 240
<211> LENGTH: 58
<212> TYPE: PRT
<213> ORGANISM: Anolis carolinensis

<400> SEQUENCE: 240

Lys Gly Gln Pro Gly Arg Pro Gly Val Pro Gly Ile Pro Gly Pro Arg
1               5                   10                  15

Gly Glu Met Gly Leu Met Gly Pro Val Gly Asn Pro Gly Leu Ser Gly
            20                  25                  30

Val Pro Gly Asn Pro Gly Ile Pro Gly Ile Arg Gly Ser Pro Gly Phe
        35                  40                  45

Ser Gly Leu Lys Gly Arg Lys Gly Ser Ser
    50                  55

<210> SEQ ID NO 241
<211> LENGTH: 59
<212> TYPE: PRT
<213> ORGANISM: Python bivittatus

<400> SEQUENCE: 241

Arg Gly Asp Pro Gly Thr Ala Gly Thr Asp Ser Thr Gln Lys Gly Pro
1               5                   10                  15

Lys Gly Gln Lys Gly Glu Leu Gly Pro Ala Gly Glu Ser Gly Arg Asp
            20                  25                  30

Gly Pro Arg Gly Asp Ala Gly Ile Gly Arg Asp Gly Gly Leu Gly
        35                  40                  45

Arg Arg Gly Gln Pro Gly Ile Lys Gly Asn Lys
    50                  55

<210> SEQ ID NO 242
<211> LENGTH: 59
<212> TYPE: PRT
<213> ORGANISM: Protobothrops mucrosquamatus

<400> SEQUENCE: 242

Arg Gly Asn Pro Gly Ser Phe Gly Thr Asp Ser Ser Asp Arg Gly Leu
1               5                   10                  15

Lys Gly Glu Lys Gly Glu Leu Gly Ser Ala Gly Glu Leu Gly Arg Asn
            20                  25                  30

Gly Pro Arg Gly Asp Ala Gly Gly Ala Gly Arg Asp Gly Ala Leu Gly
        35                  40                  45

```
Arg Arg Gly Pro Pro Gly Ile Lys Gly Asn Lys
    50                  55
```

<210> SEQ ID NO 243
<211> LENGTH: 59
<212> TYPE: PRT
<213> ORGANISM: Ophiophagus hannah

<400> SEQUENCE: 243

```
Gly Lys Pro Gly Thr Pro Gly Phe Arg Gly Glu Arg Gly Leu Met Gly
1               5                   10                  15

His Gly Gly Ser Pro Gly Leu Pro Gly Val Ser Gly Asn Pro Gly Ile
            20                  25                  30

Pro Gly Gly Arg Gly Ser Pro Gly Phe Pro Gly Ser Lys Gly Arg Lys
        35                  40                  45

Gly Ser Phe Gly Glu Lys Gly Glu Pro Gly Asp
    50                  55
```

<210> SEQ ID NO 244
<211> LENGTH: 59
<212> TYPE: PRT
<213> ORGANISM: Thamnophis sirtalis

<400> SEQUENCE: 244

```
Arg Gly Asp Pro Gly Thr Phe Gly Thr Asp Ser Thr Asp Arg Gly Pro
1               5                   10                  15

Lys Gly Glu Lys Gly Glu Leu Gly Pro Ala Gly Glu Leu Gly Arg Asp
            20                  25                  30

Gly Pro Arg Gly Asp Ala Gly Glu Ala Gly Arg Asp Gly Ser Leu Gly
        35                  40                  45

Lys Arg Gly Pro Pro Gly Ile Lys Gly Asn Lys
    50                  55
```

<210> SEQ ID NO 245
<211> LENGTH: 59
<212> TYPE: PRT
<213> ORGANISM: Latimeria chalumnae

<400> SEQUENCE: 245

```
Arg Gly Asp Pro Gly Thr Pro Gly Thr Asn Val Arg Arg Gly Pro
1               5                   10                  15

Lys Gly Gln Lys Gly Glu Ile Gly Pro Gln Gly Asp Pro Gly Asn Asp
            20                  25                  30

Gly Thr Ser Gly Thr Gly Pro Arg Gly Lys Gly Ser Ala Gly
        35                  40                  45

Arg Arg Gly Pro Pro Gly Thr Lys Gly Glu Gln
    50                  55
```

<210> SEQ ID NO 246
<211> LENGTH: 59
<212> TYPE: PRT
<213> ORGANISM: Rhincodon typus

<400> SEQUENCE: 246

```
Arg Gly Asp Pro Gly Glu Pro Gly Leu Thr Asn Ile Gln Lys Gly Asp
1               5                   10                  15

Lys Gly Gln Arg Gly Asp Met Gly Leu Val Gly Glu Thr Gly Ala Ser
            20                  25                  30

Gly Arg Pro Gly Ser Pro Gly Ala Ser Gly Arg Arg Gly Thr Gln Gly
        35                  40                  45
```

Arg Arg Gly Pro Pro Gly Ala Arg Gly Ser Lys
    50                  55

<210> SEQ ID NO 247
<211> LENGTH: 59
<212> TYPE: PRT
<213> ORGANISM: Callorhinchus milii

<400> SEQUENCE: 247

Arg Gly Asp Pro Gly Thr Ser Gly Thr Asp Asn Thr Gln Arg Gly Ile
1               5                   10                  15

Lys Gly Gln Lys Gly Asp Ser Gly Ile Ala Gly Asp Pro Gly Thr Asp
            20                  25                  30

Gly Thr Pro Gly Gln Arg Gly Pro Leu Gly Lys Asn Gly Ala Thr Gly
        35                  40                  45

Arg Arg Gly Ser Ala Gly Pro Arg Gly Asp Lys
    50                  55

<210> SEQ ID NO 248
<211> LENGTH: 54
<212> TYPE: PRT
<213> ORGANISM: Salmo salar

<400> SEQUENCE: 248

Arg Gly Asp Pro Gly Thr Thr Gly Gln Asp Asn Asn Val Ala Gly Pro
1               5                   10                  15

Lys Gly Asp Pro Gly Asp Val Gly Pro Val Gly Glu Pro Gly Asp Asp
            20                  25                  30

Gly Lys Met Gly Gly Pro Gly Glu Pro Gly Arg Thr Gly Ser Asp Gly
        35                  40                  45

Arg Arg Gly Pro Pro Gly
    50

<210> SEQ ID NO 249
<211> LENGTH: 57
<212> TYPE: PRT
<213> ORGANISM: Xenopus laevis

<400> SEQUENCE: 249

Arg Gly Asp Pro Gly Glu Pro Gly Thr Asn Ser Asn Asn Gln Gly Pro
1               5                   10                  15

Lys Gly Leu Lys Gly Asn Ser Gly Arg Gln Gly Glu Thr Gly Arg Asp
            20                  25                  30

Gly Val Gln Gly Lys Arg Gly Asp Asn Gly Pro Asn Gly Ser Gln Gly
        35                  40                  45

Arg Arg Gly Pro Pro Gly Leu Lys Gly
    50                  55

<210> SEQ ID NO 250
<211> LENGTH: 51
<212> TYPE: PRT
<213> ORGANISM: Cyprinus carpio

<400> SEQUENCE: 250

Arg Gly Asp Pro Gly Asn Pro Gly Ile Asp Asn Asn Ser Arg Gly Pro
1               5                   10                  15

Lys Gly Asp Ile Gly Ser Pro Gly Ile Gln Gly Glu Pro Gly Gln Asp
            20                  25                  30

Gly Leu Ser Gly Gln Ile Gly Asp Glu Gly Arg Pro Gly Pro Asn Gly

Arg Arg Gly
    50

<210> SEQ ID NO 251
<211> LENGTH: 529
<212> TYPE: DNA
<213> ORGANISM: Equus caballus

<400> SEQUENCE: 251

```
ggtccccgag atttctggct ttctttgtgg cgaggtcggg ggaggtgggt gcctgactgt    60
tttccccttc ctcctgctca tgccccttcc tggctttcag atcagggtcc aggtgatcga   120
ggggcgccag ctgccagggg tgaacatcaa gcctgtggtc aaggtcaccg cggccaggca   180
gaccaagcgg actcggattc acaggggaaa cagcccgctc ttcaacgagg tgggagacat   240
ggcgttttag ggctggtagc ttggtgggcc ttccagattg ggagcacccg gcagatacct   300
ggcaattctt tcagtttttg ttcatggcgc taactttggt ttgagaggtg tgccaggtcc   360
tgagtacgtt atctgaggaa ctggagagag ggttctagtt cttattcctg tcccgggctc   420
ctggtgctcc acatccctgt cttcctgtgg ggccagccac ccatgctgtc ctggagatga   480
caacctctga gaggtcaggg gtggaacacc ccagaacttg tcgagtcct              529
```

<210> SEQ ID NO 252
<211> LENGTH: 529
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252

```
ggtccccgag atttctggct ttctttgtgg cgaggtcggg ggaggtgggt gcctgactgt    60
tttccccttc ctcctgctca tgccccttcc tggctttcag atcagggtcc aggtgatcga   120
ggggcgccag ctgccagggg tgaacatcaa gcctgtggtc aaggtcaccg cggccaggca   180
gaccaagtgg actcggattc acaggggaaa cagcccgctc ttcaacgagg tgggagacat   240
ggcgttttag ggctggtagc ttggtgggcc ttccagattg ggagcacccg gcagatacct   300
ggcaattctt tcagtttttg ttcatggcgc taactttggt ttgagaggtg tgccaggtcc   360
tgagtacgtt atctgaggaa ctggagagag ggttctagtt cttattcctg tcccgggctc   420
ctggtgctcc acatccctgt cttcctgtgg ggccagccac ccatgctgtc ctggagatga   480
caacctctga gaggtcaggg gtggaacacc ccagaacttg tcgagtcct              529
```

<210> SEQ ID NO 253
<211> LENGTH: 450
<212> TYPE: DNA
<213> ORGANISM: Equus caballus

<400> SEQUENCE: 253

```
actggttgca aactcccaac tgtgatcact gacatattcc atgagtgtca ttttgtggct    60
gaaggtgtgt ttgcctggcc cggacagaaa ggagggtgat ggggccttgg gtgacaggca   120
ctgaccaaag ctctttttc taccccgcag ccggccatct accacattcc tggttttgag   180
gtaagtcttg ctcttccctc ttcttcttca aactcatggc ccgcctctgt gtgtttgcag   240
ccccctatga gctaggaagg gcagtcaggt gtataccacc accggcccgc ttcaggat    300
ggggtgggtg agggccgggg tccctggcca gctcaggcct ttcccgccct tcttccctga   360
```

```
gactcagact gtagggacct catggtcatc cagcccacgg gctctcagct gggctgcatg      420
ttagaatccc ttcggcagct tgaaaaatca                                       450

<210> SEQ ID NO 254
<211> LENGTH: 450
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 254
actggttgca aactcccaac tgtgatcact gacatattcc atgagtgtca ttttgtggct       60
gaaggtgtgt ttgcctggcc cggacagaaa ggagggtgat ggggccttgg gtgacaggca      120
ctgaccaaag ctcttttttc tacccgcag ccggccatct accacattac tggttttgag      180
gtaagtcttg ctcttccctc ttcttcttca aactcatggc ccgcctctgt gtgtttgcag      240 cccccctatga gctaggaagg gcagtcaggt gtataccacc accggcccgc cttcagggat      300
ggggtgggtg agggccgggg tccctggcca gctcaggcct ttcccgccct tcttccctga      360
gactcagact gtagggacct catggtcatc cagcccacgg gctctcagct gggctgcatg      420
ttagaatccc ttcggcagct tgaaaaatca                                       450

<210> SEQ ID NO 255
<211> LENGTH: 499
<212> TYPE: DNA
<213> ORGANISM: Equus caballus

<400> SEQUENCE: 255
ttctttggaa ctctctccag tgacactttt agctgtaaaa ttttgtgaac agattttctg       60
ctggccattc taaataacac aaaataacta tatattgtgt ttccttttta tactcactag      120
aataacttct ttatcgcctt ttatatatag gttgtattgc tgggaaaata caatgcacag      180
ggcttaggtt cagatcatga attaatgctg agatgtacca aaggacaaga atacgtcaaa      240
gtcgtcatgc aaaatgggcg aatgatggga gctgtcttaa ttggtgaaac cgatttagaa      300
gaaacatttg aaaacttgat tttaaaccag atgaatcttt cagcatatgg agaagatctg      360
ctggatccag atattgacat agaagattat tttgactaaa aaggtcattc caagaaccac      420
ataaagttcc aaataagaca aaaaagtcac acatcaataa agtaaatgat tgcactgatt      480
taatgatgac cacattgaa                                                   499

<210> SEQ ID NO 256
<211> LENGTH: 499
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 256
ttctttggaa ctctctccag tgacactttt agctgtaaaa ttttgtgaac agattttctg       60
ctggccattc taaataacac aaaataacta tatattgtgt ttccttttta tactcactag      120
aataacttct ttatcgcctt ttatatatag gttgtattgc tgggaaaata caatgcacag      180
ggcttaggtt cagatcatga attaatgctg agatgtacca aaggacaaga atacgtcaaa      240
gtcgtcatgc aaaatgggcg aatgatggga gctgtcttaa ttggtgaaac cgatttagaa      300
```

```
gaaacatttg aaaacttgat tttaaaccag atgaatcttt cagcatatgg agaagatctg       360
ctgcatccag atattgacat agaagattat tttgactaaa aaggtcattc caagaaccac       420
ataaagttcc aaataagaca aaaaagtcac acatcaataa agtaaatgat tgcactgatt       480
taatgatgac cacattgaa                                                    499

<210> SEQ ID NO 257
<211> LENGTH: 704
<212> TYPE: DNA
<213> ORGANISM: Equus caballus

<400> SEQUENCE: 257
agacctcggg cccatggtac gatgctcctt gttcccagac tctcctgtgc tggaggccag        60
agaaacaaag ctcacactgg ctcgccaggg gccgaaggac catggaagtg gtctttgagg       120
ctggggagca tatgcggtca ggaacagagg gccccgtgaa gcccaccctg tgtgcccatg       180
aaggacgttt ccattgtgga acagaagcaa gccctaccga gaggagcttc ttctgggcag       240
aagttgtgct ctttagatat ttacgaaagc gcttgtcaag ccaaaggctg tggggcggg       300 cacgtaccta agtctagcgc acctcacgac agagtaccga ccttcctctg cctatccatc      360
ccttttcctg tagtgtctcg tgcaatattc cagagttcct gctcttcttt gcagatgaaa      420
atcttacacc aatttttcttc cccacgccag ggtctgcctg ggagtgatgg tgtctcggga     480
agtcctggag aaccagggag ggacgtgagt gtctcttaca gctttggagg gaggtggcgg      540
ggcctctgtg ctggtattta gcaggtgccc tccagatctt ccagacactg cctggggcgt      600
tgttacccag caactctttg tttaaagaat ttaaagagat ttctgaaacc tttgtcaccc      660
aaatcttgat gcttatggaa aacattcgtc cttattgttt gatc                       704

<210> SEQ ID NO 258
<211> LENGTH: 704
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 258
agacctcggg cccatggtac gatgctcctt gttcccagac tctcctgtgc tggaggccag        60
agaaacaaag ctcacactgg ctcgccaggg gccgaaggac catggaagtg gtctttgagg       120
ctggggagca tatgcggtca ggaacagagg gccccgtgaa gcccaccctg tgtgcccatg       180
aaggacgttt ccattgtgga acagaagcaa gccctaccga gaggagcttc ttctgggcag       240
aagttgtgct ctttagatat ttacgaaagc gcttgtcaag ccaaaggctg tggggcggg       300 cacgtaccta agtctagcgc acctcacgac agagtaccga ccttcctctg cctatccatc      360
ccttttcctg tagtgtctcg tgcaatattc cagagttcct gctcttcttt gcagatgaaa      420
atcttacacc aatttttcttc cccacgccag ggtctgcctg cgagtgatgg tgtctcggga     480
agtcctggag aaccagggag ggacgtgagt gtctcttaca gctttggagg gaggtggcgg      540
ggcctctgtg ctggtattta gcaggtgccc tccagatctt ccagacactg cctggggcgt      600
tgttacccag caactctttg tttaaagaat ttaaagagat ttctgaaacc tttgtcaccc      660
aaatcttgat gcttatggaa aacattcgtc cttattgttt gatc                       704

<210> SEQ ID NO 259
<211> LENGTH: 11
<212> TYPE: DNA
```

```
<213> ORGANISM: Equus caballus

<400> SEQUENCE: 259
ccaagcggac t                                                           11

<210> SEQ ID NO 260
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
ccaagtggac t                                                           11

<210> SEQ ID NO 261
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
ccaagtggac t                                                           11

<210> SEQ ID NO 262
<211> LENGTH: 11
<212> TYPE: DNA
<213> ORGANISM: Equus caballus

<400> SEQUENCE: 262
accaggaatg t                                                           11

<210> SEQ ID NO 263
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
accaggaatg t                                                           11

<210> SEQ ID NO 264
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
accagtaatg t                                                           11
```